(12) United States Patent
Bialas

(10) Patent No.: US 12,167,961 B2
(45) Date of Patent: Dec. 17, 2024

(54) METHODS AND SYSTEMS FOR ALIGNING A COMMISSURE OF A PROSTHETIC HEART VALVE WITH A COMMISSURE OF A NATIVE VALVE

(71) Applicant: EDWARDS LIFESCIENCES CORPORATION, Irvine, CA (US)

(72) Inventor: Michael R. Bialas, Lake Forest, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 0 days.

(21) Appl. No.: 18/113,833

(22) Filed: Feb. 24, 2023

(65) Prior Publication Data

US 2023/0190456 A1  Jun. 22, 2023

Related U.S. Application Data

(63) Continuation of application No. PCT/US2021/047056, filed on Aug. 23, 2021.
(Continued)

(51) Int. Cl.
*A61F 2/24* (2006.01)
*A61B 50/30* (2016.01)
(Continued)

(52) U.S. Cl.
CPC ............ *A61F 2/24* (2013.01); *A61B 50/30* (2016.02); *A61F 2/2418* (2013.01);
(Continued)

(58) Field of Classification Search
CPC ........ A61F 2/24; A61F 2/2433; A61F 2/2418; A61F 2/2436; A61B 19/00; A61B 50/30
See application file for complete search history.

(56) References Cited

U.S. PATENT DOCUMENTS

| 519,297 A | 5/1894 | Bauer |
| 3,557,947 A | 1/1971 | Greenwell |

(Continued)

FOREIGN PATENT DOCUMENTS

| DE | 19532846 A1 | 3/1997 |
| DE | 19907646 A1 | 8/2000 |

(Continued)

*Primary Examiner* — Matthew W Schall
(74) *Attorney, Agent, or Firm* — Klarquist Sparkman, LLP; Sean Seung Kyu Kim

(57) ABSTRACT

Methods and systems for rotationally aligning a commissure of a prosthetic heart valve with a commissure of a native valve are disclosed. In some examples, a method can comprise advancing a distal end portion of a delivery apparatus toward a native valve; visualizing under fluoroscopy and for a selected imaging view, a position of a radiopaque marker on the distal end portion relative to a guidewire extending through the delivery apparatus, the marker circumferentially offset from a selected commissure of the radially compressed prosthetic valve by a predetermined amount that is determined based on the selected imaging view; rotating the delivery apparatus until the marker is centered along the guidewire; and advancing the distal end portion into the native valve and inflating the balloon to radially expand and implant the prosthetic valve in the native valve such that the selected commissure is aligned with a commissure of the native valve.

12 Claims, 80 Drawing Sheets

Related U.S. Application Data

(60) Provisional application No. 63/138,890, filed on Jan. 19, 2021, provisional application No. 63/069,567, filed on Aug. 24, 2020.

(51) Int. Cl.
*A61M 25/10* (2013.01)
*A61F 2/95* (2013.01)
*A61F 2/958* (2013.01)

(52) U.S. Cl.
CPC .......... *A61F 2/2436* (2013.01); *A61M 25/10* (2013.01); *A61F 2/2433* (2013.01); *A61F 2/9517* (2020.05); *A61F 2002/9583* (2013.01); *A61F 2220/0025* (2013.01); *A61F 2220/0075* (2013.01); *A61F 2230/0002* (2013.01); *A61F 2250/0098* (2013.01)

(56) References Cited

U.S. PATENT DOCUMENTS

| | | |
|---|---|---|
| 4,035,849 A | 7/1977 | Angell et al. |
| 4,349,498 A | 9/1982 | Ellis et al. |
| 4,592,340 A | 6/1986 | Boyles |
| 4,930,341 A | 6/1990 | Euteneuer |
| 4,955,895 A | 9/1990 | Sugiyama et al. |
| 4,994,077 A | 2/1991 | Dobben |
| 5,015,231 A | 5/1991 | Keith et al. |
| 5,053,007 A | 10/1991 | Euteneuer |
| 5,059,177 A | 10/1991 | Towne et al. |
| 5,137,512 A | 8/1992 | Burns et al. |
| 5,176,698 A | 1/1993 | Burns et al. |
| 5,192,297 A | 3/1993 | Hull |
| 5,205,413 A | 4/1993 | Cautereels et al. |
| 5,266,073 A | 11/1993 | Wall |
| 5,325,845 A | 7/1994 | Adair |
| 5,352,236 A | 10/1994 | Jung et al. |
| 5,358,496 A | 10/1994 | Ortiz et al. |
| 5,411,552 A | 5/1995 | Andersen et al. |
| 5,417,707 A | 5/1995 | Parkola |
| 5,554,185 A | 9/1996 | Block et al. |
| 5,569,294 A | 10/1996 | Parkola |
| 5,584,852 A | 12/1996 | Parkola |
| 5,591,195 A | 1/1997 | Taheri et al. |
| 5,599,305 A | 2/1997 | Hermann et al. |
| 5,632,760 A | 5/1997 | Sheiban et al. |
| 5,639,274 A | 6/1997 | Fischell et al. |
| 5,728,068 A | 3/1998 | Leone et al. |
| 5,749,890 A | 5/1998 | Shaknovich |
| 5,782,809 A | 7/1998 | Umeno et al. |
| 5,824,042 A | 10/1998 | Lombardi et al. |
| 5,824,044 A | 10/1998 | Quiachon et al. |
| 5,840,081 A | 11/1998 | Andersen et al. |
| 5,908,405 A | 6/1999 | Imran et al. |
| 5,916,147 A | 6/1999 | Boury |
| 5,944,690 A | 8/1999 | Falwell et al. |
| 5,961,536 A | 10/1999 | Mickley et al. |
| 5,968,068 A | 10/1999 | Dehdashtian et al. |
| 6,019,777 A | 2/2000 | Mackenzie |
| 6,027,510 A | 2/2000 | Alt |
| 6,033,380 A | 3/2000 | Butaric et al. |
| 6,033,381 A | 3/2000 | Kontos |
| 6,110,146 A | 8/2000 | Berthiaume et al. |
| 6,132,450 A | 10/2000 | Hanson et al. |
| 6,143,016 A | 11/2000 | Bleam et al. |
| 6,162,208 A | 12/2000 | Hipps |
| 6,168,614 B1 | 1/2001 | Andersen et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,235,050 B1 | 5/2001 | Quiachon et al. |
| 6,251,092 B1 | 6/2001 | Qin et al. |
| 6,379,372 B1 | 4/2002 | Dehdashtian et al. |
| 6,383,171 B1 | 5/2002 | Gifford et al. |
| 6,454,799 B1 | 9/2002 | Schreck |
| 6,458,153 B1 | 10/2002 | Bailey et al. |
| 6,461,382 B1 | 10/2002 | Cao |
| 6,468,219 B1 | 10/2002 | Njemanze |
| 6,471,672 B1 | 10/2002 | Brown et al. |
| 6,500,147 B2 | 12/2002 | Omaleki et al. |
| 6,514,228 B1 | 2/2003 | Hamilton et al. |
| 6,514,280 B1 | 2/2003 | Gilson |
| 6,527,979 B2 | 3/2003 | Constantz et al. |
| 6,540,782 B1 | 4/2003 | Snyders |
| 6,579,305 B1 | 6/2003 | Lashinski |
| 6,582,462 B1 | 6/2003 | Andersen et al. |
| 6,612,482 B2 | 9/2003 | Ross |
| 6,613,067 B1 | 9/2003 | Johnson |
| 6,652,578 B2 | 11/2003 | Bailey et al. |
| 6,730,118 B2 | 5/2004 | Spenser et al. |
| 6,733,525 B2 | 5/2004 | Yang et al. |
| 6,749,584 B2 | 6/2004 | Briggs et al. |
| 6,764,504 B2 | 7/2004 | Wang et al. |
| 6,767,362 B2 | 7/2004 | Schreck |
| 6,830,584 B1 | 12/2004 | Seguin |
| 6,893,460 B2 | 5/2005 | Spenser et al. |
| 6,908,481 B2 | 6/2005 | Cribier |
| 6,960,186 B1 | 11/2005 | Fukaya et al. |
| 7,011,094 B2 | 3/2006 | Rapacki et al. |
| 7,018,406 B2 | 3/2006 | Seguin et al. |
| 7,018,408 B2 | 3/2006 | Bailey et al. |
| 7,105,013 B2 | 9/2006 | Durcan |
| 7,137,993 B2 | 11/2006 | Acosta et al. |
| 7,276,084 B2 | 10/2007 | Yang et al. |
| 7,318,278 B2 | 1/2008 | Zhang et al. |
| 7,320,702 B2 | 1/2008 | Hammersmark et al. |
| 7,320,704 B2 | 1/2008 | Lashinski et al. |
| 7,374,571 B2 | 5/2008 | Pease et al. |
| 7,393,360 B2 | 7/2008 | Spenser et al. |
| 7,435,257 B2 | 10/2008 | Lashinski et al. |
| 7,510,575 B2 | 3/2009 | Spenser et al. |
| 7,585,321 B2 | 9/2009 | Cribier |
| 7,594,926 B2 | 9/2009 | Linder et al. |
| 7,597,709 B2 | 10/2009 | Goodin |
| 7,618,446 B2 | 11/2009 | Andersen et al. |
| 7,658,727 B1 | 2/2010 | Fernandes et al. |
| 7,694,814 B1 | 4/2010 | Cristobal et al. |
| 7,763,063 B2 | 7/2010 | Arbefeuille et al. |
| 7,780,723 B2 | 8/2010 | Taylor |
| 7,785,366 B2 | 8/2010 | Maurer et al. |
| 7,874,426 B2 | 1/2011 | Castellani |
| 7,959,661 B2 | 6/2011 | Hijlkema et al. |
| 8,007,605 B2 | 8/2011 | Arbefeuille et al. |
| 8,014,849 B2 | 9/2011 | Peckham |
| 8,029,556 B2 | 10/2011 | Rowe |
| 8,062,345 B2 | 11/2011 | Ouellette et al. |
| 8,062,349 B2 | 11/2011 | Moore et al. |
| 8,070,790 B2 | 12/2011 | Berra et al. |
| 8,167,932 B2 | 5/2012 | Bourang et al. |
| 8,292,943 B2 | 10/2012 | Berra et al. |
| 8,308,790 B2 | 11/2012 | Arbefeuille et al. |
| RE43,882 E | 12/2012 | Hopkins et al. |
| 8,449,595 B2 | 5/2013 | Ouellette et al. |
| 8,449,606 B2 | 5/2013 | Eliasen et al. |
| 8,475,523 B2 | 7/2013 | Duffy |
| 8,500,792 B2 | 8/2013 | Berra |
| 8,568,472 B2 | 10/2013 | Marchand et al. |
| 8,636,788 B2 | 1/2014 | Arbefeuille et al. |
| 8,694,076 B2 | 4/2014 | Eidenschink et al. |
| 8,740,963 B2 | 6/2014 | Arbefeuille et al. |
| 8,889,211 B2 | 11/2014 | Owens et al. |
| 8,983,577 B2 | 3/2015 | Hansis et al. |
| 8,998,981 B2 | 4/2015 | Tuval et al. |
| 9,061,119 B2 | 6/2015 | Le et al. |
| 9,089,422 B2 | 7/2015 | Ryan et al. |
| 9,107,736 B2 | 8/2015 | Bei et al. |
| 9,114,010 B2 | 8/2015 | Gaschino et al. |
| 9,119,716 B2 | 9/2015 | Lee et al. |
| 9,173,755 B2 | 11/2015 | Berra et al. |
| 9,198,786 B2 | 12/2015 | Moore et al. |
| 9,220,617 B2 | 12/2015 | Berra |
| 9,233,015 B2 | 1/2016 | Geusen et al. |
| 9,248,016 B2 | 2/2016 | Oba et al. |
| 9,320,631 B2 | 4/2016 | Moore et al. |

(56) References Cited

U.S. PATENT DOCUMENTS

| | | |
|---|---|---|
| 9,333,104 B2 | 5/2016 | Ouellette et al. |
| 9,370,422 B2 | 6/2016 | Wang |
| 9,370,643 B2 | 6/2016 | Hedberg et al. |
| 9,387,075 B2 | 7/2016 | Bortlein et al. |
| 9,387,106 B2 | 7/2016 | Stante et al. |
| 9,408,734 B2 | 8/2016 | Arbefeuille et al. |
| 9,408,735 B2 | 8/2016 | Arbefeuille et al. |
| 9,561,124 B2 | 2/2017 | Arbefeuille et al. |
| 9,579,197 B2 | 2/2017 | Duffy et al. |
| 9,597,214 B2 | 3/2017 | Heraty et al. |
| 9,655,712 B2 | 5/2017 | Berra et al. |
| 9,662,206 B2 | 5/2017 | Bortlein et al. |
| 9,744,034 B2 | 8/2017 | Braido et al. |
| 9,795,477 B2 | 10/2017 | Tran et al. |
| 9,877,857 B2 | 1/2018 | Arbefeuille et al. |
| 9,883,961 B2 | 2/2018 | Heraty et al. |
| 9,907,686 B2 | 3/2018 | Ouellette et al. |
| 9,913,743 B2 | 3/2018 | Arbefeuille et al. |
| 9,925,080 B2 | 3/2018 | Arbefeuille et al. |
| 9,931,207 B2 | 4/2018 | Oba et al. |
| 9,943,407 B2 | 4/2018 | Tuval et al. |
| 9,980,818 B2 | 5/2018 | Chau et al. |
| 10,016,579 B2 | 7/2018 | Campbell et al. |
| 10,028,830 B2 | 7/2018 | Wang |
| 10,034,787 B2 | 7/2018 | Chobotov et al. |
| 10,105,250 B2 | 10/2018 | Berra |
| 10,154,921 B2 | 12/2018 | Stante et al. |
| 10,182,930 B2 | 1/2019 | Moore et al. |
| 10,213,291 B2 | 2/2019 | Berra et al. |
| 10,293,085 B2 | 5/2019 | Orlowski |
| 10,299,948 B2 | 5/2019 | Bohn et al. |
| 10,390,929 B2 | 8/2019 | Arbefeuille et al. |
| 10,524,904 B2 | 1/2020 | O'Connell et al. |
| 10,543,116 B2 | 1/2020 | Bohn et al. |
| 10,639,148 B2 | 5/2020 | Braido et al. |
| 10,646,365 B2 | 5/2020 | Berra et al. |
| 10,709,559 B2 | 7/2020 | Delaloye et al. |
| 10,709,591 B2 | 7/2020 | Fox et al. |
| 10,722,352 B2 | 7/2020 | Spence |
| 10,751,178 B2 | 8/2020 | Reynolds et al. |
| 10,806,570 B2 | 10/2020 | Tuval et al. |
| 10,828,157 B2 | 11/2020 | Bortlein et al. |
| 10,842,623 B2 | 11/2020 | Chau et al. |
| 10,869,758 B2 | 12/2020 | Ganesan et al. |
| 10,905,860 B2 | 2/2021 | Goto et al. |
| 10,918,509 B2 | 2/2021 | Moore et al. |
| 10,945,827 B2 | 3/2021 | Berra et al. |
| 11,013,626 B2 | 5/2021 | Chobotov et al. |
| 11,026,786 B2 | 6/2021 | Tuval et al. |
| 11,103,341 B2 | 8/2021 | Arbefeuille et al. |
| 11,167,065 B2 | 11/2021 | Orlowski |
| 11,173,286 B2 | 11/2021 | Campbell et al. |
| 11,259,945 B2 | 3/2022 | Berra |
| 11,273,038 B2 | 3/2022 | Tang et al. |
| 11,285,029 B2 | 3/2022 | Bohn et al. |
| 11,413,173 B2 | 8/2022 | Arbefeuille et al. |
| 11,432,884 B1 | 9/2022 | Spence |
| 11,464,659 B2 | 10/2022 | Fox et al. |
| 11,484,370 B1 | 11/2022 | Spence |
| 11,596,537 B2 | 3/2023 | Berra et al. |
| 11,612,481 B2 | 3/2023 | Ganesan et al. |
| 11,622,854 B2 | 4/2023 | Spence |
| 11,642,220 B2 | 5/2023 | Börtlein et al. |
| 11,730,597 B2 | 8/2023 | Alon et al. |
| 11,801,131 B2 | 10/2023 | Baldwin |
| 11,813,158 B2 | 11/2023 | Arbefeuille et al. |
| 11,857,444 B2 | 1/2024 | Bohn et al. |
| 2001/0002445 A1 | 5/2001 | Vesely |
| 2001/0007082 A1 | 7/2001 | Dusbabek et al. |
| 2002/0010146 A1 | 1/2002 | Garvey et al. |
| 2002/0032481 A1 | 3/2002 | Gabbay |
| 2002/0058995 A1 | 5/2002 | Stevens |
| 2002/0165461 A1 | 11/2002 | Hayzelden et al. |
| 2003/0040792 A1 | 2/2003 | Gabbay |
| 2003/0050694 A1 | 3/2003 | Yang et al. |
| 2003/0074044 A1 | 4/2003 | Randby et al. |
| 2003/0120341 A1 | 6/2003 | Shennib et al. |
| 2003/0203915 A1 | 10/2003 | Fang et al. |
| 2004/0093061 A1 | 5/2004 | Acosta et al. |
| 2004/0122515 A1 | 6/2004 | Chu |
| 2004/0132805 A1 | 7/2004 | Garvey |
| 2004/0133263 A1 | 7/2004 | Dusbabek et al. |
| 2004/0143197 A1 | 7/2004 | Soukup et al. |
| 2004/0186563 A1 | 9/2004 | Lobbi |
| 2004/0186565 A1 | 9/2004 | Schreck |
| 2004/0260389 A1 | 12/2004 | Case et al. |
| 2005/0063907 A1 | 3/2005 | Brandon et al. |
| 2005/0079200 A1 | 4/2005 | Rathenow et al. |
| 2005/0080474 A1 | 4/2005 | Andreas et al. |
| 2005/0096736 A1 | 5/2005 | Osse et al. |
| 2005/0137689 A1 | 6/2005 | Salahieh et al. |
| 2005/0143817 A1 | 6/2005 | Hunter et al. |
| 2005/0149160 A1 | 7/2005 | McFerran |
| 2005/0203614 A1 | 9/2005 | Forster et al. |
| 2005/0203617 A1 | 9/2005 | Forster et al. |
| 2005/0245894 A1 | 11/2005 | Zadno-Azizi |
| 2006/0025857 A1 | 2/2006 | Bergheim et al. |
| 2006/0282150 A1 | 12/2006 | Olson et al. |
| 2007/0003753 A1 | 1/2007 | Asgari |
| 2007/0005131 A1 | 1/2007 | Taylor |
| 2007/0013094 A1 | 1/2007 | Bischofsberger et al. |
| 2007/0073389 A1 | 3/2007 | Bolduc et al. |
| 2007/0088431 A1 | 4/2007 | Bourang et al. |
| 2007/0100356 A1 | 5/2007 | Lucatero et al. |
| 2007/0112422 A1 | 5/2007 | Dehdashtian |
| 2007/0203566 A1 | 8/2007 | Arbefeuille et al. |
| 2007/0203575 A1 | 8/2007 | Forster et al. |
| 2007/0219612 A1 | 9/2007 | Andreas et al. |
| 2007/0239254 A1 | 10/2007 | Chia et al. |
| 2007/0244546 A1 | 10/2007 | Francis |
| 2007/0265700 A1 | 11/2007 | Eliasen et al. |
| 2008/0031103 A1 | 2/2008 | Horinouchi et al. |
| 2008/0065011 A1 | 3/2008 | Marchand et al. |
| 2008/0077226 A1 | 3/2008 | Ouellette et al. |
| 2008/0097404 A1 | 4/2008 | Yribarren et al. |
| 2008/0103520 A1 | 5/2008 | Selkee |
| 2008/0125853 A1 | 5/2008 | Bailey et al. |
| 2008/0140107 A1 | 6/2008 | Bei et al. |
| 2008/0146999 A1 | 6/2008 | Tanaka et al. |
| 2008/0255507 A1 | 10/2008 | Mushtaha |
| 2008/0268014 A1 | 10/2008 | Garvey et al. |
| 2008/0275540 A1 | 11/2008 | Wen |
| 2008/0294230 A1 | 11/2008 | Parker |
| 2009/0024428 A1 | 1/2009 | Hudock, Jr. |
| 2009/0069886 A1 | 3/2009 | Suri et al. |
| 2009/0069889 A1 | 3/2009 | Suri et al. |
| 2009/0088836 A1 | 4/2009 | Bishop et al. |
| 2009/0138079 A1 | 5/2009 | Tuval et al. |
| 2009/0149947 A1 | 6/2009 | Frohwitter |
| 2009/0157175 A1 | 6/2009 | Benichou |
| 2009/0192585 A1 | 7/2009 | Bloom et al. |
| 2009/0192591 A1 | 7/2009 | Ryan et al. |
| 2009/0222082 A1 | 9/2009 | Lock et al. |
| 2009/0228093 A1 | 9/2009 | Taylor et al. |
| 2009/0276040 A1 | 11/2009 | Rowe et al. |
| 2009/0281619 A1 | 11/2009 | Le et al. |
| 2009/0299456 A1 | 12/2009 | Melsheimer |
| 2009/0319037 A1 | 12/2009 | Rowe et al. |
| 2009/0326094 A1 | 12/2009 | Samkov |
| 2010/0030318 A1 | 2/2010 | Berra |
| 2010/0036472 A1 | 2/2010 | Papp |
| 2010/0036473 A1 | 2/2010 | Roth |
| 2010/0049313 A1 | 2/2010 | Alon et al. |
| 2010/0076402 A1 | 3/2010 | Mazzone et al. |
| 2010/0076541 A1 | 3/2010 | Kumoyama |
| 2010/0082089 A1 | 4/2010 | Quadri et al. |
| 2010/0094394 A1 | 4/2010 | Beach et al. |
| 2010/0121425 A1 | 5/2010 | Shimada |
| 2010/0121436 A1* | 5/2010 | Tuval ............... A61B 34/20 623/2.17 |
| 2010/0145431 A1 | 6/2010 | Wu et al. |
| 2010/0161036 A1 | 6/2010 | Pintor et al. |
| 2010/0174363 A1 | 7/2010 | Castro |
| 2010/0198347 A1 | 8/2010 | Zakay et al. |

(56) References Cited

U.S. PATENT DOCUMENTS

| | | |
|---|---|---|
| 2010/0241071 A1 | 9/2010 | Atanasoska et al. |
| 2010/0274344 A1 | 10/2010 | Dusbabek et al. |
| 2010/0274351 A1 | 10/2010 | Rolando et al. |
| 2011/0015729 A1 | 1/2011 | Jimenez et al. |
| 2011/0054596 A1 | 3/2011 | Taylor |
| 2011/0137331 A1 | 6/2011 | Walsh et al. |
| 2011/0160846 A1 | 6/2011 | Bishop et al. |
| 2011/0208288 A1 | 8/2011 | Arbefeuille et al. |
| 2011/0245911 A1 | 10/2011 | Quill et al. |
| 2011/0251683 A1 | 10/2011 | Tabor |
| 2012/0022629 A1 | 1/2012 | Perera et al. |
| 2012/0123529 A1 | 5/2012 | Levi et al. |
| 2012/0136367 A1 | 5/2012 | Pacetti et al. |
| 2012/0158129 A1 | 6/2012 | Duffy et al. |
| 2012/0205367 A1 | 8/2012 | Kawai et al. |
| 2012/0239142 A1 | 9/2012 | Liu et al. |
| 2012/0323315 A1 | 12/2012 | Bruchman et al. |
| 2013/0030519 A1 | 1/2013 | Tran et al. |
| 2013/0073032 A1 | 3/2013 | Wang |
| 2013/0178931 A1 | 7/2013 | Fargahi |
| 2013/0233746 A1 | 9/2013 | Mason |
| 2013/0282110 A1 | 10/2013 | Schweich, Jr. et al. |
| 2013/0317598 A1 | 11/2013 | Rowe et al. |
| 2014/0005777 A1 | 1/2014 | Anderl et al. |
| 2014/0014530 A1 | 1/2014 | Lin |
| 2014/0066896 A1 | 3/2014 | Tilson et al. |
| 2014/0194920 A1 | 7/2014 | Krahbichler |
| 2014/0207231 A1 | 7/2014 | Hacohen et al. |
| 2014/0257466 A1 | 9/2014 | Board et al. |
| 2014/0277428 A1 | 9/2014 | Skemp et al. |
| 2014/0296962 A1 | 10/2014 | Cartledge et al. |
| 2014/0324161 A1 | 10/2014 | Tegels et al. |
| 2014/0358224 A1 | 12/2014 | Tegels et al. |
| 2015/0068928 A1 | 3/2015 | Turner |
| 2015/0112427 A1 | 4/2015 | Schweich, Jr. et al. |
| 2015/0142101 A1 | 5/2015 | Coleman et al. |
| 2015/0209140 A1 | 7/2015 | Bell et al. |
| 2015/0265402 A1 | 9/2015 | Centola et al. |
| 2015/0313701 A1 | 11/2015 | Krahbichler |
| 2016/0058540 A1 | 3/2016 | Don Michael |
| 2016/0135310 A1 | 5/2016 | Kawai |
| 2016/0213441 A1 | 7/2016 | Connolly |
| 2016/0228241 A1 | 8/2016 | Al-Jilaihawi et al. |
| 2016/0270914 A1 | 9/2016 | Krans et al. |
| 2016/0278922 A1 | 9/2016 | Braido et al. |
| 2016/0287385 A1 | 10/2016 | Liu et al. |
| 2016/0296324 A1 | 10/2016 | Bapat et al. |
| 2016/0317288 A1 | 11/2016 | Rogers et al. |
| 2016/0331525 A1 | 11/2016 | Straubinger et al. |
| 2017/0065415 A1 | 3/2017 | Rupp et al. |
| 2017/0189160 A1 | 7/2017 | Krahbichler |
| 2017/0319333 A1 | 11/2017 | Tegels et al. |
| 2018/0110622 A1 | 4/2018 | Gregg et al. |
| 2018/0153689 A1 | 6/2018 | Maimon et al. |
| 2018/0282471 A1 | 10/2018 | Green et al. |
| 2018/0344456 A1 | 12/2018 | Barash et al. |
| 2019/0008635 A1 | 1/2019 | Francis et al. |
| 2019/0247177 A1 | 8/2019 | Kim |
| 2019/0298968 A1 | 10/2019 | Morin |
| 2019/0307591 A1 | 10/2019 | Folan |
| 2020/0093597 A1 | 3/2020 | O'Connell et al. |
| 2020/0123294 A1 | 4/2020 | Jiang et al. |
| 2020/0289259 A1 | 9/2020 | Christianson et al. |
| 2020/0306040 A1 | 10/2020 | Fung et al. |
| 2020/0306044 A1 | 10/2020 | Ratz et al. |
| 2020/0390550 A1 | 12/2020 | Delaloye et al. |
| 2021/0030533 A1 | 2/2021 | Tamir et al. |
| 2021/0046291 A1 | 2/2021 | Sardesai et al. |
| 2021/0068956 A1 | 3/2021 | Gale et al. |
| 2021/0186694 A1 | 6/2021 | Baldwin |
| 2021/0196442 A1 | 7/2021 | Giordano et al. |
| 2021/0220626 A1 | 7/2021 | Sardesai et al. |
| 2021/0251750 A1 | 8/2021 | Rumpca et al. |
| 2021/0251752 A1 | 8/2021 | Tuval et al. |
| 2021/0275299 A1 | 9/2021 | Peterson et al. |
| 2021/0275331 A1 | 9/2021 | Chobotov et al. |
| 2021/0290387 A1 | 9/2021 | Murad et al. |
| 2021/0315694 A1 | 10/2021 | Vidlund et al. |
| 2021/0330459 A1 | 10/2021 | Christianson et al. |
| 2021/0346154 A1 | 11/2021 | Kaleta et al. |
| 2022/0000601 A1 | 1/2022 | Khairkhahan et al. |
| 2022/0032015 A1 | 2/2022 | Campbell et al. |
| 2022/0054256 A1 | 2/2022 | Huddleston et al. |
| 2022/0054264 A1 | 2/2022 | McGuinn et al. |
| 2022/0287837 A1 | 9/2022 | Alkhatib |
| 2022/0296369 A1 | 9/2022 | Kheradvar et al. |
| 2022/0338981 A1 | 10/2022 | Alkhatib |
| 2022/0361907 A1 | 11/2022 | Osterbauer et al. |
| 2022/0362017 A1 | 11/2022 | Tang et al. |
| 2022/0362042 A1 | 11/2022 | Fox et al. |
| 2022/0401241 A1 | 12/2022 | Arbefeuille et al. |
| 2023/0012858 A1 | 1/2023 | Nollert et al. |
| 2023/0029387 A1 | 1/2023 | Yadav et al. |
| 2023/0030110 A1 | 2/2023 | Hake et al. |
| 2023/0038809 A1 | 2/2023 | Clapp et al. |
| 2023/0147309 A1 | 5/2023 | Berra et al. |
| 2023/0190456 A1 | 6/2023 | Bialas |
| 2023/0200986 A1 | 6/2023 | Chung et al. |
| 2023/0200988 A1 | 6/2023 | Ganesan et al. |
| 2023/0210657 A1 | 7/2023 | Murad |
| 2023/0277308 A1 | 9/2023 | Spence |
| 2023/0380966 A1 | 11/2023 | Le et al. |

FOREIGN PATENT DOCUMENTS

| | | |
|---|---|---|
| EP | 0592410 B1 | 10/1995 |
| EP | 0850607 A1 | 7/1998 |
| EP | 1554990 A2 | 7/2005 |
| EP | 1684819 A2 | 8/2006 |
| EP | 1776938 | 5/2009 |
| EP | 1772120 | 8/2011 |
| EP | 2395935 | 12/2011 |
| EP | 2397112 | 12/2011 |
| EP | 2614794 | 7/2013 |
| EP | 2736450 | 6/2014 |
| EP | 2755715 | 7/2014 |
| EP | 2651335 | 10/2014 |
| EP | 1673033 | 1/2015 |
| EP | 1986573 | 9/2015 |
| EP | 2349123 | 11/2015 |
| EP | 2950752 A2 | 12/2015 |
| EP | 2950832 A1 | 12/2015 |
| EP | 2254512 | 1/2016 |
| EP | 2967858 A2 | 1/2016 |
| EP | 3019122 | 5/2016 |
| EP | 2611476 | 8/2016 |
| EP | 2397106 | 11/2016 |
| EP | 2394689 | 6/2017 |
| EP | 2755602 | 8/2017 |
| EP | 3223757 | 10/2017 |
| EP | 3009102 | 1/2018 |
| EP | 3222317 | 11/2018 |
| EP | 2259757 | 3/2019 |
| EP | 3524207 | 8/2019 |
| EP | 3634322 | 4/2020 |
| EP | 2723436 | 11/2020 |
| EP | 3576670 | 12/2020 |
| EP | 3796867 | 3/2021 |
| EP | 3852692 A2 | 7/2021 |
| EP | 2421572 | 9/2021 |
| EP | 2358307 | 12/2021 |
| EP | 4018967 | 6/2022 |
| EP | 3206631 | 7/2022 |
| EP | 4076283 | 10/2022 |
| EP | 3579905 | 11/2022 |
| EP | 4088691 | 11/2022 |
| EP | 4090290 | 11/2022 |
| EP | 2861189 | 12/2022 |
| FR | 2815844 A1 | 5/2002 |
| WO | 9117720 A1 | 11/1991 |
| WO | 9829057 A1 | 7/1998 |
| WO | 9912483 A1 | 3/1999 |
| WO | 0149213 A2 | 7/2001 |
| WO | 0154625 A1 | 8/2001 |

(56) References Cited

FOREIGN PATENT DOCUMENTS

| WO | 0176510 A2 | 10/2001 |
|---|---|---|
| WO | 0222054 | 3/2002 |
| WO | 0236048 A1 | 5/2002 |
| WO | 0247575 A2 | 6/2002 |
| WO | 02060352 | 8/2002 |
| WO | 03030776 A2 | 4/2003 |
| WO | 03047468 | 6/2003 |
| WO | 2004019825 A1 | 3/2004 |
| WO | 2005084595 A1 | 9/2005 |
| WO | 2005102015 A2 | 11/2005 |
| WO | 2006032051 A2 | 3/2006 |
| WO | 2006111391 A1 | 10/2006 |
| WO | 2006138173 A2 | 12/2006 |
| WO | 2007047488 A2 | 4/2007 |
| WO | 2007067942 A1 | 6/2007 |
| WO | 2010121076 A2 | 10/2010 |
| WO | 2014162306 A2 | 10/2014 |
| WO | 2022046654 A1 | 3/2022 |
| WO | WO 2022/261184 | 12/2022 |
| WO | 2023012680 A1 | 2/2023 |

\* cited by examiner

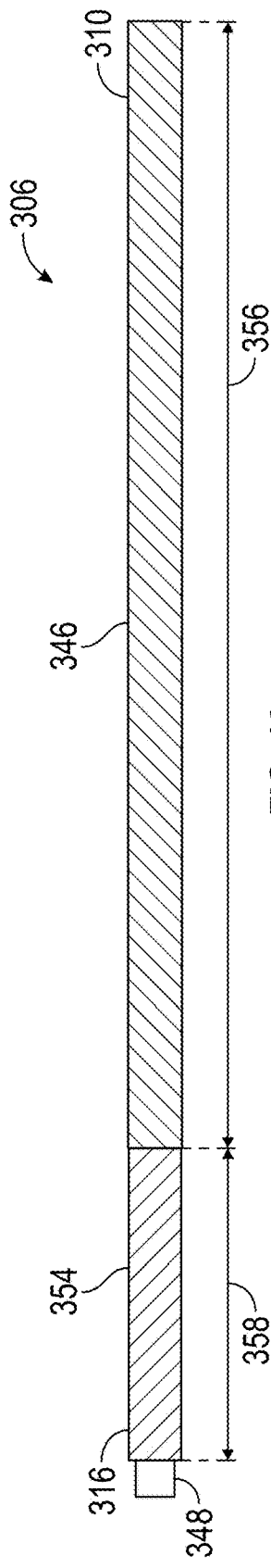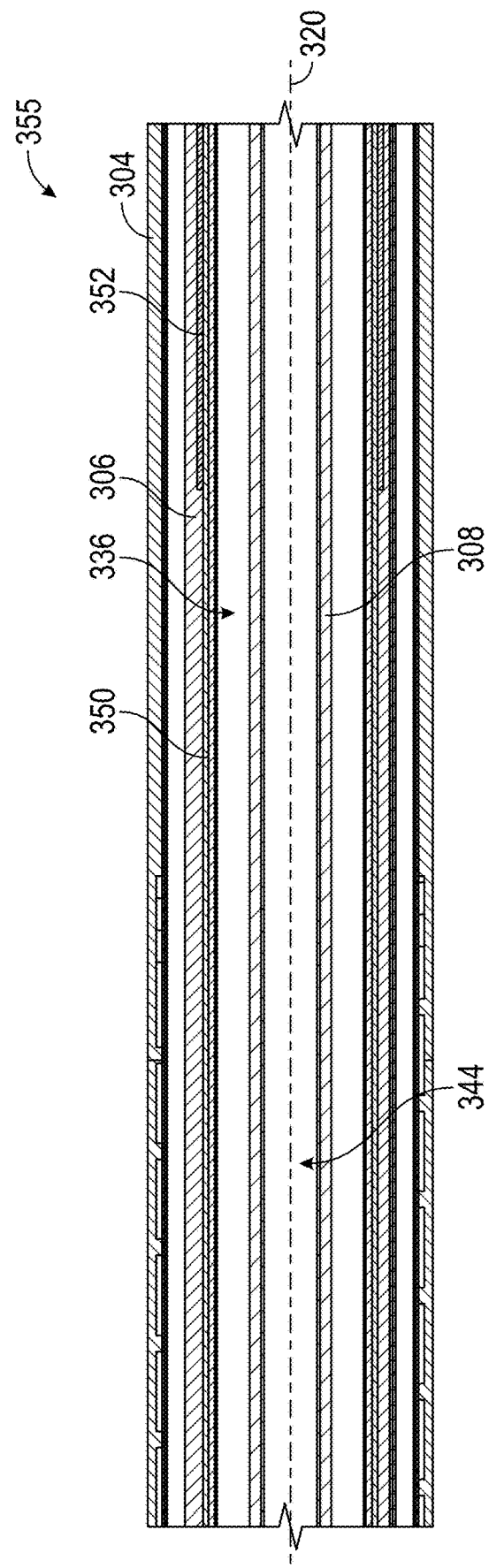

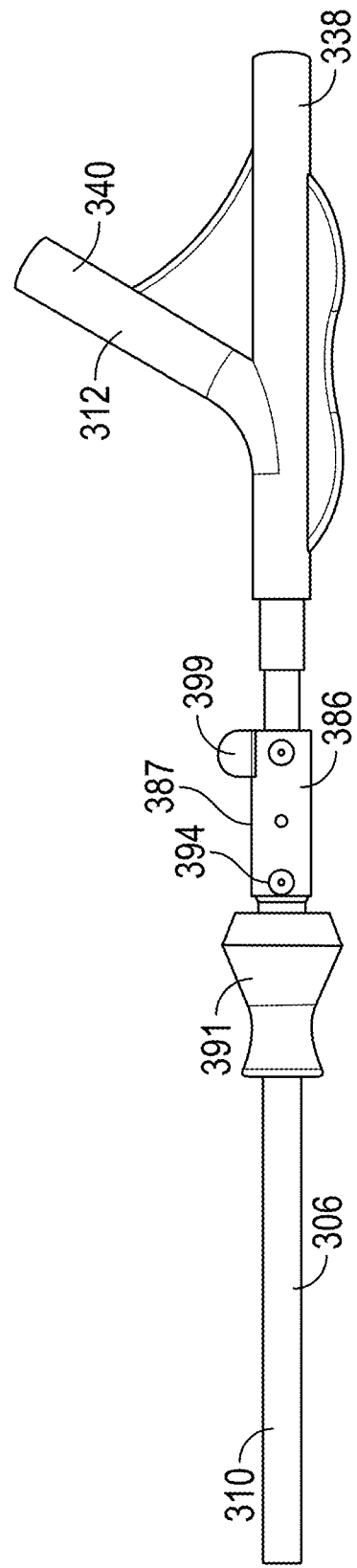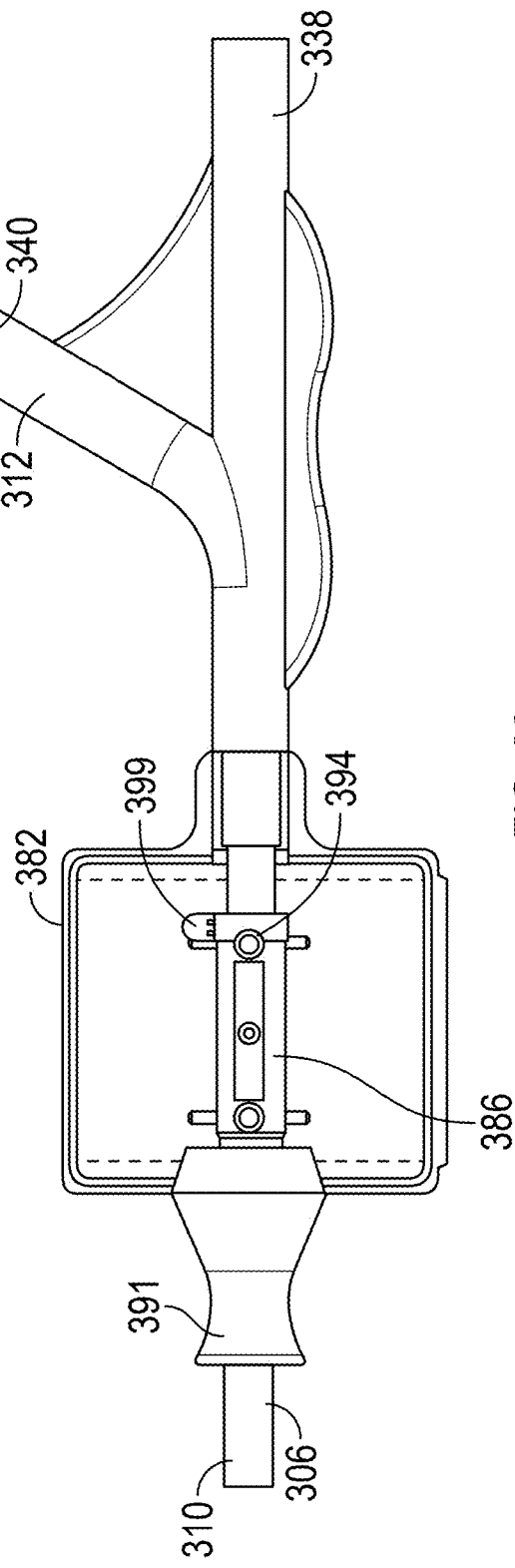
FIG. 21
FIG. 22

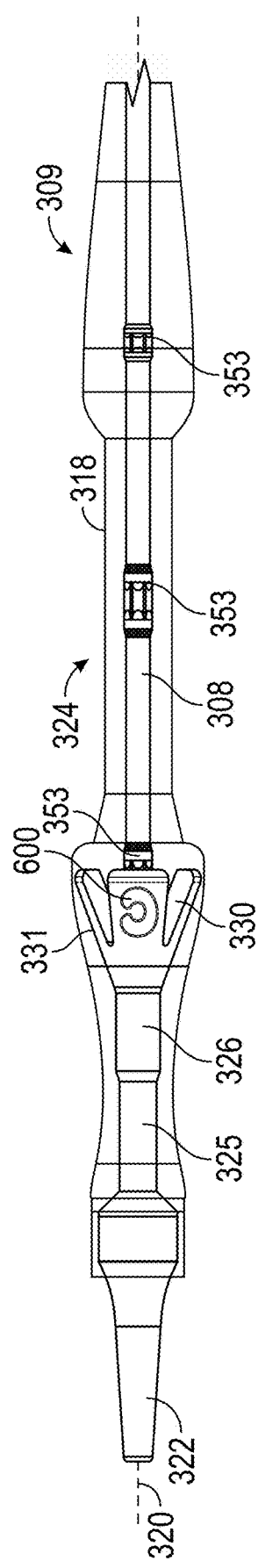
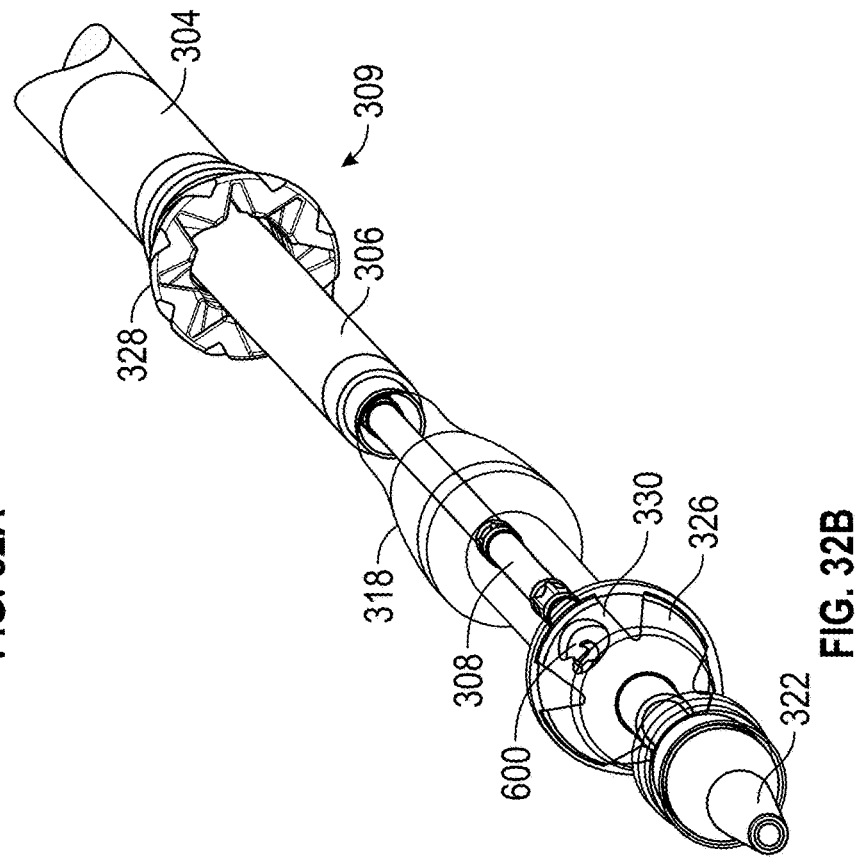

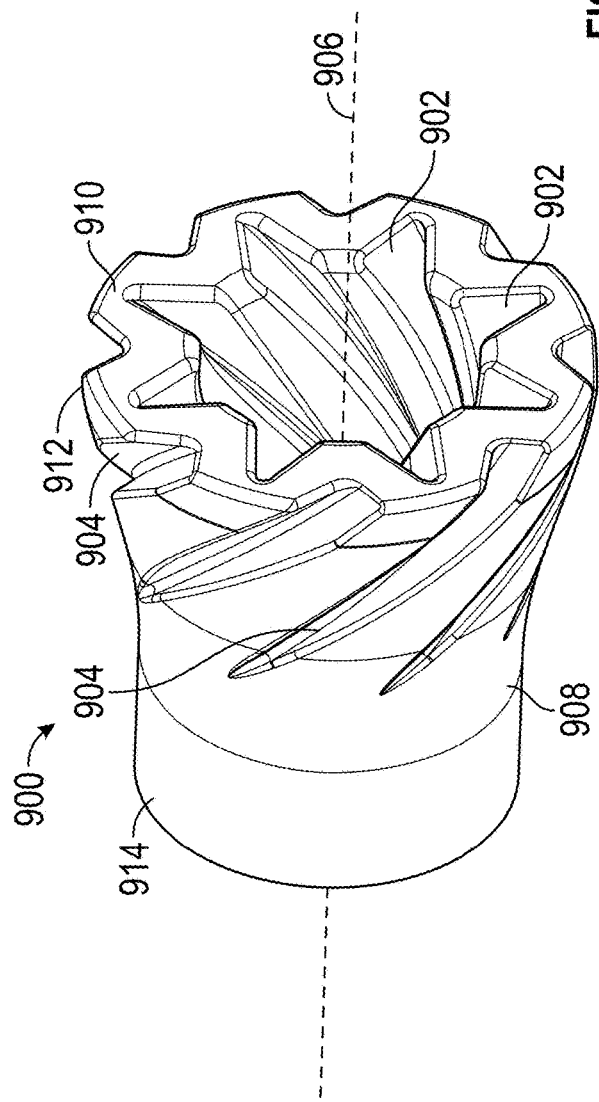
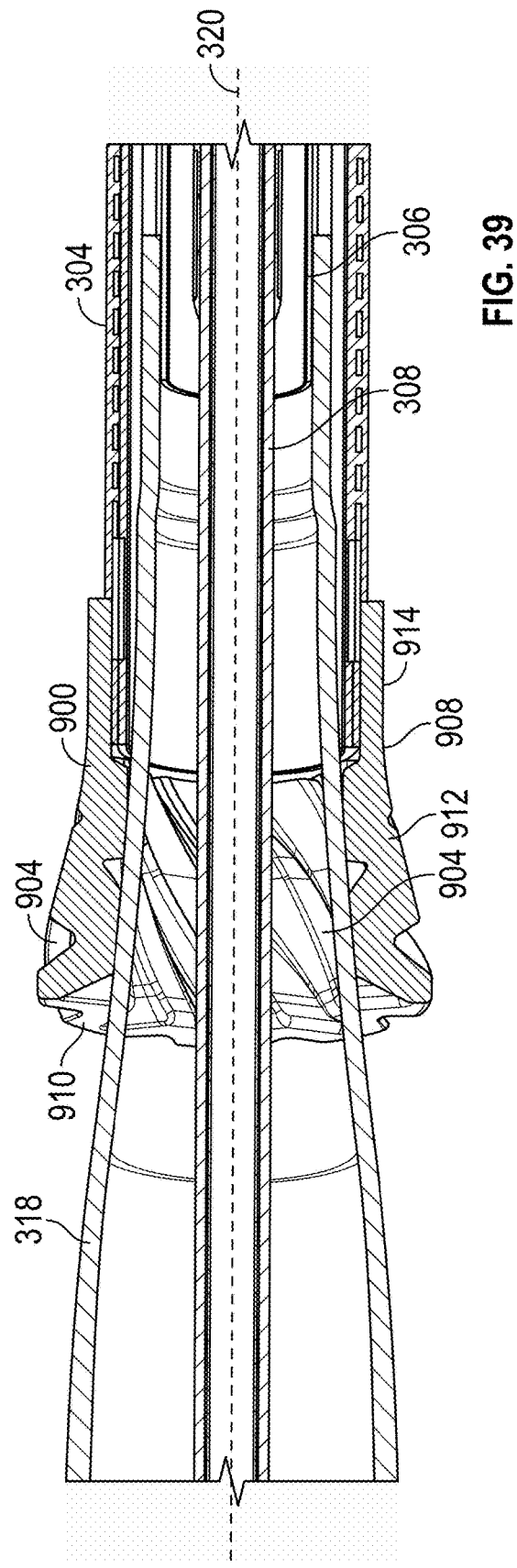

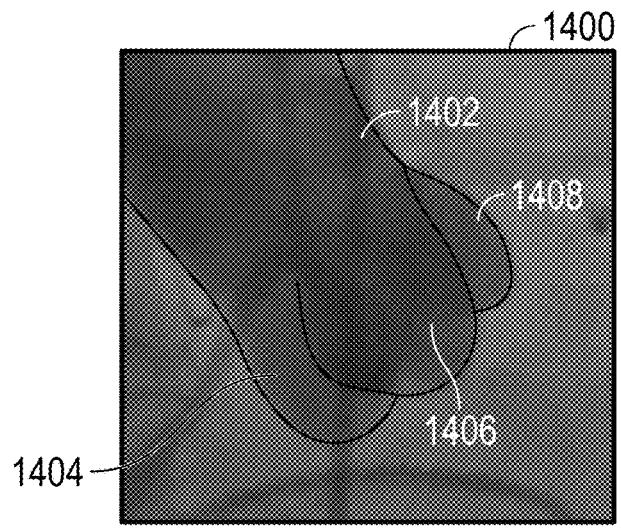
FIG. 58
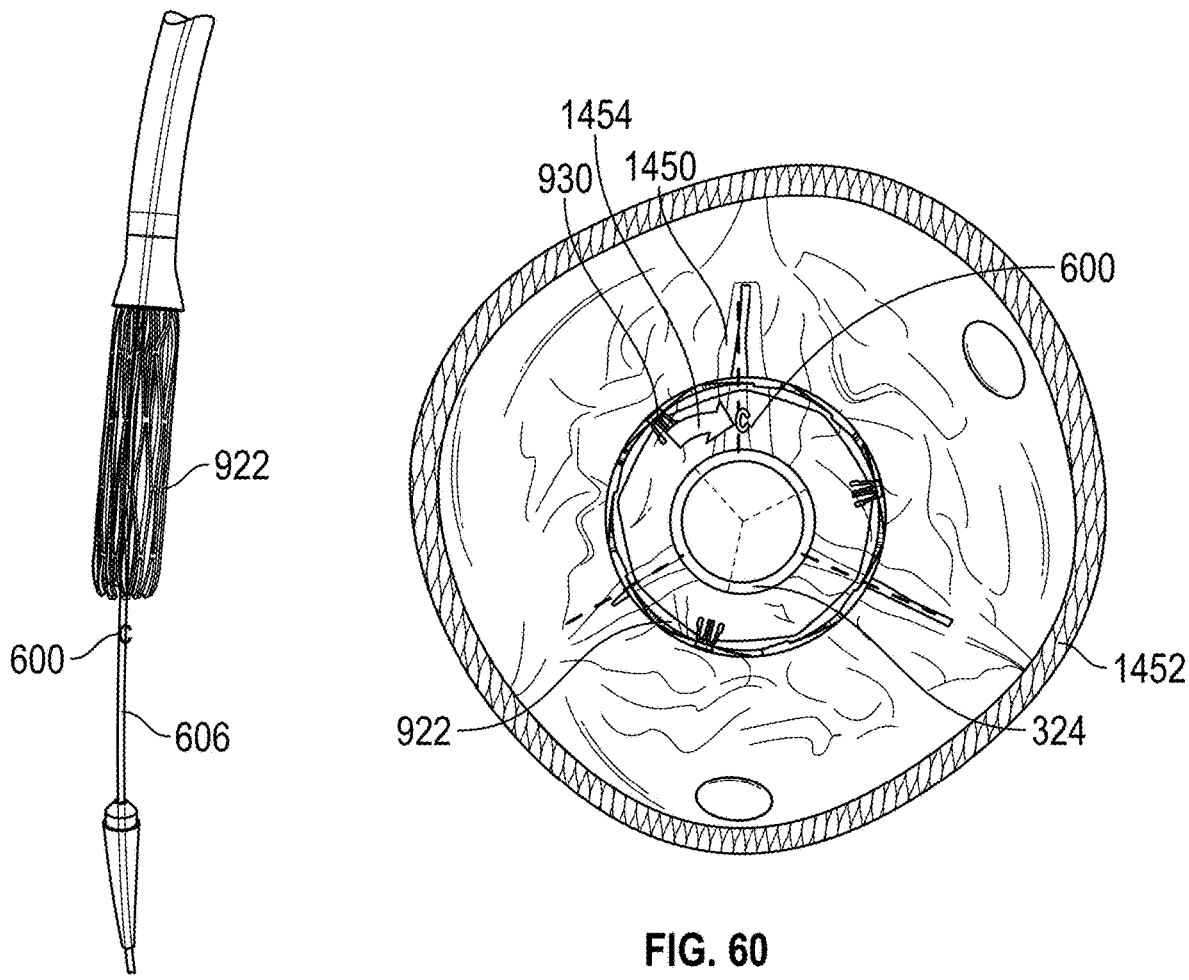
FIG. 59
FIG. 60

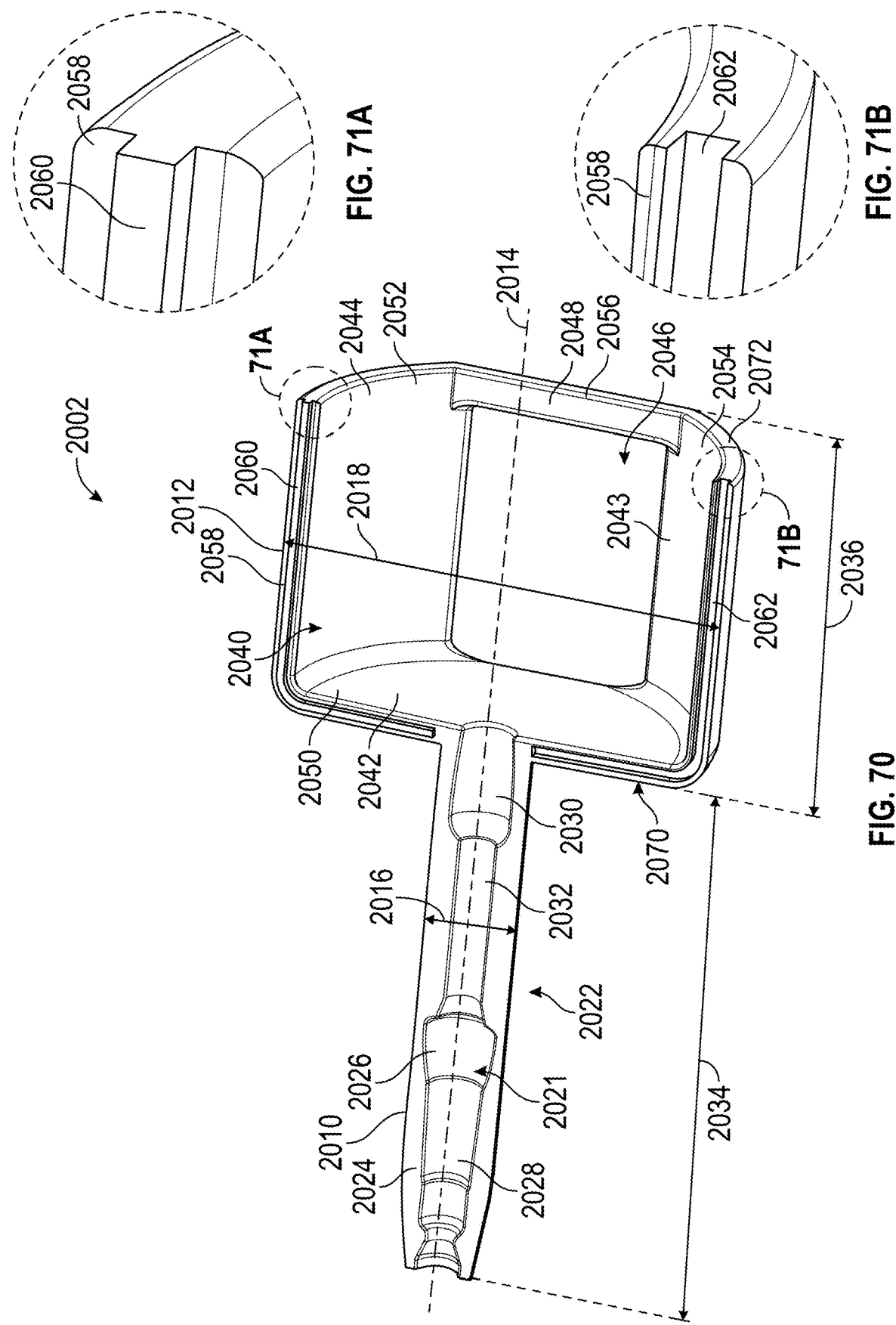

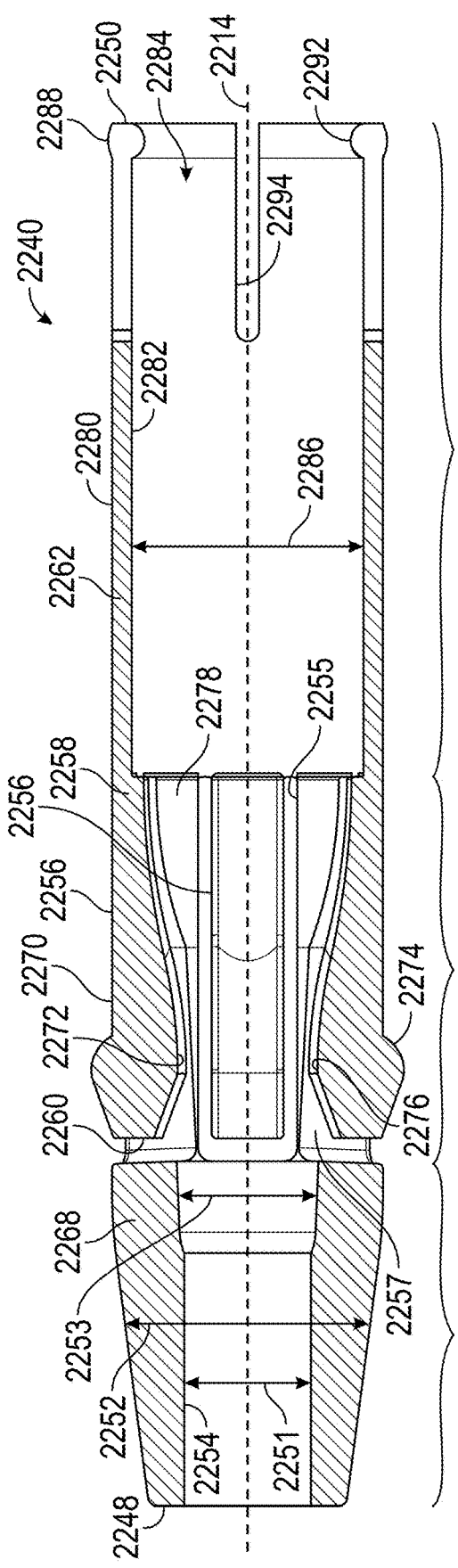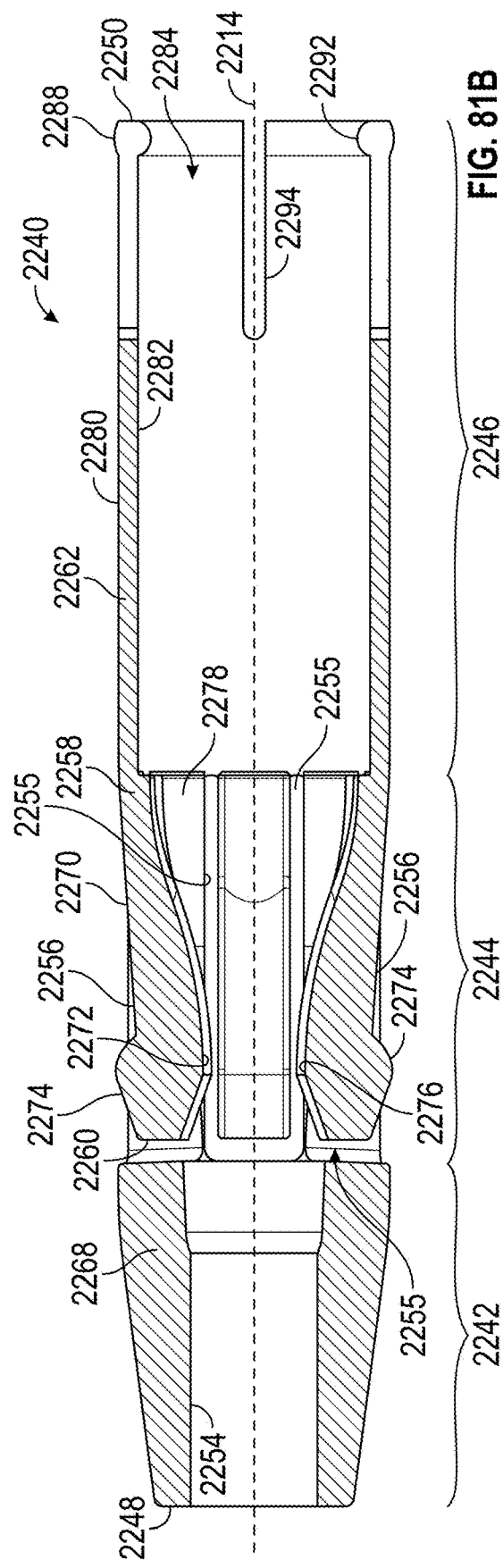
FIG. 81A
FIG. 81B

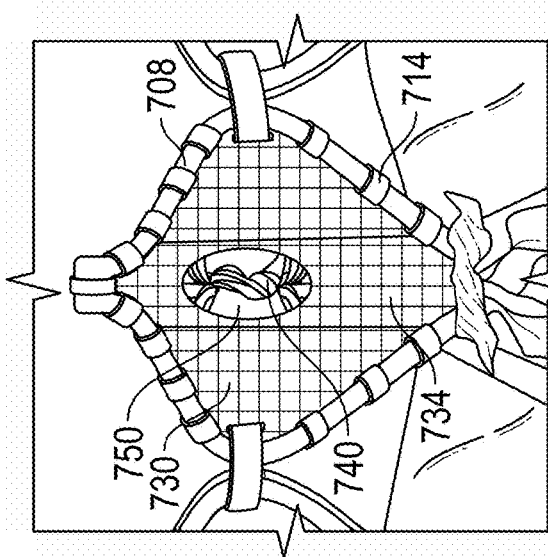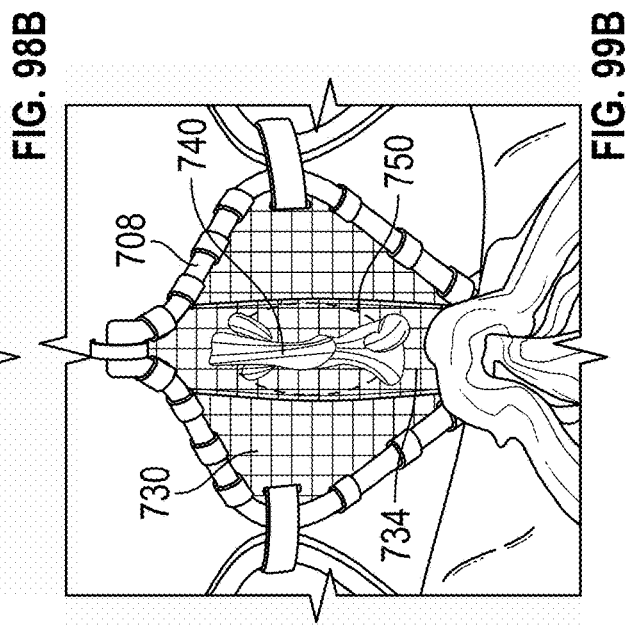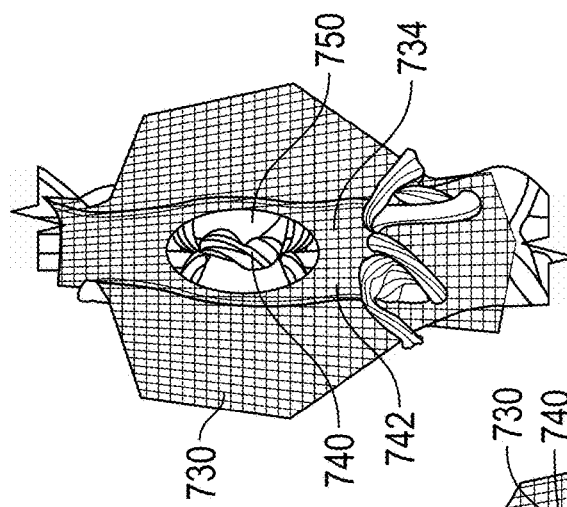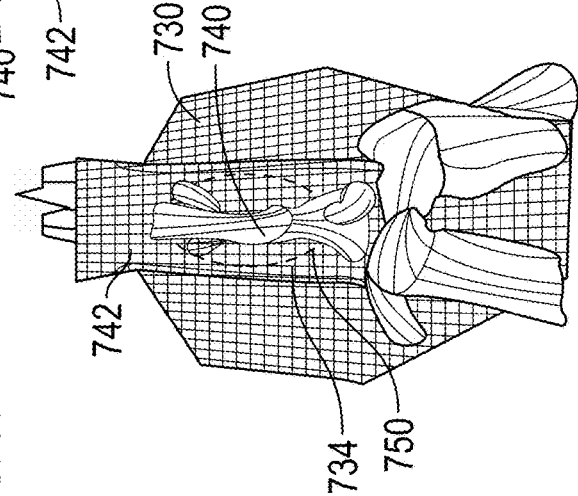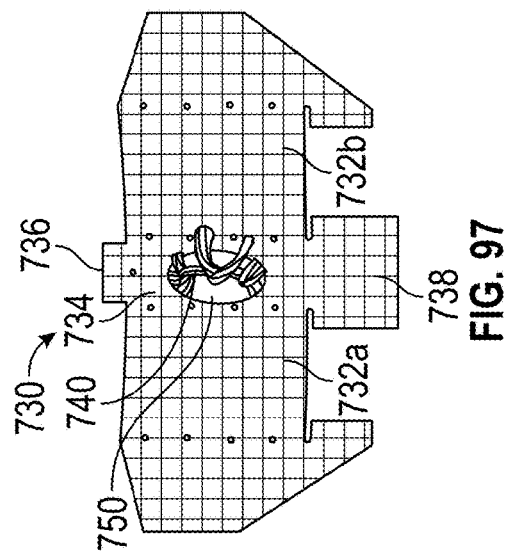

METHODS AND SYSTEMS FOR ALIGNING A COMMISSURE OF A PROSTHETIC HEART VALVE WITH A COMMISSURE OF A NATIVE VALVE

CROSS REFERENCE TO RELATED APPLICATIONS

This application is a continuation of PCT Application No. PCT/US2021/047056, filed Aug. 23, 2021, which claims the benefit of U.S. Provisional Patent Application Nos. 63/138,890, filed Jan. 19, 2021, and 63/069,567, filed Aug. 24, 2020, which are incorporated by reference herein in their entireties. PCT Application Nos. PCT/US2021/047063 and PCT/US2021/047068 are also incorporated by reference herein in their entireties.

FIELD

The present disclosure relates to prosthetic heart valves and methods for deploying a balloon-expandable prosthetic heart valve at a native valve with a delivery apparatus such that a commissure of the radially expanded prosthetic heart valve is aligned with a commissure of the native valve.

BACKGROUND

The human heart can suffer from various valvular diseases. These valvular diseases can result in significant malfunctioning of the heart and ultimately require repair of the native valve or replacement of the native valve with an artificial valve. There are a number of known repair devices (e.g., stents) and artificial valves, as well as a number of known methods of implanting these devices and valves in humans. Percutaneous and minimally-invasive surgical approaches are used in various procedures to deliver prosthetic medical devices to locations inside the body that are not readily accessible by surgery or where access without surgery is desirable. In one specific example, a prosthetic heart valve can be mounted in a crimped state on the distal end of a delivery device and advanced through the patient's vasculature (e.g., through a femoral artery and the aorta) until the prosthetic valve reaches the implantation site in the heart. The prosthetic valve is then expanded to its functional size, for example, by inflating a balloon on which the prosthetic valve is mounted.

When deploying the prosthetic valve at the native valve by inflating the balloon of the delivery device, the radially expanded prosthetic valve is deployed at a random radial orientation relative to the native valve. As such, in some embodiments, one of the commissures of the prosthetic valve may be arranged in front of (e.g., adjacent to) a coronary ostium of the aorta. This arrangement may reduce coronary access (e.g., blood flow to the coronary arteries from the aorta) and/or create difficulties during future cardiovascular interventions that aim to maintain or increase coronary access.

Accordingly, a need exists for improved delivery apparatuses and methods for deploying balloon-expandable prosthetic heart valves in a desired rotational orientation relative to the native valve, such that prosthetic heat valve commissures are in alignment with the native valve commissures.

SUMMARY

Described herein are embodiments of improved prosthetic valve delivery apparatuses and methods for delivering a prosthetic valve to and implanting the prosthetic valve at a native valve of a heart of a patient with one or more selected commissures of the prosthetic valve in alignment with one or more corresponding commissures of the native valve. In some embodiments, the disclosed delivery apparatuses include an inflatable balloon that the prosthetic valve can be mounted around, in a radially compressed state, for delivery to the native valve. After reaching the native valve, a portion of the delivery apparatus and/or the prosthetic valve can be rotationally aligned at or proximate to the native valve such that after deploying the prosthetic valve via inflating the balloon of the delivery apparatus, one or more commissures of the prosthetic valve are aligned (e.g., in a circumferential direction) with one or more commissures of the native valve.

In one representative embodiment, a delivery apparatus comprises a first shaft configured to rotate around a central longitudinal axis of the delivery apparatus to rotationally align a prosthetic valve mounted on the delivery apparatus with native anatomy at a target implantation site; a second shaft extending through the first shaft and having a distal end portion extending distally beyond a distal end portion of the first shaft; an inflatable balloon coupled to the distal end portion of the first shaft; and a polymeric body mounted on the distal end portion of the second shaft and a radiopaque marker mounted on or embedded within the polymeric body.

In another representative embodiment, a medical assembly for replacing a native valve of a heart comprises a delivery apparatus. The delivery apparatus comprises: a first shaft configured to rotate around a central longitudinal axis of the delivery apparatus; a second shaft extending through the first shaft and having a distal end portion extending distally beyond a distal end portion of the first shaft; an inflatable balloon coupled to the distal end portion of the first shaft; and a radiopaque marker arranged on a distal end portion of the delivery apparatus. The medical assembly further comprises a prosthetic heart valve mounted in a radially compressed configuration onto and around the balloon. The marker is offset, in a circumferential direction relative to the central longitudinal axis, from a location of a selected commissure of the prosthetic heart valve. The first shaft is configured to rotate to rotationally align the marker at the native valve such that, after inflating the balloon to radially expand the prosthetic heart valve, the prosthetic heart valve is implanted with the selected commissure of the prosthetic heart valve circumferentially aligned with a target commissure of the native valve.

In another representative embodiment, a delivery apparatus comprises a handle portion and a rotatable shaft extending distally from the handle portion and having a proximal end portion that extends proximally from the handle portion to an adaptor. The adaptor includes a body connected to the proximal end portion, a first port extending axially from the body, and a second port extending at an angle from the body, in a direction intersecting a central longitudinal axis of the delivery apparatus. The delivery apparatus further comprises a knob mounted on the proximal end portion of the rotatable shaft, distal to the adaptor, the knob configured to rotate the rotatable shaft. The delivery apparatus further comprises an inflatable balloon coupled to a distal end portion of the rotatable shaft and configured to inflate upon receiving inflation fluid from the second port.

The foregoing and other objects, features, and advantages of the disclosed technology will become more apparent from the following detailed description, which proceeds with reference to the accompanying figures.

BRIEF DESCRIPTION OF THE DRAWINGS

FIG. 12 is a schematic view of an embodiment of an intermediate shaft of the delivery apparatus of FIG. 9.

FIG. 13 is a cross-sectional side view of a detail portion of coaxial shafts of the delivery apparatus of FIG. 11.

FIG. 21 is a side view of the anchor of FIG. 18, mounted on the proximal end portion of the intermediate shaft.

FIG. 22 is a side view of the knob of FIG. 15, mounted on the proximal end portion of the intermediate shaft with one housing portion of the outer housing removed to show the anchor.

FIG. 32A a side view of an exemplary delivery apparatus with the asymmetric marker of FIG. 30 arranged on or embedded within a distal shoulder of the delivery apparatus.

FIG. 32B is a perspective view of the exemplary delivery apparatus of FIG. 32A with the asymmetric marker of FIG. 30 arranged on or embedded within the distal shoulder of the delivery apparatus.

FIG. 38 is a perspective view of an embodiment of a distal tip portion for an outer shaft of a delivery apparatus including a plurality of helical internal expansion grooves.

FIG. 39 is a cross-sectional view of the distal tip portion of FIG. 38 mounted on a distal end of the outer shaft and arranged over a portion of an inflatable balloon of the delivery apparatus.

FIG. 58 illustrates an exemplary fluoroscopic image of a native valve viewed with a standard, three-cusp imaging view.

FIG. 59 illustrates an exemplary fluoroscopic image of a distal end portion of a delivery apparatus including an asymmetric radiopaque marker, where the marker is centered along a guidewire extending through the delivery apparatus and appears in a forward-readable orientation, thereby indicating the marker is in a direct back of the imaging view.

FIG. 60 is a schematic illustrating a desired rotational positioning of a distal end portion of a delivery apparatus, including a prosthetic valve mounted thereon, at a native valve with an asymmetric radiopaque marker of the delivery apparatus aligned with a target commissure of the native valve and a selected commissure of the prosthetic valve circumferentially offset from the marker by a predetermined amount.

FIG. 70 is a perspective view of a shell member of the balloon cover of FIG. 60, the shell member configured to matingly engage with another shell member of the balloon cover to form an outer shell of the balloon cover.

FIG. 71A is a detail view of a portion of a mating edge of the shell member of FIG. 70 which includes an elongate protrusion.

FIG. 71B is a detail view of another portion of the mating edge of the shell member of FIG. 70 which includes an elongate groove.

FIG. 81A is a cross-sectional side view of the depression sleeve of FIG. 78 in an unflexed or resting configuration.

FIG. 81B is a cross-sectional side view of the depression sleeve of FIG. 78 in a flexed or radially inward configuration.

FIG. 93 is a cross-sectional side view of the release sleeve of FIG. 92.

FIG. 94 is a perspective view of an embodiment of an adaptor insert of the shaft connector release assembly of FIG. 89.

FIG. 95 is a side view of the adaptor insert of FIG. 94.

FIG. 96 is a cross-sectional side view of the adaptor insert of FIG. 95.

FIG. 97 shows an exemplary radiopaque marker sewn to a central portion of an attachment member, the attachment member configured to form a commissure with commissure tabs of adjacent leaflets of the prosthetic heart valve and configured to be arranged across a cell of a prosthetic heart valve and secured to struts forming the cell.

FIG. 98A shows the marker secured to an outer surface of the attachment member of FIG. 97 and the commissure tabs secured to an inner surface of the attachment member.

FIG. 99B shows the attachment member of FIG. 98A attached to the struts of the cell and the marker facing away from the commissure.

FIG. 99A shows the marker secured to an inner surface of the attachment member of FIG. 97 and the commissure tabs secured to an inner surface of the attachment member.

FIG. 99B shows the attachment member of FIG. 99B attached to the struts of the cell and the marker facing toward the commissure.

FIG. 100 shows an exemplary embodiment of a marker positioned against an elongate flap of an attachment member, the attachment member configured to form a commissure with commissure tabs of adjacent leaflets of the prosthetic heart valve and configured to be arranged across a cell of a prosthetic heart valve and secured to struts forming the cell.

FIGS. 101A-101E show a process for sewing the marker to the attachment member of FIG. 100 using one or more fasteners used to secure the commissure tabs of the leaflets to the attachment member.

FIG. 102 is a perspective view of another embodiment of a rotatable knob mounted on a proximal end portion of an intermediate shaft of a delivery apparatus, the knob configured to rotate the intermediate shaft, thereby rotating an inflatable balloon and prosthetic heart valve radially compressed onto the balloon.

Figure 102:
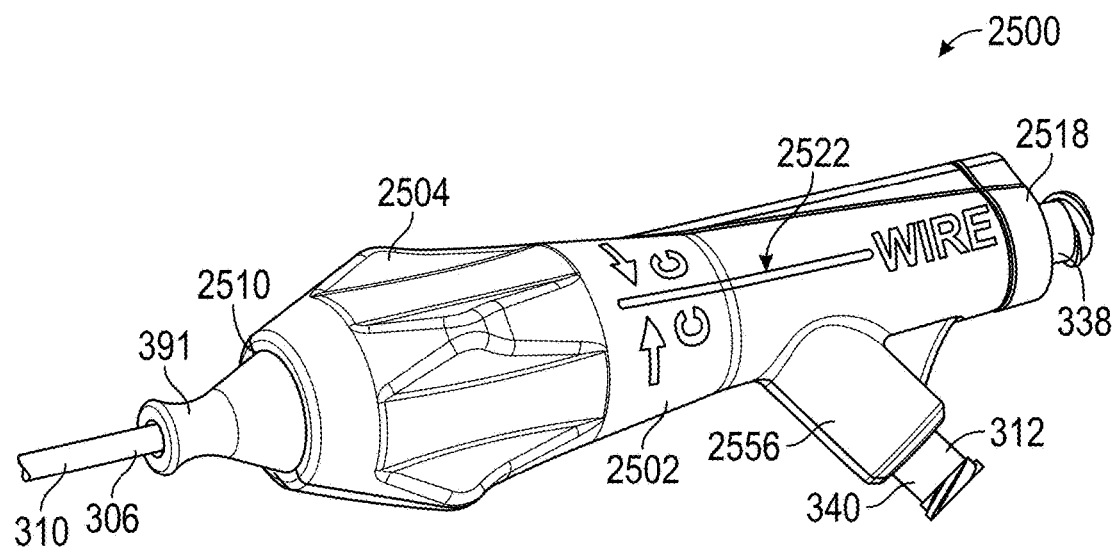
Figure 103:
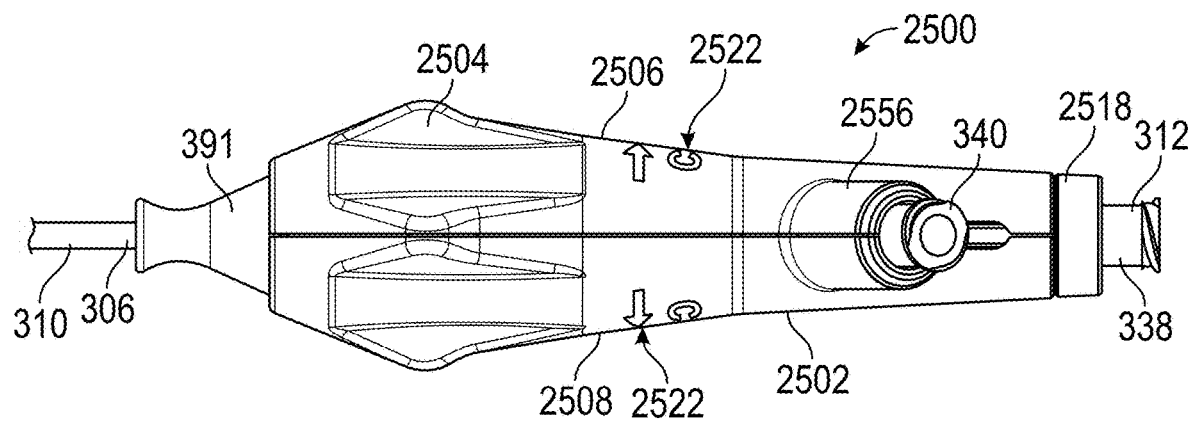

FIG. 103 is a side view of the knob of FIG. 102.

Figure 104:
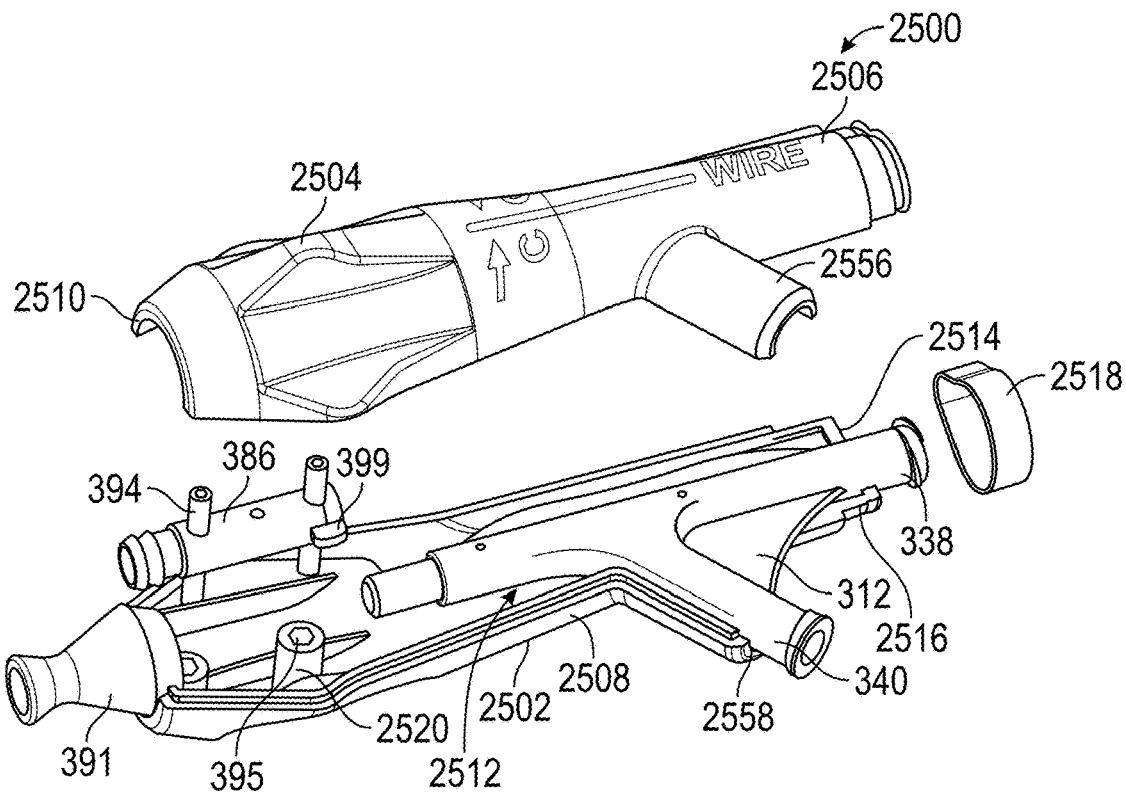

FIG. 104 is a first exploded view of the know of FIG. 102 that shows two housing portions of the knob which enclose an anchor and adaptor therein.

Figure 105:
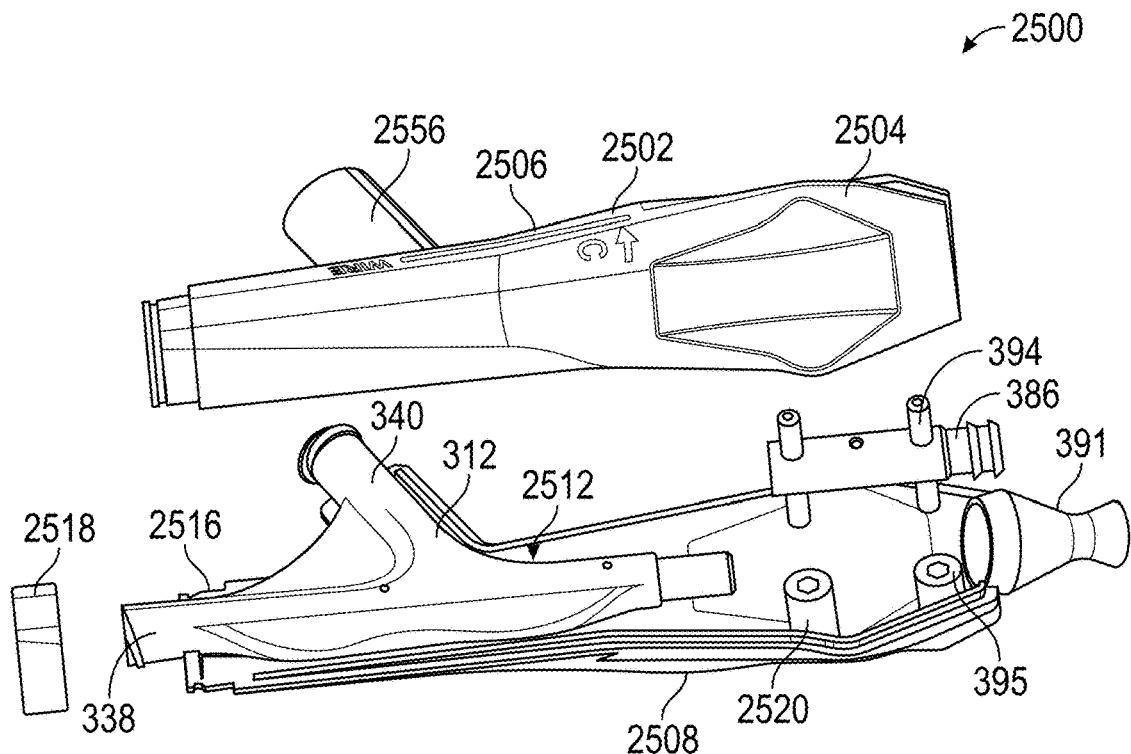

FIG. 105 is a second exploded view of the knob of FIG. 102.

Figure 106:
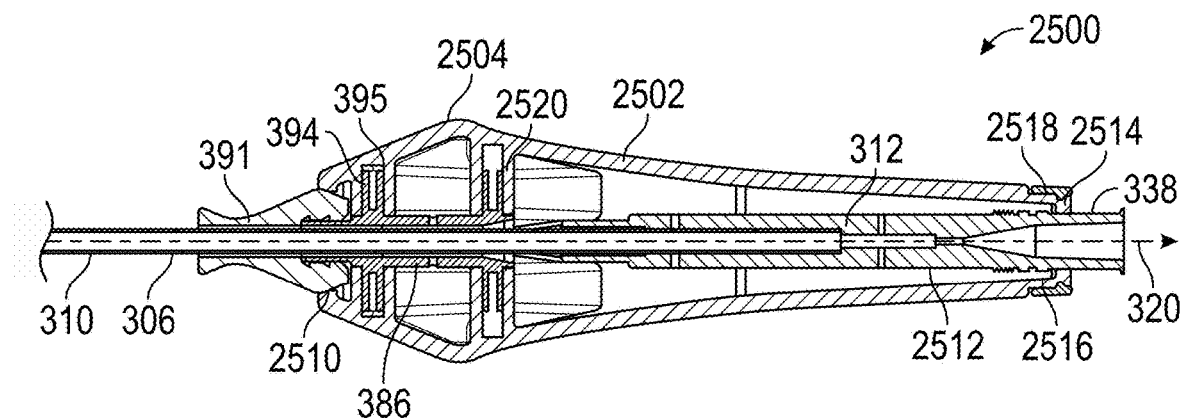

FIG. 106 is a first cross-sectional side view of the knob of FIG. 102 that shows the anchor and adaptor inside the housing of the knob.

Figure 107:
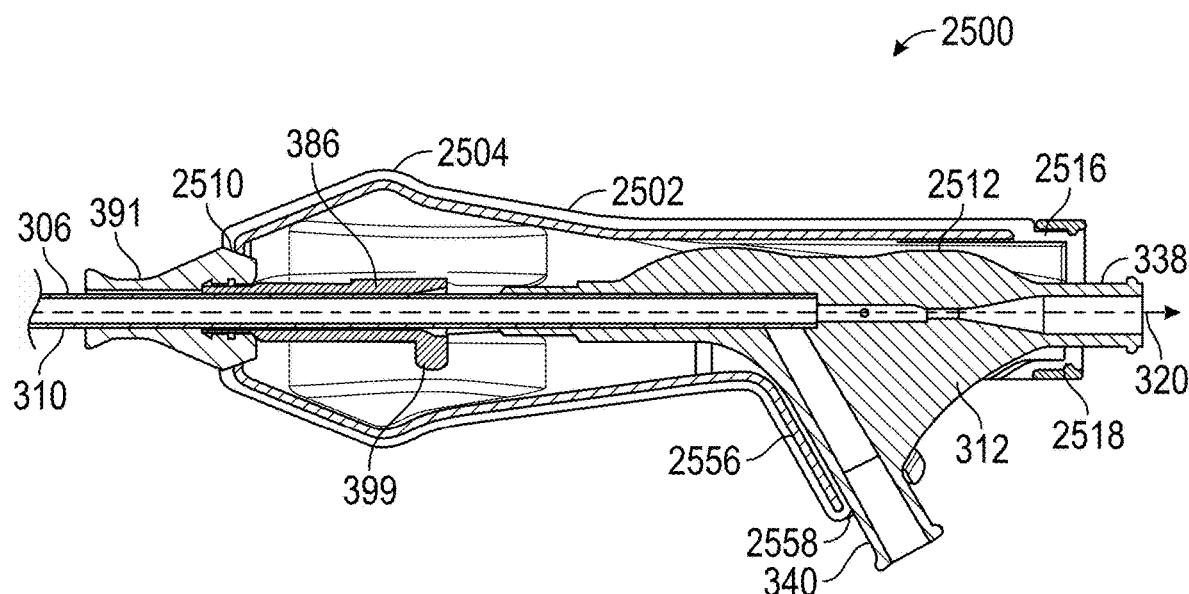

FIG. 107 is a second cross-sectional side view of the knob of FIG. 102 that shows an aligning tab of the anchor and the adaptor inside the housing of the knob.

Figure 108:
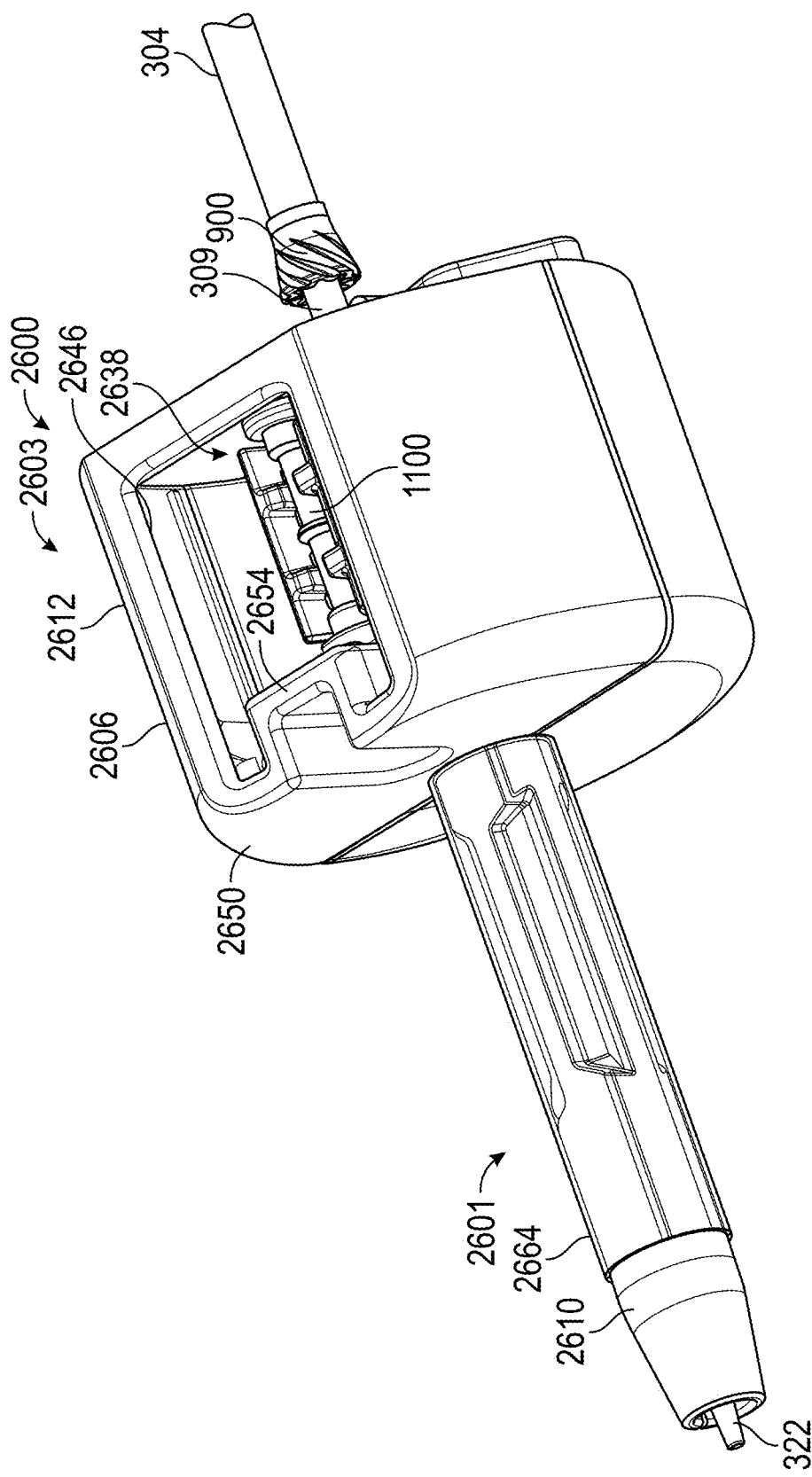

FIG. 108 is a perspective view of another embodiment of a balloon cover for a distal end portion of delivery apparatus which is configured to cover an inflatable balloon and a positioning device mounted on the distal end portion.

Figure 109:
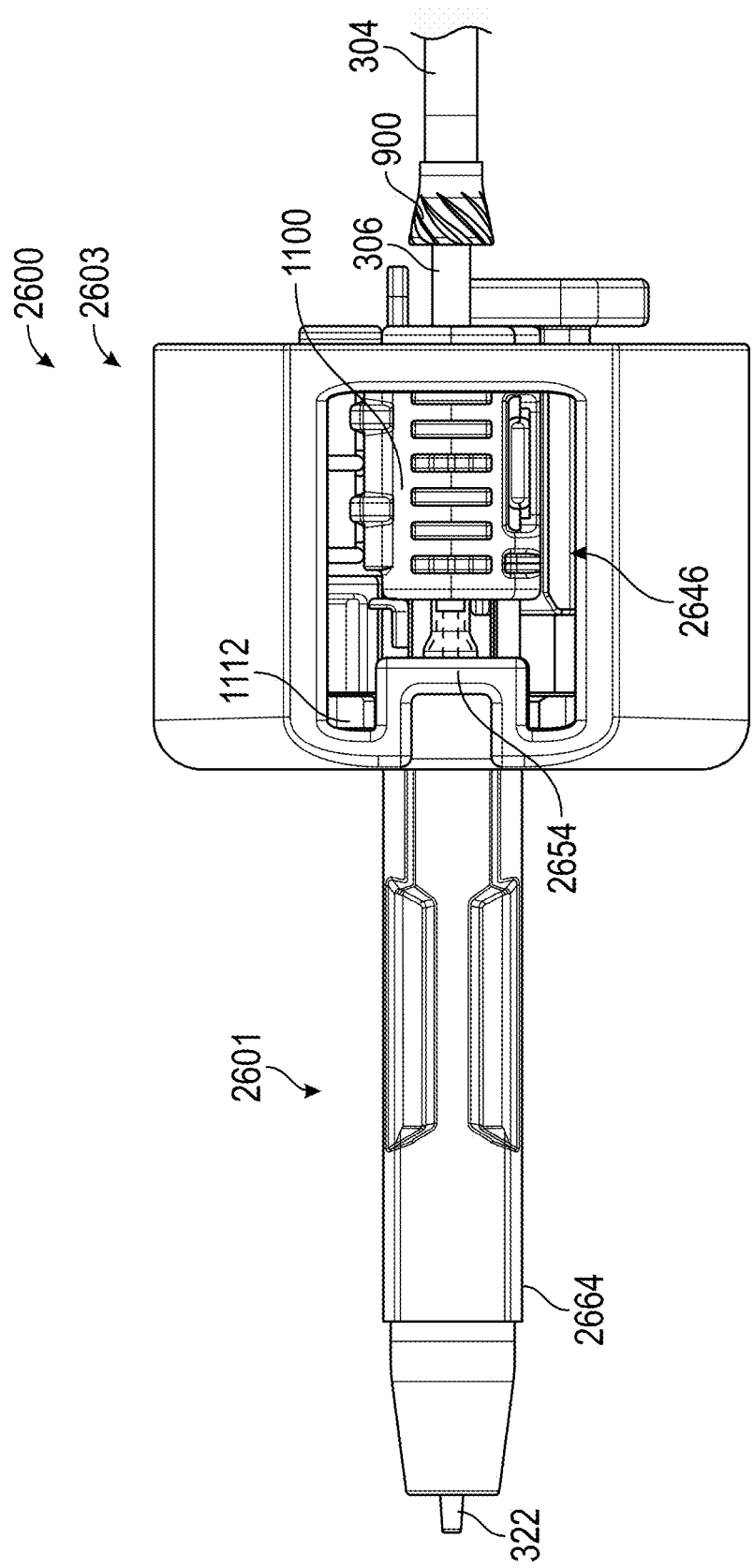

FIG. 109 is a side view of the balloon cover of FIG. 108.

Figure 110:
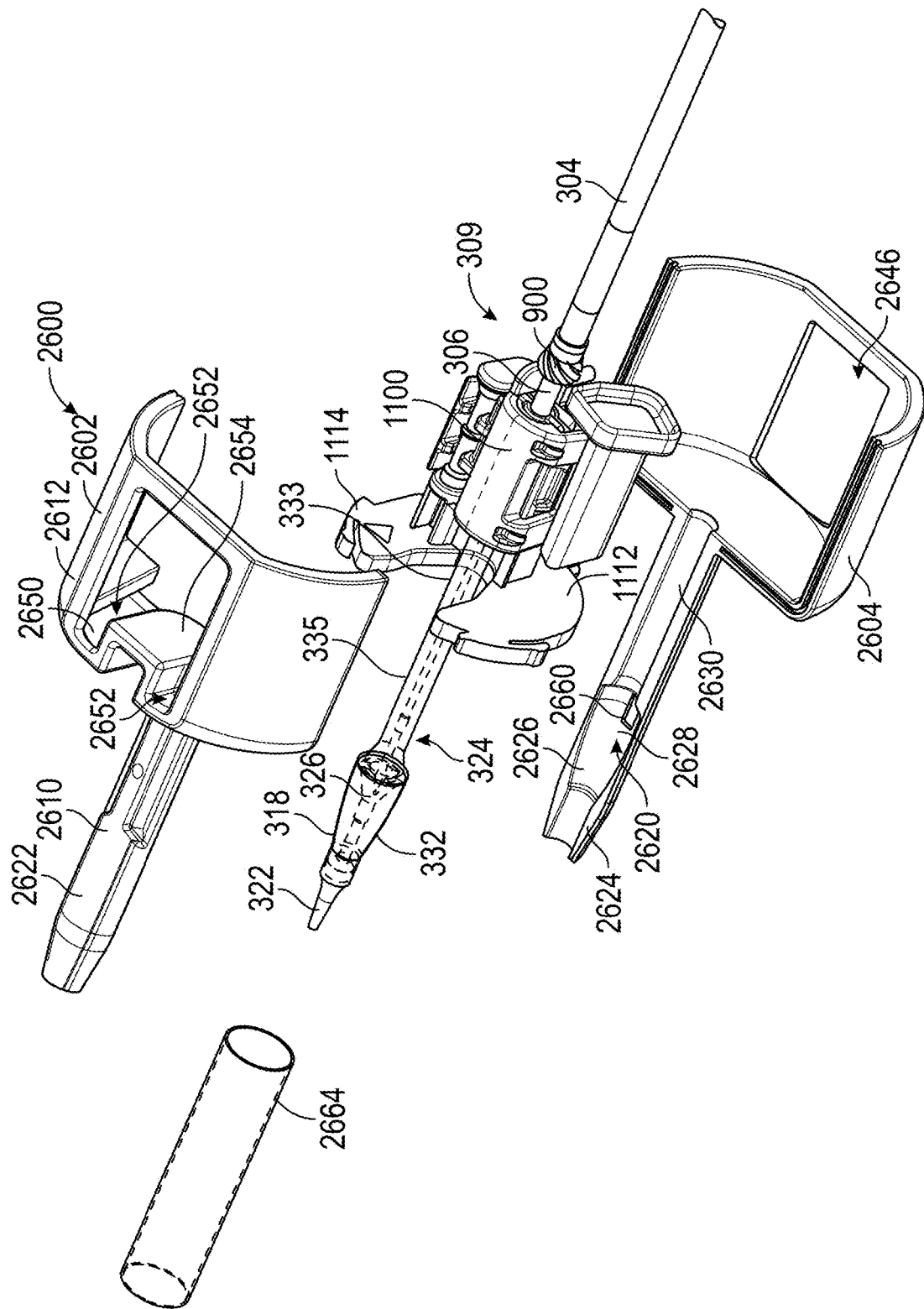

FIG. 110 is an exploded view of the balloon cover of FIG. 108.

Figure 111:
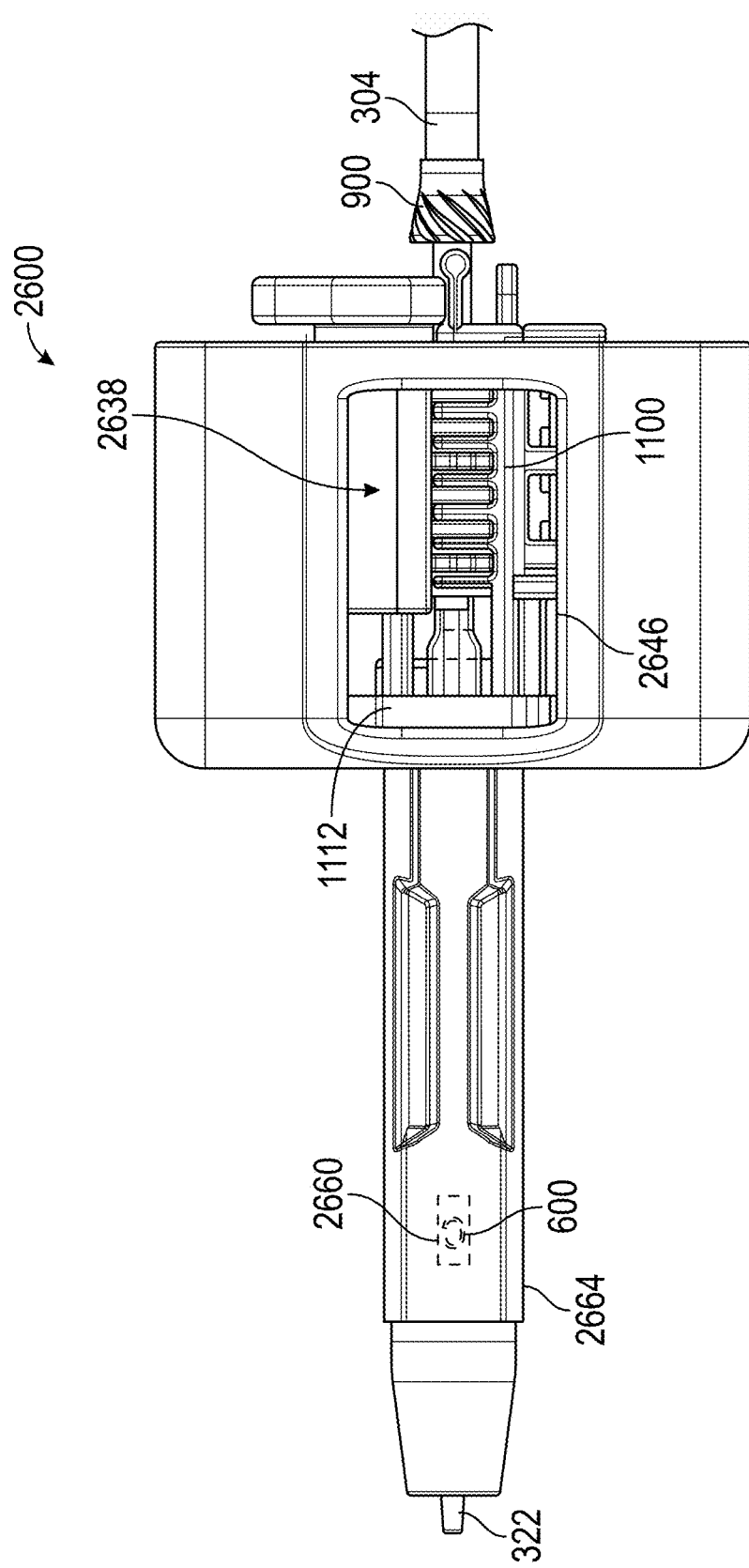

FIG. 111 is another side view of the balloon cover of FIG. 108 that shows a sleeve covering a portion of the balloon cover that includes a viewing window for an underlying radiopaque marker on the distal end portion of the delivery apparatus.

Figure 112:
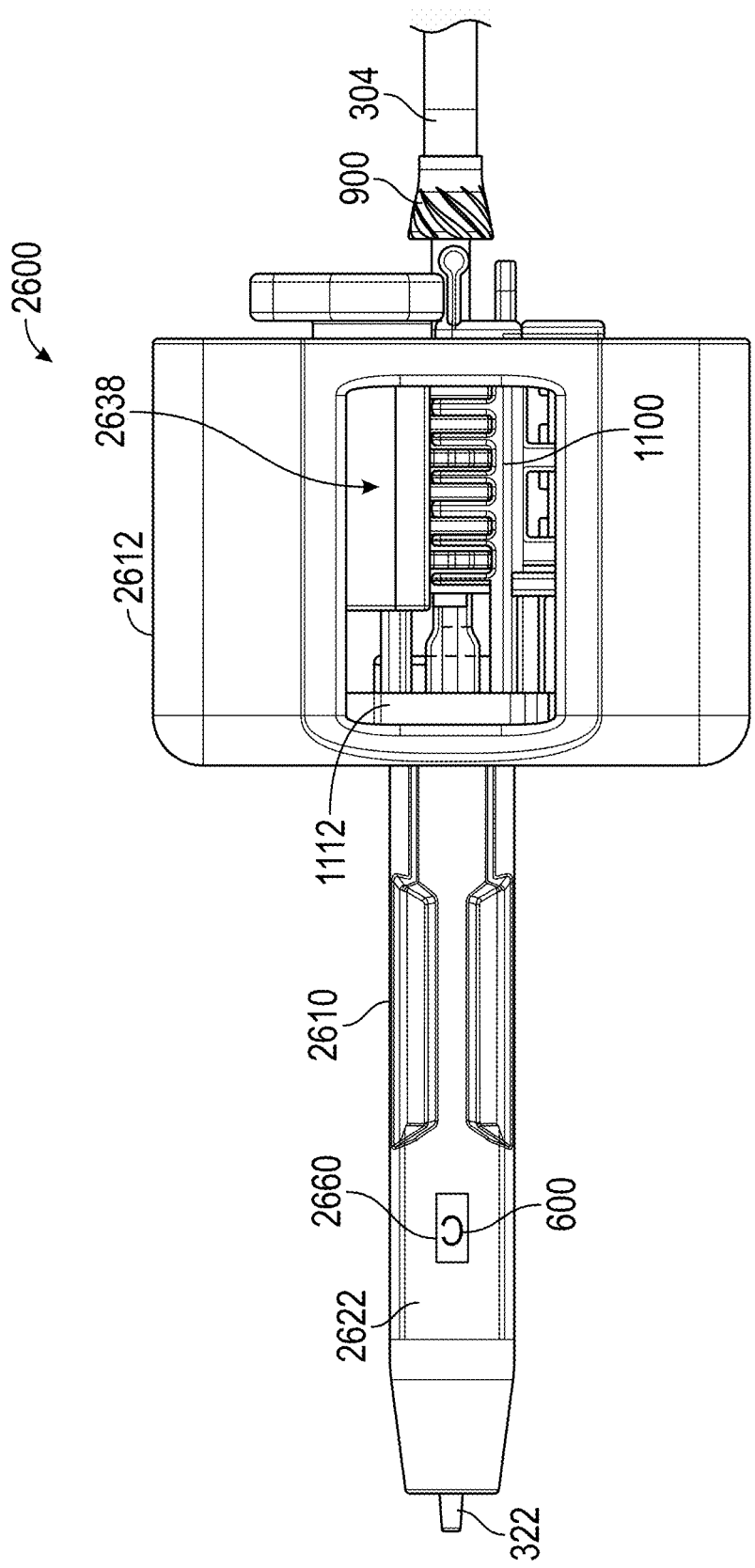

FIG. 112 is another side view of the balloon cover of FIG. 111 with the sleeve removed such that the viewing window and the underlying radiopaque marker on the distal end portion of the delivery apparatus are visible.

Figure 113:
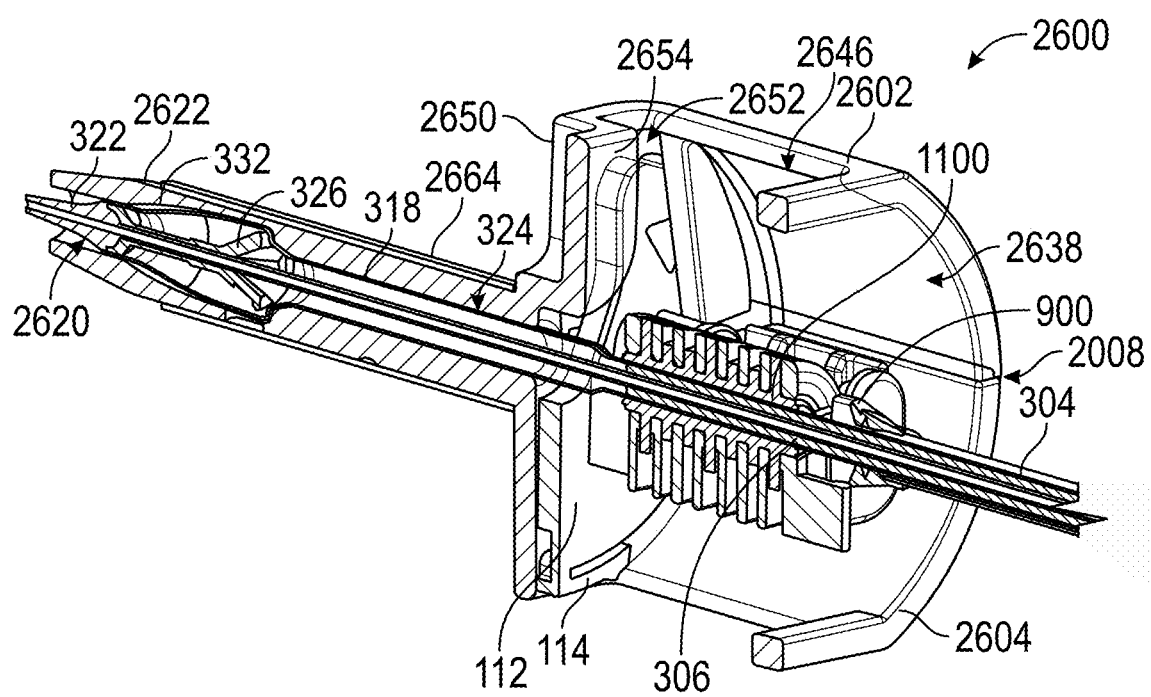

FIG. 113 is a cross-sectional perspective view of the balloon cover of FIG. 108.

Figure 114:
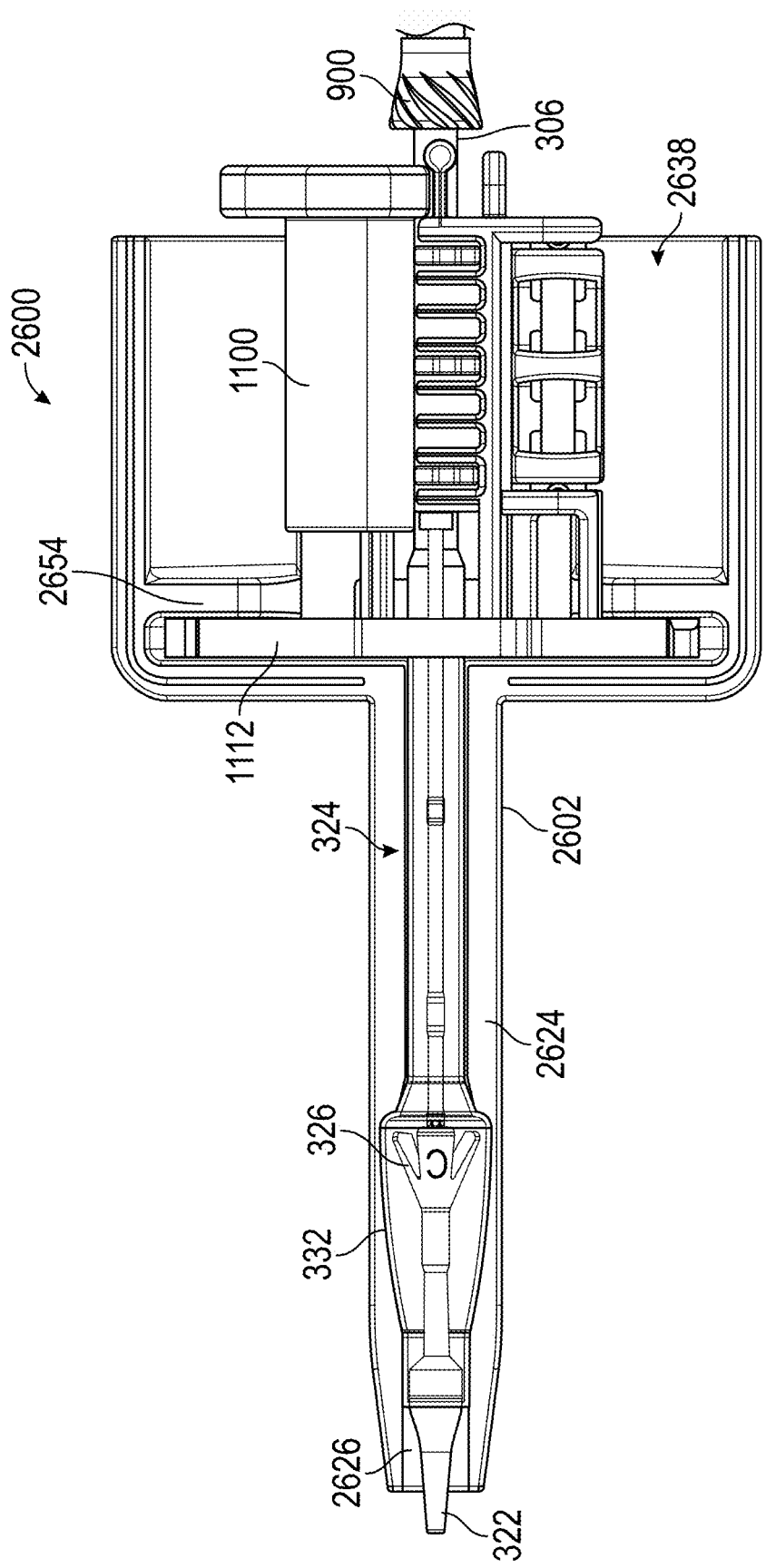

FIG. 114 is a partial cross-sectional side view of the balloon cover of FIG. 108.

DETAILED DESCRIPTION

General Considerations

For purposes of this description, certain aspects, advantages, and novel features of the embodiments of this disclosure are described herein. The described methods, systems, and apparatus should not be construed as limiting in any way. Instead, the present disclosure is directed toward all novel and non-obvious features and aspects of the various disclosed embodiments, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present, or problems be solved.

Features, integers, characteristics, compounds, chemical moieties, or groups described in conjunction with a particular aspect, embodiment or example of the disclosure are to be understood to be applicable to any other aspect, embodiment or example described herein unless incompatible therewith. All of the features disclosed in this specification (including any accompanying claims, abstract, and drawings), and/or all of the steps of any method or process so disclosed, may be combined in any combination, except combinations where at least some of such features and/or steps are mutually exclusive. The disclosure is not restricted to the details of any foregoing embodiments. The disclosure extends to any novel one, or any novel combination, of the features disclosed in this specification (including any accompanying claims, abstract, and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods, systems, and apparatus can be used in conjunction with other systems, methods, and apparatus.

As used herein, the terms "a," "an," and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A," "B," "C," "A and B," "A and C," "B and C," or "A, B, and C."

As used herein, the term "coupled" generally means physically coupled or linked and does not exclude the presence of intermediate elements between the coupled items absent specific contrary language.

Directions and other relative references (e.g., inner, outer, upper, lower, etc.) may be used to facilitate discussion of the drawings and principles herein, but are not intended to be limiting. For example, certain terms may be used such as "inside," "outside,", "top," "down," "interior," "exterior," and the like. Such terms are used, where applicable, to provide some clarity of description when dealing with relative relationships, particularly with respect to the illustrated embodiments. Such terms are not, however, intended to imply absolute relationships, positions, and/or orientations. For example, with respect to an object, an "upper" part can become a "lower" part simply by turning the object over. Nevertheless, it is still the same part and the object remains the same. As used herein, "and/or" means "and" or "or," as well as "and" and or.

As used herein, with reference to the prosthetic heart valve and the delivery apparatus, "proximal" refers to a position, direction, or portion of a component that is closer to the user and/or a handle of the delivery apparatus that is outside the patient, while "distal" refers to a position, direction, or portion of a component that is further away from the user and/or the handle of the delivery apparatus and closer to the implantation site. The terms "longitudinal" and "axial" refer to an axis extending in the proximal and distal directions, unless otherwise expressly defined. Further, the term "radial" refers to a direction that is arranged perpendicular to the axis and points along a radius from a center of an object (where the axis is positioned at the center, such as the longitudinal axis of the prosthetic valve).

Examples of the Disclosed Technology

Described herein are examples of prosthetic valve delivery apparatuses and methods for delivering and implanting a radially expandable prosthetic valve at a native valve of a heart such that commissures of the prosthetic valve are circumferentially aligned within commissures of the native valve.

Also described herein are examples of balloon covers configured to receive a distal end portion of a delivery apparatus therein. In some embodiments, such balloon covers can be configured to create a specified shape of an inflatable balloon overlying a portion of the distal end portion of the delivery apparatus.

Also described herein are assemblies for coupling a rotatable shaft of the delivery apparatus to an adaptor of the delivery apparatus that is configured to receive inflation fluid for the inflatable balloon of the delivery apparatus.

In some embodiments, a delivery apparatus can include a first shaft that is configured to rotate around a central longitudinal axis of the delivery apparatus to rotationally align a prosthetic valve mounted on the delivery apparatus with native anatomy at a target implantation site. The delivery apparatus can further include a second shaft extending through the first shaft and having a distal end portion extending distally beyond a distal end portion of the first shaft. In some embodiments one or more polymeric bodies, such as one or more balloon shoulders and/or a nose cone can be mounted on the distal end portion of the second shaft. The delivery apparatus can further include an inflatable balloon coupled to the distal end portion of the first shaft. In some embodiments, a shoulder, or another polymeric body of the delivery apparatus, can be arranged within the balloon and a radiopaque marker can be mounted on or embedded within the shoulder at a location spaced radially outward from an outer surface of the distal end portion of the second shaft. The marker can be reflection asymmetric along an axis that is parallel to the central longitudinal axis of the delivery apparatus. The shoulder can be configured such that when the prosthetic valve is mounted on the balloon in a radially compressed state, the shoulder resists movement of the prosthetic valve relative to the balloon in an axial direction.

In this way, the delivery apparatus can be configured to rotationally align the radially compressed prosthetic valve at the native valve such that prosthetic valve is implanted with commissures of the prosthetic valve in alignment (e.g., circumferential alignment) with commissures of the native valve. For example, rotating the first shaft can result in rotation of the balloon and the radially compressed prosthetic valve mounted thereon. In some embodiments, the first shaft can be rotated at or proximate to the native valve until the marker on the shoulder or alternate polymeric body of the delivery apparatus is aligned with a desired landmark of the native anatomy and/or a guidewire, within a selected imaging view.

Prosthetic valves disclosed herein can be radially compressible and expandable between a radially compressed configuration and a radially expanded configuration. Thus, the prosthetic valves can be crimped on a delivery apparatus in the radially compressed configuration during delivery, and then expanded to the radially expanded configuration once the prosthetic valve reaches the implantation site. In some embodiments, the prosthetic valve can be deployed from the delivery apparatus at the implantation site (e.g., a native valve of a heart) via inflating an inflatable balloon of the delivery apparatus.

Figure 1:
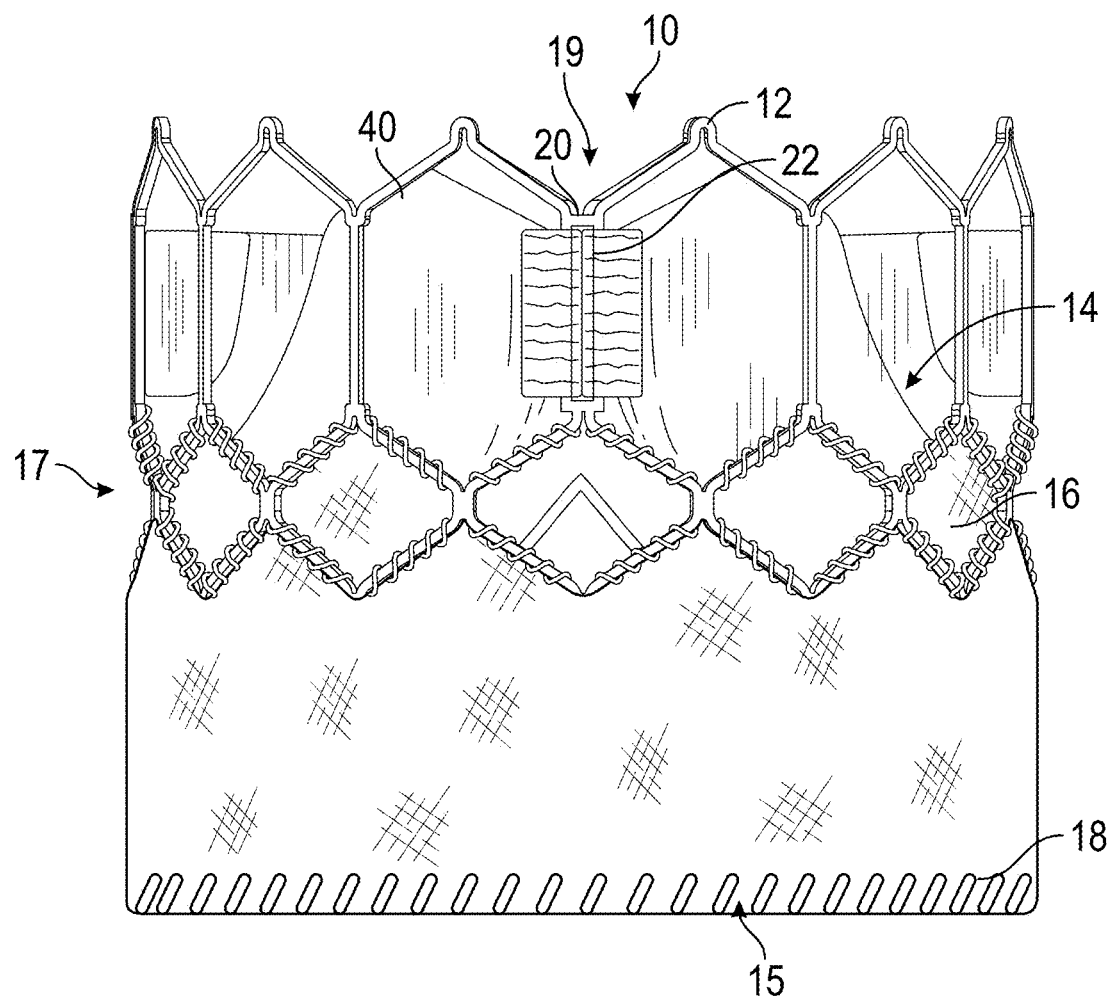
FIG. 1 is a perspective view of a prosthetic heart valve, according to one embodiment.

FIG. 1 shows a prosthetic heart valve (e.g., prosthetic valve) 10, according to one embodiment. The illustrated prosthetic valve is adapted to be implanted in the native aortic annulus, although in other embodiments it can be adapted to be implanted in the other native annuluses of the heart (e.g., the pulmonary, mitral, and tricuspid valves). The prosthetic valve can also be adapted to be implanted in other tubular organs or passageways in the body. The prosthetic valve 10 can have four main components: a stent or frame 12, a valvular structure 14, an inner skirt 16, and a perivalvular outer sealing member or outer skirt 18. The prosthetic valve 10 can have an inflow end portion 15, an intermediate portion 17, and an outflow end portion 19.

The valvular structure 14 can comprise three leaflets 40, collectively forming a leaflet structure, which can be arranged to collapse in a tricuspid arrangement, although in other embodiments there can be greater or fewer number of leaflets (e.g., one or more leaflets 40). The leaflets 40 can be secured to one another at their adjacent sides to form commissures 22 of the valvular (e.g., leaflet) structure 14. The lower edge of valvular structure 14 can have an undulating, curved scalloped shape and can be secured to the inner skirt 16 by sutures (not shown). In some embodiments, the leaflets 40 can be formed of pericardial tissue (e.g., bovine pericardial tissue), biocompatible synthetic materials, or various other suitable natural or synthetic materials as known in the art and described in U.S. Pat. No. 6,730,118, which is incorporated by reference herein.

The frame 12 can be formed with a plurality of circumferentially spaced slots, or commissure windows 20 that are adapted to mount the commissures 22 of the valvular structure 14 to the frame. The frame 12 can be made of any of various suitable plastically-expandable materials (e.g., stainless steel, etc.) or self-expanding materials (e.g., nickel titanium alloy (NiTi), such as nitinol), as known in the art. When constructed of a plastically-expandable material, the frame 12 (and thus the prosthetic valve 10) can be crimped to a radially collapsed configuration on a delivery catheter and then expanded inside a patient by an inflatable balloon or equivalent expansion mechanism. When constructed of a self-expandable material, the frame 12 (and thus the prosthetic valve 10) can be crimped to a radially collapsed configuration and restrained in the collapsed configuration by insertion into a sheath or equivalent mechanism of a delivery catheter. Once inside the body, the prosthetic valve can be advanced from the delivery sheath, which allows the prosthetic valve to expand to its functional size.

Suitable plastically-expandable materials that can be used to form the frame 12 include, without limitation, stainless steel, a biocompatible, high-strength alloys (e.g., a cobalt-chromium or a nickel-cobalt-chromium alloys), polymers, or combinations thereof. In particular embodiments, frame 12 is made of a nickel-cobalt-chromium-molybdenum alloy, such as MP35N® alloy (SPS Technologies, Jenkintown, Pennsylvania), which is equivalent to UNS R30035 alloy (covered by ASTM F562-02). MP35N® alloy/UNS R30035 alloy comprises 35% nickel, 35% cobalt, 20% chromium, and 10% molybdenum, by weight. Additional details regarding the prosthetic valve 10 and its various components are described in WIPO Patent Application Publication No. WO 2018/222799, which is incorporated herein by reference.

Figure 2A:
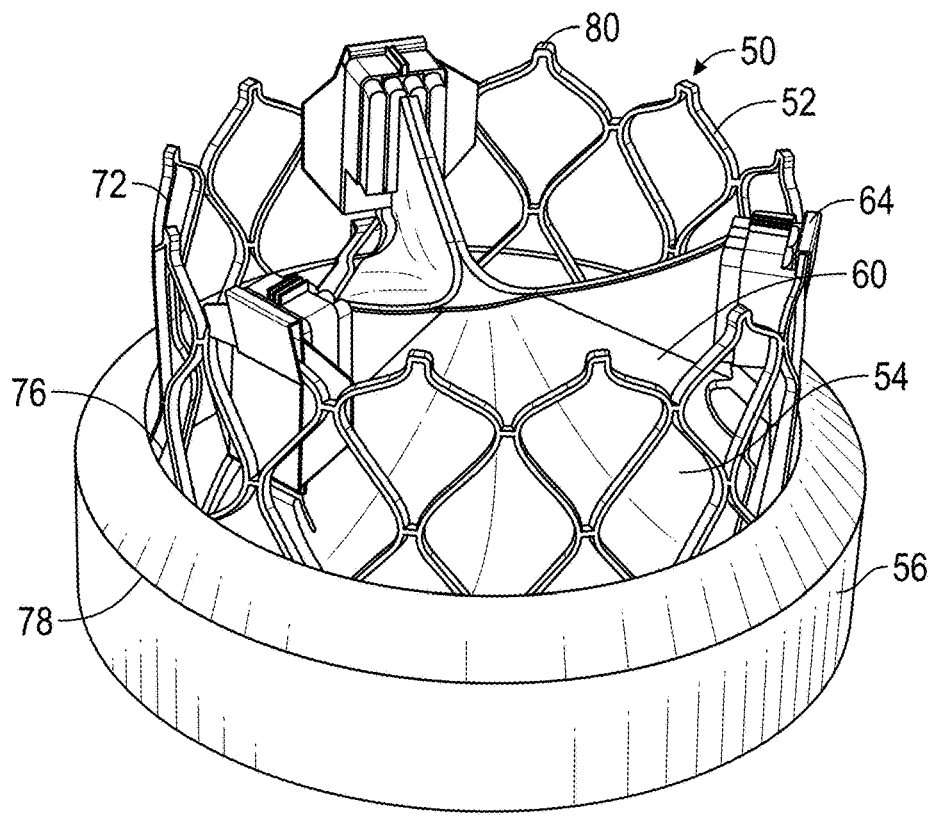
FIG. 2A is a perspective view of a prosthetic heart valve, according to another embodiment.
Figure 2B:
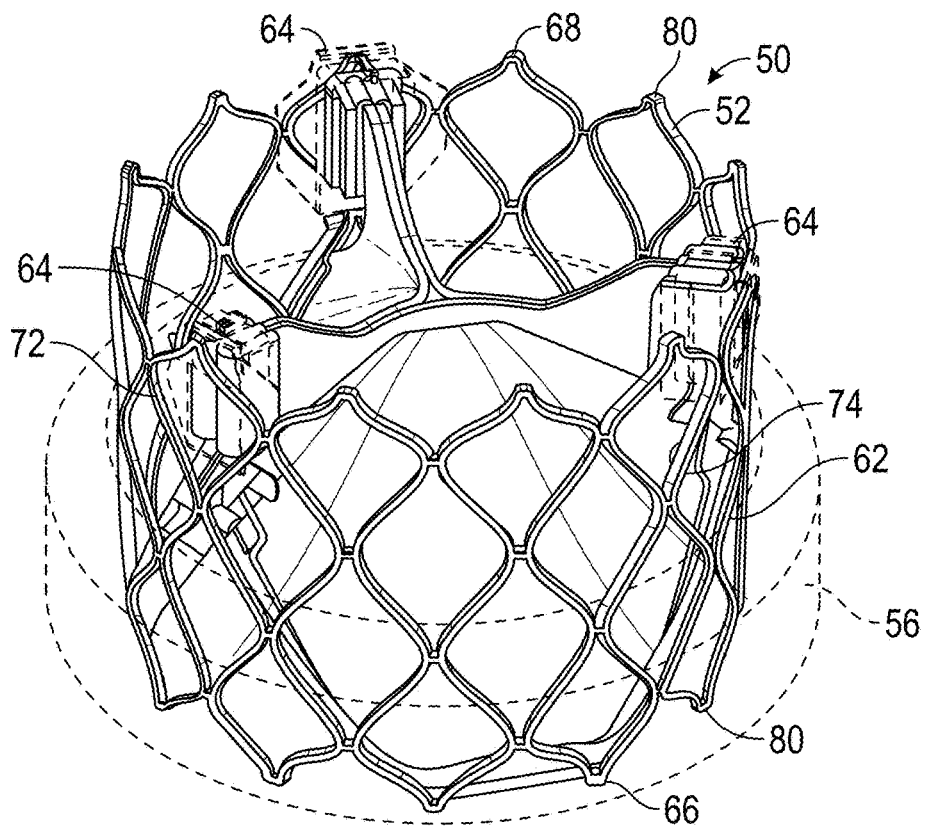
FIG. 2B is a perspective view of the prosthetic valve of FIG. 2A with the components on the outside of the frame shown in transparent lines for purpose of illustration.

FIG. 2A is a perspective view of a prosthetic heart valve 50, according to another embodiment. The prosthetic valve 50 can have three main components: a stent or frame, 52, a valvular structure 54, and a sealing member 56. FIG. 2B is a perspective view of the prosthetic valve 50 with the components on the outside of the frame 52 (including the sealing member 56) shown in transparent lines for purposes of illustration.

Figure 16:
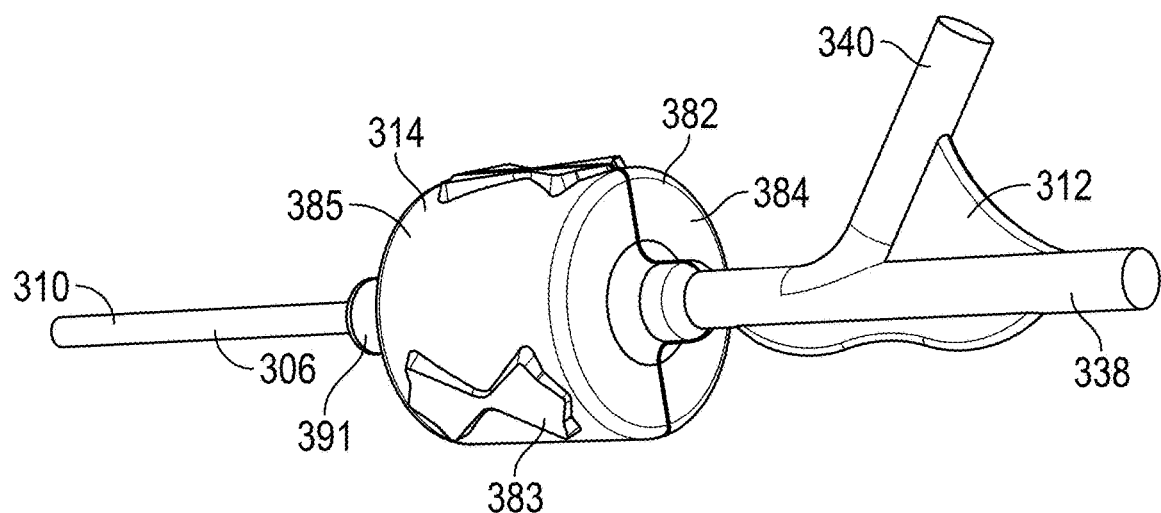
FIG. 16 is a second perspective view of the knob of FIG. 15.
Figure 17:
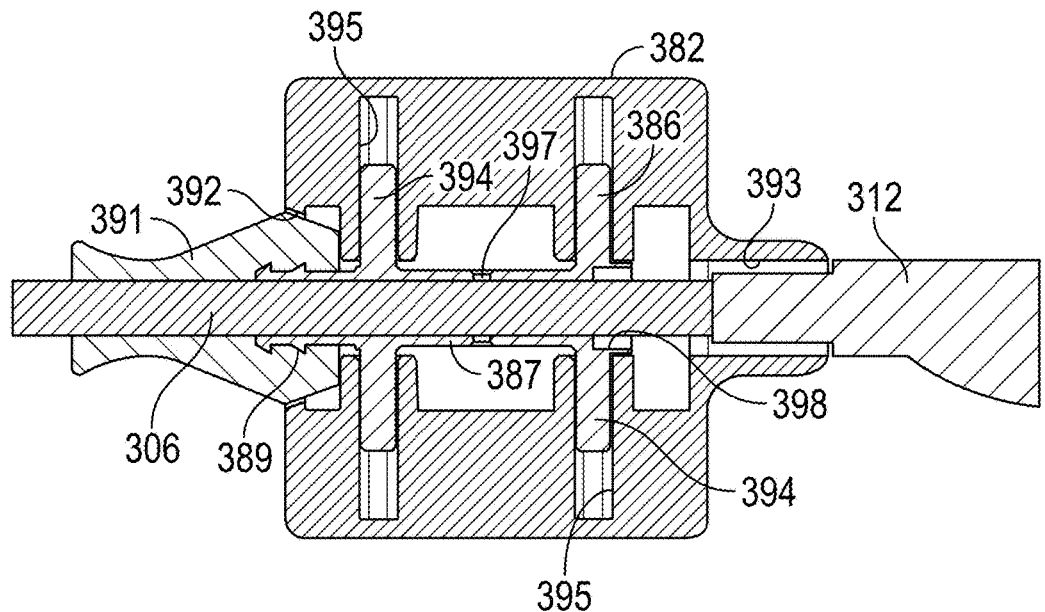
FIG. 17 is a cross-sectional side view of the knob of FIG. 15.

Like the valvular structure 14 of FIG. 1, the valvular structure 54 can comprise three leaflets 60, collectively forming a leaflet structure, which can be arranged to collapse in a tricuspid arrangement. Each leaflet 60 can be coupled to the frame 52 along its inflow edge 62 (the lower edge in the figures; also referred to as "cusp edges") and at commissures 64 of the valvular structure 54 where adjacent portions (e.g., commissure tabs) of two leaflets are connected to each other. In some embodiments, the commissures 64 can comprise an attachment member (e.g., comprising fabric, flexible polymer, or the like) arranged across a cell (e.g., commissure cell) of the frame 52, the cell formed by struts of the frame. The attachment member can be secured to the struts of the frame forming the cell and the adjacent portions of the two leaflets can be connected to the attachment member to form the commissure 64 (e.g., as shown in FIGS. 16 and 17, as described further below).

A reinforcing element (not shown), such as a fabric strip, can be connected directly to the cusp edges of the leaflets and to the struts of the frame to couple the cusp edges of the leaflets to the frame.

Similar to the frame 12 of FIG. 1, the frame 52 can be made of any of various suitable plastically-expandable materials or self-expanding materials, as known in the art and described above. The frame 52 in the illustrated embodiment comprises a plurality of circumferentially extending rows of angled struts 72 defining rows of cells, or openings, 74 of the frame. The frame 52 can have a cylindrical or substantially cylindrical shape having a constant diameter from an inflow end 66 to an outflow end 68 of the frame as shown, or the frame can vary in diameter along the height of the frame, as disclosed in U.S. Patent Publication No. 2012/0239142, which is incorporated herein by reference.

The frame 52, at each of the inflow end 66 and the outflow end 68, may comprise a plurality of apices 80 spaced apart from one another around a circumference of the frame 52.

The sealing member 56 in the illustrated embodiment is mounted on the outside of the frame 52 and functions to create a seal against the surrounding tissue (e.g., the native leaflets and/or native annulus) to prevent or at least minimize paravalvular leakage. The sealing member 56 can comprise an inner layer 76 (which can be in contact with the outer surface of the frame 52) and an outer layer 78. The sealing member 56 can be connected to the frame 52 using suitable techniques or mechanisms. For example, the sealing member 56 can be sutured to the frame 52 via sutures that can extend around the struts 72 and through the inner layer 76. In alternative embodiments, the inner layer 76 can be mounted on the inner surface of the frame 52, while the outer layer 78 is on the outside of the frame 52.

The outer layer 78 can be configured or shaped to extend radially outward from the inner layer 76 and the frame 52 when the prosthetic valve 50 is deployed. When the prosthetic valve is fully expanded outside of a patient's body, the outer layer 78 can expand away from the inner layer 76 to create a space between the two layers. Thus, when implanted inside the body, this allows the outer layer 78 to expand into contact with the surrounding tissue.

Additional details regarding the prosthetic valve 50 and its various components are described in U.S. Patent Publication No. 2018/0028310, which is incorporated herein by reference.

Figure 3:
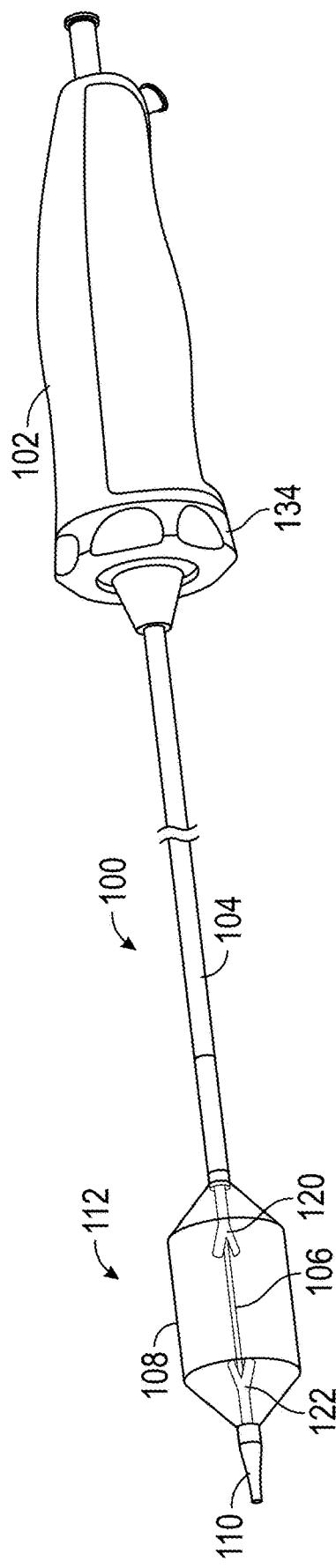
FIG. 3 is a perspective view of a delivery apparatus for a prosthetic heart valve, according to an embodiment.

FIG. 3 shows a delivery device (e.g., apparatus) 100, according to an embodiment, that can be used to implant an expandable prosthetic heart valve (e.g., prosthetic valve 10 or 50), or another type of expandable prosthetic medical device (such as a stent). In some embodiments, the delivery device 100 is specifically adapted for use in introducing a prosthetic valve into a heart.

The delivery device 100 in the illustrated embodiment of FIG. 3 is a balloon catheter comprising a handle 102, a steerable, outer shaft 104 extending from the handle 102, an intermediate shaft extending from the handle 102 coaxially through the steerable outer shaft 104, and an inner shaft 106 extending from the handle 102 coaxially through the intermediate shaft and the steerable, outer shaft 104, an inflatable balloon (e.g., balloon) 108 extending from a distal end of the intermediate shaft, and a nosecone 110 arranged at a distal end of the delivery device 100. A distal end portion 112 of the delivery device 100 includes the balloon 108, the nosecone 110, and a balloon shoulder assembly. A prosthetic medical device, such as a prosthetic heart valve may be mounted on a valve retaining portion of the balloon 108, as described further below with reference to FIGS. 9-11, 41, and 42. As described further below, the balloon shoulder assembly is configured to maintain the prosthetic heart valve or other medical device at a fixed position on the balloon 108 during delivery through the patient's vasculature. In some embodiments, the balloon shoulder assembly can include a proximal shoulder 120 and/or a distal shoulder 122.

The handle 102 can include a steering mechanism configured to adjust the curvature of the distal end portion of the delivery device. In the illustrated embodiment, for example, the handle 102 includes an adjustment member, such as the illustrated rotatable knob 134, which in turn is operatively coupled to the proximal end portion of a pull wire (not shown). The pull wire extends distally from the handle 102 through the outer shaft 104 and has a distal end portion affixed to the outer shaft at or near the distal end of the outer shaft 104. Rotating the knob 134 is effective to increase or decrease the tension in the pull wire, thereby adjusting the curvature of the distal end portion of the delivery device.

Figure 4:
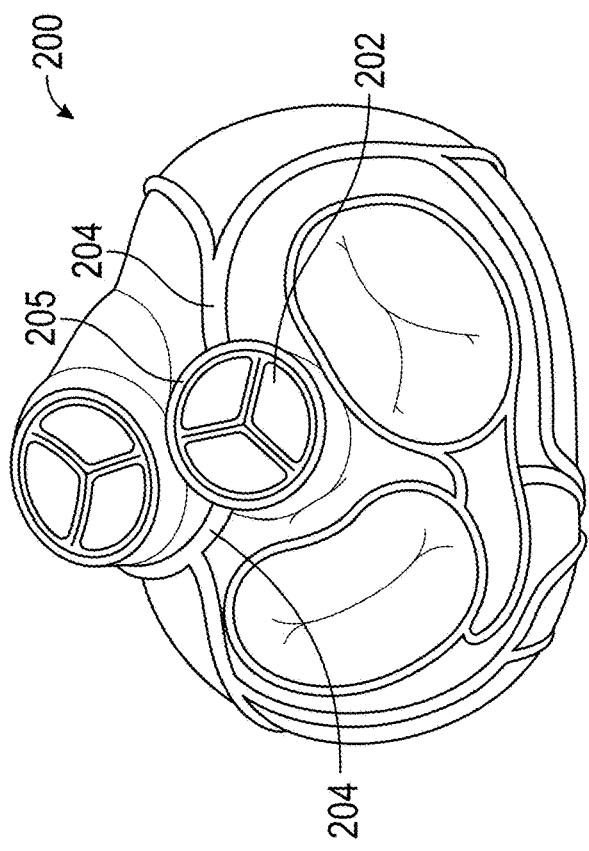
FIG. 4 is a schematic of an exemplary heart showing a position of coronary arteries relative to an aortic valve.

In some embodiments, the delivery apparatus (or another, similar delivery apparatus) can be configured to deploy and implant a prosthetic heart valve (e.g., prosthetic valve 10 of FIG. 1 or prosthetic heart valve 50 of FIGS. 2A and 2B) in the native aortic annulus of a native aortic valve. An exemplary heart 200 including an aortic valve 202 is shown in FIG. 4. As shown in FIG. 4, two coronary arteries (e.g., the left coronary artery and the right coronary artery) 204 are coupled to and branch off from the aorta 205, proximate to the aortic valve 202. The coronary arteries 204 carry oxygenated blood from the aorta to the muscle of the heart 200.

Figure 5A:
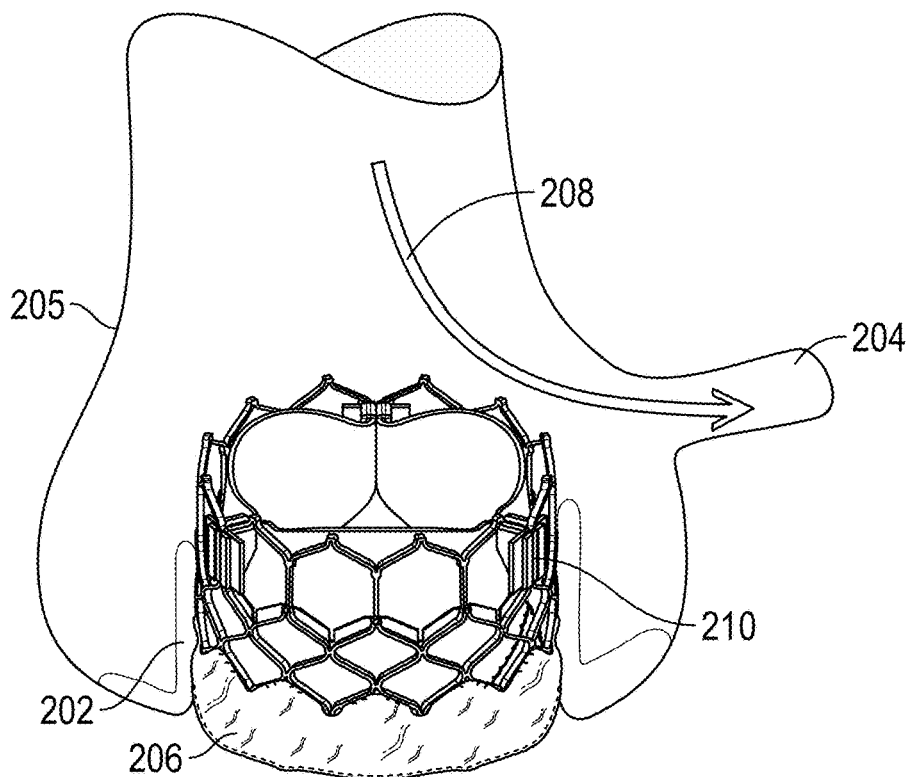
FIG. 5A illustrates an exemplary positioning of a prosthetic valve in an aortic valve, relative to a coronary artery.
Figure 5B:
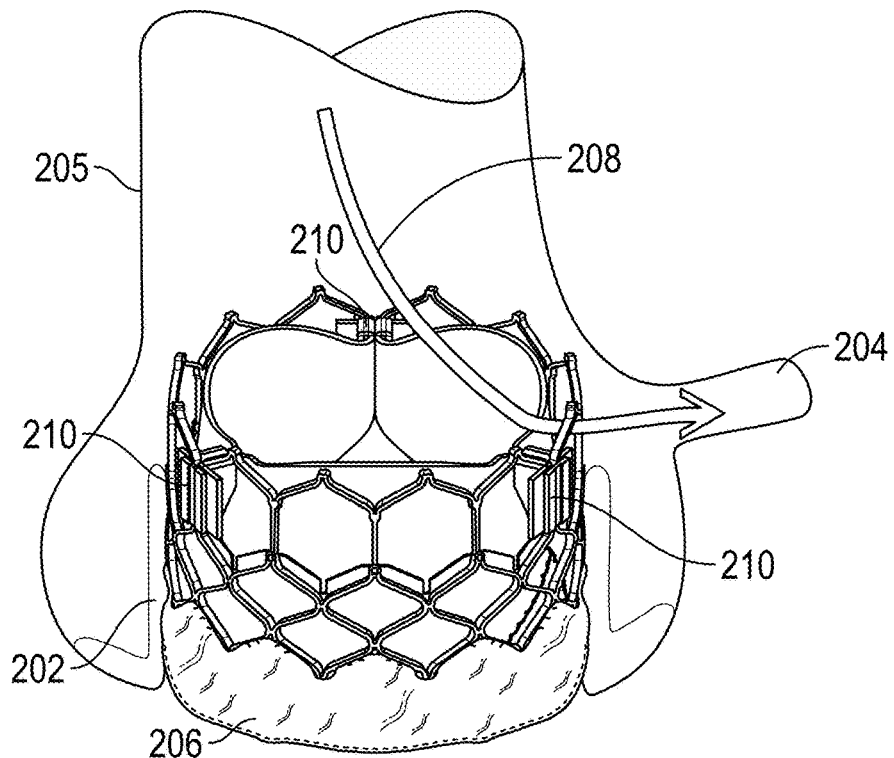
FIG. 5B illustrates another exemplary positioning of a prosthetic valve in an aortic valve, relative to a coronary artery, where the prosthetic valve at least partially inhibits blood flow to the coronary artery.

As shown in FIG. 5A, since the prosthetic heart valve 206 is implanted in the native aortic annulus of the aortic valve 202, blood flow 208 may exit the prosthetic heart valve 206, flow into the aorta 205, and then flow over top of the outflow end of the prosthetic heart valve 206 and/or through open cells (e.g., open cells that are not constantly covered by leaflets of the prosthetic heart valve) in the frame of the prosthetic heart valve 206, to the coronary artery 204 (only one shown in FIGS. 5A and 5B). Depending on a patient's anatomy, the prosthetic heart valve may cover (e.g., be placed in front of) at least a portion of the opening to the coronary artery 204, as shown in the example depicted in FIG. 5B. The interference with blood flow to the coronary arteries 204 can be further exacerbated when a commissure 210 of the prosthetic heart valve 206 is arranged in front of (e.g., adjacent to) an opening to one of the coronary arteries 204 (FIG. 5B). For example, since adjacent leaflets are coupled together at the commissures 210, the commissures 210 block and/or reduce blood flow through the cells to which they are coupled. Thus, less oxygenated blood flow can reach the coronary arteries and the heart muscle.

Figure 6A:
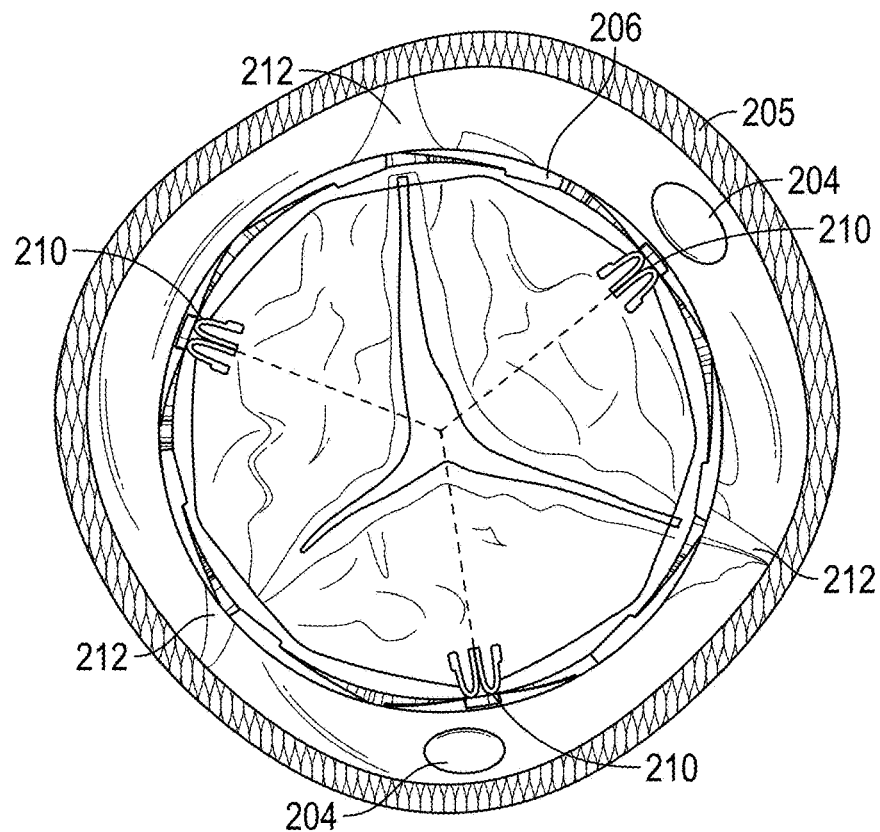
FIG. 6A is a cross-sectional view of an aortic valve illustrating a first positioning of a prosthetic valve within the aortic valve where commissures of the prosthetic valve at least partially block one or more openings to the coronary arteries.
Figure 6B:
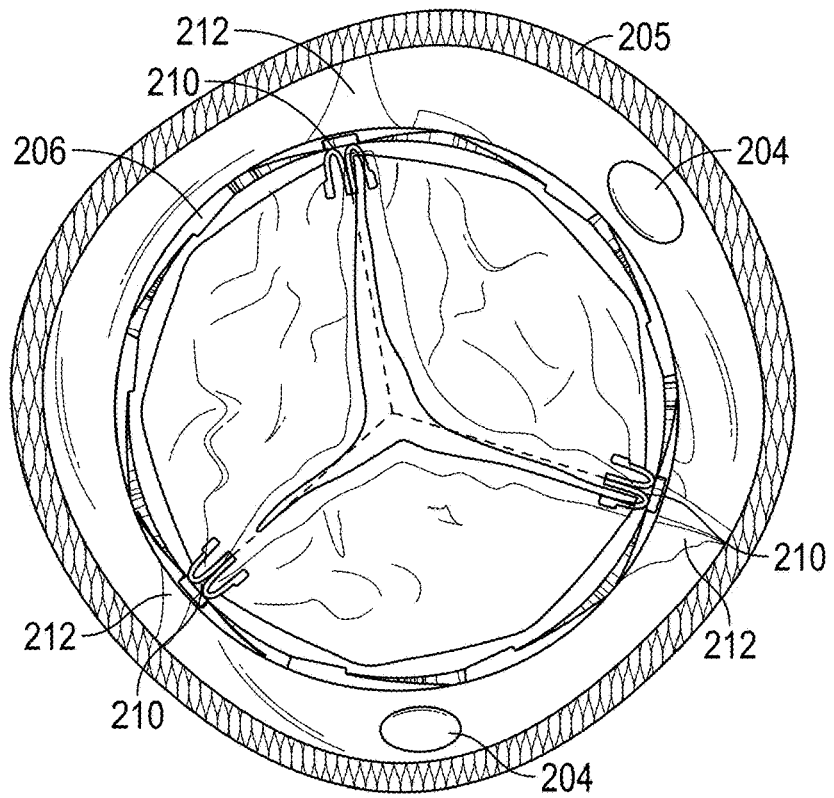
FIG. 6B is a cross-sectional view of an aortic valve illustrating a second positioning of a prosthetic valve within the aortic valve where commissures of the prosthetic valve are circumferentially aligned with native commissure of the aortic valve, thereby maintaining access to the coronary arteries.

Thus, instead of deploying the prosthetic heart valve with the delivery apparatus in a random rotational orientation relative to the aorta 205, which may result in commissures 210 of the prosthetic heart valve 206 being arranged in front of the coronary arteries 204 (as shown in FIG. 6A), it may be desirable to deploy the prosthetic heart valve 206 in an targeted rotational orientation where the commissures 210 are positioned away from and do not block the coronary arteries 204 (as shown in FIG. 6B). For example, as shown in FIG. 6B, the delivery apparatus can be configured to deploy the prosthetic heart valve 206 such that commissures 210 of the radially expanded prosthetic heart valve 206 are circumferentially aligned with the native commissures 212 of the aortic valve 202.

As explained further below, the delivery apparatus can be configured to control the rotational positioning of the prosthetic heart valve 206 relative to the native valve, to achieve the commissure alignment shown in the example of FIG. 6B, thereby increasing blood flow access to the coronary arteries 204. Additionally, this positioning of the prosthetic heart valve can facilitate a later, leaflet cutting procedure that provides increased blood flow to the coronary arteries, as shown in FIGS. 7-8B.

Figure 7:
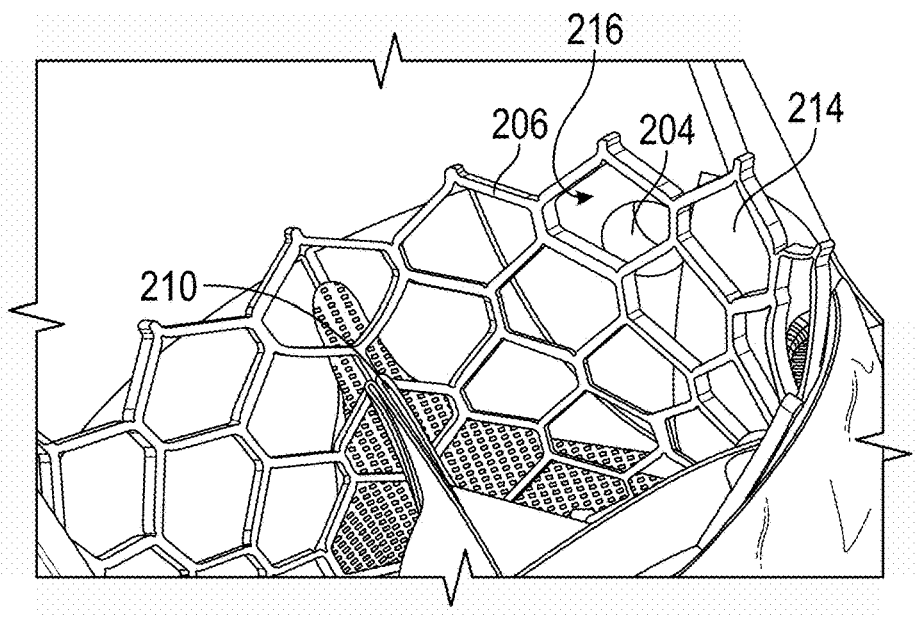
FIG. 7 illustrates a leaflet-cutting procedure where a leaflet of a native aortic valve can be split at a location of an entrance to a coronary artery when a prosthetic heart valve is implanted within the aortic valve to enable increased blood flow to enter the coronary artery.

For example, as shown in FIG. 7, a native leaflet 214 of the native valve (e.g., aortic valve 202) can be split (e.g., cut) longitudinally (relative to a central longitudinal axis of the prosthetic heart valve 206) at a location of an entrance to a coronary artery 204. This enables increased blood flow to enter the coronary artery 204 from the aorta, through one or more open (e.g., not covered by leaflets) cells 216 of the prosthetic heart valve 206.

Figure 8A:
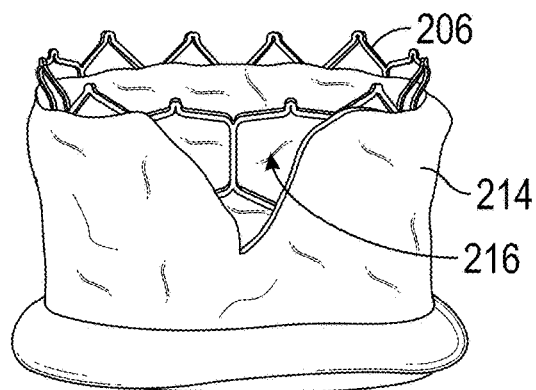
FIG. 8A illustrates an exemplary prosthetic heart valve and an example of how splitting a native leaflet surrounding the prosthetic heart valve at a region of a frame of the prosthetic heart valve that is between two adjacent commissures results in open cells in front of an entrance to a coronary artery.
Figure 8B:
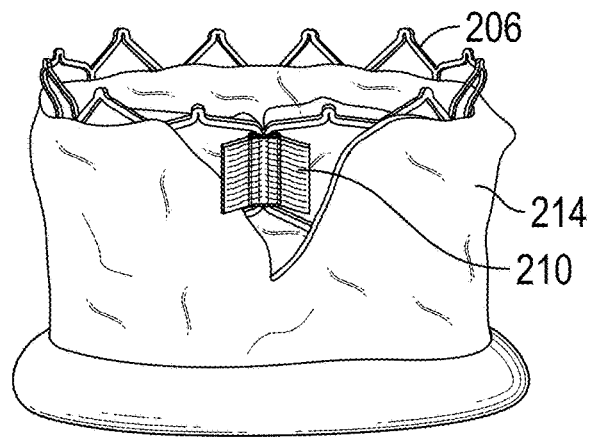
FIG. 8B illustrates the exemplary prosthetic heart valve of FIG. 8A and how splitting the native leaflet in a region of the frame of the prosthetic heart valve that includes a commissure does not result in open cells being arranged in front of the entrance to the coronary artery.

As shown in FIG. 8A, splitting a native leaflet 214 (shown surrounding the prosthetic heart valve 206 in FIGS. 8A and 8B) at a region of a frame of the prosthetic heart valve 206 that is between two adjacent commissures 210 results in open cells 216 that can receive blood flow therethrough. However, as shown in FIG. 8B, splitting the native leaflet 214 in a region of the frame of the prosthetic heart valve 206 that includes the commissure 210 (e.g., due to the commissure 210 being positioned in front of the entrance to the coronary artery 204), does not result in open cells 216 being arranged in front of the entrance to the coronary artery 204. Instead, the commissure 210 can continue to block blood flow to the coronary artery 204.

Thus, it is desirable to have delivery apparatuses and methods for deploying radially expandable prosthetic heart valves in a desired rotational orientation relative to the native valve, such that prosthetic heat valve commissures are in alignment with the native valve commissures.

Figure 9:
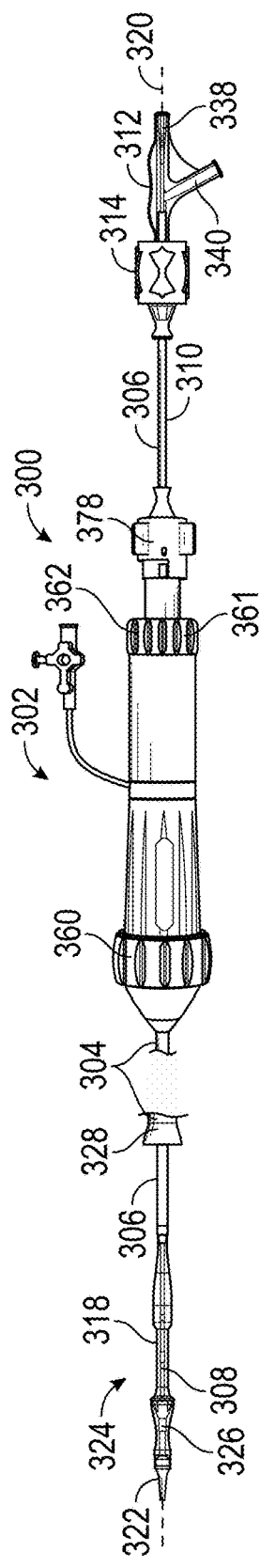
FIG. 9 is a side view of an embodiment of a delivery apparatus configured to deliver and implant a radially expandable prosthetic heart valve at an implantation site.
Figure 68:
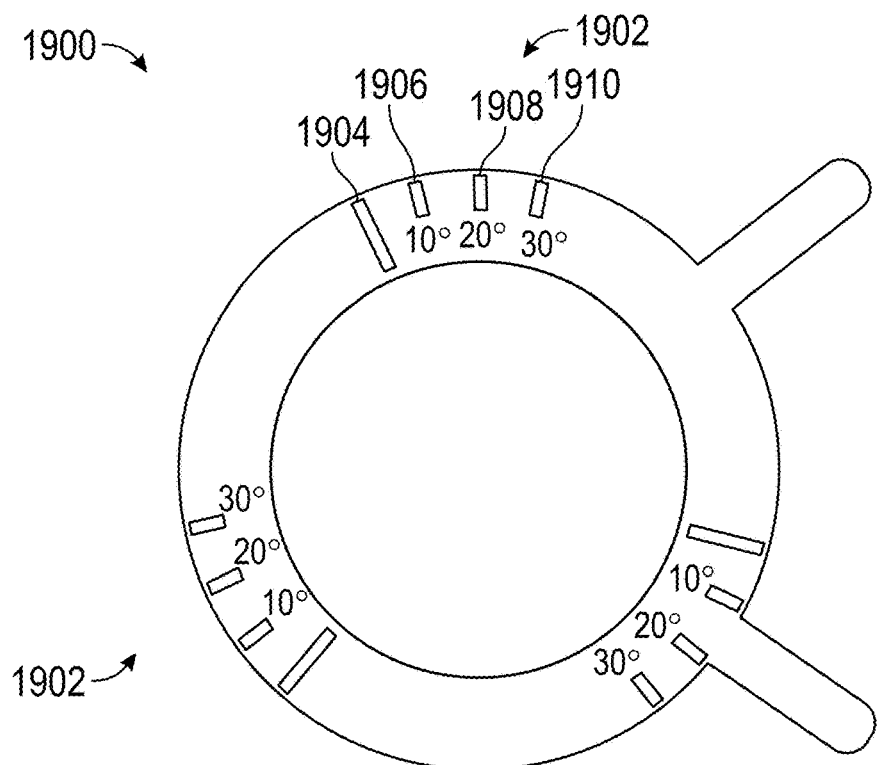
FIG. 68 illustrates another embodiment of an alignment ring including one or more sets of graduated alignment markers.

FIGS. 9-68 show embodiments of delivery apparatuses, methods, and related components, for implanting a radially expandable prosthetic heart valve in a native valve with a delivery apparatus such that commissures of the prosthetic heart valve are aligned with commissures of the native valve. In some embodiments, the prosthetic valve and delivery apparatuses are configured such that the prosthetic valve is deployed from the delivery apparatus at the native valve via inflating a balloon of the delivery apparatus.

FIGS. 9-14 show a delivery apparatus 300, according to an embodiment, that can be used to implant an expandable prosthetic heart valve (e.g., prosthetic valve 10 of FIG. 1 or prosthetic valve 50 of FIGS. 2A-2B), or another type of expandable prosthetic medical device (such as a stent). In some embodiments, the delivery apparatus 300 is specifically adapted for use in introducing a prosthetic valve into a heart. As described further below, the delivery apparatus 300 can be configured to rotate the prosthetic valve, mounted on the delivery apparatus in a radially compressed state, at the target implantation site (e.g., at a native valve of the heart) to achieve commissure alignment between the native valve and prosthetic valve after deploying the prosthetic valve.

Figure 14:
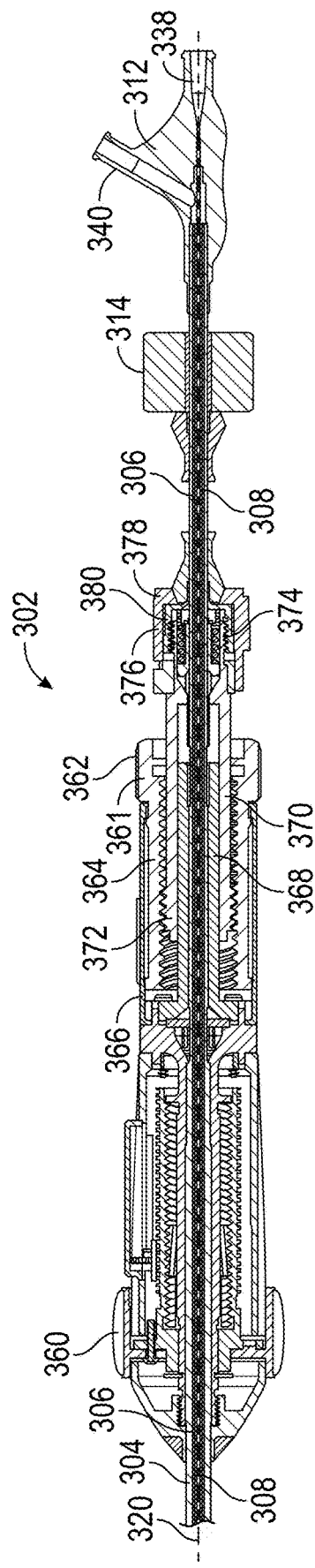
FIG. 14 is a cross-sectional side view of a handle of the delivery apparatus of FIG. 9.

Similar to the delivery device 100 of FIG. 3, the delivery apparatus 300 is a balloon catheter comprising a handle 302 and a steerable, outer shaft 304 extending distally from the handle 302 (FIGS. 9 and 14). The delivery apparatus 300 can further comprise an intermediate shaft 306 (which also may be referred to as a balloon shaft) that extends proximally from the handle 302 (FIGS. 9 and 14) and distally from the handle 302, the portion extending distally from the handle 302 also extending coaxially through the outer shaft 304. Additionally, the delivery apparatus 300 can further comprise an inner shaft 308 extending distally from the handle 302 coaxially through the intermediate shaft 306 and the outer shaft 304 (as show in the detail portion 355 in FIG. 13) and proximally from the handle 302 coaxially through the intermediate shaft 306.

As described further below, the outer shaft 304 and the intermediate shaft 306 are configured to translate (e.g., move) longitudinally, along the central longitudinal axis 320, relative to one another to facilitate delivery and positioning of a prosthetic valve at an implantation site in a patient's body.

The intermediate shaft 306 can include a proximal end portion 310 that extends proximally from a proximal end of the handle 302, to an adaptor 312 (FIGS. 9 and 14). A rotatable knob 314 can be mounted on the proximal end portion 310 (FIGS. 9 and 14) and can be configured to rotate the intermediate shaft 306 around a central longitudinal axis 320 of the delivery apparatus 300 and relative to the outer shaft 304, as described further below with reference to FIGS. 15-22.

The adaptor 312 can include a first port 338 configured to receive a guidewire therethrough and a second port 340 configured to receive fluid (e.g., inflation fluid) from a fluid source. The second port 340 can be fluidly coupled to an inner lumen of the intermediate shaft 306, as described further below.

The intermediate shaft 306 can further include a distal end portion 316 that extends distally beyond a distal end of the outer shaft 304 (FIGS. 10 and 11) when a distal end of the outer shaft 304 is positioned away from an inflatable balloon 318 of the delivery apparatus (e.g., as described further below with reference to FIGS. 38-41). A distal end portion of the inner shaft 308 can extend distally beyond the distal end portion 316 of the intermediate shaft 306 (FIG. 10).

The balloon 318 is coupled to the distal end portion 316 of the intermediate shaft 306. For example, in some embodiments, a proximal end portion of the balloon 318 is coupled to and/or around a distal end 348 of the intermediate shaft 306 (FIGS. 10 and 11).

The balloon 318 can comprise a distal end portion (or section) 332, a proximal end portion (or section) 333, and an intermediate portion (or section) 335, the intermediate portion 335 disposed between the distal end portion 332 and the proximal end portion 333.

Figure 10:
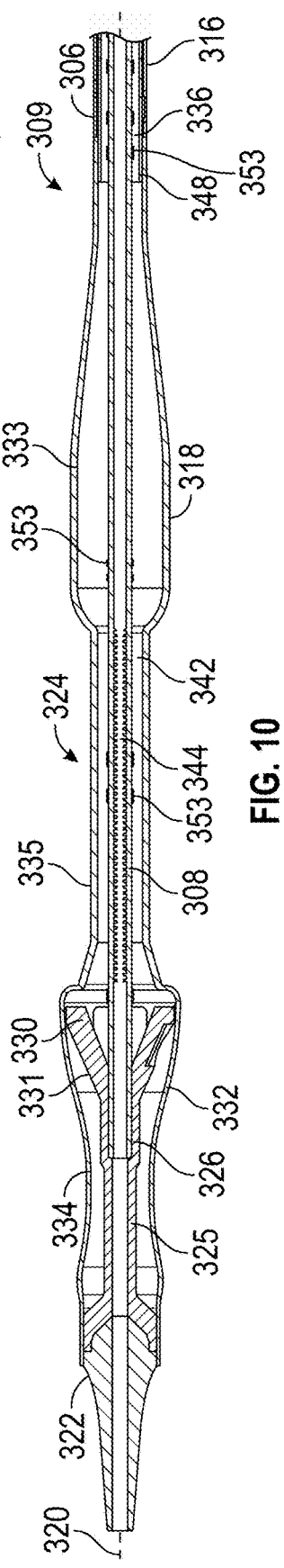
FIG. 10 is a cross-sectional side view of a distal end portion of the delivery apparatus of FIG. 9.
Figure 11:
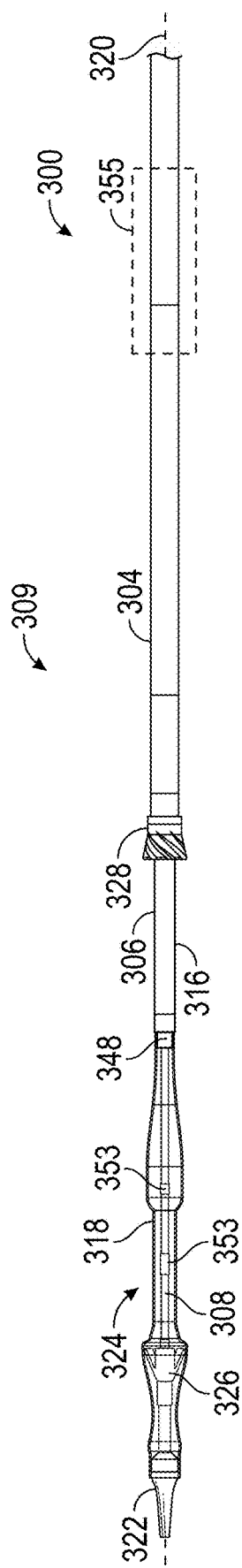
FIG. 11 is a side view of the distal end portion of the delivery apparatus of FIG. 9, illustrating a distal tip portion of an outer shaft of the delivery apparatus.
Figure 41:
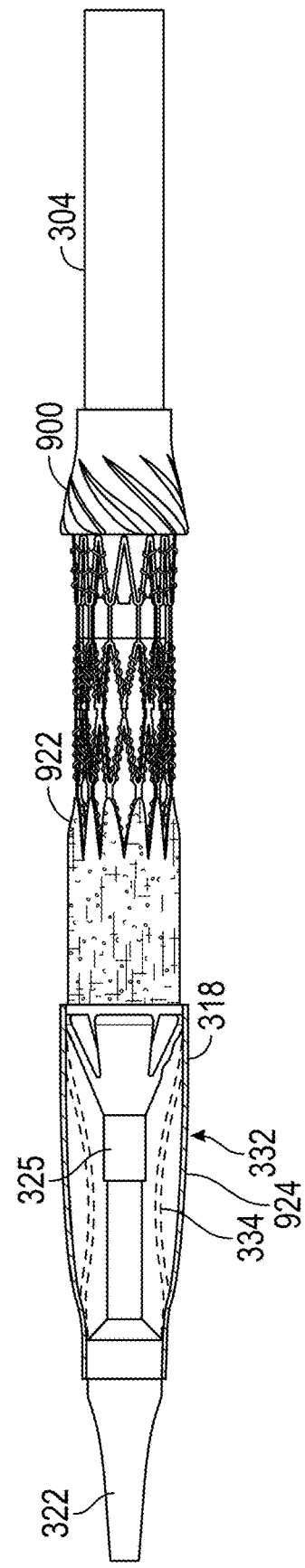
FIG. 41 is a side view of the distal end portion of the delivery apparatus of FIG. 40, illustrating a state of the distal end portion of the inflatable balloon when the distal tip portion is arranged over the proximal end portion of the balloon and a prosthetic valve is mounted on a valve mounting portion of the delivery apparatus.
Figure 42:
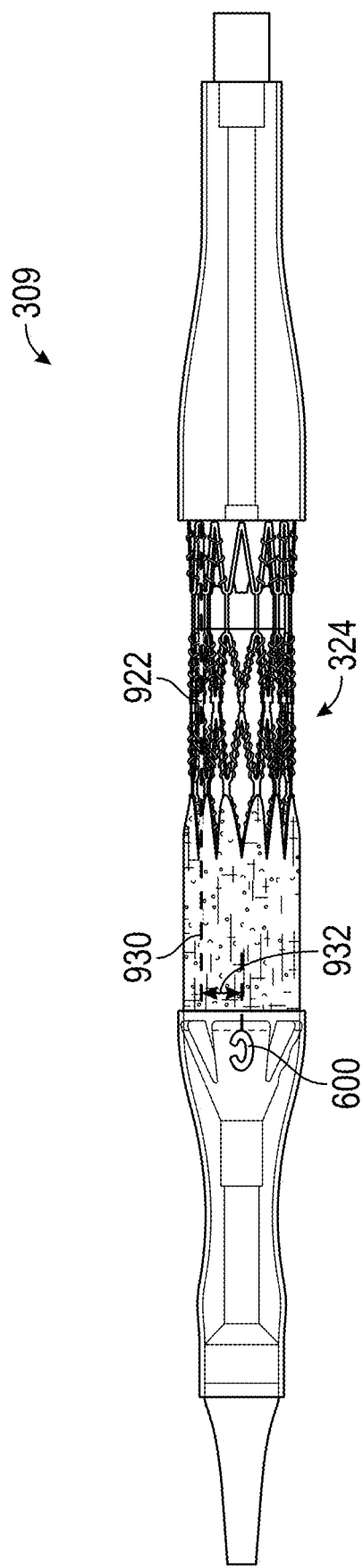
FIG. 42 is a side view of a distal end portion of an exemplary delivery apparatus with a prosthetic valve mounted on and around a valve mounting portion of the distal end portion of the delivery apparatus, in a radially compressed state, with a selected commissure of the prosthetic valve circumferentially offset from a radiopaque marker on the delivery apparatus by a predetermined amount.

In some embodiments, a distal end of the distal end portion 332 of the balloon 318 can be coupled to a distal end of the delivery apparatus 300, such as to a nose cone 322 (as shown in FIGS. 9-11), or to an alternate component at the distal end of the delivery apparatus 300 (e.g., a distal shoulder). In some embodiments, the intermediate portion 335 of the balloon 318 can overlay a valve mounting portion 324 of a distal end portion 309 of the delivery apparatus 300, the distal end portion 332 can overly a distal shoulder 326 of the delivery apparatus 300, and the proximal end portion 333 can surround a portion of the inner shaft 308 (FIG. 10). The valve mounting portion 324 and the intermediate portion 335 of the balloon 318 can be configured to receive a prosthetic heart valve in a radially compressed state (e.g., as shown in FIGS. 41 and 42, as described further below).

As described further below, rotation of the intermediate shaft 306 results in rotation of the balloon 318 and the prosthetic valve mounted thereon for rotational positioning of the prosthetic valve relative to the native anatomy at the target implantation site.

The balloon shoulder assembly is configured to maintain the prosthetic heart valve or other medical device at a fixed position on the balloon 318 during delivery through the patient's vasculature. The balloon shoulder assembly can include a distal shoulder 326 (FIGS. 9-11) arranged within a distal end portion of the balloon 318 and coupled to the distal end portion of the inner shaft 308. The distal shoulder 326 can be configured to resist movement of the prosthetic valve or other medical device mounted on the valve mounting portion 324 distally, in an axial direction (e.g., along central longitudinal axis 320), relative to the balloon 318.

For example, in some embodiments, the distal shoulder 326 can include a flared portion 331 arranged adjacent to the valve mounting portion 324 (FIG. 10). In some embodiments, the flared portion 331 can include a plurality of wings 330 that flare radially outward from a base (e.g., shaft) portion 325 of the distal shoulder 326 (FIG. 10), toward the valve mounting portion 324 (as discussed in more detail below with reference to FIGS. 28, 32A-32B, and 40-42).

The outer shaft 304 can include a distal tip portion 328 mounted on its distal end (FIGS. 9 and 11). In some embodiments, the distal tip portion 328 can be configured as a flex adaptor including a plurality of inner and outer helical grooves, as described further below with reference to FIGS. 38-41. The outer shaft 304 and the intermediate shaft 306 can be translated axially relative to one another to position the distal tip portion 328 adjacent to a proximal end of the valve mounting portion 324, when a prosthetic valve is mounted in the radially compressed state on the valve mounting portion 324 and during delivery of the prosthetic valve to the target implantation site (e.g., as shown in FIG. 41). As such, the distal tip portion 328 can be configured to resist movement of the prosthetic valve relative to the balloon 318 proximally, in the axial direction, relative to the balloon 318, when the distal tip portion 328 is arranged adjacent to a proximal side of the valve mounting portion 324.

In some embodiments, the nose cone 322 can be disposed distal to and be coupled to the distal shoulder 326. In some embodiments, the nose cone 322 can be coupled to the distal end portion of the inner shaft 308.

In some embodiments, the delivery apparatus 300 can comprise one or more markers or marker bands 353 that are configured to indicate to a user a location of a specified component of the delivery apparatus. In some embodiments, the one or more marker bands 353 can radiopaque. In some embodiments, one or more marker bands 353 can be radially compressed (e.g., crimped) onto the inner shaft 308 (FIGS. 10 and 11 and also shown in FIGS. 32A and 40).

As shown in FIG. 10, the distal end portion 332 of the balloon 318 can include a radial depression 334 that is depressed inward, toward the central longitudinal axis 320, relative to an outermost radial surface of the distal shoulder 326 and an outermost radial surface of the nose cone 322. The radial depression 334 is described in further detail below with reference to FIGS. 40 and 41.

As shown in the detail, cross-sectional view of a selected portion 355 (from FIG. 11) of the delivery apparatus 300 of FIG. 13, an annular space 336 can be defined between an outer surface of the inner shaft 308 and an inner surface of the intermediate shaft 306. In some embodiments, the annular space 336 can be referred to as an inner lumen of the intermediate shaft 306. In some embodiments, the annular space 336 can be configured to receive fluid from a fluid source via the second port 340 of the adaptor 312 (e.g., the annular space 336 is in fluid communication with the second port 340 of the adaptor 312). The annular space 336 can be fluidly coupled to a fluid passageway 342 formed between the outer surface of the distal end portion of the inner shaft 308 and an inner surface of the balloon 318 (FIG. 10). As such, fluid from the fluid source can flow to the fluid passageway 342 from the annular space 336 to inflate the balloon 318 and radially expand and deploy the prosthetic valve.

An inner lumen 344 of the inner shaft 308 (FIG. 13) can be configured to receive a guidewire therethrough, for navigating the distal end portion 309 of the delivery apparatus 300 to the target implantation site. As introduced above, the first port 338 of the adaptor 312 can be coupled to the inner lumen 344 and configured to receive the guidewire. For example, the distal end portion 309 of the delivery apparatus 300 can be advanced over the guidewire, to the target implantation site. Exemplary guidewires are shown in FIGS. 29, 31A-31B, 34A-34B, and 59, as described further below.

As shown in the schematic of the intermediate shaft 306 in FIG. 12 and the detail, cross-sectional view of the selected portion 355 (FIG. 11) of the delivery apparatus 300 in FIG. 13, in some embodiments, the intermediate (e.g., balloon) shaft 306 can include two layers of a braided (or coil) material that are configured to increase the torque resistance of the intermediate shaft 306 so that it can withstand rotation at the target implantation site. The braided or coil material can comprise a more rigid braided or coiled material, such as metal or polyethylene terephthalate (PET).

For example, the intermediate shaft 306 can be broken in a first portion 346 that has a first length 356 and a second portion 354 that has a second length 358, the first length 356 longer than the second length 358 (FIG. 12). The first length 356 can be a majority of a total length of the intermediate shaft 306. In some embodiments, the second length 358 can be in a range of 4 to 10 inches, 4 to 8 inches, or 5 to 7 inches. In some embodiments, the second length 358 can be approximately 6 inches. Thus, the first portion 346 can extend from the proximal end portion 310 of the intermediate shaft 306 to a distance (e.g., second length 358) away from the distal end 348 of the intermediate shaft 306.

The two layers of the braided material of the intermediate shaft 306 can include a first braided layer 350 that extends along an entire length of the intermediate shaft 306 (up until the distal end 348), along both the first portion 346 and the second portion 354 (FIG. 13). The two layers of the braided material of the intermediate shaft 306 can further include a second braided layer 352 that extends a majority of the entire length of the intermediate shaft 306, along the first portion 346 (FIG. 13). However, the second braided layer 352 stops before the second portion 354 (FIGS. 12 and 13). This can allow the distal, second portion 354 of the intermediate shaft 306 to have increased flexibility at the distal end portion 316.

In alternate embodiments, the second braided layer 352 can extend the entire length of the intermediate shaft 306. In some alternate embodiments, the intermediate shaft 306 can include more than two layers of braided material, such as three.

As shown in FIGS. 9 and 14, the handle 302 can include a steering mechanism configured to adjust the curvature of the distal end portion 309 of the delivery apparatus 300. In the illustrated embodiment, for example, the handle 102 includes an adjustment member, such as the illustrated rotatable knob 360, which in turn is operatively coupled to the proximal end portion of a pull wire. The pull wire can extend distally from the handle 302 through the outer shaft 304 and has a distal end portion affixed to the outer shaft 304 at or near the distal end of the outer shaft 304. Rotating the knob 360 can increase or decrease the tension in the pull wire, thereby adjusting the curvature of the distal end portion 309 of the delivery apparatus 300. Further details on steering or flex mechanisms for the delivery apparatus can be found in U.S. Pat. No. 9,339,384, which is incorporated by reference herein.

The handle 302 can further include an adjustment mechanism 361 including an adjustment member, such as the illustrated rotatable knob 362, and a shaft 364 extending distally into a housing 366 of the handle 302. The adjustment mechanism 361 is configured to adjust the axial position of the intermediate shaft 306 relative to the outer shaft 304 (FIGS. 9 and 14). In some embodiments, as shown in FIG. 14, an inner support 368 is mounted within the housing 366 on the intermediate shaft 306 and an inner shaft 370 (also referred to as a slider or sliding mechanism) is mounted on the inner support 368. The inner shaft 370 has a distal end portion 372 formed with external threads that mate with internal threads that extend along the inner surface of the shaft 364. The inner shaft 370 further includes a proximal end portion 374 that mounts and interfaces with a locking mechanism 376, which is configured to retain (e.g., lock) the position of the intermediate shaft 306 relative to the handle 302. The inner shaft 370 can be coupled to the inner support 368 such that rotation of shaft 364 causes the inner shaft 370 to move axially within the handle 302. The locking mechanism 376 can include another adjustment member, configured as a rotatable knob 378 housing an inner nut 380 with inner threads that engage the external threads of the proximal end portion 374 of the inner shaft 370.

To restrain movement of the intermediate shaft 306 for fine positioning of the prosthetic valve mounted on the distal end portion of the delivery apparatus 300, the knob 378 is rotated, which in turn causes rotation of the inner nut 380. As a result, the inner nut 380 translates in the distal direction along the external threads on the proximal end portion 374 of the inner shaft 370. As the nut 380 is moved distally, additional components of the locking mechanism 376 are configured to frictionally engage the intermediate shaft 306, thereby retaining the intermediate shaft 306 relative to the inner shaft 370. In the locked position, rotation of the knob 362 causes the inner shaft 370 and the intermediate shaft 306 to move axially relative to the outer shaft 304 (either in the proximal or distal direction, depending on the direction the knob 362 is rotated).

Rotating the knob 378 in the opposite direction from the locked position to the unlocked position allows axial and rotational movement of the intermediate shaft relative to the inner shaft 370 and the proximal end portion of the handle 302. Further details on the adjustment mechanism 361 and locking mechanism 376 of the handle 302 can be found in U.S. Pat. No. 9,339,384, which is incorporated by reference herein.

As introduced above, the knob 314 of handle 302 can be configured to rotate the intermediate (e.g., balloon) shaft 306, thereby rotating the balloon 318 mounted to the intermediate shaft 306 and a radially compressed prosthetic valve mounted on the balloon 318, around the valve mounting portion 324. Thus, rotating the knob 314 can rotate the prosthetic valve, around the central longitudinal axis 320, into a desired orientation relative to the native anatomy at the target implantation site.

FIGS. 15-22 show various views of an embodiment of the knob 314, which is configured to rotate the intermediate shaft 306 upon rotation of the knob 314. In alternate embodiments, a differently configured rotatable knob or other adjustment mechanism can be used in place of knob 314, in order to rotate the intermediate shaft 306 of the delivery apparatus 300.

Figure 15:
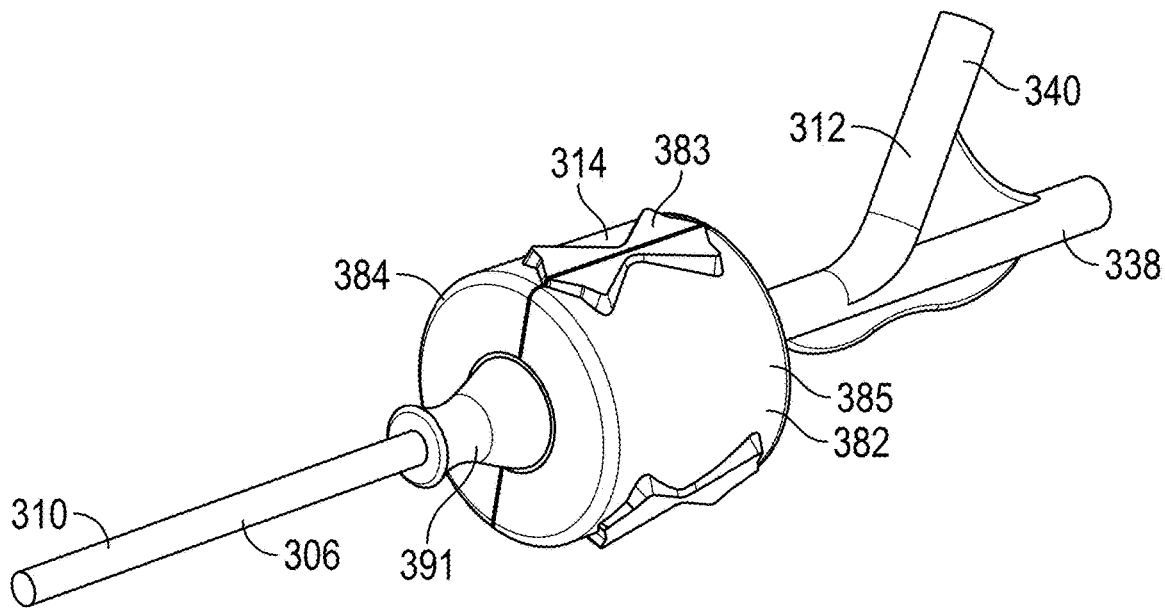
FIG. 15 is a first perspective view of an embodiment of a rotatable knob mounted on a proximal end portion of an intermediate shaft of a delivery apparatus, the knob configured to rotate the intermediate shaft, thereby rotating an inflatable balloon and prosthetic heart valve radially compressed onto the balloon.

As shown in the perspective views of FIGS. 15 and 16 (and FIGS. 9 and 14, as described above), the knob 314 can be mounted on the proximal end portion 310 of the intermediate shaft 306, distal to the adaptor 312. In some embodiments, the knob 314 can be directly coupled to and/or arranged around a portion or an entirety of the adaptor 312 (e.g., as shown in FIGS. 102-107, described further below). In alternate embodiments, the knob 314 can be spaced axially away from the adaptor 312.

The knob 314 can include an outer housing 382 arranged around (e.g., housing) one or more internal components of the knob 314 (FIGS. 15-17 and 20). In some embodiments, the outer housing 382 can include one or more gripping elements 383 configured to increase traction or grip for a user rotating the knob 314. In some embodiments, the one or more gripping elements 383 can be raised elements or features that extend outward from an outer surface of the outer housing 382 and are spaced apart from one another around a circumference of the outer housing 382. In alternate embodiments, the one or more gripping elements 383 can be raised ridges and/or depressed indentations in the outer housing 382.

Figure 20:
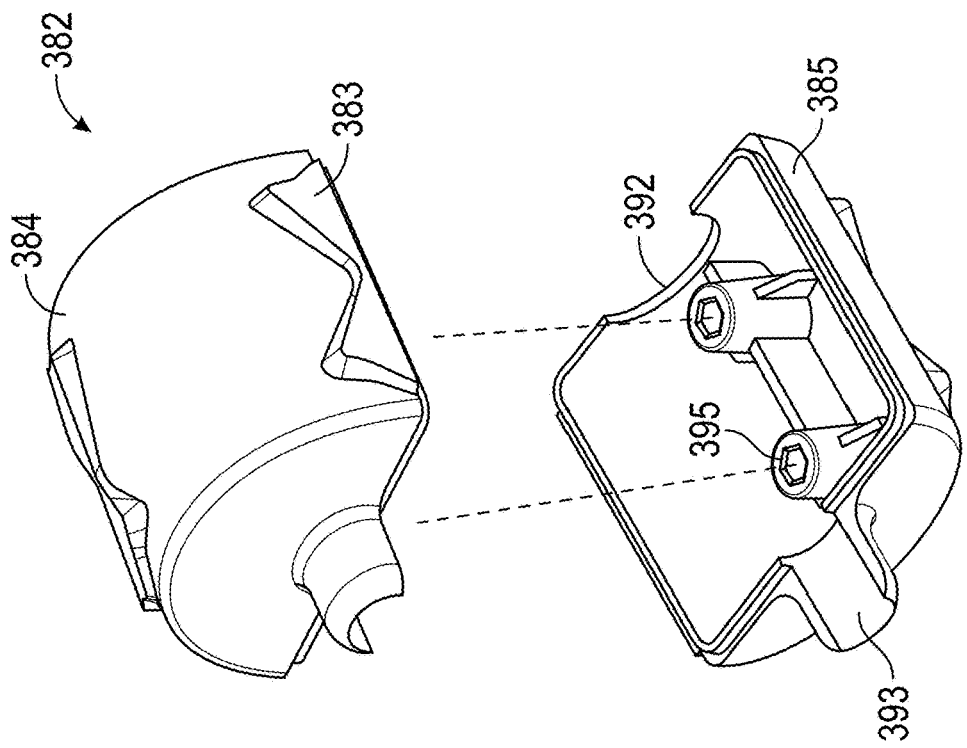
FIG. 20 is an exploded view of an outer housing of the knob of FIG. 15.

In some embodiments, in order to increase an ease of assembly of the knob 314, the outer housing 382 can be split into two or more mating components. For example, in some embodiments, as shown in FIGS. 15, 16, and 20, the outer housing 382 can comprise a first housing portion 384 and a second housing portion 385 that are configured to be removably coupled to one another. For example, each of the first housing portion 384 and the second housing portion 385 can include a corresponding mating interface configured to couple to the first housing portion 384 and the second housing portion 385 to one another. In this way, the first housing portion 384 and the second housing portion 385 can be coupled to one another, around the intermediate shaft 306 and internal components of the knob 314, thereby forming the knob (e.g., knob assembly) 314.

Figure 18:
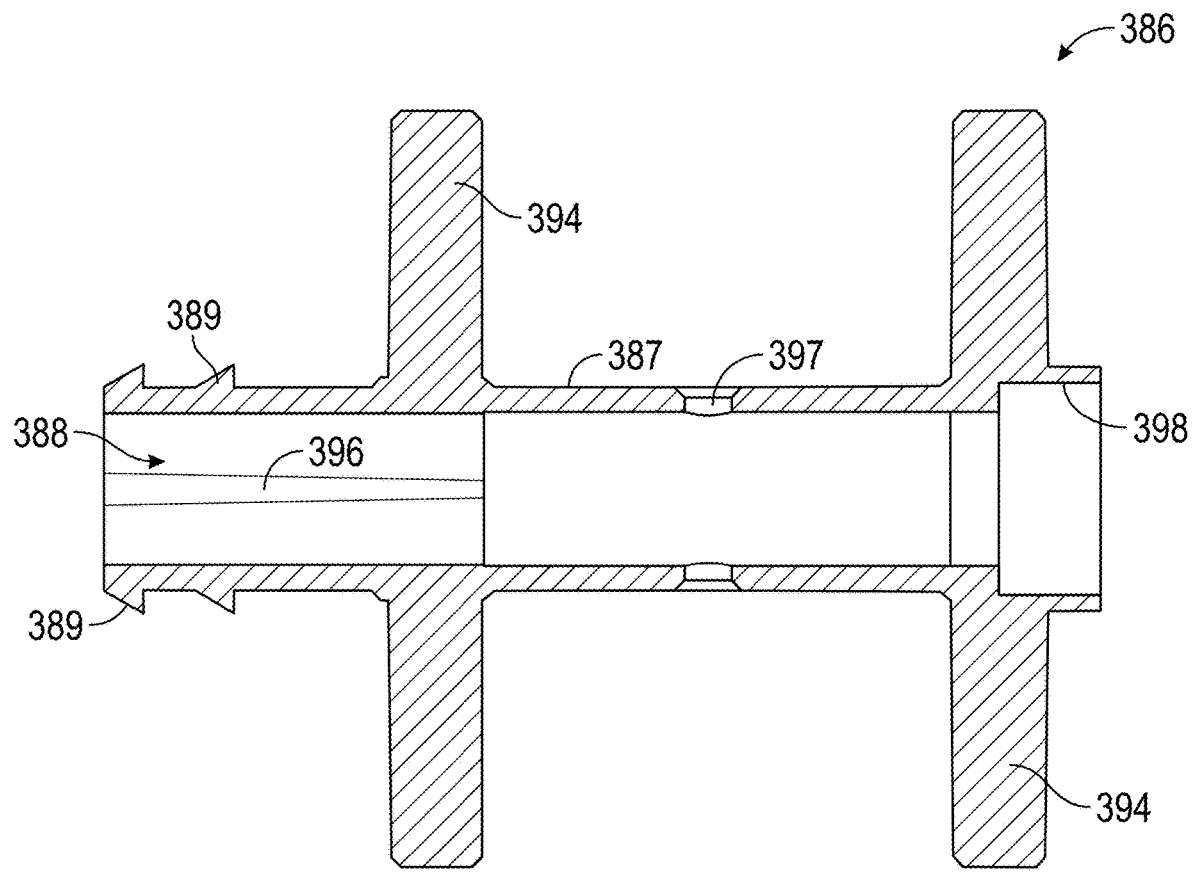
FIG. 18 is a cross-sectional view of an anchor of the knob of FIG. 15, the anchor configured to couple the knob to the intermediate shaft.
Figure 19:
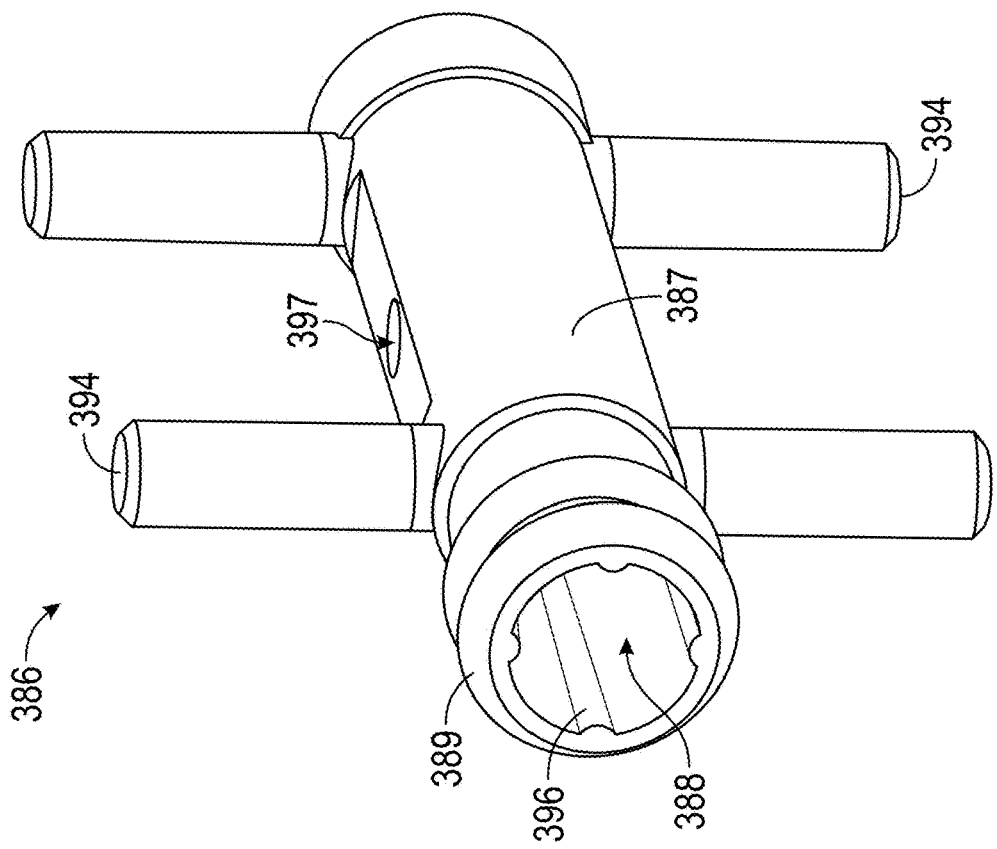
FIG. 19 is a perspective view of the anchor of FIG. 18.

The knob 314 can further comprise an anchor 386 arranged within the outer housing 382 and configured to anchor (e.g., couple) the knob 314 to the proximal end portion 310 of the intermediate shaft 306 (FIGS. 17-19). FIG. 19 shows a cross-sectional view of the knob 314 with the anchor 386 coupled to the intermediate shaft 306 and the outer housing 382 coupled around the anchor 386. FIGS. 18 and 19 show a cross-sectional view and perspective view, respectively, of the anchor 386.

As shown in FIGS. 17-19, the anchor 386 can comprise a shaft portion 387 defining an inner lumen 388 configured to receive and couple around the intermediate shaft 306. In some embodiments, the inner lumen 388 has a relatively constant inner diameter.

In some embodiments, a distal end of the shaft portion 387 can include one or more radial extensions 389 extending around at least a portion of a circumference of the shaft portion 387 (FIGS. 17-19). In some embodiments, one or more or each of the radial extensions 389 can extend around an entire circumference of the shaft portion 387. In some embodiments, the one or more radial extensions 389 can be configured as annular barbs that are axially spaced apart from one another.

The one or more radial extensions 389 can be configured to mate with an interior of a sleeve element (which can also be referred to as a strain relief element) 391 (FIG. 17). In some embodiments, the sleeve element 391 can be arranged around a portion of the proximal end portion 310 of the intermediate shaft 306 and the outer housing 382 can include a wider, first aperture 392 configured to receive therein and/or clamp around a proximal end of the sleeve element 391 (FIGS. 15-17). The sleeve element 391 can be configured to relieve strain between the knob and the proximal end portion of the second shaft. In some embodiments, the sleeve element 391 can comprise a flexible and/or elastic material such as an elastic polymeric material (e.g. rubber).

The outer housing 382 can further include a narrower, second aperture (e.g., channel) 393 configured to receive a distal portion of the adaptor 312 (FIGS. 17 and 20).

As shown in FIGS. 17-19, the anchor 386 can comprise one or more or a plurality of extension portions (e.g., shafts or pins) 394 that are configured to mate with (e.g., extend into and/or couple with) corresponding channels or apertures 395 arranged in the outer housing 382 (FIGS. 17 and 20). The extension portions 394 can be spaced apart from one another and extend radially outward from the shaft portion 387 of the anchor 386.

In some embodiments, as shown in FIGS. 17-19, the anchor 386 can comprise two extension portions 394 extending from each of two opposite sides of the anchor 386. However, in alternate embodiments, the anchor 386 can comprise more or less than four extension portions 394. A number of the apertures 395 can be the same as the number of extension portions 394.

In some embodiments, the apertures 395 and a mating portion of the corresponding extension portions 394 can have a hexagonal shape. However, in alternate embodiments, other shapes are possible, such as rectangular, square, or the like.

In some embodiments, the anchor 386 can be configured for bonding (e.g., UV bonding) to an outer surface of the intermediate shaft 306. For example, in some embodiments, the shaft portion 387 of the anchor 386 can include one or more centering ribs 396 spaced apart around a circumference of the inner lumen 388 and extending along the inner lumen 388 (FIGS. 18 and 19). In some embodiments, the shaft portion 387 can include a viewing aperture 397 (e.g., configured as a window) that can allow a user to view an alignment and/or bonding between the anchor 386 and the intermediate shaft 306 (FIGS. 18 and 19). For example, as shown in FIG. 17, the aperture 397 can extend between an outer surface and an inner surface of the shaft portion 387 and arranged in a central portion of the shaft portion 387. In some embodiments, a proximal end portion of the shaft portion 387 of the anchor 386 can include a counterbore 398 (FIGS. 17 and 18). The counterbore 398 can enable enhanced UV bonding between the anchor 386 and the intermediate shaft 306.

Figures 28, 29:
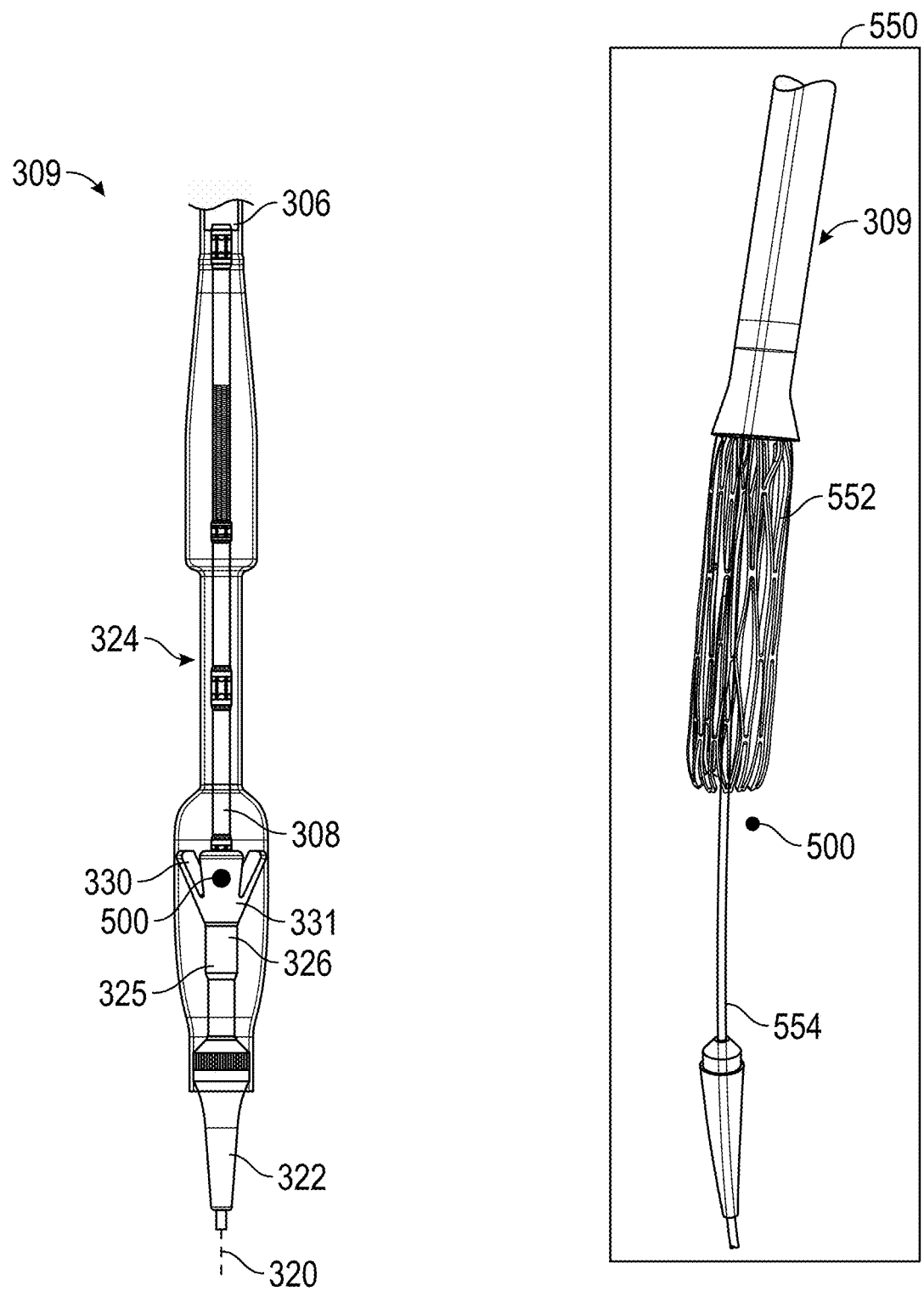
FIG. 28 illustrates a side view of a distal end portion of a delivery apparatus with an exemplary radiopaque marker positioned on and/or embedded within a polymeric body of the distal end portion of the delivery apparatus.
FIG. 29 illustrates an exemplary fluoroscopic image of the distal end portion of the delivery apparatus, including the radiopaque marker, of FIG. 28.
Figure 33:
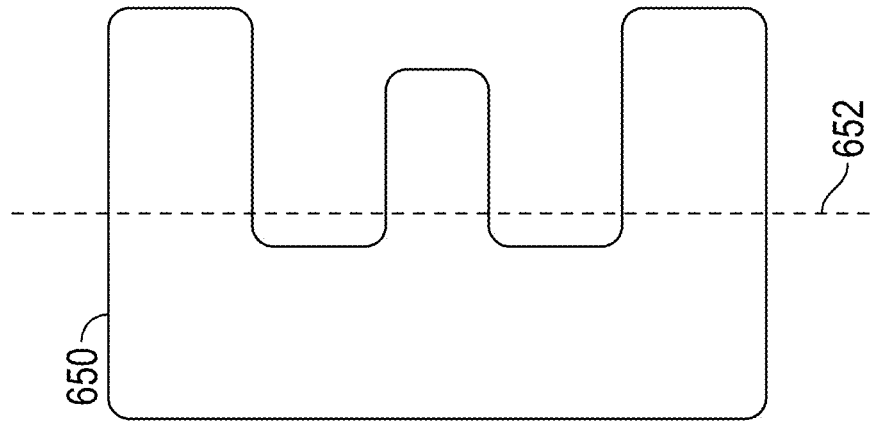
FIG. 33 illustrates another embodiment of an asymmetric radiopaque marker that allows a user to differentiate between two different positions of the marker within an imaging view.

The knob 314 can also include an aligning tab or extension 399 (FIGS. 21-22) configured to align the adaptor 312 with a radiopaque marker arranged on the distal end portion 309 of the delivery apparatus 300 (e.g., the marker 500 shown in FIG. 28, the marker 600 shown in FIGS. 32A-32B, or the marker 650 shown in FIG. 33). In some embodiments, as shown in FIGS. 21 and 22, the aligning tab 399 can extend radially outward from the anchor 386. In some embodiments, the aligning tab 399 can extend radially outward from the shaft portion 387 of the anchor 386 in a direction that is arranged perpendicular to a direction in which the extension portions 394 extend radially outward from the shaft portion 387 of the anchor 386. As described further below, during assembly, the aligning tab 399 can be aligned with the second port 340 of the adaptor 312, such that they extend outwardly relative to the central longitudinal axis 320 in a relatively same direction (e.g., both pointing outward from a same side of the intermediate shaft 306, as shown in FIGS. 21 and 22).

In some embodiments, the knob 314 can be assembled to the proximal end portion 310 of the intermediate (e.g., balloon) shaft 306 in the following manner. However, it should be noted that the below-described method of assembly is exemplary and alternate assembly methods can be possible.

In some embodiments, during assembly, the sleeve element 391 can be mounted on and/or around the proximal end portion 310 of the intermediate shaft 306. Then, the anchor 386 can be positioned on and around the intermediate shaft 306, adjacent to the sleeve element 391. In some embodiments, when the intermediate shat 306 is resting on a relatively planar surface (e.g., a table), the delivery apparatus 300 can be positioned such that the radiopaque marker on the distal end portion 309 is pointing up (e.g., away from the table, which would appear in the plane of the page in FIG. 21) and the anchor 386 can be positioned such that the aligning tab 399 is pointing away from the user (e.g., the person assembling the apparatus), as shown in FIG. 21. For example, in FIG. 21, the planar surface of table may be in the plane of the page. After this portion of the alignment is complete, the anchor 386 can be bonded (e.g., via UV bonding) to the intermediate shaft 306 and the sleeve element 391 can then be positioned over the radial extensions 389 of the anchor 386.

In some embodiments, the assembly method can further include bonding the adaptor 312 to the intermediate shaft 306 such that the second port 340 is pointing in a same direction as the aligning tab 399 and/or the second port 340 and the aligning tab 399 are circumferentially aligned, relative to a circumference of the intermediate shaft 306 (FIGS. 21 and 22). In this way, during an implantation procedure, a user may know an initial (e.g., starting) position of the radiopaque marker on the distal end portion 309 of the delivery apparatus 300, within a patient. This may enable easier and faster rotational positioning of the radiopaque marker, and thus the prosthetic valve, at the target implantation site, as described further below.

The outer housing 382 can then be positioned around the anchor 386 (FIG. 22). In some embodiments, this can include positioning the first housing portion 384 and the second housing portion 385 around the anchor 386 and coupling them to one another.

FIGS. 102-107 show various views of another embodiment of a knob (or handle) 2500 which is configured to rotate the intermediate shaft 306 of the delivery apparatus 300 upon rotation of the knob 2500. The knob 2500 (which can also be referred to as a handle or valve rotation control (VRC)) can be similar in function to the knob 314 (and include the same or similar internal components, as described further below), except an outer housing 2502 of the knob 2500 is larger and configured to include or enclose an adaptor (such as or similar to adaptor 312). Thus, in one specific embodiment, the delivery apparatus 300 of FIG. 9 includes the knob 2500 instead of the knob 314.

As shown in the perspective and side views of FIGS. 102 and 103, respectively, the knob 2500 can be mounted on the proximal end portion 310 of the intermediate shaft 306 and surround or include therein the adaptor 312 (or another, similar adaptor). For example, as shown in FIGS. 102-107, the knob 2500 is arranged around and encloses therein the adaptor 312 such that a user cannot grab or rotate the adaptor 312 independent of the knob 2500.

In some embodiments, the outer housing 2502 can include one or more gripping elements 2504 configured to increase traction or grip for a user rotating the knob 2500. In some embodiments, as shown in FIGS. 102-107, the one or more gripping elements 2504 can be raised elements or features that extend radially outward from an outer surface of the outer housing 2502 and are spaced apart from one another around a circumference of the outer housing 2502. In alternate embodiments, the one or more gripping elements 2504 can be raised ridges and/or depressed indentations in the outer housing 2502.

In some embodiments, in order to increase an ease of assembly of the knob 2500, the outer housing 2502 can be split into two or more mating components. For example, in some embodiments, as shown in FIG. 103 and the exploded view of FIGS. 104 and 105, the outer housing 2502 can comprise a first housing portion 2506 and a second housing portion 2508 that are configured to be removably coupled to one another. For example, each of the first housing portion 2506 and the second housing portion 2508 can include a corresponding mating interface configured to couple the first housing portion 2506 and the second housing portion 2508 to one another. In this way, the first housing portion 2506 and the second housing portion 2508 can be coupled to one another, around the intermediate shaft 306 and internal components of the knob 2500, thereby forming the knob (e.g., knob assembly) 2500.

Similar to the knob 314 of FIGS. 15-22, the knob 2500 can comprise the anchor 386 arranged within the outer housing 2502 and configured to anchor (e.g., couple) the knob 2500 to the proximal end portion 310 of the intermediate shaft 306 (as shown in the cross-sectional side views of FIGS. 106 and 107). For example, the anchor 386 is configured to couple around the intermediate shaft 306 and interface with the sleeve element 391, as described above with reference to FIGS. 15-22 (and shown in FIGS. 106 and 107).

As described above with reference to FIGS. 15-22, the outer housing 1502 is configured to couple around and to the anchor 386 and receive and/or clamp around a proximal end of the sleeve element 391. For example, similar to the outer housing 382 of knob 314, the outer housing 2502 can comprise a first aperture 2510 (formed by the two halves of the outer housing 2502 when the two halves are coupled together) configured to receive therein and/or clamp around the proximal end of the sleeve element 391 (FIGS. 104-107).

The outer housing 2502 can further include an internal cavity 2512 (at its proximal end) configured to receive the adaptor 312 therein (FIGS. 104-107). The outer housing 2502 can include a second aperture 2514 (formed by the two halves of the outer housing 2502 when the two halves are coupled together) that is configured to fit around the first port 338 of the adaptor 312 (FIGS. 104-107). A proximal end of the first port 338 can extend proximally out of and away from a proximal end 2516 of the outer housing 2502 of the knob 2500. In some embodiments, the outer housing 2502 comprises a cap 2518 configured to couple around the proximal end 2516 when the first housing portion 2506 and the second housing portion 2508 are arranged together, thereby coupling the first housing portion 2506 and the second housing portion 2508 to one another and forming the closed outer housing 2502 (FIGS. 102, 103, 106, and 107).

The outer housing 2502 can further include an extension portion 2556 that extends outward at an angle from a main body of the outer housing 2502. A portion of the internal cavity 2512 can be formed within the extension portion 2556 and configured to receive the second port 340 of the adaptor 312. In some embodiments, the extension portion 2556 can include a third aperture 2558 (formed by the two halves of the outer housing 2502 when the two halves are coupled together) that is configured to fit around the second portion 340 (FIGS. 104 and 107). An open end of the second port 340 can extend out of and away from the third aperture 2558.

In alternate embodiments, instead of receiving the adaptor 312 within the internal cavity 2512, the adaptor and outer housing 2502 can be integrated together (e.g., formed or molded as one piece).

Similar to the knob 314, as described above with reference to FIGS. 15-22, the outer housing 2502 of the knob 2500 can comprise one or more apertures 395 that are arranged on an interior of the outer housing 2502 and configured to receive and mate with the one or more extension portions 394 of the anchor 386 (FIGS. 104-106). In some embodiments, each aperture 395 can be arranged in a radial extension member 2520 extending from an inner surface of the outer housing 2502 (FIGS. 104-106).

In some embodiments, as described above with reference to FIGS. 21-22, the anchor 386 can include the aligning tab 399 which can extend radially outward from the anchor 386 (FIGS. 104 and 107). As described above and as shown in FIGS. 104 and 107, during assembly, the aligning tab 399 can be aligned with the second port 340 of the adaptor 312, such that they extend outwardly relative to the central longitudinal axis 320 in a relatively same direction (e.g., both pointing outward from a same side of the intermediate shaft 306, as shown in FIGS. 104 and 107).

In some embodiments, the knob 2500 can be assembled to the proximal end portion 310 of the intermediate (e.g., balloon) shaft 306 in the same or a similar manner to the knob 314, as described above with reference to FIGS. 15-22.

For example, in some embodiments, during assembly, the sleeve element 391 can be mounted on and/or around the proximal end portion 310 of the intermediate shaft 306. Then, the anchor 386 can be positioned on and around the intermediate shaft 306, adjacent to the sleeve element 391. In some embodiments, when the intermediate shat 306 is resting on a relatively planar surface (e.g., a table), the delivery apparatus 300 can be positioned such that the radiopaque marker on the distal end portion 309 is pointing up (e.g., away from the table) and the anchor 386 can be positioned such that the aligning tab 399 is pointing away from the user. After this portion of the alignment is complete, the anchor 386 can be bonded (e.g., via UV bonding) to the intermediate shaft 306 and the sleeve element 391 can then be positioned over the radial extensions 389 of the anchor 386.

In some embodiments, the assembly method can further include bonding the adaptor 312 to the intermediate shaft 306 such that the second port 340 is pointing in a same direction as the aligning tab 399 and/or the second port 340 and the aligning tab 399 are circumferentially aligned, relative to a circumference of the intermediate shaft 306. In this way, during an implantation procedure, a user may know an initial (e.g., starting) position of the radiopaque marker on the distal end portion 309 of the delivery apparatus 300, within a patient. This may enable easier and faster rotational positioning of the radiopaque marker, and thus the prosthetic valve, at the target implantation site, as described further below.

The outer housing 2502 can then be positioned around the anchor 386 and the adaptor 312 (FIGS. 104-107). In some embodiments, this can include positioning the first housing portion 2506 and the second housing portion 2508 around and coupling them to the anchor 386, thereby coupling distal ends of the first housing portion 2506 and the second housing portion 2508 to one another. The cap 2518 can then be coupled to the proximal end 2516 of the knob 2500, thereby coupling proximal ends of the first housing portion 2506 and the second housing portion 2508 to one another. These connections may allow for the first housing portion 2506 and the second housing portion 2508 to be held together without using adhesive or additional fasteners.

In some embodiments, the outer housing 2502 can comprise one or more indicators 2522 (e.g., markings) that indicate to a user which way the knob 2500 should be rotated in order to align the radiopaque marker on the distal end portion of the delivery apparatus (e.g., marker 500 or any of the other markers described herein) with the guidewire running through a center of the delivery apparatus (e.g., under fluoroscopy during an implantation procedure, as described herein). For example, in some embodiments, each indicator 2522 can comprise a printed marking including a line representing the guidewire, a visual representation of the radiopaque marker on either side of the line (e.g., the "C" markers as shown), and an arrow on either side of the line indicating to the user which way to rotate the knob 2500 if the radiopaque marker does not appear aligned with the guidewire in the selected imaging view during the implantation procedure, as described further herein (e.g., during the method at 1308, as described below with reference to FIG. 57).

For example, if the radiopaque marker on the distal end portion of the delivery apparatus (e.g., marker 600 or another marker described herein) appears to be on a first side of the guidewire in the fluoroscopic imaging view, the user may rotate the knob 2500 in a first direction (as indicated by a first arrow of the indicator 2522) and if the radiopaque marker appears to be on an opposite, second side of the guidewire in the imaging view, the user may rotate the knob 2500 in an opposite, second direction (as indicated by a second arrow of the indicator 2522) in order to position the marker in alignment with the guidewire during the implantation procedure. In some embodiments, as shown in FIGS. 102 and 103, each of the first housing portion 2506 and the second housing portion 2508 can include an indicator 2522 and the two indicators 2522 (one on each housing portion) can be arranged 180 degrees apart from one another around the knob 2500.

In some embodiments, the presence of the knob 314 or the knob 2500 for rotating the intermediate shaft 306 to achieve a desired rotational positioning of the prosthetic valve at the target implantation site may reduce a likelihood of the user holding onto and using the adaptor 312 to rotate the intermediate shaft 306 and prosthetic valve. Such force or torque applied to the adaptor 312 may result in damage to the adaptor 312. Further, by fully encasing or enclosing the adaptor 312 within the knob 2500, as shown in FIGS. 102-107, a user is prevented from holding onto and applying torque to the adaptor 312.

In some embodiments, to further deter a user from holding and rotating the adaptor 312 for rotationally aligning the prosthetic valve, a portion of the adaptor 312 itself can be rotatable relative to the intermediate shaft 306 and a remainder of the adaptor 312.

For example, FIGS. 23-27 show an embodiment of a proximal end portion 400 of a delivery apparatus, including an adaptor 402 comprising a first port 404 and a second (e.g., inflation) port 406 that is configured to rotate. In some embodiments, the proximal end portion 400 can be used as the proximal end portion of the delivery apparatus 300 of FIGS. 9 and 14. Further, in some embodiments, the proximal end portion 400 can include similar components to those described above with reference to FIGS. 9 and 14, and thus, are labeled similarly in FIG. 23.

Figure 23:
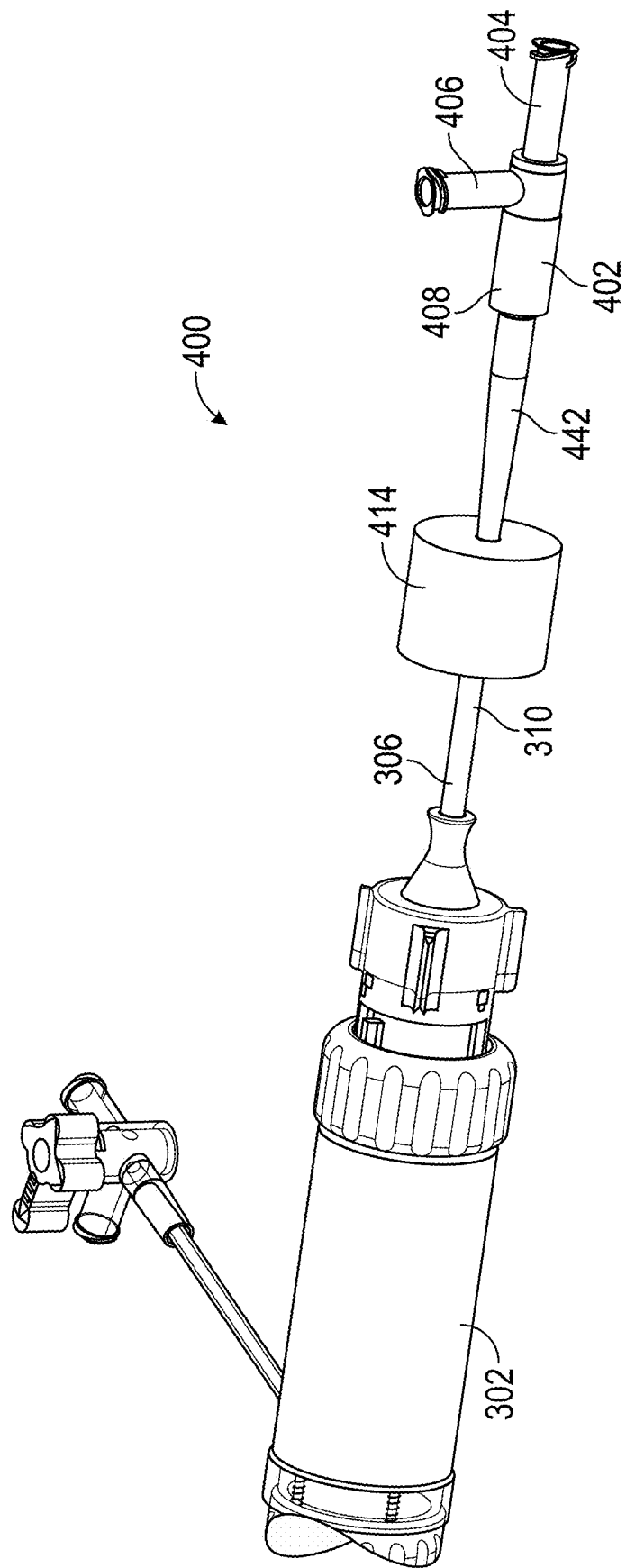
FIG. 23 is a perspective view of an embodiment of a proximal end portion of a delivery apparatus, including a handle, rotatable knob, and an adaptor.

As shown in FIG. 23, the proximal end portion 400 can include a handle (e.g., handle portion), such as the handle 302 described above with reference to FIGS. 9 and 14. However, in alternate embodiments, an alternate handle configuration can be possible. A rotatable shaft, such as the intermediate (e.g., balloon) shaft 306, can extend distally from the handle 302 (as shown in FIGS. 9 and 14) and have a proximal end portion 310 that extends proximally from the handle 302 to the adaptor 402 (FIG. 23). Additionally, a rotatable knob 414 can be mounted on the proximal end portion 310 of the intermediate shaft 306, distal to the adaptor 402. The knob 414 can be configured to rotate the intermediate shaft 306. In some embodiments, the knob 414 can be knob 314, as described above with reference to FIGS. 15-22.

The adaptor 402 can further comprise an adaptor body (e.g., body) 408. The adaptor body 408 can be coupled (e.g., connected) to the proximal end portion 310 of the intermediate shaft 306 (FIGS. 23 and 26). For example, the adaptor body 408 can include a first inner channel 410 (FIG. 25) configured to receive a proximal end of the intermediate shaft 306 therein (FIG. 26).

In some embodiments, an additional adaptor 442 can be arranged around the intermediate shaft 306, between the knob 414 and the adaptor body 408 (FIGS. 23 and 26).

Figure 24:
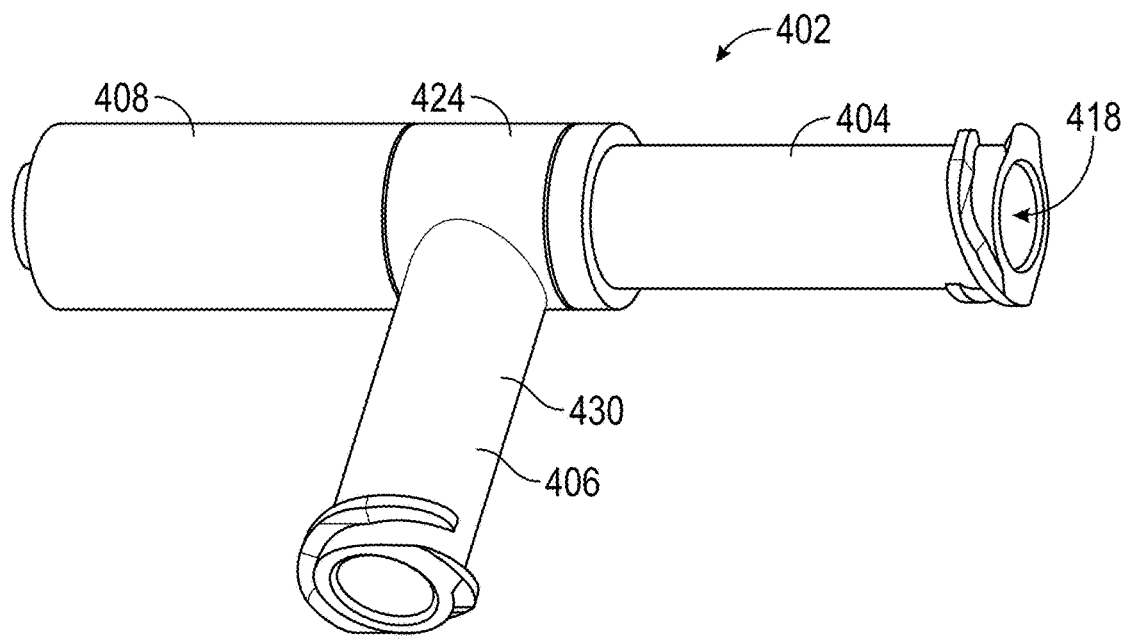
FIG. 24 is a perspective view of the adaptor in FIG. 23, the adaptor comprising a first port and a second port that is configured to rotate relative to a body of the adaptor and the first port.
Figure 25:
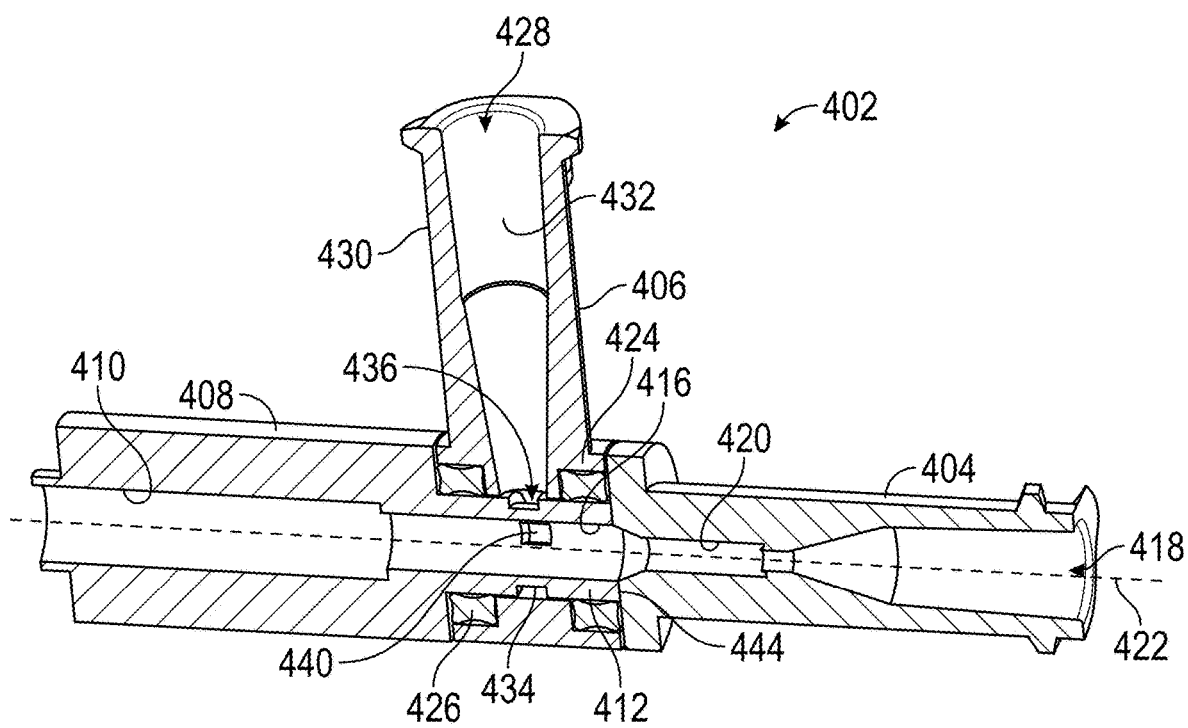
FIG. 25 is a cross-sectional view of the adaptor of FIG. 24.
Figure 26:
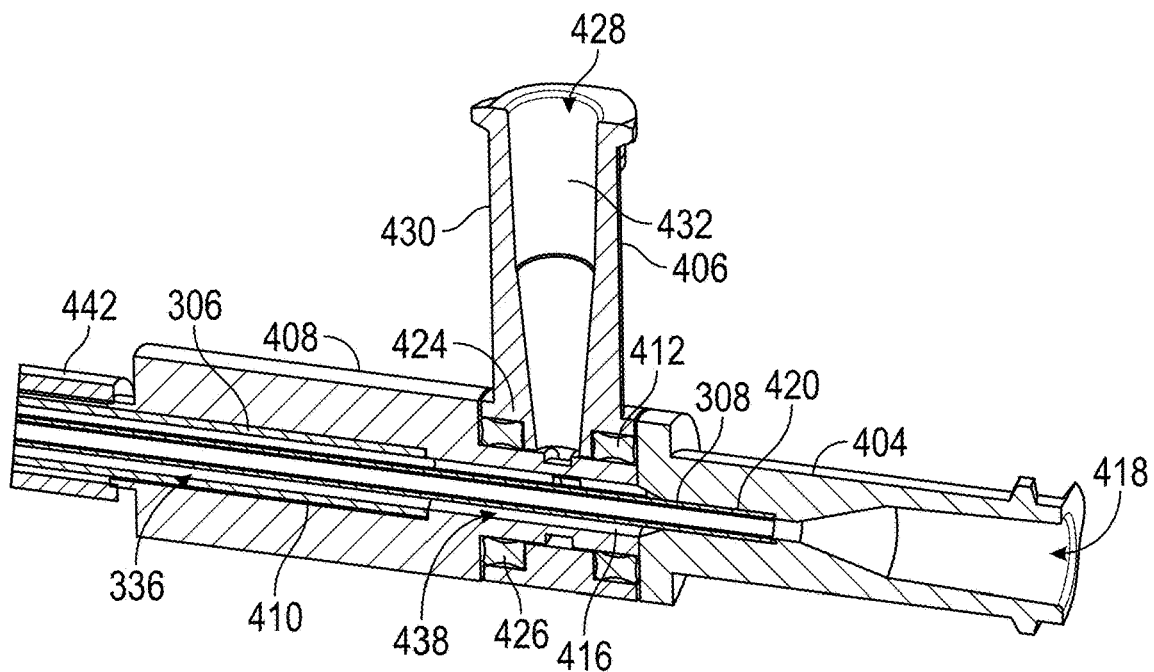
FIG. 26 is a cross-sectional view of the adaptor of FIG. 24, mounted on the proximal end portion of the delivery apparatus.
Figure 27:
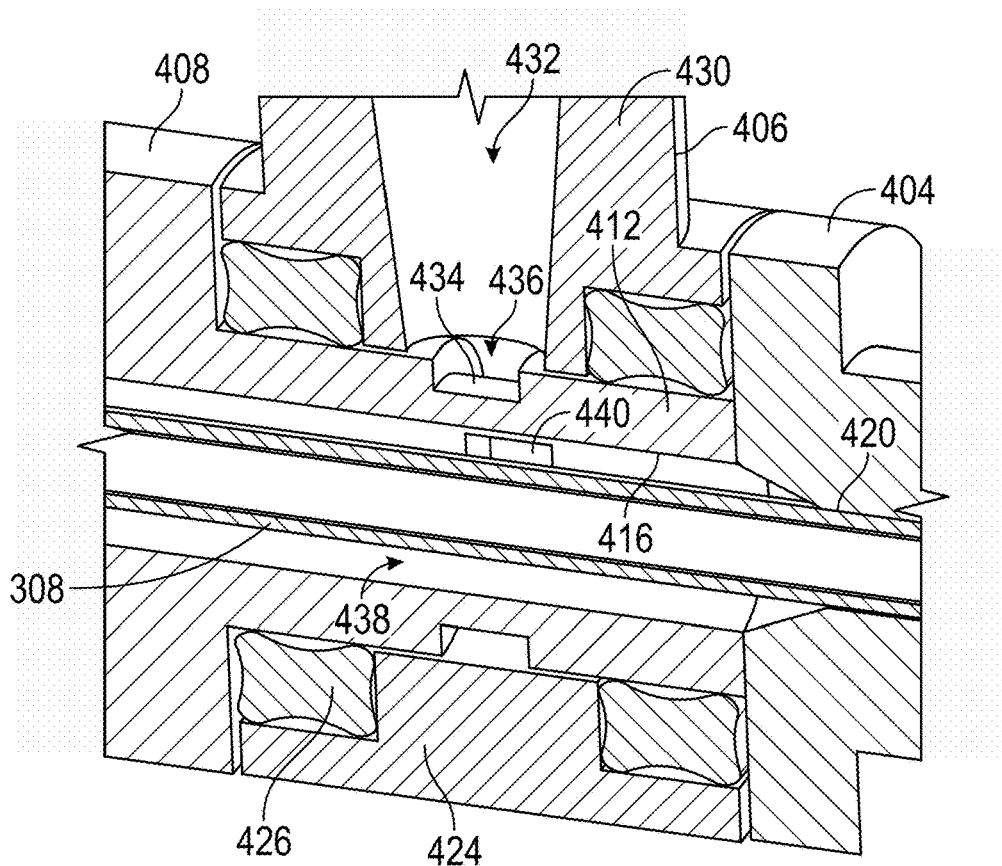
FIG. 27 is a detail, cross-sectional view of a portion of the adaptor of FIG. 26 including a rotating interface between the second port and the body of the adaptor.

The first port 404 can extend axially from the adaptor body 408 (FIGS. 24-26). In some embodiments, the first port 404 can be directly and/or rigidly coupled to a proximal portion 412 of the adaptor body 408 defining a second inner channel 416 of the adaptor body 408 (FIGS. 25-27). For example, in some embodiments, the first port 404 and the proximal portion 412 can be bonded together (e.g., via welding or an adhesive) at joint 444 (FIG. 25).

In some embodiments, the first port 404 can be configured as a guidewire port that is adapted to receive a guidewire. For example, in some embodiments, a guidewire can be inserted into an opening 418 in the first port 404 and extend through the inner shaft 308, the inner shaft 308 received within and extending through the second inner channel 416 and the first inner channel 410. For example, as shown in FIGS. 26 and 27, a proximal end of the inner shaft 308 can be arranged and fit within a distal channel 420 of the first port 404 (FIGS. 25-27). A guidewire can then be inserted into the opening 418 and extend through an inner lumen defined by the inner shaft 308.

The second port 406 can extend radially outward from the adaptor body 408, in a direction intersecting a central longitudinal axis 422 of the adaptor 402 and a central longitudinal axis (e.g., central longitudinal axis 320) of the delivery apparatus (FIG. 25). In some embodiments, the second port 406 can extend radially outward from the adaptor body 408 at an angle that is between 10 and 90 degrees from the central longitudinal axis 422. In some embodiments, the second port 406 can extend radially outward from the adaptor body 408 in a direction that is perpendicular to the central longitudinal axis 422.

The second port 406 is rotatably coupled to the adaptor body 408. For example, as shown in FIGS. 25-27, the second port 406 can be rotatably coupled to the proximal portion 412 of the adaptor body 408. In some embodiments, the second port 406 can include a base portion 424 arranged around the proximal portion 412 of the adaptor body 408.

A seal 426 can be arranged between the base portion 424 and the proximal portion 412 of the adaptor body 408 (FIGS. 25-27). In some embodiments, the seal 426 can be a circumferential or ring-like seal that extends around an outer surface of the proximal portion 412 of the adaptor body 408 (e.g., around the circumference). In some embodiments, the seal 426 can comprise one or more O-ring seals or a quad ring seal.

The second port 406 can further include an inner channel (forming an inner lumen) 432 extending from an opening 428 in the second port 406, through a shaft portion 430 of the second port 406, and through a portion of the base portion 424 connected with the shaft portion 430. The shaft portion 430 can extend radially outward from one side of the base portion 424.

The proximal portion 412 of the adaptor body 408 can include an annular groove 434 defining an annular channel 436 extending around at least a portion of a circumference of the proximal portion 412 of the adaptor body 408 (as best seen in FIGS. 25 and 27). In some embodiments, the annular channel 436 can fluidly couple the inner channel 432 to an annular space 438 defined between the outer surface of the inner shaft 308 and inner surface of the proximal portion 412 of the adaptor body 408 (FIGS. 26 and 27).

In some embodiments, one or more apertures 440 extending radially inward from the annular groove 434 can fluidly connect the annular space 438 with the inner channel 432 (FIGS. 25 and 27). The annular space 438 can be fluidly coupled to the annular space 336 defined between the outer surface of the inner shaft 308 and the inner surface of the intermediate shaft 306 (FIG. 26). In alternate embodiments, the annular groove 434 can extend through a thickness of the proximal portion 412 of the adaptor body 408 in order to fluidly couple the inner channel 432 with the annular space 438.

In this way, fluid (e.g., inflation fluid) can flow from the inner channel 432, to the annular space 438, to the annular space 336, and into the inflatable balloon (e.g., balloon 318 described above with reference to FIGS. 9-14), while allowing the second port 406 to rotate around the adaptor body 408 (e.g., around the central longitudinal axis 422). As a result, a user may be deterred from attempting to rotate the intermediate shaft 306 via rotating the adaptor 402 (e.g., since doing so may result in the second port 406 rotating around the adaptor body 408). Further, rotating the second port 406 can avoid torque from being applied to the adaptor body 408 and the first port 404, thereby increasing a durability and longevity of the adaptor 402 and preventing a bond between the adaptor 402 and the intermediate shaft 306 from being compromised. As a result, a likelihood of more effective and consistent deployment of the balloon (e.g., balloon 318) via injection of an inflation fluid via the second port 406 can be increased. Further still, having a rotatable second port 406 can allow a user to position the second port 406 in a variety of positions (for injecting the inflation fluid) without causing unwanted movement of the delivery apparatus.

As described above with reference to FIGS. 9-27, the delivery apparatus 300 and/or similarly configured delivery apparatuses can include one or more features that facilitate the rotational alignment of a radially compressed prosthetic valve, arranged on a distal end portion of the delivery apparatus, at the target implantation site.

As introduced above, it may be desirable to implant a prosthetic heart valve in a native valve with a delivery apparatus (such as delivery apparatus 300 of FIGS. 9-14) such that commissures of the prosthetic heart valve are aligned with commissures of the native valve. In some embodiments, in order to facilitate the desired rotational positioning of the prosthetic heart valve relative to the native valve, a radiopaque marker that is visible under medical imaging can be arranged on or embedded in a portion of the distal end portion (such as a polymeric body mounted on a distal end portion of a shaft) of the delivery apparatus which is disposed proximate to the valve mounting portion (e.g., valve mounting portion 324) of the delivery apparatus, and thus the radially compressed prosthetic valve. As described further below, in some embodiments, the radiopaque marker can be configured to indicate a location of a selected commissure of the prosthetic valve after radially expanding the prosthetic valve via inflating a balloon of the delivery apparatus (e.g., balloon 318 of FIGS. 9-11).

FIGS. 28-34B show embodiments of a radiopaque marker arranged on or embedded in a portion of a delivery apparatus, such as delivery apparatus 300 shown in FIGS. 9-14. Though delivery apparatus 300 is shown by way of example in FIGS. 28, 29, and 32A-32B, in alternate embodiments, the radiopaque marker can be arranged on or embedded within a portion of an alternate delivery apparatus configured to deliver a radially compressed prosthetic valve to a target implantation site. In some embodiments, the portion of the delivery apparatus that the radiopaque marker is arranged on or embedded within can be a polymeric body mounted on a shaft at the distal end portion of the delivery apparatus. For example, the polymeric body can be one or more of a proximal shoulder, a distal shoulder (e.g., distal shoulder 326 in FIGS. 9-11), or a nose cone (e.g., nose cone 322 in FIGS. 9-11) mounted to an inner shaft of the delivery apparatus and/or to another polymeric body mounted to the inner shaft.

FIG. 28 shows a radiopaque marker 500 positioned on and/or embedded within a polymeric body of distal end portion of a delivery apparatus (e.g., delivery apparatus 300 shown as an example in FIGS. 28 and 29). In some embodiments, as shown in FIG. 28, the distal shoulder 326 of the distal end portion 309 of the delivery apparatus 300 can include the marker 500 arranged on and/or embedded therein.

As shown in FIG. 28 and explained above with reference to FIGS. 9-11, the inflatable balloon 318 is arranged over (e.g., overlays) the distal shoulder 326 and the valve mounting portion 324. The nose cone 322 is arranged at a distal end of the delivery apparatus 300 and is arranged adjacent (and distal to) the distal shoulder 326. As explained above, the valve mounting portion 324 is configured to receive a radially compressed prosthetic valve thereon, around the balloon 318. The distal shoulder 326 can be configured such that when a prosthetic valve is mounted on the balloon 318 in a radially compressed state, at the valve mounting portion 324, the distal shoulder 326 resists movement of the prosthetic valve relative to the balloon 318 in an axial direction (which is arranged along and relative to the central longitudinal axis 320 of the delivery apparatus 300).

The nose cone 322 and/or the distal shoulder 326 may comprise one or more polymeric materials, and thus, may be referred to herein as polymeric bodies. In some embodiments, the distal end portion 309 of the delivery apparatus 300 can have additional polymeric bodies or components, such as a proximal shoulder arranged on an opposite side of the valve mounting portion 324 from the distal shoulder 326.

The marker 500 can be configured to be visible under medical imaging. For example, the marker 500 can comprise a radiopaque material that is configured to be visible under medical imaging, such as fluoroscopy and/or other types of X-ray imaging. In some embodiments, the marker 500 can comprise a radiopaque or other material that is configured to be visible under Mill, ultrasound, and/or echocardiogram. The polymeric body, such as the distal shoulder 326, that the marker 500 is arranged on and/or embedded within can be configured such that it is not radiopaque. As a result, the marker 500 can be more easily visible under imaging, as described further below with reference to FIG. 29.

Though the marker 500 is shown positioned on and/or embedded within the distal shoulder 326 in FIG. 28, in alternate embodiments, the marker 500 can be arranged on and/or embedded within another polymeric body or component of the distal end portion 309 of the delivery apparatus. For example, in some embodiments, the marker 500 can be positioned on and/or embedded within the nose cone 322 or a proximal shoulder of a delivery apparatus (e.g., proximal shoulder 120 shown in FIG. 3).

The marker 500 can have various shapes or patterns. For example, though the marker 500 is shown in FIGS. 28 and 29 as a dot, in alternate embodiments, the marker 500 can be configured as a different shape or symbol, such as a circle, rectangle, star, square, triangle, "X", or the like. Additional embodiments of the shape of the marker are described below with reference to FIGS. 30-34B.

As shown in FIG. 28, the marker 500 is arranged on and/or embedded within a portion of the distal shoulder 326. In some embodiments, the portion of the distal shoulder 326 in which the marker 500 is arranged on and/or embedded within may be a portion of the distal shoulder 326 that is disposed closer to (e.g., adjacent to) the valve mounting portion 324 than a remaining portion of the distal shoulder 326. Thus, when the radially compressed prosthetic valve is arranged on the valve mounting portion 324, the marker 500 may be arranged proximate and adjacent to the prosthetic valve.

In some embodiments, as shown in FIG. 28, the distal shoulder 326 can comprise the base portion 325 and the flared portion 331. The flared portion 331 can extend radially outward from the base portion 325, toward the valve mounting portion 324. The marker 500 can be arranged on and/or be embedded within the flared portion 331, thereby orienting the marker 500 radially outward from an outer surface of the inner shaft 308. In alternate embodiments, the marker 500 can be arranged on and/or embedded within the base portion 325.

In some embodiments, as shown in FIG. 28, the flared portion 331 can comprise the plurality of wings 330 (which can also be referred to as extension portions) that extend radially outward from the base portion 325, at an angle relative to the central longitudinal axis 320. The wings 330 can be spaced apart from one another around a circumference of the flared portion 331. As shown in FIG. 28, in some embodiments, the marker 500 can be positioned on or embedded in one of the wings 330. In some embodiments, the marker 500 can be centered on one of the wings 330, such that it is centered along the central longitudinal axis 320.

In some embodiments, the marker 500 can be a single (e.g., the only) radiopaque marker arranged on the distal shoulder 326. In some embodiments, the marker 500 can be the only (or single) radiopaque marker arranged on the distal end portion 309 of the delivery apparatus 300.

In some embodiments, the distal end portion 309 of the delivery apparatus 300 can include additional radiopaque markers (in addition to marker 500).

Arranging the marker 500 on or in the distal shoulder 326, or another polymeric body of the distal end portion of the delivery apparatus, can allow the marker 500 to be more visible under imaging, such as fluoroscopy, since a remainder of the distal shoulder 326 can be less or non-radiopaque, and thus, can be less, or not, visible in the fluoroscopic image. For example, as shown in the exemplary fluoroscopic image 550 of FIG. 29, the marker 500 is visible under fluoroscopy and stands out since the distal shoulder is not radiopaque (other than the marker 500). In contrast, the prosthetic valve frame 552 is radiopaque and visible under imaging. Thus, a radiopaque marker positioned on and/or in the prosthetic valve itself may be more difficult to see under imaging since the valve frame appears relatively dark in the image 550.

As also shown in FIG. 29, a guidewire 554 extending through a center of the distal end portion 309 of the delivery apparatus (e.g., through the inner lumen of the inner shaft 308) is visible under fluoroscopy and the marker 500 is positioned radially outward of the guidewire 554 (e.g., due to the marker 500 being positioned on the flared portion 331 of the distal shoulder 326). This further increases the visibility of the marker 500 under imaging, during an implantation procedure. Additionally, as described further below, when the marker 500 is arranged in a direct back or direct front of the imaging view, the marker 500 can appear to overlap the guidewire.

Additionally, arranging the marker 500 on or in the distal shoulder 326 (or another polymeric body of the distal end portion of the delivery apparatus) can allow for more accurate alignment with the commissures of the native valve. For example, as described further below, it may be desirable to rotationally align the marker 500 with a target commissure of the native valve, prior to crossing the leaflets of the native valve. Thus, when rotating the distal end portion 309 of the delivery apparatus, including the distal shoulder 326 and the prosthetic valve, to align the marker 500 with the target commissure of the native valve, it may be advantageous for the marker 500 to be arranged as far distal on the delivery apparatus as possible so that it is positioned as close as possible to the target commissure of the native valve. As shown in FIG. 28, the distal shoulder 326 (and the nose cone 322) is one of the most distal components of the delivery apparatus 300 and is arranged further distal than the radially compressed prosthetic valve (e.g., further distal than the valve mounting portion 324, as seen in FIG. 28).

Arranging the marker 500 on or in the distal shoulder 326 (or another polymeric body of the delivery apparatus that is positioned offset from the prosthetic valve, in the axial direction) also allows the marker 500 to be offset, in a circumferential direction, from a selected commissure of the prosthetic valve. For example, as described further below, since the prosthetic valve rotates upon inflation of the inflatable balloon 318, the marker 500 can be offset in the circumferential direction from the selected commissure of the prosthetic valve to compensate for this rotation. As a result, after deployment of the prosthetic valve, the selected commissure of the prosthetic valve may be aligned with the target commissure of the native valve. If the prosthetic valve itself had an offset marker, this may be confusing after valve deployment since the maker would be visible but not actually mark the selected commissure of the prosthetic valve.

Further still, providing the marker 500 on or in the distal shoulder 326 (or another portion of the delivery apparatus, proximate to the valve mounting portion 324) may avoid having to add an additional component to the relatively permanent implant (e.g., prosthetic valve). Additionally, changes to the marker 500 (e.g., design changes) on the delivery apparatus may be more easily implemented on the delivery apparatus than if the marker 500 were on the valve (e.g., due to valve testing as a result of any design modifications to the prosthetic valve).

During an implantation procedure, a selected imaging view (e.g., fluoroscopic imaging view) can be used to visualize the distal end portion of the delivery apparatus, including the marker 500 and the radially compressed prosthetic valve (e.g., frame 552) relative to the surrounding native anatomy. Based on an existing knowledge of a location of a selected commissure of the native valve (in which the prosthetic valve is to be implanted) within the selected imaging view, a user can rotationally align the distal end portion of the delivery apparatus at the target implantation site, such that the marker 500 is aligned with the known location of the selected commissure, in the selected imaging view, or such that the marker 500 is arranged in a certain position within the selected imaging view (e.g., direct back) and deploying the prosthetic valve in such an orientation will result in commissure alignment between the prosthetic valve and the native valve.

Figure 61:
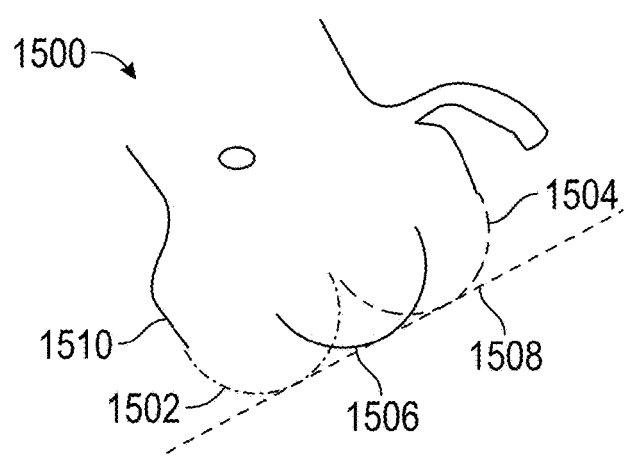
FIG. 61 is a schematic of an embodiment of a three-cusp imaging view of a native valve which can be used for visualizing a delivery apparatus in a patient's heart during an implantation procedure and rotationally aligning a prosthetic valve mounted on the delivery apparatus.
Figure 63:
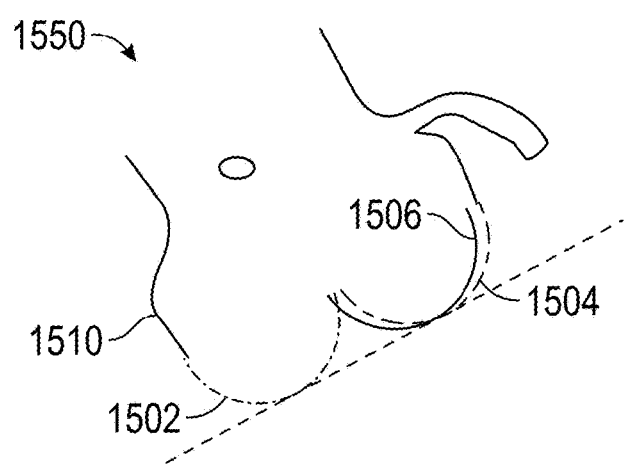
FIG. 63 is a schematic of an embodiment of a right/left cusp overlap imaging view of a native valve which can be used for visualizing a delivery apparatus in a patient's heart during an implantation procedure and rotationally aligning a prosthetic valve mounted on the delivery apparatus.
Figure 64:
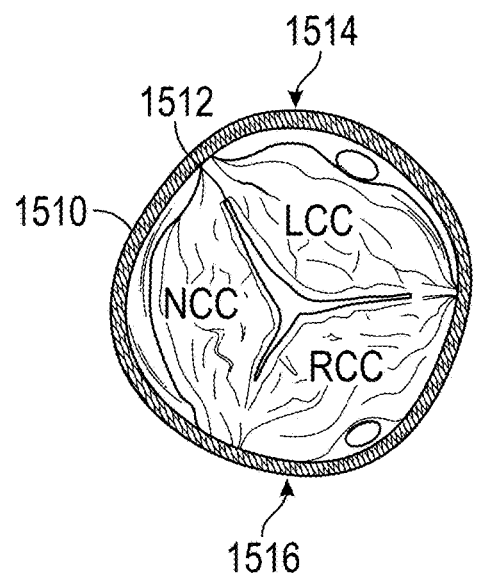
FIG. 64 is a cross-sectional view of a native valve, illustrating a location of commissures of the native valve within the imaging view of FIG. 63.

For example, in some imaging views, the selected commissure of the native valve can be arranged in a direct back of the imaging view. Thus, by aligning the marker 500 on the delivery apparatus with the direct back of the imaging view, the prosthetic valve can be implanted within the native valve with commissure alignment between the native valve and prosthetic valve. Exemplary fluoroscopic imaging views obtained during a prosthetic valve implantation procedure and used to guide the delivery apparatus proximate to the native valve are shown in FIGS. 58, 61, and 63, as described further below.

To enable the desired positioning of the marker within the selected imaging view, in some embodiments, the marker can be configured as an asymmetric marker which is then aligned with a guidewire extending through the delivery apparatus, along a central longitudinal axis of the delivery apparatus. For example, the asymmetric marker can be reflection asymmetric along an axis that is parallel to the central longitudinal axis of the delivery apparatus. In this way, under medical imaging, such as fluoroscopy, a position of the marker within the imaging view, relative to the guidewire (e.g., a front vs. a back of the imaging view), can be more easily discerned.

FIGS. 30-34B show example embodiments of such an asymmetric marker that allows a user to differentiate between two different positions of the marker within the imaging view. For example, in some embodiments, the asymmetric marker is configured such that a user viewing the imaging view can differentiate between the marker being positioned in a front or a back of the fluoroscopic imaging view. The markers shown in FIGS. 30-34B can be positioned on the delivery apparatus, as described above with reference to FIGS. 28 and 29. For example, in some embodiments, the markers shown in FIGS. 30-34B can replace marker 500 (FIGS. 28 and 29) on the distal shoulder 326 or an alternate polymeric body of the distal end portion 309 of the delivery apparatus.

In some embodiments, the asymmetric marker can be a letter of the alphabet (e.g., as shown in FIGS. 30-34B), a number, a symbol, a shape, or the like, that is reflection asymmetric along an axis that is parallel to the central longitudinal axis of the delivery apparatus. For example, the asymmetric marker can have a first orientation where it can be read "correctly" or forward (e.g., not backward) and a second orientation that is approximately 180 degrees rotated around the axis from the first orientation, which results in the marker appearing backward to a reader (e.g., user).

Figure 30:
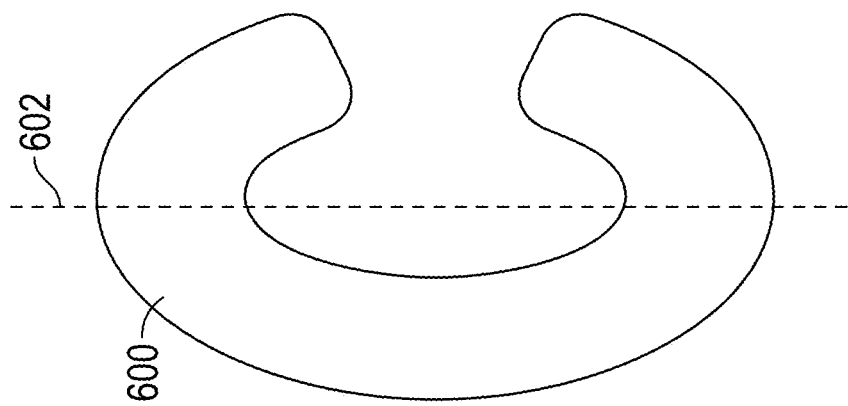
FIG. 30 illustrates an embodiment of an asymmetric radiopaque marker that allows a user to differentiate between two different positions of the marker within an imaging view.

FIG. 30 shows a first exemplary embodiment of an asymmetric marker 600 that is shaped as a letter "C" and can be configured similarly to marker 500 of FIG. 28 (e.g., radiopaque). The C-shaped asymmetric marker 600 is reflection asymmetric across a longitudinal axis 602 which, when positioned on a delivery apparatus (e.g., delivery apparatus 300), as described above with reference to FIG. 28, is parallel to the central longitudinal axis of the delivery apparatus. For example, in FIG. 30, the C-shaped asymmetric marker 600 is in a first orientation which is its forward-readable orientation (e.g., appears in its correct, not backward, orientation to a reader). If the C-shaped asymmetric marker 600 were rotated by approximately 180 degrees around its longitudinal axis 602, the C-shaped asymmetric marker 600 would be in a second orientation and the "C" would appear backward (e.g., flipped). These two orientations of the C-shaped asymmetric marker 600 can be seen in a medical imaging view (e.g., using fluoroscopy), as explained further herein. The two orientations of the C-shaped asymmetric marker (and other asymmetric markers described herein) can be mirror images of one another.

Figure 31B:
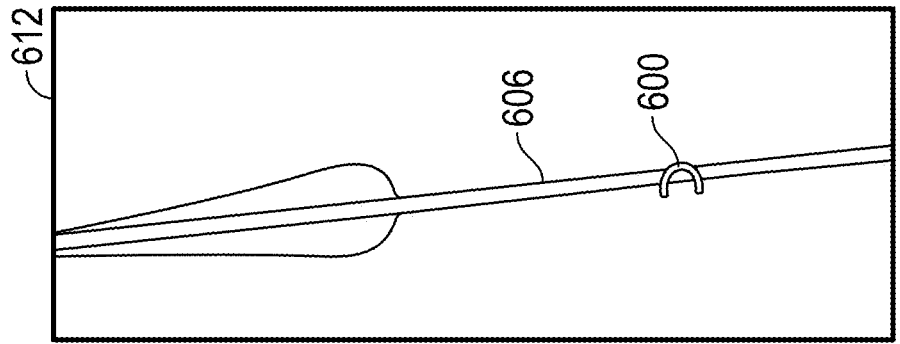
FIG. 31B is an exemplary fluoroscopic image illustrating a guidewire extending through a distal end portion of a delivery apparatus and the asymmetric marker of FIG. 30 arranged on or embedded within a portion of the distal end portion of the delivery apparatus and in a second orientation relative to the guidewire.
Figure 31A:
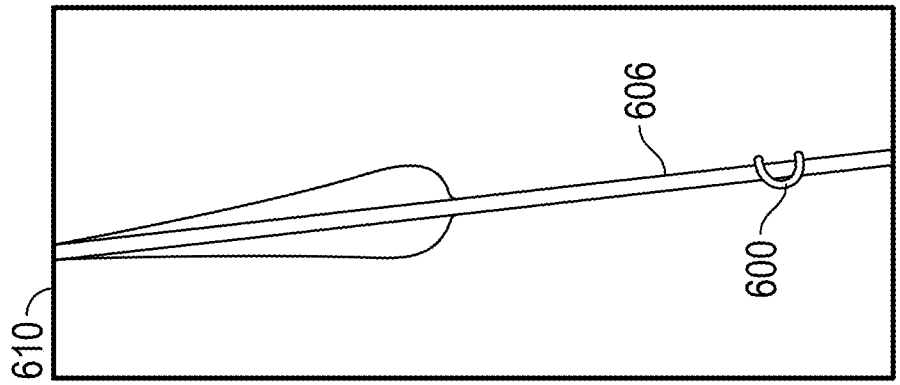
FIG. 31A is an exemplary fluoroscopic image illustrating a guidewire extending through a distal end portion of a delivery apparatus and the asymmetric marker of FIG. 30 arranged on or embedded within a portion of the distal end portion of the delivery apparatus and in a first orientation relative to the guidewire.

FIGS. 31A and 31B show exemplary fluoroscopic images 610 and 612, respectively, of a guidewire 606 extending through a distal end portion of a delivery apparatus (e.g., distal end portion 309 of delivery apparatus 300) and the C-shaped asymmetric marker 600 arranged on or embedded within a portion of the distal end portion of the delivery apparatus (e.g., the distal shoulder 326, as shown in FIG. 28). As shown in the first fluoroscopic image 610 of FIG. 31A, the C-shaped asymmetric marker 600 is aligned with (e.g., overlapping) the guidewire 606 and the "C" is readable, in its first (forward) orientation. In some embodiments, this position of the marker 600 shown in FIG. 31A may indicate the marker 600 is arranged behind the guidewire 606 within the first fluoroscopic imaging view 610, and thus, in the direct back of the imaging view. In alternate embodiments, the position of the marker shown in FIG. 31A may indicate the marker is arranged in front of the guidewire 606, and thus, in the direct front of the imaging view.

In contrast, when the delivery apparatus is rotated by approximately 180 degrees from its orientation shown in FIG. 31A, the C-shaped asymmetric marker 600 is correspondingly rotated and appears in its second (backward) orientation wherein the "C" is backward, as shown in FIG. 31B. In some embodiments, the position of the marker 600 shown in FIG. 31B may indicate the marker 600 is arranged in front of the guidewire 606 within the imaging view, and thus, in the direct front of the imaging view. In alternate embodiments, the position of the marker 600 shown in FIG. 31B may indicate the marker is arranged behind the guidewire 606, and thus, in the direct back of the imaging view.

In this way, by viewing an orientation of a reflection asymmetric marker, such as marker 600, relative to the guidewire 606, within a selected imaging view, the position of the marker 600 at an implantation site (e.g., proximate to the target native valve) can be more easily and quickly determined. Further details on rotationally aligning the marker relative to a guidewire such that the prosthetic valve is implanted with commissures in aligned with commissures of the native valve is explained below with reference to FIGS. 57-60.

FIGS. 32A and 32B show a side view and perspective view, respectively, of an exemplary positioning of the asymmetric marker 600 (shaped as the letter "C") on and/or embedded within the distal shoulder 326 of the distal end portion 309 of the delivery apparatus 300. As shown in FIGS. 32A and 32B, the marker 600 can be positioned on the distal shoulder 326 (e.g., on a wing 330, in some embodiments) such that when the delivery apparatus is arranged within a patient's vasculature, and a longitudinal imaging view similar to the view of image 550 in FIG. 29 is used to visualize the delivery apparatus, the C-shape of the marker 600 will be read in the backward orientation when the marker 600 is in the direct front of the imaging view and the marker 600 will be read in the forward orientation when the marker 600 is positioned in the direct back of the imaging view.

In alternate embodiments, the marker 600 can be oriented differently on the distal shoulder that what is shown in FIGS. 32A and 32B, such that the marker 600 is rotated by 180 degrees and is instead read in the forward orientation when the marker 600 is in the direct front of the imaging view.

Figure 34B:
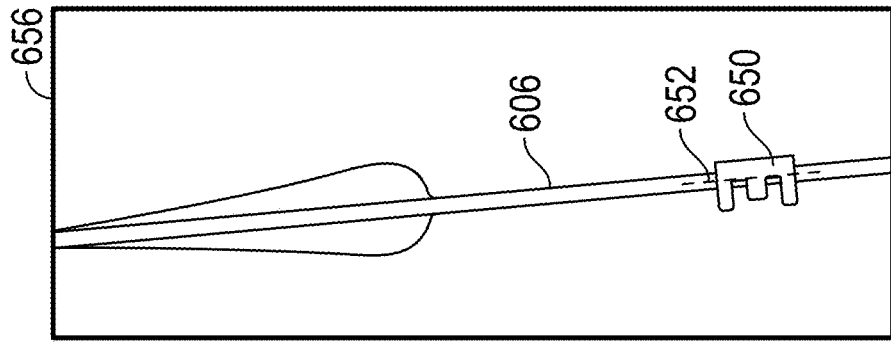
FIG. 34B is an exemplary fluoroscopic image illustrating a guidewire extending through a distal end portion of a delivery apparatus and the asymmetric marker of FIG. 33 arranged on or embedded within a portion of the distal end portion of the delivery apparatus and in a second orientation relative to the guidewire.
Figure 34A:
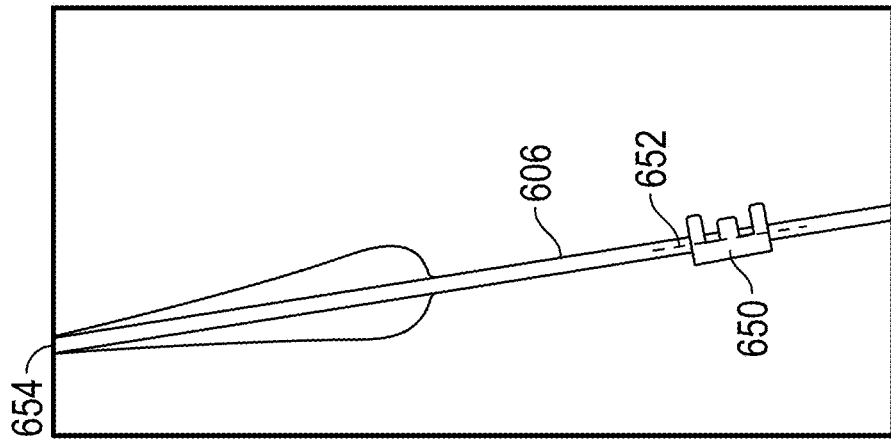
FIG. 34A is an exemplary fluoroscopic image illustrating a guidewire extending through a distal end portion of a delivery apparatus and the asymmetric marker of FIG. 33 arranged on or embedded within a portion of the distal end portion of the delivery apparatus and in a first orientation relative to the guidewire.

FIGS. 33-34B show a second exemplary embodiment of an asymmetric marker 650 that is shaped as a letter "E" and can be configured similarly to marker 500 of FIG. 28 (e.g., radiopaque). FIG. 33 shows the E-shaped asymmetric marker 650 alone while FIGS. 34A and 34B show fluoroscopic images of the E-shaped asymmetric marker 650, on a delivery apparatus, in two different orientations relative to the guidewire 606.

The E-shaped asymmetric marker 650 may be configured and function similarly to the marker 600, as described above with reference to FIGS. 30-32B, other than its overall shape (e.g., E instead of C shape). For example, the E-shaped asymmetric marker 650 can be reflection asymmetric across a longitudinal axis 652 which, when positioned on a delivery apparatus, is parallel to the central longitudinal axis of the delivery apparatus.

Similarly to marker 600, the E-shaped asymmetric marker 650 has a first orientation which is its forward (or "correct") readable orientation (as shown in FIG. 33 and the first image 654 of FIG. 34A). The E-shaped asymmetric marker 650 also has a second orientation, which is rotated by approximately 180 degrees around its longitudinal axis 652 from the first orientation. In the second orientation, the "E" appears backward (as shown in the second image 656 of FIG. 34B). These two orientations of the E-shaped asymmetric marker 650 can be seen with medical imaging (e.g., fluoroscopy), as shown in FIGS. 34A and 34B and explained further herein.

In some embodiments, the E-shaped asymmetric marker 650 can replace the marker 600 on the delivery apparatus shown in FIGS. 32A and 32B.

In yet other embodiments, an asymmetric marker can be shaped as another letter (other than "C" or "E", such as "P" or "F"), a number, a symbol, a shape, or the like, which is reflection asymmetric, as described above, and has two differentiable orientations when rotated approximately 180 degrees around its reflection asymmetric axis.

In some embodiments, the asymmetric marker (e.g., marker 600 or marker 650) arranged on or embedded within the distal end portion of the delivery apparatus (such as the distal shoulder 326) can comprise a radiopaque material. In some embodiments, the radiopaque material comprises metal.

In some embodiments, the asymmetric markers described herein can comprise tantalum. In some embodiments, the asymmetric markers described herein can comprise another type of radiopaque material or combination of materials, such as one or more of iodine, barium, barium sulfate, tantalum, bismuth, or gold.

In some embodiments, the asymmetric markers described herein can comprise a platinum-iridium alloy. In some embodiments, an alloy proportion of the platinum-iridium alloy is 90:10. In some embodiments, the alloy proportion of the platinum-iridium alloy is in a range of 75:25 to 95:5. In some embodiments, the alloy proportion of the platinum-iridium alloy is in a range of 85:15 to 95:5.

In some embodiments, instead of or in addition to being positioned on the distal end portion of the delivery apparatus, a radiopaque marker can be positioned on a prosthetic valve, such as on or near a commissure of the prosthetic valve, as shown in FIGS. 35A-35P and 97-101E. As a result, a location of a selected commissure of the radially compressed prosthetic valve can be identified by medical imaging during a valve implantation procedure and rotationally aligned with the native anatomy at the target implantation site.

In embodiments where radiopaque markers are disposed both on the distal end portion of the delivery apparatus (as described above) and on the prosthetic valve (at or near the commissure, as described below), a first radiopaque marker on the delivery apparatus can be visualized during the valve implantation procedure to rotationally align the first marker with the native anatomy and deploy the prosthetic valve such that its commissure are aligned with commissures of the native valve. Then a second radiopaque marker on the prosthetic valve can be visualized after implantation (e.g., during future interventions to locate the prosthetic valve commissures and/or to confirm the location of the prosthetic valve commissures relative to the native valve commissures). In some embodiments, the second radiopaque marker at the commissure of the prosthetic valve can be more easily visualized after radial expansion of the prosthetic valve (after implantation).

Figure 35A:
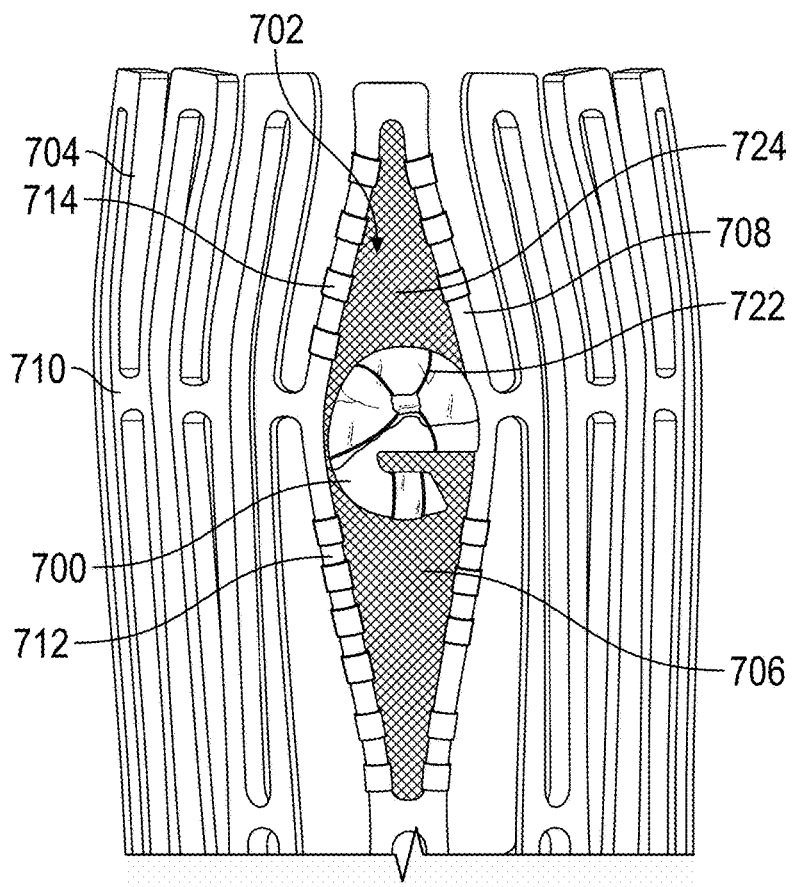
FIG. 35A illustrates an exemplary embodiment of a radiopaque marker attached to a commissure of a prosthetic valve, the prosthetic valve in a radially compressed configuration.
Figure 35B:
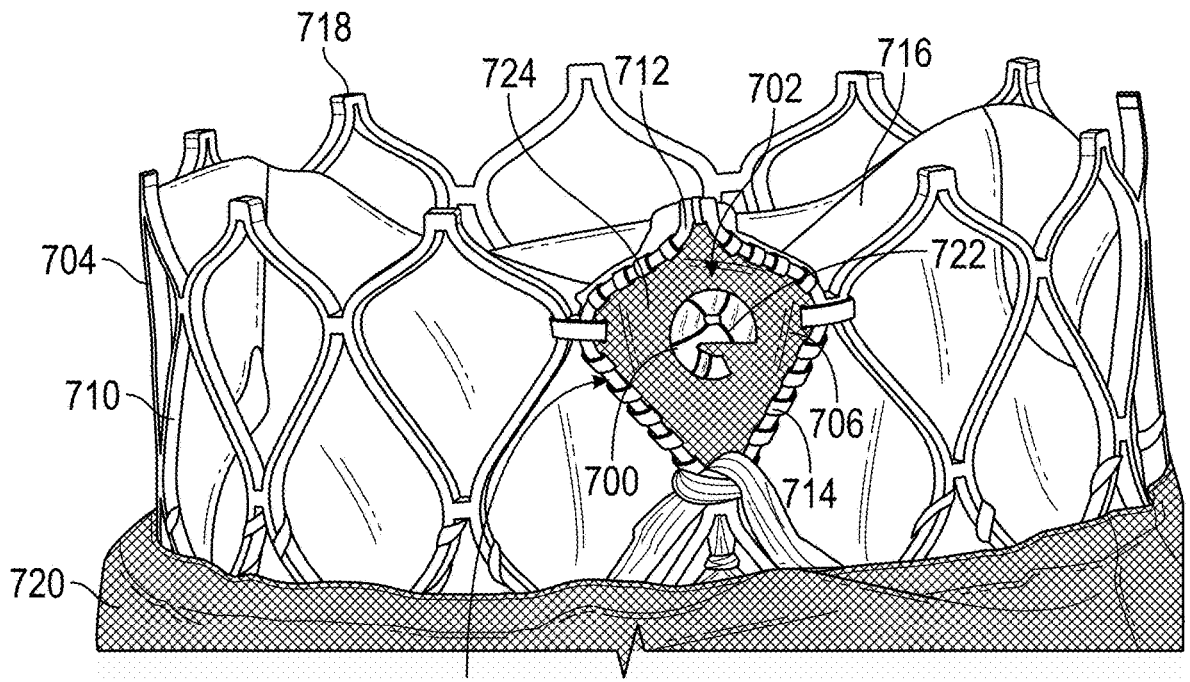
FIG. 35B illustrates the prosthetic valve of FIG. 35A in a radially expanded configuration.

An exemplary embodiment of a radiopaque marker 700 attached to a commissure 702 of a prosthetic valve 704 (which may be similar to any of the prosthetic valves described herein, such as prosthetic valve 10 of FIG. 1 or prosthetic valve 50 of FIGS. 2A and 2B), is shown in FIGS. 35A and 35B. FIG. 35A shows the prosthetic valve 704 in a radially compressed configuration (e.g., state), such as when it is arranged around and crimped onto a delivery apparatus, and FIG. 35B shows the prosthetic valve 704 in a radially expanded configuration (e.g., state).

As introduced above with reference to FIGS. 2A and 2B and as shown in FIGS. 35A and 35B, in some embodiments, commissures 702 of the prosthetic valve 704 can comprise an attachment member 706 arranged across a cell (e.g., commissure cell) 708 of the frame 710 of the prosthetic valve 704. In some embodiments, the attachment member can comprise a fabric, flexible polymer, or the like arranged across the cell 708. As explained herein, the cell 708 can be formed by struts 712 of the frame 710. The attachment member 706 can be arranged across the cell 708 and secured to the struts 712 of the frame 710 forming the cell 708 via fasteners 714 (e.g., sutures). Additionally, adjacent portions of two leaflets 716 of the prosthetic valve 704 can be connected to the attachment member 706 to form the commissure 702.

In some embodiments, the commissure tabs of two adjacent leaflets 716 are coupled to the attachment member 706, on an inner surface (shown in FIG. 35E, as described below) of the attachment member 706, and the marker 700 is disposed on an outer surface 724 of the attachment member 706. The inner surface can be arranged opposite the outer surface 724, facing an interior of the prosthetic valve 704.

In some embodiments, as shown in FIGS. 35A and 35B, the marker 700 can be arranged on a central region of the commissure cell 708. For example, in some embodiments, the marker 700 can be sewn to a central region of the attachment member 706 via one or more fasteners (e.g., sutures) 722.

In some embodiments, the marker 700 can be shaped and positioned such that it fits within the cell 708 when the frame 710 is in the radially compressed configuration, as shown in FIG. 35A.

In some embodiments, the commissure cell 708 can be arranged at an outflow end 718 of the prosthetic valve 704.

In some embodiments, the marker 700 comprises tantalum, or another radiopaque material described herein or known in the art, which is formed or laser cut into a shape that is reflection asymmetric across the axis, similar to as described above with reference to FIGS. 28-34B.

In some embodiments, the prosthetic valve 704 includes a skirt 720 (FIG. 35B) arranged around the frame 710 of the prosthetic valve 704, at an inflow end of the prosthetic valve 704 (e.g., an end arranged opposite the outflow end 718). As shown in FIGS. 35A and 35B, when the commissure cell 708 is arranged at the outflow end 718 of the prosthetic valve 704, the commissure cell 708 including the marker 700 can be spaced away, in an axial direction, from the skirt 720.

FIGS. 35C-35H show another exemplary embodiment of attachment of a radiopaque marker 750 to a commissure within a cell 708 of a prosthetic valve. The prosthetic valve shown in FIGS. 35C-35H can be the same prosthetic valve 704 as shown in FIGS. 35A and 35B, and thus FIGS. 35C-35H are labeled accordingly. However, in FIGS. 35C-35H, there are two attachment members arranged across the cell 708 and attached to the struts 712 forming the cell 708. The commissure tabs 754 of the leaflets 716 and the marker 750 can be sutured to different attachment members of the two attachment members.

For example, the attachment member 706 to which the commissure tabs 754 of the leaflets 716 are attached can be a first attachment member 706 (FIGS. 35C, 35D, and 35H) and the marker 750 can be attached to a second attachment member 752 (FIGS. 35C-35G).

The marker 750 can be similar to the marker 700 and the other radiopaque markers described herein. For example, the marker 750 can be configured (e.g., shaped and sized) such that it fits within the cell 708 when the frame 710 is in the radially compressed configuration (e.g., as shown in FIG. 35A).

Figure 35C:
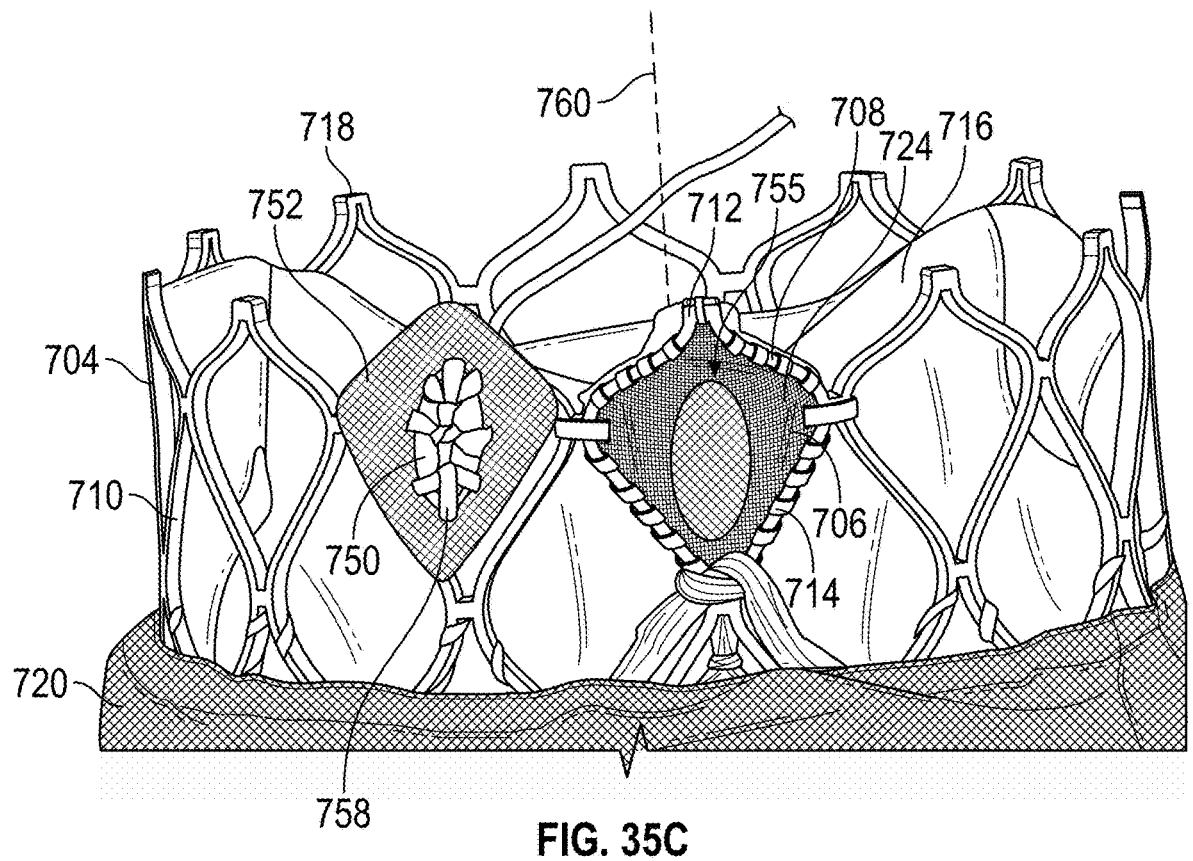
FIG. 35C illustrates an exemplary prosthetic heart valve with a first attachment member arranged across a cell of the prosthetic heart valve and secured to struts forming the cell, and a radiopaque marker secured to a second attachment member that is configured to be attached to the struts forming the cell, where commissure tabs of adjacent leaflets of the prosthetic heart valve are secured to the first attachment member to form a commissure
Figure 35D:
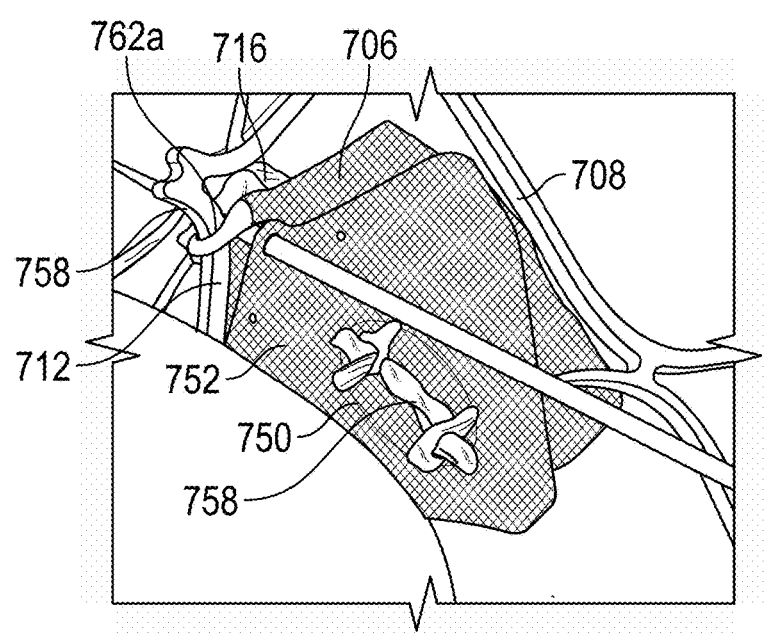
FIGS. 35D-35F illustrate the first attachment member and the second attachment member being attached to the struts forming the cell at the same time with the same sutures.
Figure 35E:
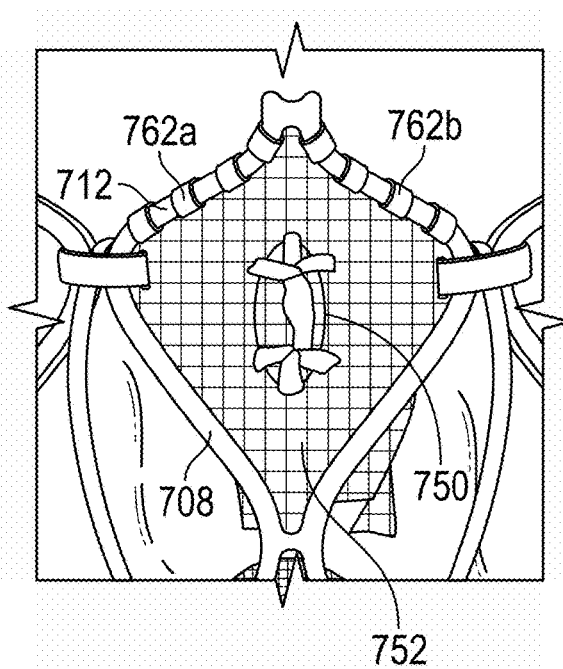
Figure 35F:
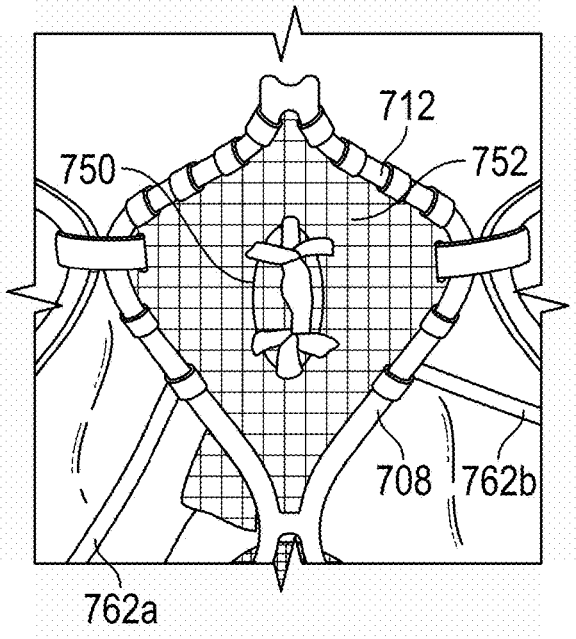
Figure 35G:
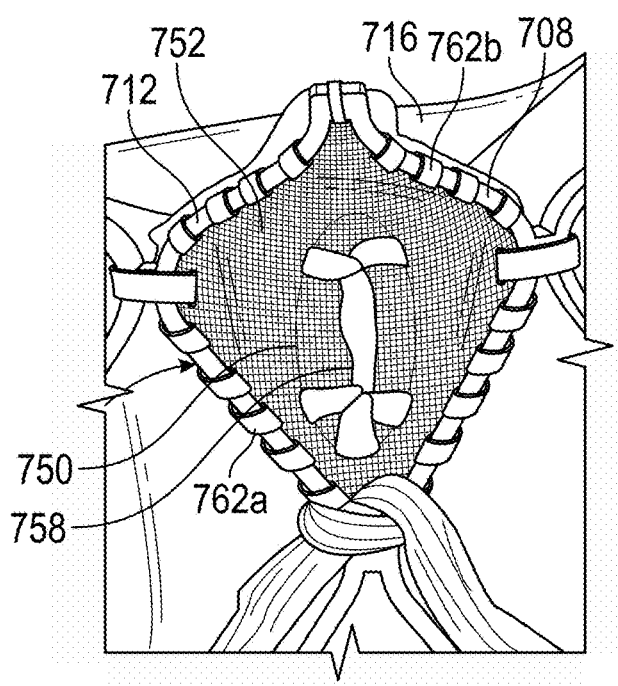
FIG. 35G illustrates the marker of FIG. 35C, attached to the second attachment member that is attached to the struts forming the cell of the prosthetic valve, in front of the first attachment member of the commissure.
Figure 35H:
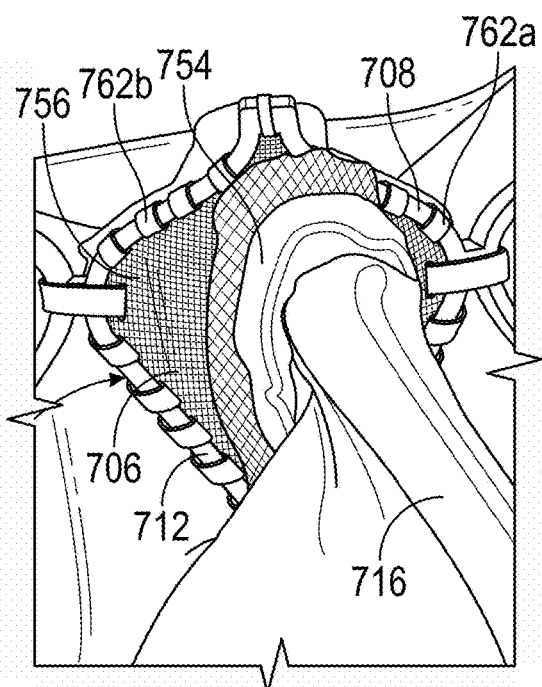
FIG. 35H illustrates an inner surface of the commissure and the first attachment member attached to the cell of the prosthetic valve.
Figure 35I:
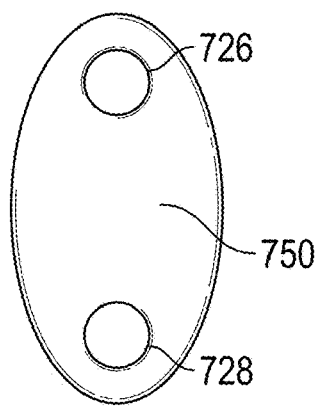
FIG. 35I illustrates an exemplary radiopaque marker configured to be attached to a commissure within a cell of a prosthetic valve.

An exemplary embodiment of the marker 750 is shown in FIG. 35I. The marker 750 can be oval-shaped with a first (upper) aperture 726 and a second (lower) aperture 728 configured to receive fasteners (e.g., sutures) for securing the marker 750 to an attachment member, as described further below. In some embodiments, the marker can include more or less than two apertures (e.g., one, three, four, or the like) for receiving fasteners. In some embodiments, the marker 750 can have a different shape configured to fit within the cell 708 when the frame 710 is radially compressed, such as one of the other marker shapes and embodiments described herein (e.g., with reference to FIGS. 35A, 35B, and 35J-35P).

In some embodiments, the marker 750 can be shaped as a letter of the alphabet (e.g., as shown in FIGS. 35A and 35B).

In some embodiments, the marker 750 can be reflection asymmetric across an axis that is parallel to a central longitudinal axis 760 of the frame 710 (e.g., as shown in FIGS. 35A and 35B).

As shown in FIG. 35C, the first attachment member 706 can be secured to the struts 712 forming the cell 708 via fasteners (e.g., sutures) 714. Commissure tabs 754 of two adjacent leaflets 716 can be coupled to the first attachment member 706, at an inner surface 756 of the first attachment member 706, as shown in FIG. 35H (commissure tabs 754 are identified by region 755 in FIG. 35C). For example, commissure tabs 754 can be sutured directly to the inner surface 756 of the first attachment member 706 or via one or more intervening layers of fabric between commissure tabs 754 and the first attachment member 706.

As also shown in FIG. 35C, the marker 750 is secured to the second attachment member 752 via one or more fasteners 758 (e.g., sutures) that can extend through the first aperture 726 and second aperture 728 in the marker 750 (FIG. 35I). In some embodiments, the marker 750 can be sewn, with the fasteners 758, to a central region of the second attachment member 752.

In other embodiments, the marker 750 can have another number of apertures or a different shape configured to receive the fasteners 758 for securing the marker 750 to the second attachment member 752. For example, in some embodiments, the marker 750 can be ring-shaped (e.g., shaped as the letter, "O").

FIG. 35C shows the marker 750 attached to the second attachment member 752, but before the second attachment member 752 is assembled to the frame 710. FIG. 35G shows the marker 750 and the second attachment member 752 after the second attachment member 752 is positioned at the commissure cell 708, such that the marker is disposed between the first attachment member 706 and the second attachment member 752, and sutured to the struts of the frame with one or more sutures 762. In this way, opposite sides of the second attachment member 752 are shown in FIGS. 35C and 35G.

In some embodiments, as shown in FIG. 35G, the second attachment member 752 can be arranged, relative to the frame 710, such that an exposed metal material of the marker 750 faces the frame 710 and the outer surface 724 of the first attachment member 706.

Thus, when the second attachment member 752 is arranged across the cell 708 and attached to the struts 712 forming the cell 708, as shown in FIG. 35G, the marker 750 can be sandwiched (e.g., disposed) between the second attachment member 752 and the first attachment member 706.

In some embodiments, the second attachment member 752 can comprise a fabric material, similar to or the same as the first attachment member 706.

In some embodiments, the second attachment member 752 can be secured to the struts 712 via additional fasteners (e.g., sutures).

In other embodiments, as shown in FIGS. 35D-35F, the second attachment member 752 and the first attachment member 706 can be secured to the struts 712 at the same time and with the same fasteners (e.g., sutures 762). For example, in some embodiments, after securing the commissure tabs 754 of two adjacent leaflets 716 to the first attachment member, a top portion of the first attachment member 706 can be initially secured to an upper strut 712 of the cell 708 with a first suture 762a (FIG. 35D). The second attachment member 752, with the marker 750 secured thereto, can then be aligned with the first attachment member 706 (FIGS. 35D and 35E). The first suture 762a can then be passed through both the first attachment member 706 and the second attachment member 752 and around the struts 712 on a first side of the cell 708 (FIGS. 35D-35G), thereby forming a single load bearing stitch line from the top to the bottom of the cell 708. Similarly, a second suture 762b can be passed through both the first attachment member 706 and the second attachment member 752 and around the struts 712 on a second side of the cell 708 (FIGS. 35E-35G), thereby forming another single load bearing stitch line from the top to the bottom of the cell 708.

In this way, the second attachment member 752 is arranged outside of the first attachment member 706 relative to an outer surface of the frame 710 and the central longitudinal axis 760 of the frame 710 (FIG. 35C). As a result, metal-on-frame contact between the marker 750 and the frame 710 and/or any abrasive contact between the marker 750 and an outside (e.g., outer surface) of the frame 710 can be avoided. Further, by securing the marker 750 to the outer, second attachment member 752, contact between the marker 750 and the leaflets (which are secured to the inner, first attachment member 706) is also avoided.

In some embodiments, the marker 750 can be secured to the struts 712 with a sewing pattern that avoids the tissue of the leaflets 716. In some embodiments, the additional material provided by the second attachment member 752 can also protect knot tails and sutures used to secure commissure tabs 754 to the first attachment member 706, thereby making the commissure more robust and durable.

As described above, due to its positioning on the frame 710 and its radiopaque nature, the marker 750 can provide identification (e.g., visibility) of the commissure during an implantation procedure, thereby enabling a desired commissure alignment, as described herein. Further, such a radiopaque marker 750 can also provide identification of a location of the commissure of the prosthetic valve, following implantation and during any future interventional procedures.

Figure 35J:
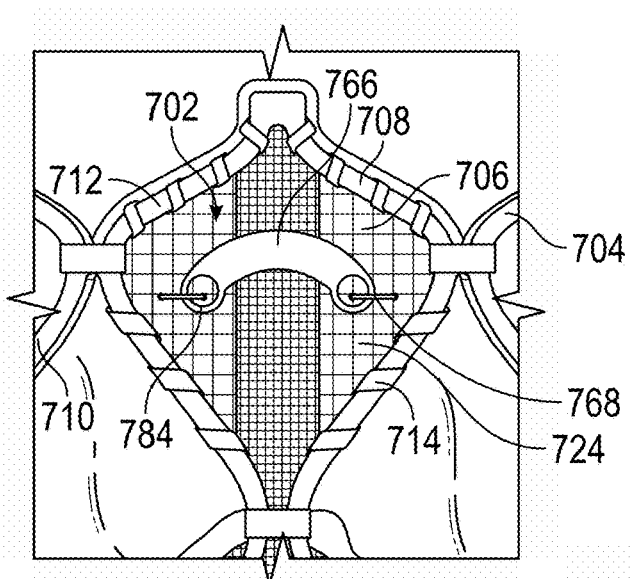
FIG. 35J illustrates another exemplary embodiment of a radiopaque marker attached to a commissure within a cell of a prosthetic valve.
Figure 35K:
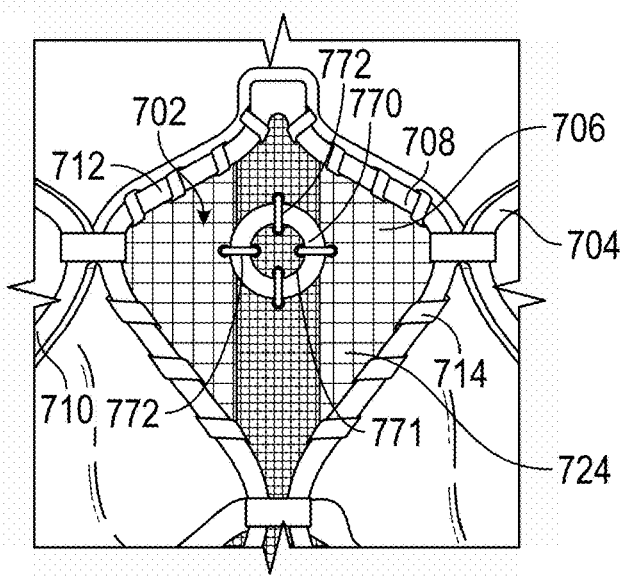
FIG. 35K illustrates another exemplary embodiment of a radiopaque marker attached to a commissure within a cell of a prosthetic valve.
Figure 35L:
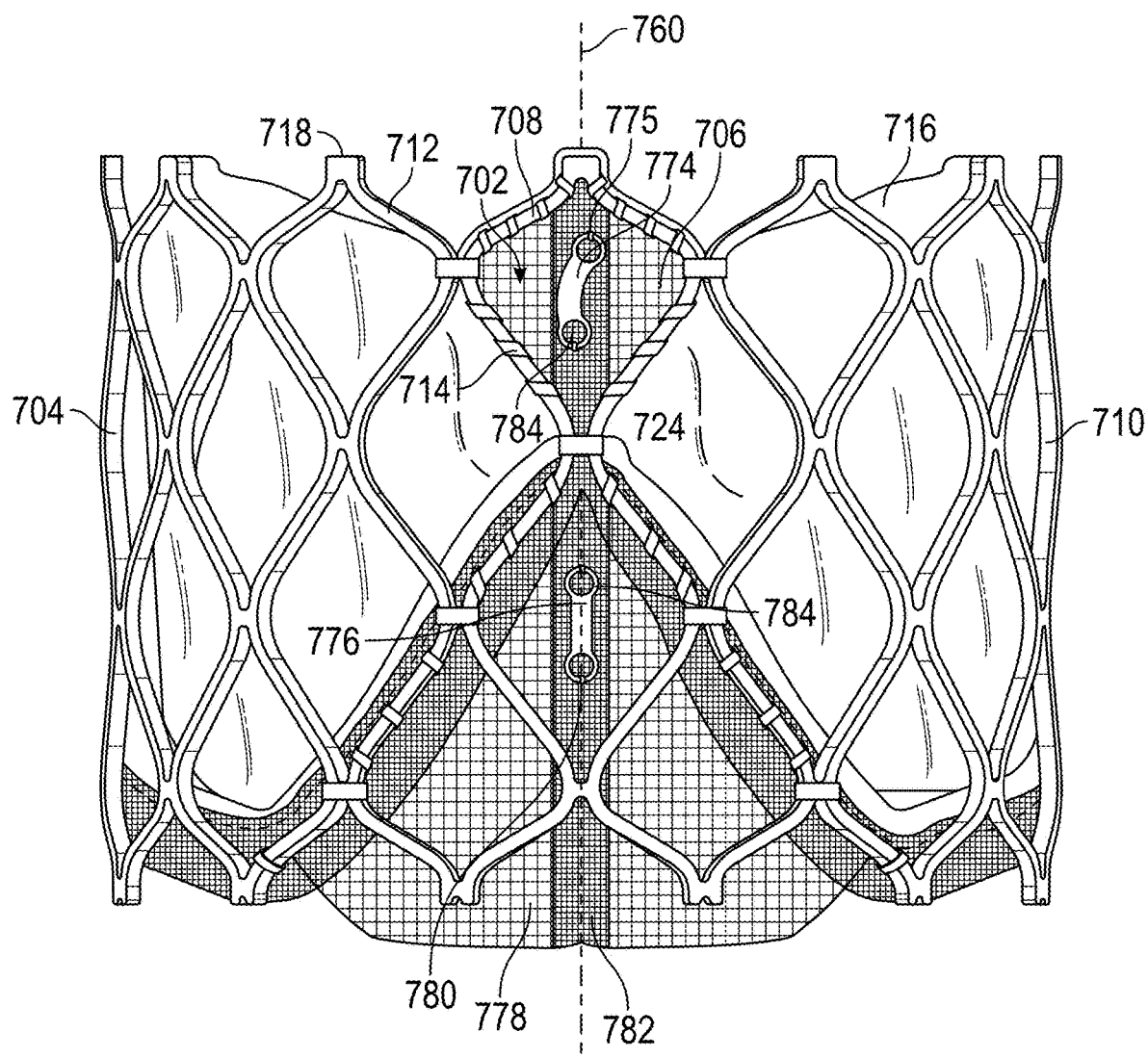
FIG. 35L illustrates another exemplary embodiment of a radiopaque marker attached to a commissure within a cell of a prosthetic valve and a radiopaque marker attached to a skirt extending across an inner surface of a frame of the prosthetic valve, directly below the commissure.

FIGS. 35J-35P show additional embodiments of radiopaque markers configured to be attached to a commissure within a cell 708 of a prosthetic valve, attached to an additional attachment member which is then attached to the cell 708, or attached to an additional skirt or fabric material, directly below a location of a commissure (e.g., as shown in FIG. 35L). For example, in some embodiments, any of the markers shown in FIGS. 35J-35P can replace the marker 700 on the prosthetic valve 704 (FIGS. 35A-35B) or the marker 750 on the second attachment member 752 (FIGS. 35C-H). Further, any of the markers shown in FIGS. 35A-35P can be attached to an additional skirt or fabric material, directly and/or axially below the location of the commissure (as shown in FIG. 35L).

The exemplary markers shown in FIGS. 35J-35P have different shapes or configurations. In some embodiments, a shape of the marker and/or a mounting location on the valve for the marker can be selected based on a geometry and space restrictions of the valve (e.g., size of cells of the frame). In certain embodiments, one or more of the markers shown in FIGS. 35J-35P can be shaped and sized to fit within the cell 708, both when the frame 710 of the prosthetic valve is in its radially compressed and radially expanded configurations.

FIG. 35J shows an exemplary embodiment of a radiopaque marker 766 secured to the attachment member 706 arranged across the cell 708 of the frame 710 with one or more fasteners (e.g., sutures) 768. As shown in FIG. 35J, the marker 766 is arc-shaped, with its longest dimension arranged in the circumferential direction (e.g., across a width of the cell 708). However, in alternate embodiments, the marker 766 can be oriented differently within the cell 708, such as with its longest dimension in the axial direction (e.g., as shown in FIG. 35L, as described below).

FIG. 35K shows an exemplary embodiment of a radiopaque marker 770 secured to the attachment member 706 arranged across the cell 708 of the frame 710 with one or more fasteners (e.g., sutures) 772. The marker 770 is annular or "o"-shaped. For example, the marker 770 can include a central aperture 771 and the one or more fasteners 772 can extend through the central aperture 771, around the marker 770, and through the material of the attachment member 706. In some embodiments, the marker 770 can be centered on the attachment member 706.

FIG. 35L shows an exemplary embodiment of a radiopaque marker 774 secured to the attachment member 706 arranged across the cell 708 of the frame 710 with one or more fasteners (e.g., sutures) 775 and a radiopaque marker 776 secured to one or more skirts 778 that extend across an inner surface of the frame 710 with one or more fasteners (e.g., sutures) 780. In some embodiments, the one or more skirts 778 can include a plurality of skirts 778, each secured to a cusp edge of corresponding leaflet 716 and folded over to extend across struts 712 of the frame 710 disposed between cusp edges of adjacent leaflets 716. Thus, in some embodiments, the marker 776 can be secured to an overlapping portion 782 of two adjacent skirts 778 which is disposed axially below the commissure 702. In certain embodiments, the prosthetic valve 704 may have only one of the markers 774 and 776 secured to the frame 710. As shown in the embodiment of FIG. 35L, the markers 774 and 776 are arranged to extend in a direction of the central longitudinal axis 760 of the frame 710 of the prosthetic valve 704 (e.g., the longest dimension of the marker 774 and the marker 776 extends in the axial direction, relative to the central longitudinal axis 760. The marker 774 can be the same or similar to the marker 766 shown in FIG. 35J, but rotated such that its longest dimension extends in the axial direction.

Each of the markers 766, 770, 774, and 776 (FIGS. 35J-35L) can include one or more mounting apertures 784 configured to receive one or more fasteners (e.g., fasteners 768, 772, 775, or 780) for securing the marker to the attachment member 706 or the one or more skirts 778. As shown in FIGS. 35J-35L, the mounting apertures 784 can be circular. However, in alternate embodiments, the mounting apertures 784 can have a different shape (e.g., oblong, rectangular, triangular, or the like) and/or size (e.g., a diameter or width smaller than a width of the marker).

FIGS. 35M-35P show additional exemplary embodiments of radiopaque markers that are reflection asymmetric along an axis that is parallel to the central longitudinal axis of the frame 710 of the prosthetic valve 704. As a result, the markers shown in FIGS. 35M-35P can provide an indication of a position of the commissure 702, relative to a guidewire (as explained herein), under fluoroscopic imaging.

Figure 35M:
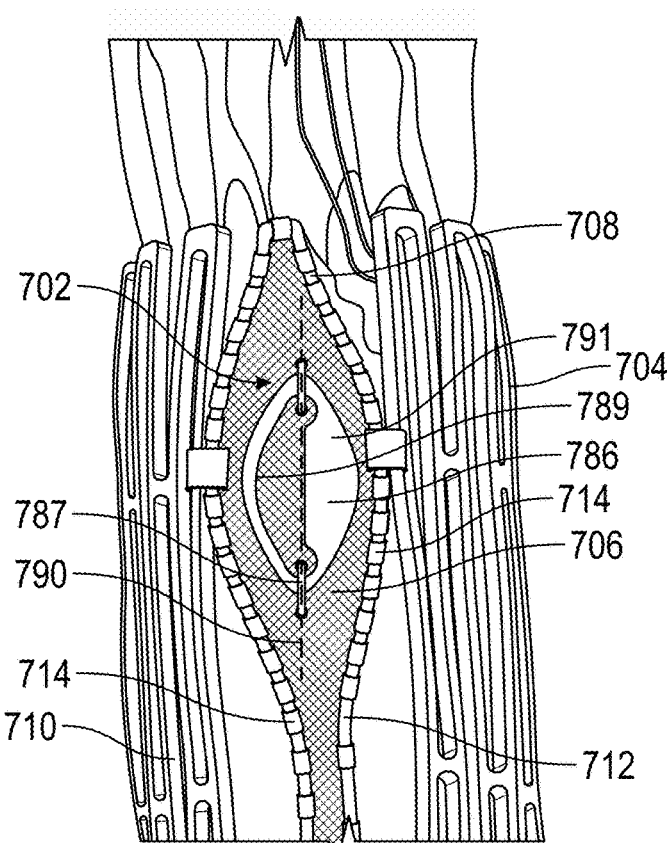
FIG. 35M illustrates another exemplary embodiment of a radiopaque marker attached to a commissure within a cell of a prosthetic valve, the prosthetic valve in a radially compressed configuration.

For example, FIG. 35M shows an exemplary embodiment of a radiopaque marker 786 secured to the attachment member 706 arranged across the cell 708 of the frame 710 with one or more fasteners (e.g., sutures) 787. The marker 786 comprises an elongate cut-out or aperture 789 disposed on a first side of the marker 786 (relative to a central longitudinal axis 790 of the marker 786). Thus, on an opposite, second side of the marker 786 (across the axis 790), the marker 786 comprises a solid material portion 791. The one or more fasteners 780 extend through the aperture 789, around the marker 786, and into the attachment member 706. Since the solid material portion 791 and the aperture 789 are disposed on opposite sides of the marker 786, relative to the axis 790, the marker 786 is reflection asymmetric across the axis 790.

Figure 35N:
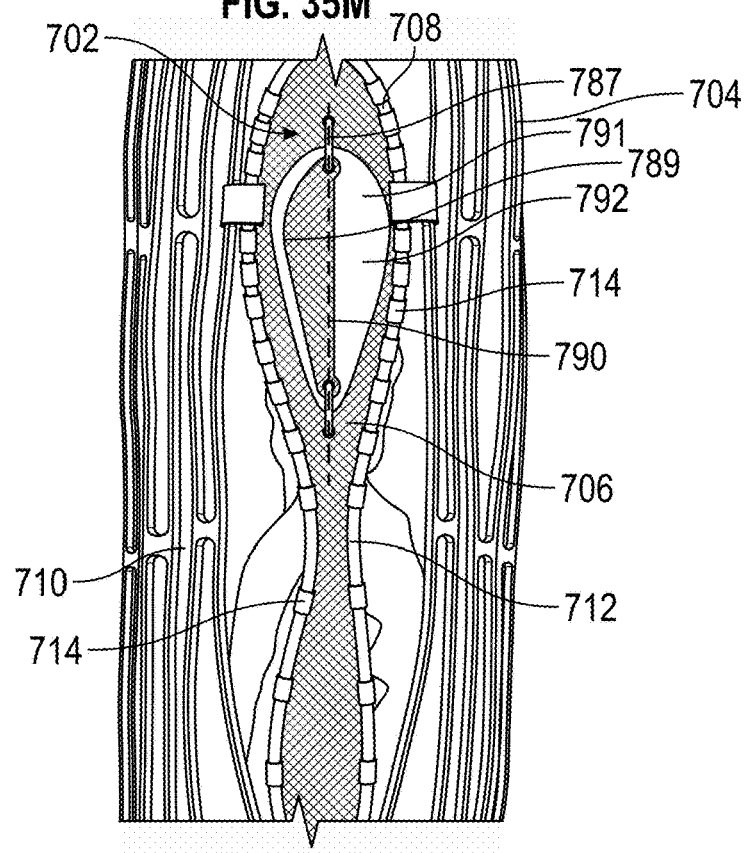
FIG. 35N illustrates another exemplary embodiment of a radiopaque marker attached to a commissure within a cell of a prosthetic valve, the prosthetic valve in a radially compressed configuration.

FIG. 35N shows another exemplary embodiment of a radiopaque marker 792 secured to the attachment member 706 arranged across the cell 708 of the frame 710 with one or more fasteners (e.g., sutures) 787 and is configured similar to marker 786 (FIG. 35M). For example, marker 792 also includes an aperture 789 disposed across the axis 790 of the marker 792 from the solid material portion 791. However, the aperture 789 and solid material portion 791 of marker 792 are shaped differently (e.g., elongated further) than marker 786.

In certain embodiments, the markers described above can be secured to the attachment member 706, in a region of or to the tissue of the leaflets (e.g., the commissure tabs 754 of the leaflets 716, as shown in FIG. 35H). For example, the underling commissure tabs of the leaflets 716 of the commissure 702 are represented in the figures as a more heavily cross-hatched, central region, on the attachment member 706. In some embodiments, the markers can be configured to attach to the attachment member 706, outside of this tissue region, thereby avoiding placing additional fasteners or sutures into the tissue of the commissure tabs of the leaflets.

Figure 35O:
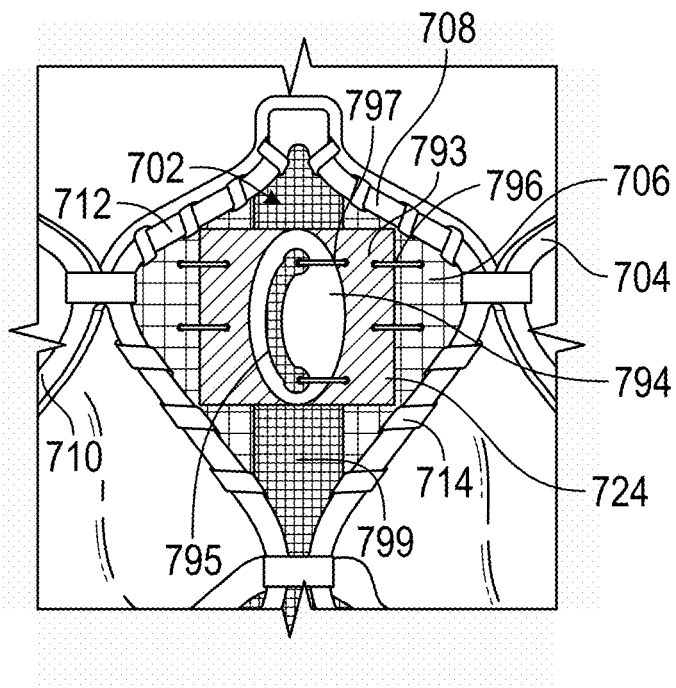
FIG. 35O illustrates an exemplary embodiment of a radiopaque marker attached to a first attachment member, the first attachment member attached to a second attachment member of a commissure within a cell of a prosthetic valve.
Figure 35P:
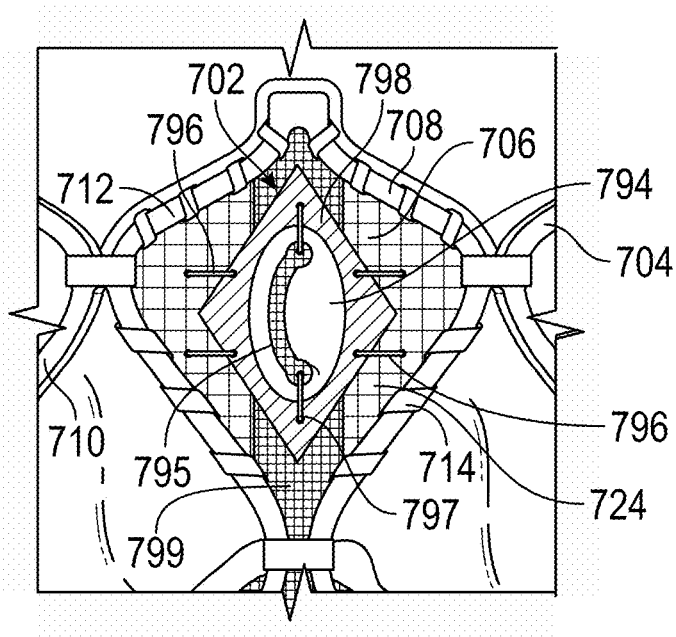
FIG. 35P illustrates another exemplary embodiment of a radiopaque marker attached to a first attachment member, the first attachment member attached to a second attachment member of a commissure within a cell of a prosthetic valve.

FIGS. 35O and 35P show exemplary embodiments of radiopaque markers that are secured to an additional attachment member (e.g., which can be cloth) and the additional attachment member is then secured to the attachment member 706, outside of the underlying tissue region 799. For example, FIG. 35O shows an exemplary embodiment of a radiopaque marker 794 secured to an additional attachment member 793 by one or more fasteners (e.g., sutures) 797 that can extend through a central aperture (or cut-out region) 795 in the marker 794. The additional attachment member 793 can be secured directly to the attachment member 706, outside of the tissue region 799, by one or more fasteners (e.g., sutures) 796. As a result, the marker 794 can be secured to the attachment member 706, through the additional attachment member 793, without securing the marker 794 itself directly to the attachment member 706.

Similarly, FIG. 35P shows another exemplary embodiment of the radiopaque marker 794 secured to an additional attachment member 798 by one or more fasteners (e.g., sutures) 797 that can extend through the central aperture (or cut-out region) 795 in the marker 794. The additional attachment member 798 can then be secured directly to the attachment member 706 by the one or more fasteners 796. As shown in FIGS. 35O and 35P, the additional attachment member 798 has a diamond shape while the additional attachment member 793 has a rectangular shape. Alternate shapes for the additional attachment members are possible (e.g., circular, square, and the like).

Exemplary methods for attaching a radiopaque marker 750 (or any of the other radiopaque markers described herein) to an attachment member configured to be attached to commissure tabs of two adjacent leaflets (thereby forming a commissure) and secured to struts 712 of a cell 708 of a frame 710 of a prosthetic heart valve, such as is shown in FIGS. 35A and 35B, are presented in FIGS. 97-101E.

FIGS. 97-99B show one embodiment where a radiopaque marker 750 is attached (e.g., sewn) directly to an attachment member 730. As shown in FIG. 97, the attachment member 730 can comprise first and second side portions 732a, 732b projecting laterally from a central portion 734 (or central region). The attachment member 730 can further comprise an upper tab 736 and a lower tab 738 projecting from upper and lower edges, respectively, of the central portion 734. Further details on attachment members for securing commissure tabs of adjacent leaflets to a cell of a frame of a prosthetic valve are described in U.S. Patent Publication No. 2018/0028310, which is incorporated by reference herein.

As shown in FIG. 97, the marker 750 is secured directly to the central portion 734 of the attachment member 730 by one or more sutures 740 (forming one or more knots on an outside of the marker 750). The attachment member 730 can then be folded and secured to the commissure tabs of the leaflets such that the marker 750 is either disposed on a radially outward facing surface 742 (e.g., facing away from the leaflets) of the attachment member 730 (FIGS. 98A and 98B) or a radially inward facing surface (e.g., the surface disposed opposite the radially outward facing surface 742 and which faces the commissure tabs of the leaflets) of the attachment member 730 (FIGS. 99A and 99B). For example, when the marker 750 is secured to the radially outward facing surface 742 of the attachment member 730, when secured to the cell 708, the marker 750 faces outward and away from the leaflets and interior of the frame 710 (FIG. 98B). In contrast, when the marker 750 is secured to the radially inward facing surface of the attachment member 730, when secured to the cell 708, the marker 750 faces inward, toward the leaflets (FIG. 99B). Thus, as shown in FIGS. 99A and 99B, the marker 750 is disposed behind the attachment member 730.

Figure 101B:
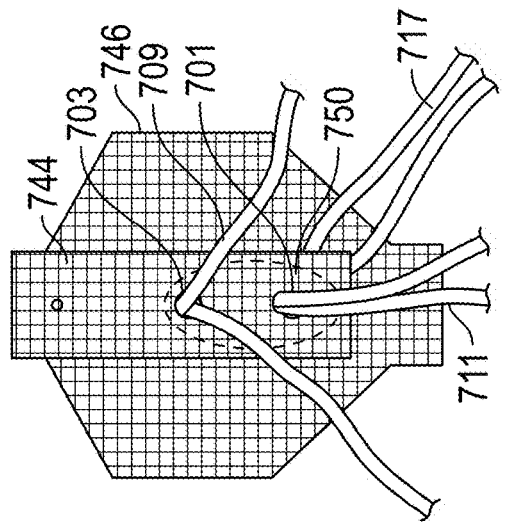
Figure 101C:
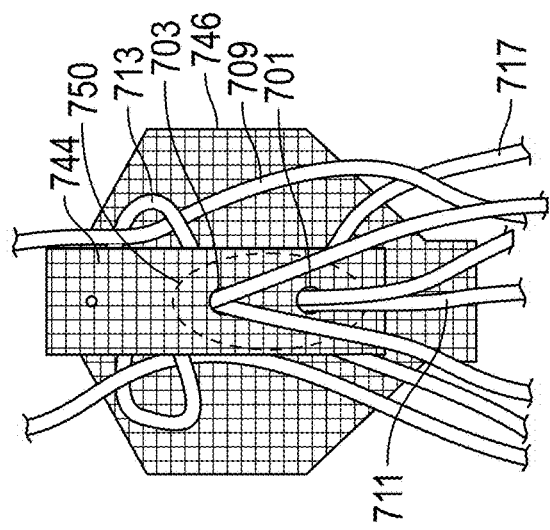
Figure 100:
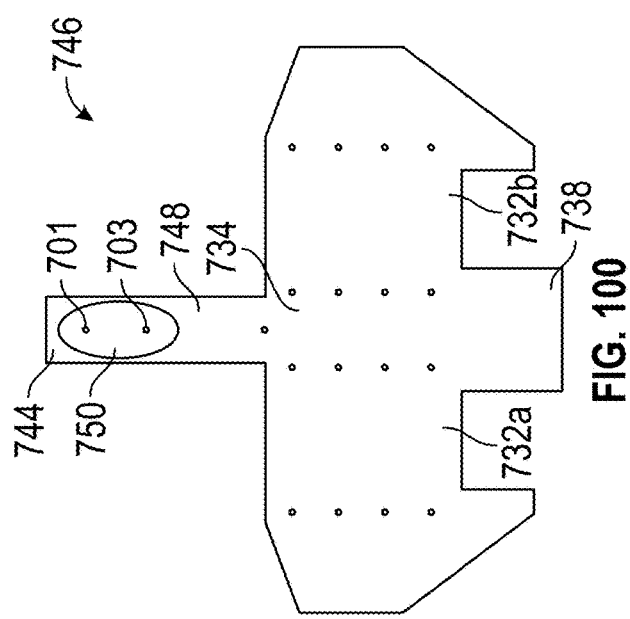
Figure 101A:
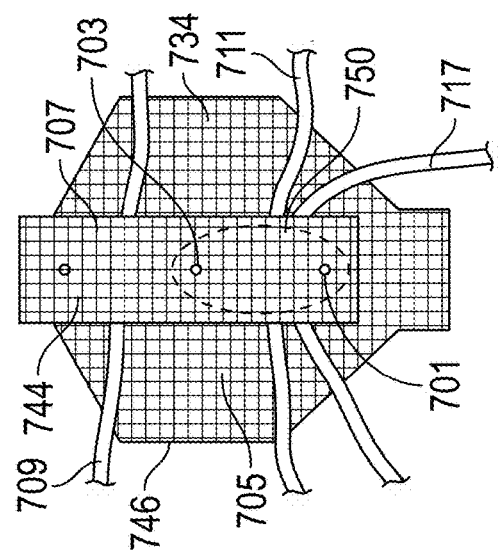
Figure 101E:
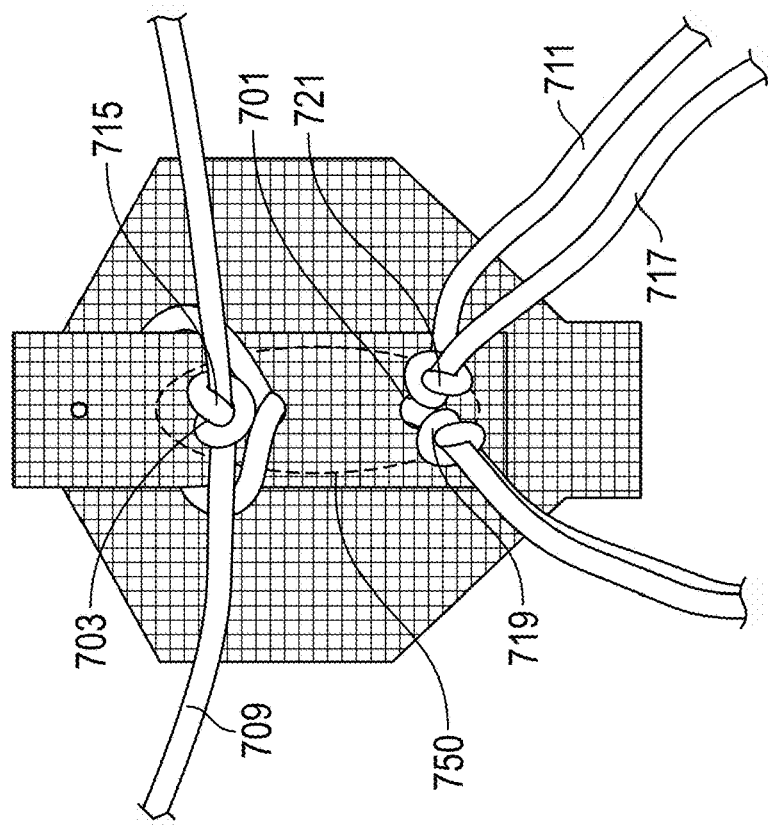

FIGS. 100-101E show another embodiment where a radiopaque marker 750 is attached (e.g., sewn) to an elongate flap 744 (or extension) of an attachment member 746. As shown in FIG. 100, the attachment member 746 is similar to the attachment member 730 of FIG. 97 except it comprises the longer flap 744 (instead of shorter upper tab 736) extending from the central portion 734. As shown in FIGS. 101A-E, the marker 750 can be attached to the flap 744 and the commissure formed with the attachment member 746 (such as the commissure 702 shown in FIGS. 32A and 32B) by one or more sutures (or other, similar fasteners) that are used to secure the commissure tabs of the adjacent leaflets to the attachment member 746 (such as shown in FIG. 35H).

For example, the marker 750 can be placed on a first surface 748 of the flap 744 (FIG. 100, which shows the marker 750 as transparent for the sake of illustration), over one or more apertures in the flap 744. In the embodiment of FIGS. 100-101E, the flap 744 includes two apertures, including a first aperture 701 and second aperture 703, which can be spaced apart based on a spacing between the first aperture 726 and the second aperture 728 of the marker 750 (e.g., such that the first aperture 726 overlaps the first aperture 701 and the second aperture 728 overlaps the second aperture 703).

The flap 744 can then be folded over an outer surface 705 of the central portion 734 of the attachment member 746, over sutures extending outward from the outer surface 705 which were used to connect the commissure tabs of the adjacent leaflets to the attachment member 746 (FIG. 101A). As such, the marker 750 is sandwiched between a second (outer) surface 707 of the flap 744 and the outer surface 705 of the central portion 734 of the attachment member 746 (FIG. 101A).

First sutures 709 can then be routed through the second aperture 728 of the marker 750 and through the second aperture 703 in the flap 744 such they extend outward and away from the second surface 707 of the flap 744 (FIG. 101B). Similarly, second sutures 711 can be routed through the first aperture 726 of the marker 750 and through the first aperture 701 in the flap 744 such they extend outward and away from the second surface 707 of the flap 744 (FIG. 101B).

Figure 101D:
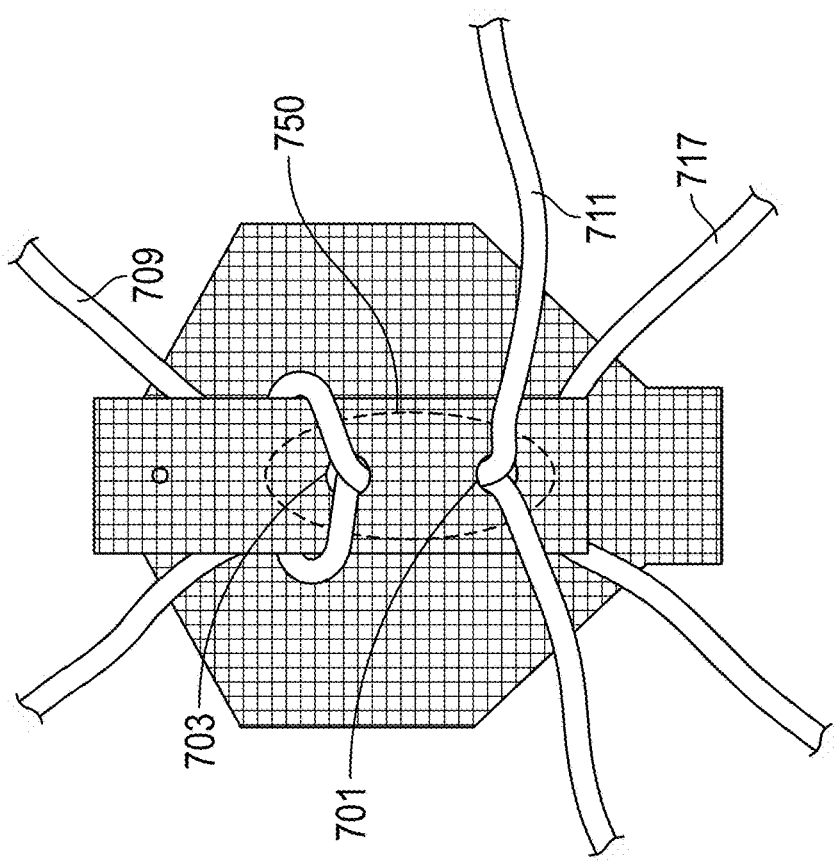

In some embodiments, free ends of the first sutures 709 can be routed through looped portions 713 of the first sutures 709 that are arranged on each side of the flap 744, beneath the flap 744 (FIG. 101C). The first sutures 709 are then tightened against the flap 744, as shown in FIG. 101D.

The free (loose) ends of the first sutures 709 can then be tied (or knotted) together to secure a first portion (top portion in the view of FIGS. 101A-101E) of the marker 750 to the attachment member 746 and the free (loose) ends of each second sutures 711 can then be tied (or knotted) together with a corresponding third suture 717 (of a pair of third sutures 717 arranged beneath the flap 744) to secure a second (e.g., bottom) portion of the marker 750 to the attachment member 746 (FIG. 101E).

In some embodiments, the first sutures 709 can be tied into one single and one double knot, thereby forming a first knotted portion 715 (FIG. 101E). Each second suture 711 can be tied into one single and two double knots with the corresponding third suture 717, thereby forming a second knotted portion 719 and a third knotted portion 721 on opposite sides of the first aperture 701 (FIG. 101E).

In this way, the marker 750 can be secured to the flap 744 of the attachment member 746 with the same sutures (or similar fixation members) that were used to secure the commissure tabs of the adjacent leaflets to an inner surface of the attachment member 746. This can simplify the assembly process of the prosthetic heart valve, thereby saving time and assembly costs.

As introduced above, a prosthetic valve can be mounted around and radially compressed (e.g., crimped) onto a valve mounting portion of a distal end portion of a delivery apparatus (e.g., valve mounting portion 324 of delivery apparatus 300 shown in FIGS. 9-11 and 32A-32B), for delivery of the valve to the target implantation site (e.g., a native valve of the heart). In some embodiments, an inflatable balloon of the delivery apparatus (e.g., balloon 318 shown in FIGS. 9-11 and 32A-32B) is pleated and wrapped in a manner that more efficiently folds the balloon material in order to minimize the folded balloon diameter. As a result, a diameter of the prosthetic valve, which is crimped in the radially compressed configuration onto the folded balloon, may also be minimized.

Figure 36:
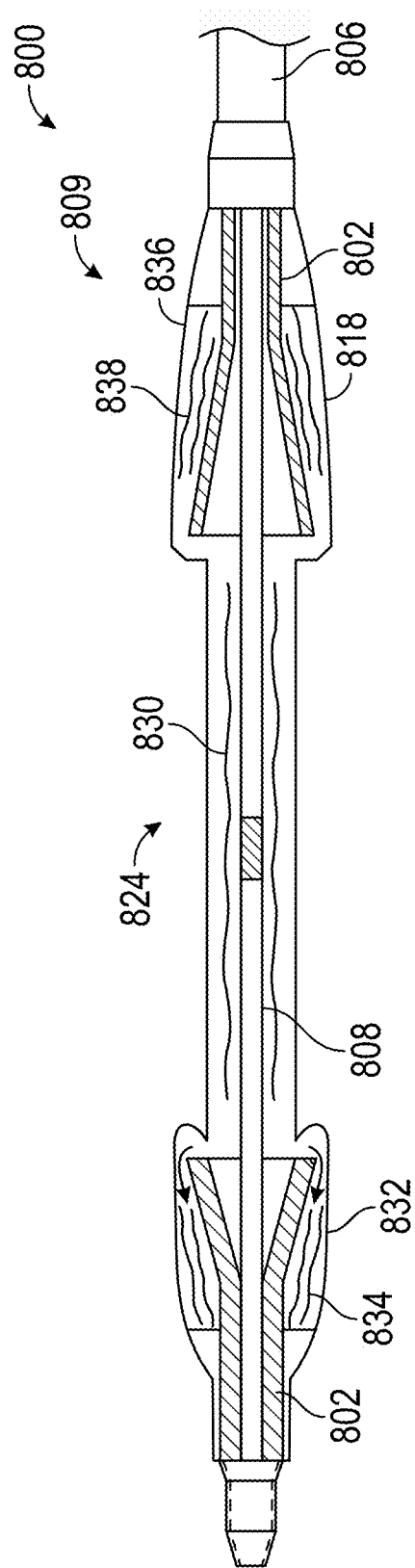
FIG. 36 illustrates an embodiment of an inflatable balloon folded around a distal end portion of a delivery apparatus.

FIG. 36 shows an embodiment of an inflatable balloon 818 folded around a distal end portion 809 of a delivery apparatus 800. The delivery apparatus 800 may be similar to delivery apparatus 300 of FIGS. 9-11 and includes one or more shoulders 802 mounted on an inner shaft 808, the inner shaft extending distally from an intermediate (e.g., balloon) shaft 806. The balloon 818 overlays a valve mounting portion 824 of the distal end portion 809 of the delivery apparatus 800. The portion of the balloon 818 at the valve mounting portion 824 can include one or more axially extending folds or pleats 830. Such axial pleats 830 can be tightly compressed in order to minimize the profile of the balloon 818 and the prosthetic heart valve crimped thereon.

In some embodiments, a distal portion 832 of the balloon 818 can include one or more axial folds or pleats 834 when the balloon 818 is in a deflated state ready for insertion into a patient's vasculature. In some embodiments, a proximal portion 836 of the balloon 818 can include one or more axial folds or pleats 838 when the balloon is in a deflated state ready for insertion into a patient's vasculature. The axial pleats 834, 838 can reduce the overall profile of the distal end portion 809 of the delivery apparatus 800 to facilitate passage of the delivery apparatus 800 through the introducer sheath and the patient's vasculature. Further details on the folding or wrapping of a balloon on a distal end portion of a delivery apparatus is described in U.S. Provisional Application No. 63/051,244, filed Jul. 13, 2020, which is incorporated by reference herein.

Figure 37:
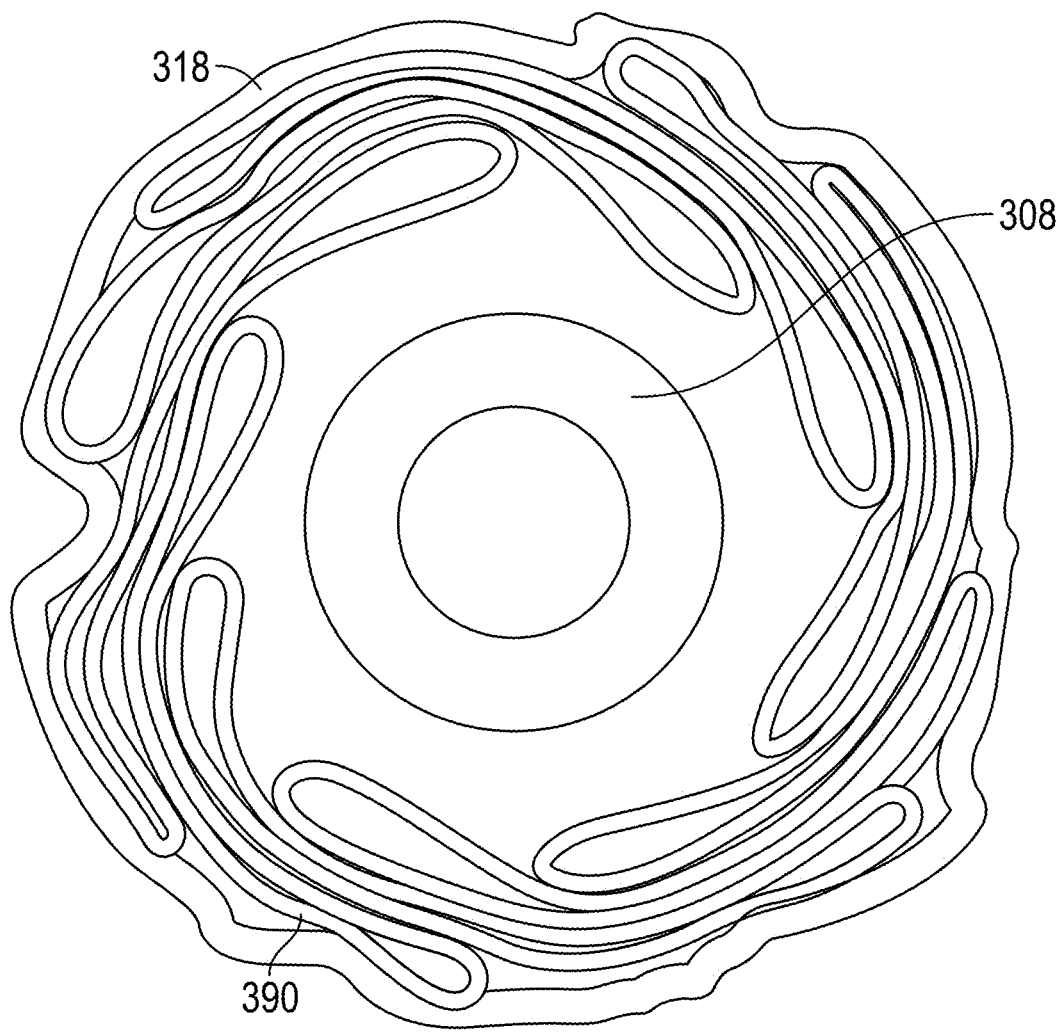
FIG. 37 is a cross-sectional view of an inflatable balloon wrapped and folded around a portion of a delivery apparatus, at a valve mounting portion of the delivery apparatus, according to an embodiment.

In some embodiments, the balloon 318 of delivery apparatus 300 shown in FIGS. 9-11, 28, and 32A-32B can be folded similarly to that of balloon 818, as described above. FIG. 37 is an exemplary, cross-sectional view of the balloon 318 of delivery apparatus 300, wrapped and folded around the inner shaft 308, at the valve mounting portion 324 of the delivery apparatus 300. As shown in FIG. 37, the balloon 318 includes a plurality of overlapping pleats or folds 390 when in its deflated configuration and when a prosthetic valve is mounted on and radially compressed around the balloon 318. The balloon 318 can be folded in such a way that the pleats 390 result in a minimized folded balloon diameter (e.g., in its deflated configuration) which can reduce a diameter of the radially compressed prosthetic valve when crimped thereon.

As introduced above with reference to FIGS. 9-11, the distal end portion 309 of the delivery apparatus 300 can include a distal tip portion 328 mounted on the distal end of the outer shaft 304. For delivery of the prosthetic valve to the target implantation site, the outer shaft 304 and the intermediate shaft (e.g., balloon shaft) 306 can be moved axially relative to one another such that the distal tip portion 328 is arranged over a proximal end portion of the balloon 318 (e.g., proximal end portion 333, as shown in FIG. 10). As a result, the distal tip portion 328 can act as a proximal shoulder on a proximal side of the valve mounting portion 324 and resist movement of the radially compressed prosthetic valve, proximally in the axial direction, during advancing the distal end portion of the delivery apparatus to the target implantation site. For example, in some embodiments, the intermediate shaft 306 can be pulled into the outer shaft 304 or the outer shaft 304 can be pushed over the intermediate shaft 306, thereby moving the proximal end portion of the balloon 318 into an interior of the distal tip portion 328. In some embodiments, the distal tip portion 328 can include internal and/or external expansion cuts or grooves that provide flexibility to the distal tip portion 328 and allow it to expand radially outward as it moves over the proximal end portion of the balloon 318, thereby increasing its ability to act as a balloon shoulder and resist axial movement of the radially compressed prosthetic valve mounted around the balloon 318 at the valve mounting portion 324.

In some embodiments, the expansion cuts of the distal tip portion arranged along an interior surface of the distal tip portion can extend axially along the interior surface (relative to the central longitudinal axis of the delivery apparatus). However, these axially extending expansion cuts can cause issues when rotating the balloon shaft (e.g., intermediate shaft 306) to which the balloon 318 is mounted (since the balloon 318 rotates as a result of the balloon shaft rotating), when rotationally aligning the distal end portion of the delivery apparatus at the target implantation site, as described herein. For example, during rotating the balloon or intermediate shaft, pleats of the folded balloon 318 (as described above with reference to FIGS. 36 and 37) can get stuck in the axially extending, interior expansion cuts of the distal tip portion. Examples of such axially extending expansion cuts can be found in U.S. Pat. No. 9,061,119, which is incorporated by reference herein.

Thus, it may be desirable to have a distal tip portion that is configured to radially expand over the proximal end portion of the balloon 318, while also allowing the balloon 318 to slide more easily within the distal tip portion, without the pleats of the balloon getting stuck, when rotating the intermediate shaft of the delivery apparatus FIGS. 38-41 show an embodiment of the distal end portion 309 of the delivery apparatus where the outer shaft 304 includes a distal tip portion 900 mounted on the distal end of the outer shaft 304 and the balloon 318 includes the radial depression 334 (FIGS. 40 and 41) in certain configurations. In some embodiments, the distal tip portion 900 can be the distal tip portion 328 of FIGS. 9 and 11.

The distal tip portion 900 can be configured as a flex adaptor including a flex portion 912 and a coupling portion (also can be referred to as a straight portion) 914. The flex portion 912 can extend from a distal end of the coupling portion 914 and be configured to flex (e.g., expand radially outward) from the distal end of the coupling portion 914. The coupling portion 914 can be coupled to and mounted around the distal end of the outer shaft 304 (FIG. 39).

The flex portion 912 can be tapered and have an outer diameter than increases in a distal direction, from the distal end of the coupling portion 914 to a distal end of the flex portion 912.

The flex portion 912 can include a plurality of internal expansion cuts or grooves 902 (also referred to herein as helical internal grooves) and a plurality of external expansion cuts or grooves 904 (also referred to herein as helical external grooves) (FIGS. 38, 39, and 41). As shown in FIGS. 38 and 39, the internal expansion grooves 902 are helical and curve around a central longitudinal axis 906, from a proximal end 908 of the flex portion 912 (e.g., where the flex portion 912 extends from the coupling portion 914) to a distal end 910 of the distal tip portion 900. The external expansion grooves 904 can also be helical and curve around the central longitudinal axis 906, from the proximal end 908 of the flex portion 912 to the distal end 910 of the distal tip portion 900.

In some embodiments, each groove of the internal expansion grooves 902 can curve from about 75 to about 110 degrees, from about 80 to about 100 degrees, or from about 85 to about 95 degrees around the central longitudinal axis 906. In some embodiments, each groove of the external expansion grooves 904 can curve from about 75 to about 110 degrees, from about 80 to about 100 degrees, or from about 85 to about 95 degrees around the central longitudinal axis 906.

In some embodiments, the internal expansion grooves 902 are spaced apart from one another and the external expansion grooves 904 are spaced apart from one another, around a circumference of the distal tip portion 900.

In some embodiments, the internal expansion grooves 902 are offset (e.g., circumferentially offset) from the external expansion grooves 904 such that a location where one external expansion groove 904 depresses into an outer surface of the distal tip portion 900 is arranged between where two adjacent grooves of the internal expansion grooves 902 depress into an inner surface of the distal tip portion 900 (FIG. 38).

The internal expansion grooves 902 and the external expansion grooves 904 are configured to allow the flex portion 912 to flex radially outward as the distal tip portion 900 is moved over a proximal end portion 333 of the balloon 318 (FIG. 40), toward the valve mounting portion 324. FIG. 41 shows the distal tip portion 900 arranged over the proximal end portion 333 of the balloon 318, during advancing a radially compressed prosthetic valve 922 (which can be similar to one of the prosthetic valves described herein), mounted on the valve mounting portion 324 of the delivery apparatus, through a patient's vasculature and to the target implantation site.

The helical shape and orientation of the internal expansion grooves 902 can be configured such that during rotating the intermediate (balloon) shaft 306 (e.g., to achieve commissure alignment at the target implantation site, as described herein), engagement between the pleats of the balloon 318 (e.g., pleats or folds 390 shown in FIG. 37) and the internal expansion grooves 902 is reduced, thereby allowing the balloon 318 to slide more easily along the inner surface of the distal tip portion 900 while the balloon 318 rotates within the distal tip portion 900. For example, the helical shape and orientation of the internal expansion grooves 902 can prevent the pleats of the balloon 318 from diving into and getting caught within the internal expansion grooves 902, as the intermediate shaft 306, and thus the balloon 318, is rotated.

Following crimping of the prosthetic valve onto the valve mounting portion 324 and advancing the distal tip portion 900 over the proximal end portion 333 of the balloon 318 (as shown in FIG. 41), fluid arranged within the proximal end portion 333 of the balloon 318 is displaced and pushed distally within the balloon 318. As a result, the distal end portion 332 of the balloon 318 can expand radially outward excessively and can cause the crimped profile (e.g., diameter) of the prosthetic valve 922 to increase. An increased crimped valve profile can result in increased resistance when pushing the delivery apparatus into and through a loader and sheath of a delivery assembly.

Figure 40:
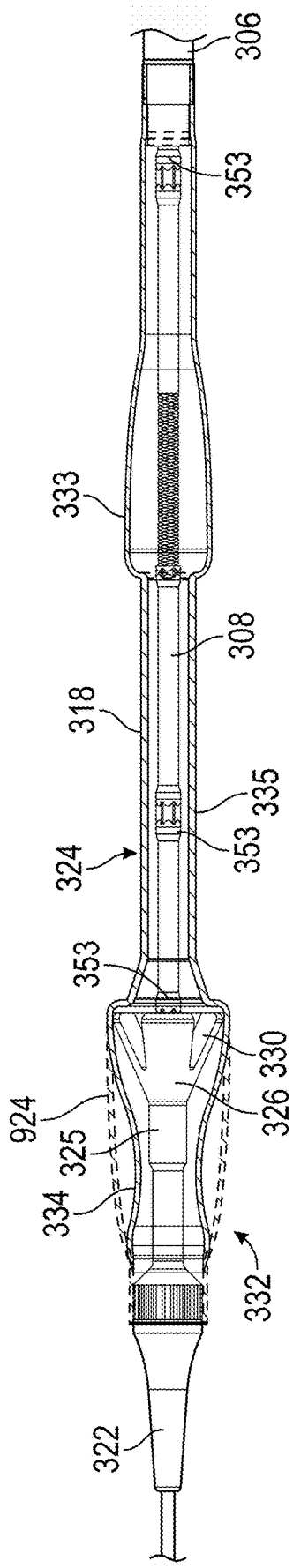
FIG. 40 is a side view of a distal end portion of delivery apparatus illustrating a radial depression in a distal end portion of an inflatable balloon of the delivery apparatus, when the distal tip portion is arranged away from a proximal end portion of the balloon.

Thus, in order to reduce or prevent the increase in the crimped profile of the prosthetic valve 922, the distal end portion 332 of the balloon 318 can be formed with a radial depression 334 that is depressed inward, toward the central longitudinal axis 320 of the delivery apparatus (FIGS. 40 and 41). In some embodiments, the radial depression 334 can be depressed inward, relative to an outermost radial surface of the distal shoulder 326. For example, as shown in FIG. 40, the distal end portion 332 of the balloon 318 can extend over a wider, flared portion 331 (e.g., which can be formed by wings 330) of the distal shoulder 326, then depress radially inward, toward the base portion 325 of the distal shoulder 326, and then extend back radially outward to a proximal end of the nose cone 322, thereby forming the radial depression. FIG. 40 shows a state of the balloon 318, including the radial depression 334 in the distal end portion 332, prior to crimping the prosthetic valve onto the valve mounting portion 324 and advancing the distal tip portion 900 over the proximal end portion 333 of the balloon 318.

After crimping of the prosthetic valve onto the valve mounting portion 324 and advancing the distal tip portion 900 over the proximal end portion 333 of the balloon 318 (as shown in FIG. 41), fluid arranged within the proximal end portion 333 of the balloon 318 is displaced and pushed distally, within the balloon 318, to the distal end portion 332 of the balloon 318. The radially depressed, distal end portion 332 of the balloon 318 can then radially expand (e.g., inflate partially) as it receives the displaced fluid to the expanded state 924 shown in FIG. 41 (solid lines) and FIG. 26 (dashed lines). The radial depression 334 can be configured (e.g., sized) so that the distal end portion 332 can receive the displaced fluid without radial expanding the portion of the balloon 318 within the valve mounting portion 324, thereby preventing the crimped profile of the prosthetic valve 922 from increasing.

Prior to inflating the balloon 318 to deploy the prosthetic valve 922 at the target implantation site, the distal tip portion 900 can be moved axially away from the prosthetic valve 922 and off the balloon 318 (either by pulling the outer shaft 304 proximally relative to the intermediate shaft 306 or by pushing the intermediate shaft 306 distally relative to the outer shaft 304). The prosthetic valve 922 can then be deployed and radially expanded by inflating the balloon 918.

When the balloon 318 is inflated (e.g., when the distal end portion of the delivery apparatus and the prosthetic valve have reached the target implantation site, such as the native valve), the balloon 318 unfurls (e.g., unwraps) into its expanded state, thereby radially expanding the prosthetic valve to its radially expanded state. As the balloon 318 expands, and its folds or pleats 390 unwrap (FIG. 37), the prosthetic valve radially expands and rotates by a predetermined (e.g., known) amount. For example, the unfolding of the pleats 390 of the balloon causes the prosthetic valve to rotate during the balloon inflation. As such, the position of the radially expanded prosthetic valve is rotated from its position on the delivery apparatus prior to inflating the balloon 318, by the predetermined amount (e.g., 10°, 20°, 30°, or the like). In some embodiments, during manufacturing of the delivery apparatus, the balloon can be wrapped and/or folded in a consistent and/or standardized manner such that a consistent amount of rotation of the prosthetic valve occurs during valve deployment (e.g., for a plurality of delivery apparatuses manufactured in a same way).

Thus, it may be desirable to mount (e.g., crimp) the prosthetic valve into its radially compressed state onto the valve mounting portion of the delivery apparatus such that a selected commissure of the prosthetic valve is offset from the marker (e.g., marker 500 of FIG. 28, marker 600 of FIGS. 30-32B, or marker 650 of FIGS. 33-34B) on the delivery apparatus by the predetermined amount, or is at least based on the predetermined amount of rotation. In this way, the circumferential offset between the marker and the selected commissure of the prosthetic valve can compensate for the valve rotation that occurs during inflation of the balloon and valve deployment. In some embodiments, the predetermined amount of offset can be at least partially based on the balloon wrapping and resulting amount of rotation of the valve that occurs during inflation of the balloon.

For example, deploying the prosthetic valve by inflating the balloon, after aligning the marker on the delivery apparatus with the guidewire within a selected imaging view (e.g., aligning the asymmetric marker with the guidewire such that the marker is arranged at the back of the selected imaging view), may cause the prosthetic valve to rotate and implant within the native valve with commissures of the prosthetic valve in alignment with commissures of the native valve (as described in further detail below). In some embodiments, the marker on the delivery apparatus can be configured to indicate a circumferential location of a selected commissure of the prosthetic valve after valve deployment.

FIG. 42 shows an example of the prosthetic valve 922 mounted on and around the valve mounting portion 324 of the distal end portion 309 of the delivery apparatus 300, in a radially compressed state, with a selected commissure (indicated by a dashed line in FIG. 42) 930 circumferentially offset from the marker 600 by a predetermined amount 932. As discussed above, upon deployment of the prosthetic valve 922 via inflating the balloon, the prosthetic valve 922 can rotate as it radially expands, by the predetermined amount 932, such that the selected commissure at 930 ends up be circumferentially aligned with the marker 600. As a result, the selected commissure at 930 of the implanted prosthetic valve can be aligned with a selected commissure of the native valve.

In alternate embodiments, the predetermined amount 932 of offset can be different from the predetermined amount of inflation of the prosthetic valve upon deployment via inflating the balloon. For example, as described further below, the predetermined amount of offset can be determined based on a desired imaging view selected for viewing the delivery apparatus in a heart during an implantation procedure (e.g., based on a known location of the target commissure of the native valve within the selected imaging view). In some embodiments, the predetermined amount of offset can be determined based on both the selected imaging view and the predetermined amount of rotation of the prosthetic valve upon deployment.

In order to mount and crimp the prosthetic valve onto the valve mounting portion of the delivery apparatus at a predetermined position and/or orientation (e.g., circumferential position and/or orientation) relative to the delivery apparatus (e.g., relative to the radiopaque marker on the distal shoulder or another portion of the distal end portion of the delivery apparatus), a mounting assembly can be used. The mounting assembly can include a first component configured to interface with an uncrimped (e.g., at least partially radially expanded) prosthetic valve and a second component configured to interface with a portion of the distal end portion of the delivery apparatus (e.g., a portion disposed proximal and/or adjacent to the valve mounting portion). The first and second components of the mounting assembly can be further configured to interface with different sides of a crimping device. As a result, the mounting assembly can hold the prosthetic valve at a predetermined orientation and/or predetermined position relative to the delivery apparatus within the crimper. Then, after crimping the prosthetic valve onto the valve mounting portion of the delivery apparatus, the prosthetic valve can be arranged in the radially compressed configuration, in a predetermined position and orientation relative to the delivery apparatus. For example, the radially compressed prosthetic valve can be arranged on the delivery apparatus such that a selected commissure of the prosthetic valve is circumferentially offset from the marker (or other desired landmark) on the delivery apparatus by the predetermined amount (e.g., as shown in FIG. 42).

FIGS. 43-52 show embodiments of various components that can be used in a mounting assembly configured to crimp a prosthetic valve (such as one of the prosthetic valves described herein) onto a valve mounting portion of a delivery apparatus (e.g., valve mounting portion 324 of delivery apparatus 300) in a predetermined position and orientation. The prosthetic valve may be crimped to the valve mounting portion of the delivery apparatus in a variety of manners. In some embodiments, a crimping device, such as the crimping device 1084 shown in FIGS. 43 and 44, can be used to crimp the prosthetic valve onto the valve mounting portion of the delivery apparatus. As described further below, the crimping device 1084 can include mating interfaces, on opposite sides of the crimping device 1084, that are configured to receive and mate with corresponding mating interfaces on first and second components of the mounting assembly.

Figure 44:
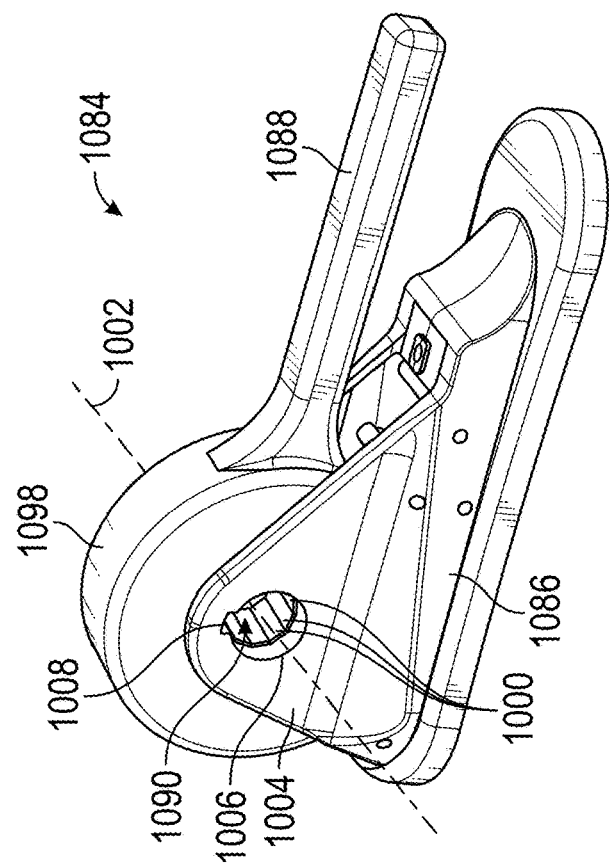
FIG. 44 is a front perspective view of the crimping device of FIG. 43.
Figure 43:
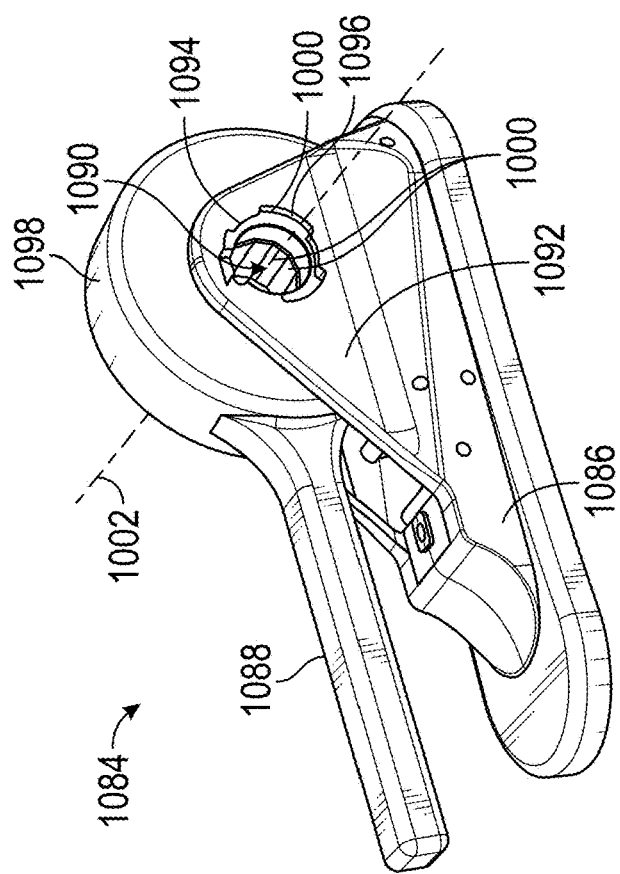
FIG. 43 is a rear perspective view of an exemplary embodiment of a crimping device configured to crimp a prosthetic valve onto a portion of a delivery apparatus.

FIG. 43 illustrates a rear perspective view of the crimping device 1084 (or a view from the proximal side of the crimping device 1084) and FIG. 44 illustrates a front perspective view of the crimping device 1084 (or a view from the distal side of the crimping device 1084). The crimping device 1084 can include a base 1086, an actuator in the form of a handle 1088, and a channel 1090 for the prosthetic valve and the delivery apparatus to be inserted into. The crimping device 1084 may include a proximal face 1092 including a proximal opening 1094 that leads into the channel 1090. The proximal opening 1094 may be configured for the delivery apparatus to be inserted into the channel 1090 therethrough.

Figure 49:
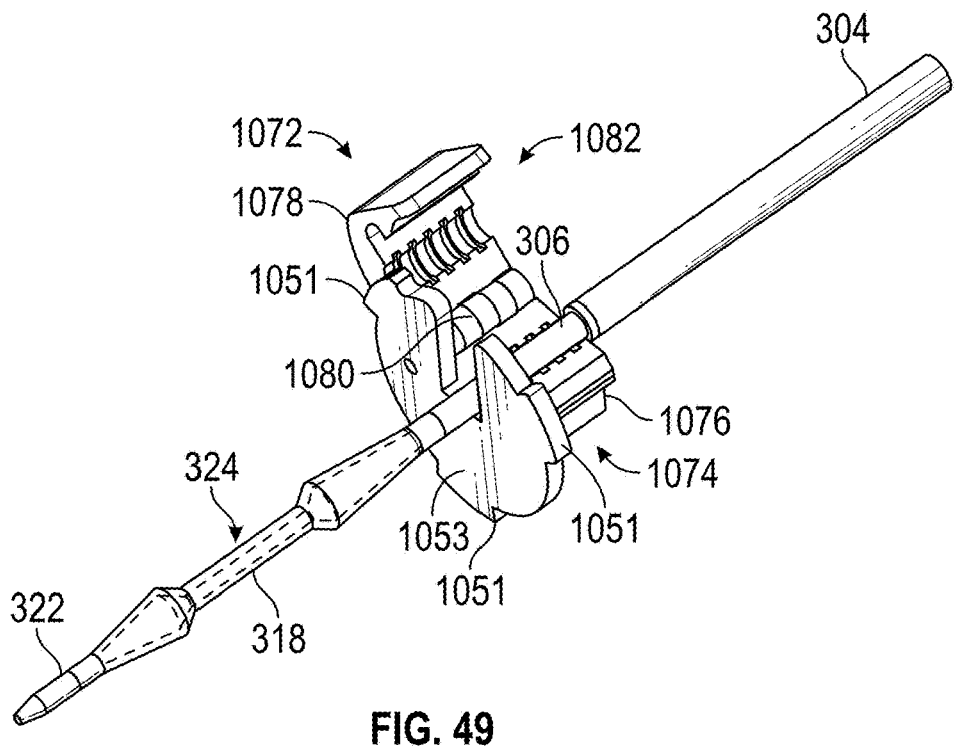
FIG. 49 is a perspective view of an embodiment of a positioning device of a mounting assembly, coupled to a distal end portion of a delivery apparatus.

In some embodiments, the proximal face 1092 can include a mating interface with mating structures 1096 in the form of cut-outs that can be configured to mate with a positioning device 1072, for example as shown in FIG. 49. For example, the mating interface can include one or more mating structures 1096.

The crimping device 1084 can further include a rotatable body 1098 configured to be rotated with rotation of the handle 1088. The crimping device 1084 may operate by a plurality of pressing surfaces 1000 surrounding the channel 1090 and being configured to apply a compressive force to radially compress a prosthetic valve positioned within the channel 1090 (e.g., prosthetic valve 922 shown in FIGS. 51 and 52, as described further below). The pressing surfaces 1000 may surround an axis 1002 of the channel 1090. The pressing surfaces 1000 may be configured such that as the rotatable body 1098 is rotated, a body presses and moves the pressing surfaces 1000 towards the center of the channel 1090 and the diameter of the channel 1090 reduces. The pressing surfaces 1000 may form an iris structure that allows the pressing surfaces 1000 to move towards the center of the channel 1090 and reduce the diameter of the channel 1090. A prosthetic valve positioned within the channel 1090 will accordingly be compressed within the channel 1090, due to the radially compressive force of the pressing surfaces 1000 against the prosthetic valve.

As shown in FIG. 44, the crimping device 1084 may include a distal face 1004 including a distal opening 1006 that leads into the channel 1090. The distal face 1004 can include a mating interface, which can comprise a cut-out portion 1008. In some embodiments, the cut-out portion 1008 can be configured as a notch, indentation, depression, or the like, in the distal face 1004. The cut-out portion 1008 can be configured (e.g., shaped) to receive an alignment device of a support body for the prosthetic valve (e.g., alignment member 1024 shown in FIG. 45, as described further below).

The distal opening 1006 can be configured for a portion of the delivery apparatus to pass therethrough during a crimping operation being performed by the crimping device 1084.

The configuration of a crimping device can be varied in alternate embodiments.

For crimping the prosthetic valve onto the valve mounting portion of the delivery apparatus, it may be desirable to maintain the leaflets (e.g., leaflets 60 of prosthetic heart valve 50 shown in FIGS. 2A and 2B) in an open position during crimping of the prosthetic valve to the delivery apparatus, thereby reducing a likelihood of degradation to the leaflets and/or attachments of the leaflets to a frame of the prosthetic valve. Thus, in some embodiments, a support body that is configured to support and/or maintain one or more leaflets of the prosthetic valve in an open position can be used as the first component of a mounting assembly that is configured to hold the prosthetic valve and position the prosthetic valve within the crimper.

Figure 45:
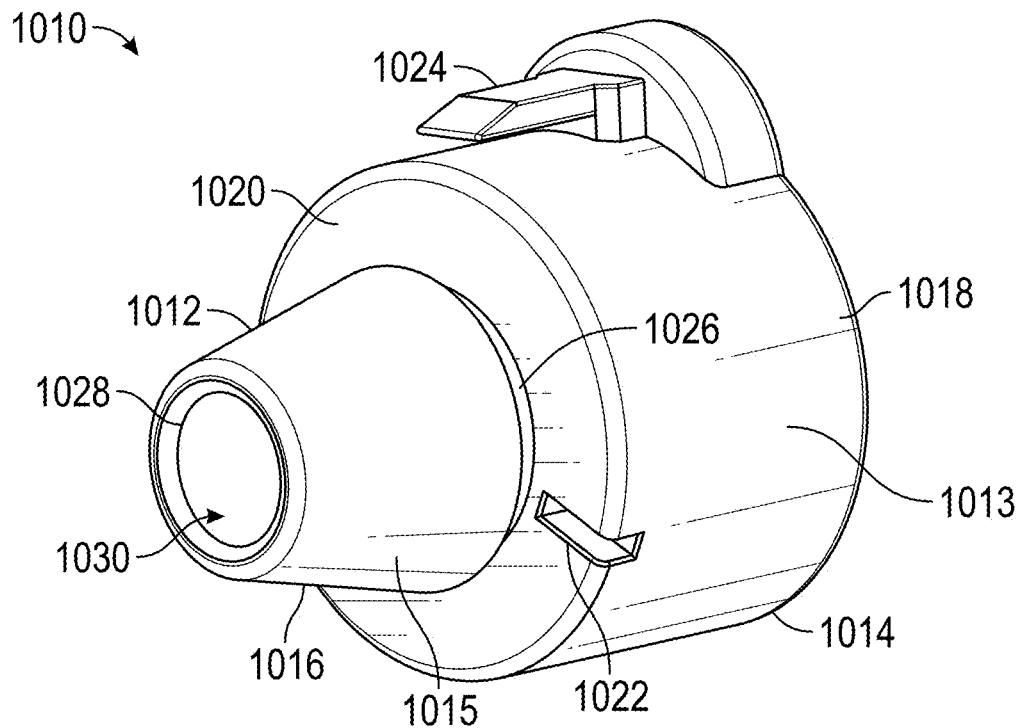
FIG. 45 is a perspective view of an embodiment of a support body for a mounting assembly configured to mount and crimp a prosthetic valve onto a delivery apparatus at a predetermined position and/or orientation relative to the delivery apparatus, the support body configured to hold the prosthetic valve in a radially expanded state.

An exemplary support body 1010 is shown in FIG. 45. The support body 1010 can be configured to be inserted into a crimping device, such as crimping device 1084 shown in FIGS. 43 and 44, and can have a support portion 1012 configured to be positioned between one or more leaflets of the prosthetic device and the delivery apparatus (e.g., delivery apparatus 300) and for supporting the one or more leaflets in an open position. The support body 1010 can comprise the support portion 1012 and a coupling portion 1013 configured to be received within and/or coupled to the crimping device. The support body 1010 can include a first end 1014 and a second end 1016. The support portion 1012 can include an outward-facing support surface 1015 that is configured to receive the prosthetic valve thereon (e.g., an interface with the valve leaflets).

Figure 47:
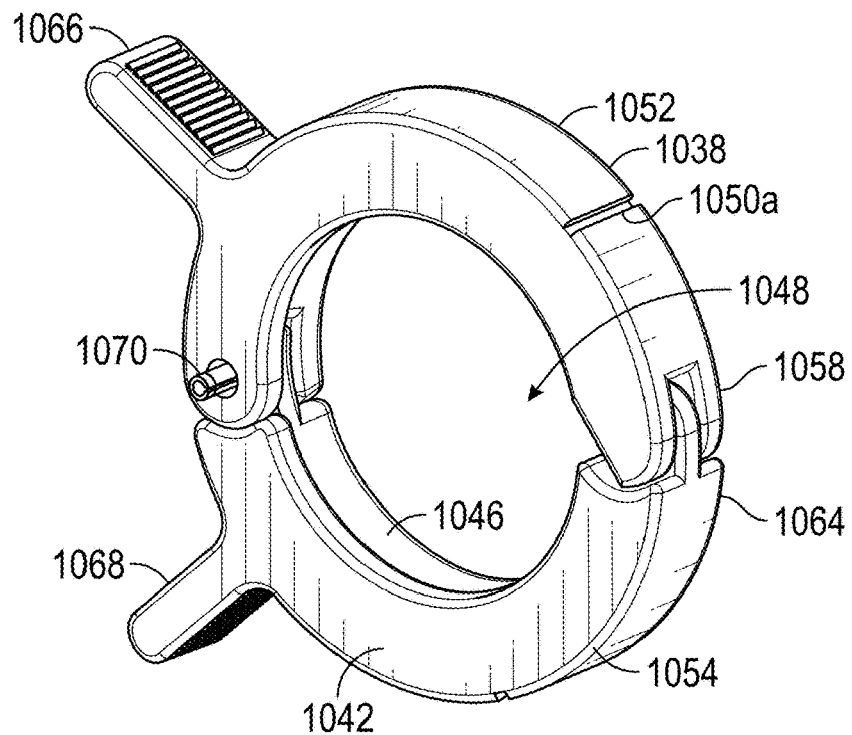
FIG. 47 is a rear perspective view of the ring body of FIG. 46.
Figure 48:
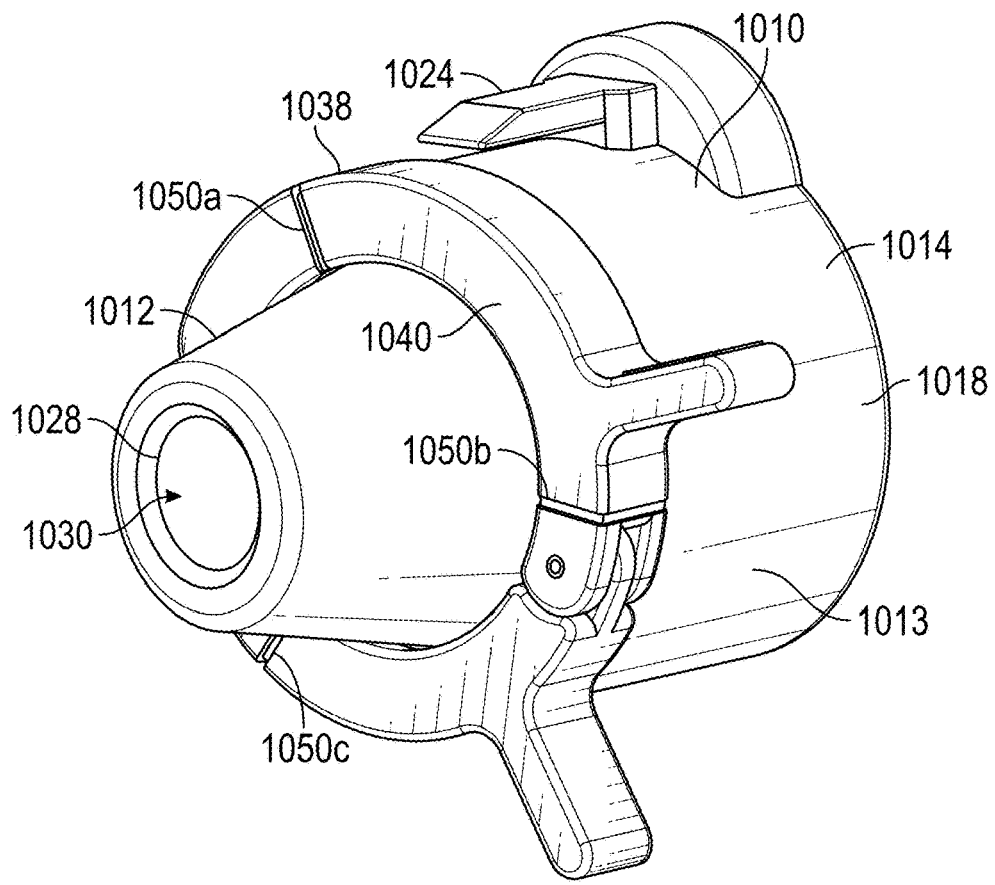
FIG. 48 is a perspective view of the ring body of FIG. 46 coupled with the support body of FIG. 45.

In some embodiments, as shown in FIG. 45, the coupling portion 1013 can have a cylindrical shape with a cylindrical outer surface 1018. The coupling portion 1013 can extend from the first end 1014 to a first (e.g., proximally facing) surface 1020 that can be arranged normal to a central longitudinal axis extending through a center of the support body 1010, from the first end 1014 to the second end 1016. The first surface 1020 can join the coupling portion 1013 to the support portion 1012, including the support surface 1015. In some embodiments, the first surface 1020 can include an alignment element, such as a recess 1022, which can be configured to receive a coupler (e.g., coupling element) 1070 of a ring body (also referred to herein as an alignment ring) 1038, as shown in FIGS. 47 and 48.

An alignment member 1024 can be arranged on the coupling portion 1013 and configured to rotationally align the support body 1010 with the crimping device 1084. The alignment member 1024 can be circumferentially positioned on the coupling portion 1013, proximate to the first end 1014, at a position that circumferentially aligns the support body 1010 in a predetermined position and orientation within the crimping device 1084.

In some embodiments, as shown in FIG. 45, the alignment member 1024 can comprise an axially extending protrusion that extends axially outward from the first end 1014 toward to the second end 1016 of the support body 1010. In other embodiments, the alignment member can have other configurations, such as a recess or other alignment feature that is configured to mate with a corresponding mating interface of the crimping device 1084 (e.g., cut-out portion 1008 shown in FIG. 44).

For example, the alignment member 1024 can be configured to insert into the cut-out portion 1008 on the distal face 1004 of the crimping device 1084 to rotationally align the support body 1010 with the crimping device 1084. The alignment member 1024 can further be configured to allow the support body 1010 to slide distally out of the cut-out portion 1008 during operation of the crimping device 1084.

The support portion 1012 can extend from the first surface 1020 to the second end 1016. The support portion 1012 includes the support surface 1015. The support portion 1012, and thus the support surface 1015, can have a tapered shape that tapers radially inward in a direction from the first surface 1020 to the second end 1016. For example, a diameter of the support portion 1012 can decrease from the first surface 1020 to the second end 1016. In some embodiments, the support portion 1012 can have a conical shape, as shown in FIG. 45. In alternate embodiments, the support portion 1012 can have another shape that tapers as described above, such as hexagonal or pyramidal.

In some embodiments, the support portion 1012 can have a greatest diameter that is less than the diameter of the cylindrical coupling portion 1013.

In some embodiments, a connector portion 1026 (FIG. 45) can join the support surface 1015 to the first surface 1020 and can have an annular shape with a relatively constant diameter.

Figure 50:
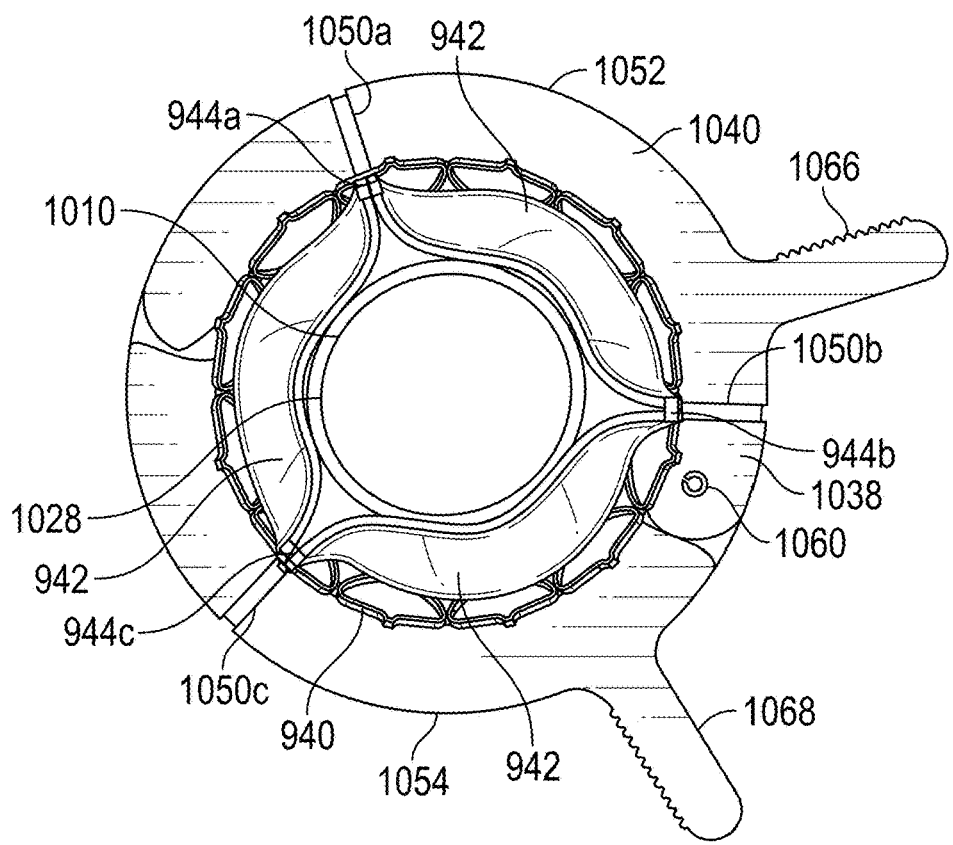
FIG. 50 is an end view of a prosthetic valve mounted on the support body of FIG. 45, with commissure aligned with corresponding indicators on the ring body of FIG. 46.

The support surface 1015 can be configured for interior surfaces of the leaflets of the prosthetic valve to contact and rest upon the support surface 1015 when the prosthetic valve is positioned around the support portion 1012 (as shown in FIG. 50). The support surface 1015 can be configured to resist the leaflets from moving to a closed position when the prosthetic valve is positioned around the support portion 1012 and within the crimping device 1084.

The tapered shape of the support portion 1012, as described above, can allow the support body 1010 to be slid distally, away from the crimping device 1084, when the pressing surfaces 1000 of the crimping device 1084 press upon the support surface 1015. As such, the tapered shape of the support portion 1012 may cause a pressing force applied by the pressing surfaces 1000 to move proximally along the tapered shape of the support surface 1015, thereby moving the support body 1010 distally and out of the crimping device 1084. The support surface 1015 can maintain the leaflets in an open position as the pressing surfaces 1000 press against the tapered support surface 1015.

Figure 52:
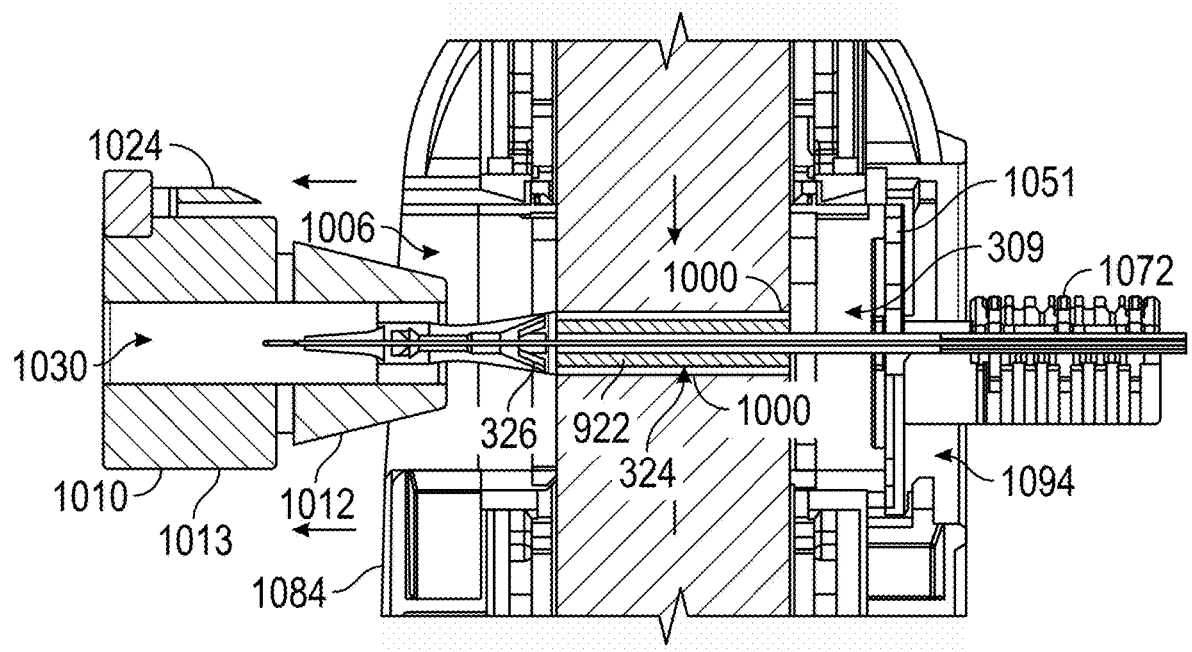
FIG. 52 is a cross-sectional view of the prosthetic valve radially compressed onto the valve mounting portion of the delivery apparatus, after performing a crimping operation with the crimping device of FIG. 43.

In this way, the support body 1010 can be configured to slide axially away from the prosthetic valve during and as a result of the crimping device 1084 crimping the prosthetic valve. The support body 1010, for example, can be configured to insert into the channel 1090 of the crimping device 1084 and slide axially away from the channel 1090 upon the crimping device 1084 crimping the prosthetic valve 922, and thus, may slide in an axially distal direction (as shown in FIG. 52).

As shown in FIG. 45, the support body 1010 can include a central aperture 1028 leading to a central channel 1030. The central aperture 1028 and central channel 1030 may be configured for the delivery apparatus to extend therethrough. An inner surface of the support portion 1012 can define the central channel 1030. The central aperture 1028 can be positioned at the second end 1016 and the central channel 1030 can extend from the second end 1016 to the first end 1014.

Figure 51:
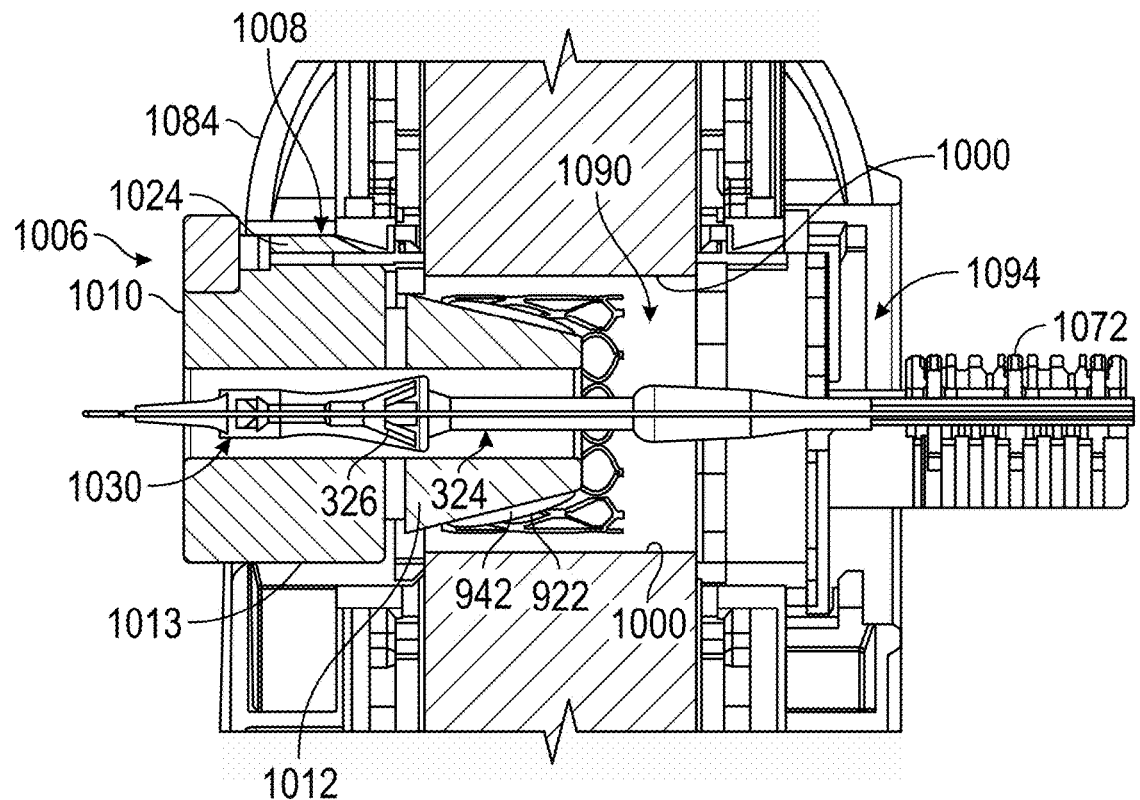
FIG. 51 is a cross-sectional view of the mounting assembly, including the support body of FIG. 45 and the positioning device of FIG. 49, coupled to and arranged within the crimping device of FIG. 43 such that the prosthetic valve is arranged in a predetermined orientation and/or position around a valve mounting portion of a distal end portion of the delivery apparatus, relative to the delivery apparatus.

In operation, the prosthetic valve 922 may be slid distally onto the support surface 1015 of the support portion 1012 of the support body 1010, with the frame 940 of the prosthetic valve 922 extending over the support surface 1015 and the inner surfaces of the leaflets 942 of the prosthetic valve being arranged against the support surface 1015 (FIGS. 50 and 51).

To align the prosthetic valve 922 in a desired circumferential orientation around the support portion 1012, and to space the prosthetic valve 922 from the first surface 1020 at a desired spacing, a ring body (which can also be referred to as an alignment ring) can be utilized and positioned upon the support body 1010.

Figure 46:
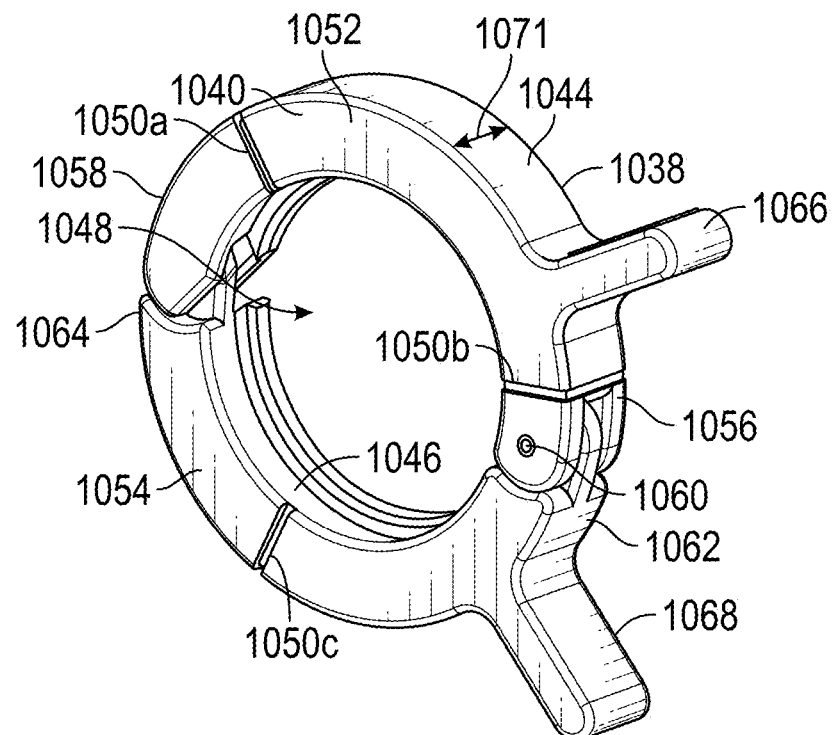
FIG. 46 is a front perspective view of an embodiment of a ring body configured to couple to the support body of FIG. 45 and circumferentially align the prosthetic valve on the support body in a desired orientation.

FIGS. 46 and 47, for example, illustrate perspective views, from different sides, of a ring body 1038 that can be utilized with the support body 1010. The ring body 1038 can be configured to couple to and extend around the support body 1010. The ring body 1038 can include a first surface (which may be a proximally facing surface) 1040 (FIG. 46), a second surface 1042 facing opposite the first surface 1040 (which may be a distally facing surface) (FIG. 47), and an outer (e.g., circumferential) surface 1044 facing radially outward and connecting the first surface 1040 to the second surface 1042. The ring body 1038 can include an inner surface 1046 facing opposite the outer surface 1044 and facing radially inward, the inner surface 1046 defining a central channel (e.g., opening or aperture) 1048 of the ring body 1038.

In some embodiments, an alignment guide can be positioned on the ring body 1038 (FIG. 46). The alignment guide can comprise one or more indicators 1050*a-c* (which may also be referred to as alignment markers) configured to indicate a desired circumferential (e.g., rotational) position of selected elements (e.g., commissures) of the prosthetic valve 922 relative to the ring body 1038 (FIGS. 46, 48, and 50). Each indicator 1050*a-c* may further indicate the desired circumferential position of the selected elements of the prosthetic valve 922 relative to the support body 1010 (e.g., when the ring body 1038 is coupled to the support body 1010, as described further below with reference to FIGS. 48 and 50).

Each indicator 1050*a-c* can comprise a marking, groove, raised element, or other form of indicator, on one or more of the first surface 1040, the second surface 1042, or the outer surface 1044 of the ring body 1038. One or more or each of the indicators 1050*a-c*, for example, can comprise a variation in the surface profile of the ring body 1038, such as a raised portion or a recessed portion (e.g., groove). The indicators 1050*a-c* shown in FIGS. 46-48 and 50, for example, each comprise recessed portions in the form of grooves on the first surface 1040 and extending to the outer surface 1044. In some embodiments, the indicators 1050*a-c* can additionally be printed upon to vary a color of the respective indicator 1050*a-c* such that the indicator is easier to visualize. In some embodiments, the indicators 1050*a-c* may solely be printed upon the ring body 1038 without use of a variation of the surface profile (e.g., without grooves).

The indicators 1050*a-c* can be circumferentially spaced apart from each other on the ring body 1038. In some embodiments, the indicators 1050*a-c* can be equally spaced apart from each other around the circumference of the ring body 1038. The circumferential position of each indicator 1050*a-c* can correspond to and indicate a desired position of one of the commissures of the prosthetic valve when the ring body 1038 is coupled to the support body 1010 and the prosthetic valve is arranged around the support portion 1012 of the support body 1010 (e.g., as shown in FIG. 50). As such, a user may position the ring body 1038 on the support body 1010 and align the commissures 944*a-c* of the prosthetic valve 922 with respective indicators 1050*a-c* (FIG. 50).

In some embodiments, the ring body 1038 can include one or more arms (which can also referred to as body portions) 1052, 1054 each extending around and defining the central channel 1048 (FIGS. 46 and 47). Each arm 1052, 1054 can have an arcuate shape forming the ring body 1038. Each arm 1052, 1054 can comprise half of the ring body 1038 or another amount as desired.

The first arm 1052 can include a first end portion 1056 (FIG. 46) and a second end portion 1058 (FIG. 47), with the first end portion 1056 positioned at a pivot 1060 (FIG. 46) that couples the first arm 1052 to the second arm 1054. The second end portion 1058 of the first arm 1052 may include a coupler for coupling to the second arm 1054. The second arm 1054 may include a first end portion 1062 (FIG. 46) positioned at the pivot 1060 and a second end portion 1064 (FIG. 47) positioned at the coupler. The coupler (also can be referred to as a coupling interface) may comprise a recess in the second end portion 1058 of the first arm 1052, and a protrusion at the second end portion 1064 of the second arm 1054. The protrusion may extend into the recess and may be held in position with an interference fit or another form of coupling. As such, the second end portions 1058, 1064 of the respective first arm 1052 and second arm 1054 may be configured to couple to each other to hold the ring body 1038 together. If desired, the ring body 1038 may be separated and removed from the support body 1010 by the second end portions 1058, 1064 being separated from each other and the arms 1052, 1054 pivoted about the pivot 1060 to an open position. For example, the ring body 1038 can be opened to be removed from the support body 1010 and can be closed to be held around and coupled to the support body 1010.

As shown in FIGS. 46 and 47, a first lever (e.g., radial extension) 1066 may extend radially outward from the first arm 1052, and a second lever (e.g., radial extension) 1068 may extend radially outward from the second arm 1054. The first lever 1066 and second lever 1068 may each be configured to be pressed to rotate the first arm 1052 or the second arm 1054 about the pivot 1060 to cause the ring body 1038 to move to the open position.

The ring body 1038 may have an axial width 1071 that may define a spacing of the prosthetic valve from the first surface 1020 of the support body 1010 (FIG. 46).

As shown in FIG. 47, the ring body 1038 can include a coupler 1070 extending axially outward from the second surface 1042. In some embodiments, the coupler 1070 can be a protrusion configured to extend into the recess 1022 of the support body 1010 (FIG. 45). In alternate embodiments, the coupler 1070 can be a differently shaped mating feature configured to mate with a corresponding feature on the support body 1010.

The coupler 1070 may be circumferentially positioned relative to the recess 1022 such that the ring body 1038 mates with the support body 1010 at a desired circumferential alignment. In this way, the coupler 1070 and the recess 1022 may rotationally align the ring body 1038 with the support body 1010 so that the prosthetic valve is circumferentially aligned in a desired orientation relative to the support body 1010 and crimping device.

In operation, the ring body 1038 can be positioned upon and/or around the support body 1010, with the indicators 1050*a-c* positioned at a desired rotational (e.g., circumferential) alignment relative to the support body 1010 (FIG. 48). The coupler 1070 shown in FIG. 47, for example, can be received within the recess 1022, thereby circumferentially aligning the ring body 1038 at a desired position relative to the support body 1010. In other embodiments, other alignment devices may be utilized to rotationally align the ring body 1038 with respect to the support body 1010 in the desired rotational alignment.

The ring body 1038 can abut the first surface 1020 of the support body 1010. The ring body 1038 can be configured to abut the prosthetic valve 922 when the prosthetic valve 922 is positioned on the support body 1010. As such, the prosthetic valve 922 may be positioned on the support surface 1015 with an end of the prosthetic valve 922 abutting the first surface 1040 of the ring body 1038 and defining a position of the prosthetic valve 922 upon the support surface 1015. The ring body 1038 accordingly may comprise a spacer configured to define a position of the prosthetic valve 922 upon the support body 1010.

In some embodiments, the ring body 1038 can be oriented in an open configuration with the arms 1052, 1054 open and then may be positioned on and around the support body 1010 with the arms 1052, 1054 closed to secure the ring body 1038 around the support body 1010. The ring body 1038 may be positioned upon the connector portion 1026 shown in FIG. 45, for example.

The prosthetic valve 922 may then be positioned around the support portion 1012 and the support surface 1015, and abutted against the first surface 1040 of the ring body 1038. The prosthetic valve 922 may be positioned upon the support surface 1015 with the commissures 944a-c circumferentially aligned with the indicators 1050a-c and an end of the prosthetic valve 922 abutting the first surface 1040 (FIG. 50).

The use of the ring body 1038 may allow the commissures 944a-c of the prosthetic valve 922 to be positioned in a desired circumferential orientation relative to the ring body 1038 and thus relative to the support body 1010 (e.g., relative to the alignment member 1024 of the support body 1010). The alignment member 1024 can then rotationally align the support body 1010 with the crimping device 1084, and thus place the commissures 944a-c of the prosthetic valve 922 in a desired rotational orientation within the crimping device 1084.

As a result, the prosthetic valve 922 can be crimped onto the delivery apparatus at a predetermined circumferential orientation relative to the delivery apparatus (e.g., relative to a radiopaque marker on the delivery apparatus, as described herein).

The support body 1010 and the ring body 1038 may each be part of an assembly or system (e.g., mounting assembly) for use in crimping a prosthetic valve having one or more leaflets to a delivery apparatus. In some embodiments, the assemblies or systems may include a positioning device 1072 configured to couple to a portion (e.g., distal end portion) of the delivery apparatus, proximal to the valve mounting portion. FIG. 49, for example, illustrates an embodiment of such a positioning device 1072 positioned proximal of the valve mounting portion 324. The positioning device 1072 includes a body 1074 including a first portion 1076 and a second portion 1078 joined at a hinge 1080. The body 1074 can include a central channel 1082 that an intermediate shaft 306 (or another shaft portion, such as the outer shaft 304) of the delivery apparatus may be positioned in, with the second portion 1078 rotating about the hinge 1080 to close the central channel 1082 and retain the delivery apparatus (e.g. the intermediate shaft 306) within the central channel 1082.

The body 1074 may further include a flange portion 1053 including one or more mating surfaces (e.g., interfaces) in the forms of flanges 1051 (FIG. 49) that are configured to engage the mating structures 1096 of the proximal face 1092 of the crimping device 1084 (FIG. 43).

The positioning device 1072 may be utilized to couple to the distal end portion 309 of the delivery apparatus and suspend the distal end portion 309 of the delivery apparatus in position within the channel 1090 of the crimping device 1084 (FIGS. 51 and 52). The positioning device 1072 accordingly may hold the delivery apparatus spaced from the pressing surfaces 1000 of the crimping device 1084, as shown in FIG. 51 for example.

Further, the positioning device 1072 may be positioned axially along the delivery apparatus such that the valve mounting portion 324 is held within a defined axial position within the channel 1090 of the crimping device 1084. In some embodiments, such a feature may further allow the distal shoulder 326 of the delivery apparatus to be positioned outside of the channel 1090 of the crimping device 1084 and distal of the channel 1090 such that the distal shoulder 326 is not pressed by the pressing surfaces 1000 during crimping. The delivery apparatus may further be held in a defined axial position relative to the prosthetic valve 922 positioned upon the support body 1010 (FIG. 51).

An exemplary method of operation of the systems disclosed herein may include the following steps. Steps may be modified, excluded, or substituted across embodiments as desired.

Initially, the ring body 1038 can be positioned upon the support body 1010 in a configuration shown in FIG. 48 for example. The ring body 1038 may be rotationally oriented upon the support body 1010 in a defined position, for example, via the coupling of the coupler 1070 shown in FIG. 47 with the recess 1022 shown in FIG. 48. As such, the prosthetic valve 922 may be positioned upon the support surface 1015 with the commissures 944a-c of the prosthetic valve 922 circumferentially aligned with the indicators 1050a-c (as shown in FIG. 50). The prosthetic valve 922 may be abutted against the ring body 1038.

With the prosthetic valve 922 positioned upon the support surface 1015, in the desired rotational alignment, the ring body 1038 may then be removed from the support body 1010, prior to crimping the prosthetic valve 922 to the delivery apparatus. For example, the levers 1066, 1068 may be pressed to rotate the arms 1052, 1054 about the pivot 1060 and open the ring body 1038.

With the ring body 1038 removed, the support body 1010 may be inserted into the crimping device 1084 with the prosthetic valve 922 positioned around the support portion 1012. FIG. 51, for example, illustrates the prosthetic valve 922 positioned on and around the support portion 1012 and the support body 1010 inserted into the channel of the crimping device 1084. The distal opening 1006 of the crimping device 1084 may be configured for the support body 1010 to be inserted into the channel 1090. The channel 1090 of the crimping device 1084 may be configured to receive the prosthetic valve 922, the support body 1010, and the distal end portion 309 of the delivery apparatus.

Upon insertion of the support body 1010 into the channel 1090 of the crimping device 1084, the alignment member 1024 can be aligned (e.g., received within) with the cut-out portion 1008 of the crimping device 1084. As such, the rotational orientation of the support body 1010 within the channel 1090 of the crimping device 1084, and accordingly the rotational orientation of the prosthetic valve 922 within the channel 1090 of the crimping device 1084, may be set in the desired position.

With the support body 1010 and the prosthetic valve 922 inserted into the channel 1090 of the crimping device 1084, the positioning device 1072 (or an alternate positioning device, as described further below) can be coupled to the distal end portion 309 of the delivery apparatus and then inserted into the proximal opening 1094 of the crimping device 1084 (FIG. 51). The flanges 1051 of the positioning device 1072 may mate with the corresponding mating structures 1096.

FIG. 51 illustrates a cross sectional view of the pressing surfaces 1000 in position around the channel 1090 of the crimping device 1084, and the support body 1010 inserted into the channel 1090 with the prosthetic valve 922 positioned around the support portion 1012.

As shown in FIG. 51, the support portion 1012 of the support body 1010 extends axially within the channel 1090, toward the proximal opening 1094 of the crimping device

1084. The support surface 1015 may be surrounded by the pressing surfaces 1000. The coupling portion 1013 of the support body 1010 can be arranged outside of and distal of the pressing surfaces 1000, and may be retained within the distal opening 1006 of the crimping device 1084. The alignment member 1024 may extend proximally into the cut-out portion 1008 of the crimping device 1084.

In FIG. 51, the valve mounting portion 324 of the delivery apparatus is positioned within the channel 1090 of the crimping device 1084. The prosthetic valve 922 is positioned within the channel 1090 and around the valve mounting portion 324 of the delivery apparatus. The support body 1010 is positioned within the channel 1090 and between the prosthetic valve 922 and the delivery apparatus. The support body 1010 supports the leaflets of the prosthetic valve 922 in an open position. The distal end portion 309 of the delivery apparatus extends distally within the interior channel 1090 of the crimping device 1084 and distally within the central channel 1030 of the support body 1010.

When inserted into the crimping device 1084, the positioning device 1072 may be coupled to the distal end portion 309 of the delivery apparatus, proximal to the valve mounting portion 324, and may be engaged with the mating structures 1096 of the proximal face 1092. The positioning device 1072 may be coupled to the distal end portion 309 of the delivery apparatus at a location such that the valve mounting portion 324 is positioned at a desired location within the channel 1090 and relative to the prosthetic valve 922. For example, as shown in FIG. 51, the prosthetic valve 922 may surround the valve mounting portion 324.

As described above, the rotational alignment of the prosthetic valve 922 relative to the distal end portion 309 of the delivery apparatus may be in a desired, predetermined orientation and/or position due to the prior use of the ring body 1038.

With the distal end portion 309 of the delivery apparatus, support body 1010, and prosthetic valve 922 in a desired position within the channel 1090, the actuator of the crimping device 1084 may be actuated to compress the prosthetic valve 922. For example, the handle 1088 may be rotated to rotate the rotatable body 1098 and move the pressing surfaces 1000 radially inward against the prosthetic valve 922 (FIGS. 43 and 44).

FIG. 52, for example, illustrates the pressing surfaces 1000 having been moved radially inward to apply a compressive force to the prosthetic valve 922. The prosthetic valve 922 is crimped to the delivery apparatus, around the valve mounting portion 324, utilizing the pressing surfaces 1000 of the crimping device 1084. As shown in FIG. 52, in its radially compressed state, the prosthetic valve 922 has increased in length, in the axial direction.

Crimping the prosthetic valve 922 to the delivery apparatus may include applying a force to the support surface 1015 of the support body 1010 with the pressing surfaces 1000, thereby causing the support body 1010 to slide axially within the channel 1090, away from the prosthetic valve 922 (FIG. 52).

For example, as described above, the tapered shape of the support portion 1012 and the support surface 1015 can cause the support body 1010 to slide distally away from the channel 1090 and away from the pressing surfaces 1000, as the pressing surfaces 1000 move radially inward. The support body 1010 is configured to releasably couple to the crimping device 1084 and slide in a direction axially away from the channel 1090 upon the crimping device 1084 crimping the prosthetic valve 922. In some embodiments, the support body 1010 may eject out from the distal opening 1006, as shown in FIG. 52. The elongate shape of the alignment member 1024 may allow the alignment member 1024 to slide out of the cut-out portion 1008.

In embodiments, the support body 1010 may not eject, but may remain coupled to the crimping device 1084 during crimping. The support body 1010, for example, may slide distally while a tether or another form of coupler keeps the support body 1010 coupled to the crimping device 1084 such that the support body 1010 does not fall.

Following the prosthetic valve 922 being crimped to the delivery apparatus, the positioning device 1072 may be disengaged from the mating structures 1096 and moved outward from the proximal opening 1094, thereby moving the delivery apparatus outward and away from the crimping device 1084. The positioning device 1072 may then be removed from the distal end portion 309 of the delivery apparatus, with the prosthetic valve 922 crimped to the delivery apparatus.

In this way, the use of a mounting assembly including the support body 1010 may allow the leaflets of the prosthetic valve 922 to remain in an open position during crimping. Such a feature may reduce the possibility of degradation to the prosthetic valve 922 occurring during crimping. Further, the tapered shape of the support surface 1015 may allow the support body 1010 to be slid outward from the crimping device via the radially inward movement of the pressing surfaces 1000, such that the support body 1010 automatically is moved outward and away from the crimped prosthetic valve 922. The support body 1010 may automatically slide axially outward such that the support surface 1015 is not positioned between the prosthetic valve 922 and the pressing surfaces 1000 following crimping. In some embodiments, the system may be configured such that a separate mechanism slides the support body 1010 distally, such that a tapered shape may not be utilized for the support surface 1015. For example, arms or gears or another form of coupler may engage the support body 1010 to move the support body 1010 away from the prosthetic valve 922.

Figure 53:
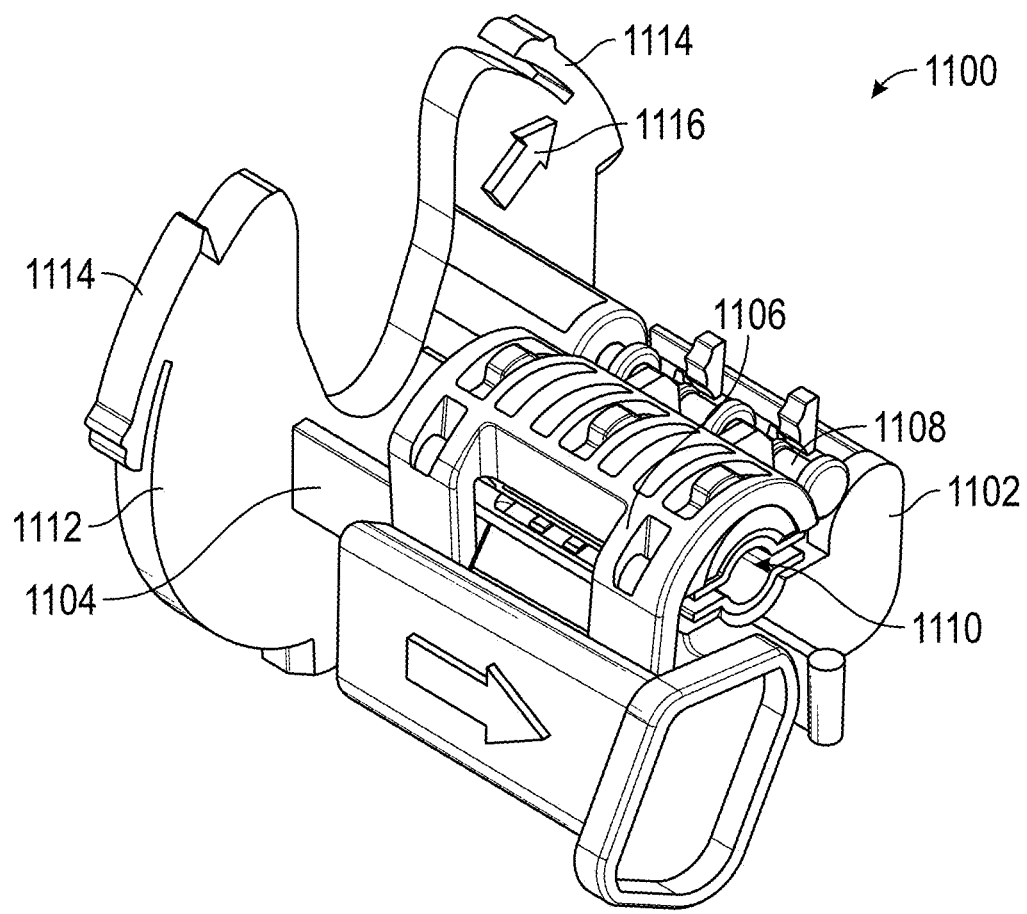
FIG. 53 is a perspective view of another embodiment of a positioning device that can be used in a mounting assembly and coupled to a crimping device.
Figure 54:
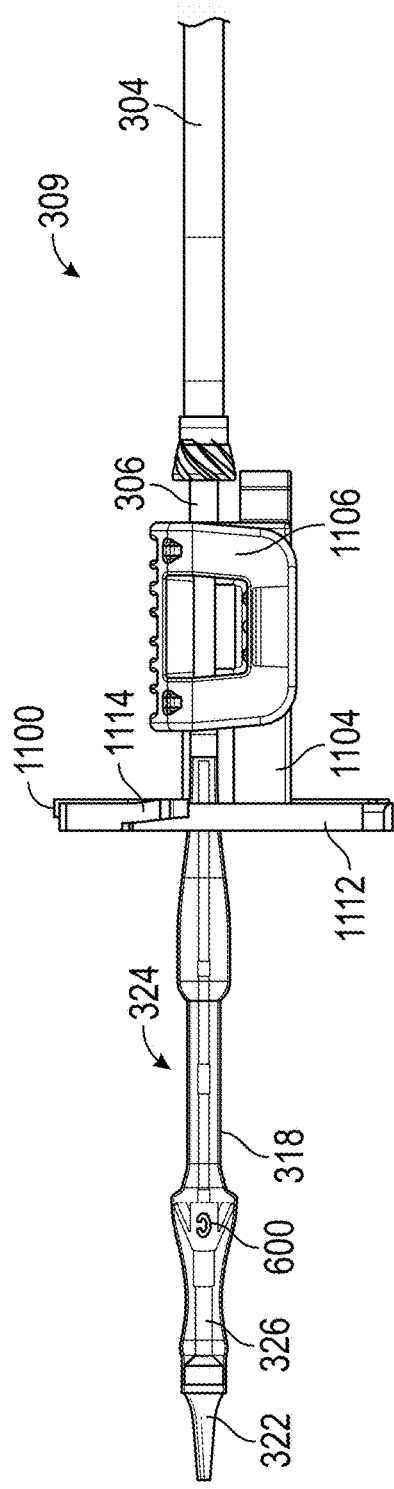
FIG. 54 is a side view of the positioning device of FIG. 53 coupled to a distal end portion of a delivery apparatus, proximal to a valve mounting portion.
Figure 55:
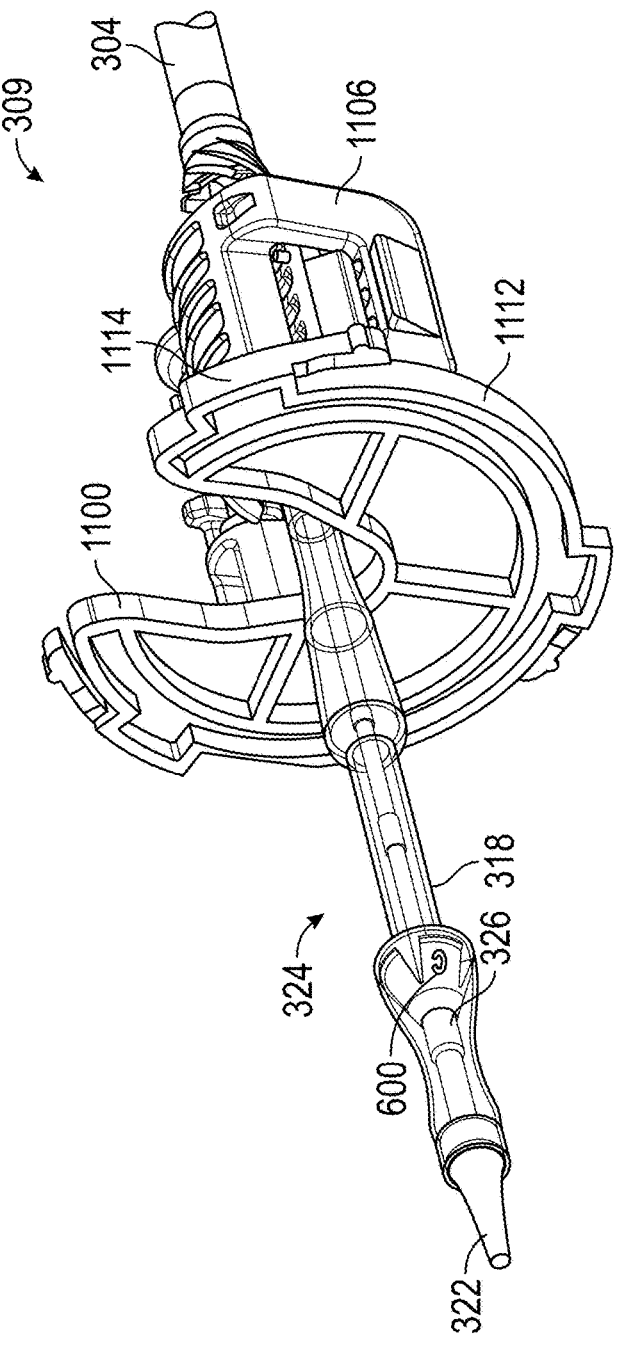
FIG. 55 is a perspective view of the positioning device of FIG. 53 coupled to the distal end portion of the delivery apparatus of FIG. 54.

In some embodiments, the mounting assembly can include a differently configured positioning device that is configured to mate with one or more mating structures (e.g., mating structures 1096 of crimping device 1084) arranged on one side of a crimping device. FIG. 53 shows another embodiment of a positioning device 1100 that can be used in a mounting assembly and coupled to a crimping device and FIGS. 54 and 55 show side and perspective views, respectively, of the positioning device 1100 coupled to the distal end portion 309 of the delivery apparatus 300, proximal to the valve mounting portion 324.

As shown in FIG. 53, the positioning device 1100 can include a body 1102 including a first portion 1104 and a second portion 1106 pivotably coupled to one another via a hinge 1108. The body 1102 can include a central channel 1110 (FIG. 53) that is configured to receive the intermediate shaft 306 (or another shaft portion, such as the outer shaft 304) of the delivery apparatus 300 (FIGS. 54 and 55).

The second portion 1106 of the body 1102 can include a flange portion 1112 extending radially outward therefrom and arranged at a distal end of the positioning device 1100. The flange portion 1112 can include one or more mating elements that are configured to mate with correspondingly shaped mating features in a side surface (e.g., proximal face) of a crimping device. In some embodiments, as shown in FIG. 53, the mating elements are configured as circumferentially extending extension portions 1114. In some embodiments, the extension portions 1114 can be spaced apart from one another around a circumference of the flange portion 1112.

In some embodiments, the flange portion 1112 can include one or more indicating elements 1116 that can indicate an orientation of insertion of the extension portions 1114 into the crimping device.

As shown in FIGS. 54 and 55, the positioning device 1100 is clamped around the intermediate shaft 306 at a location proximal to and adjacent to a proximal end portion of the balloon 318.

Alternate embodiments of mounting assemblies that are configured to crimp a prosthetic valve onto a delivery apparatus at a predetermined position and/or orientation relative to the delivery apparatus are described in International Patent Application No. PCT/US19/28831, which is incorporated by reference herein.

Figure 56:
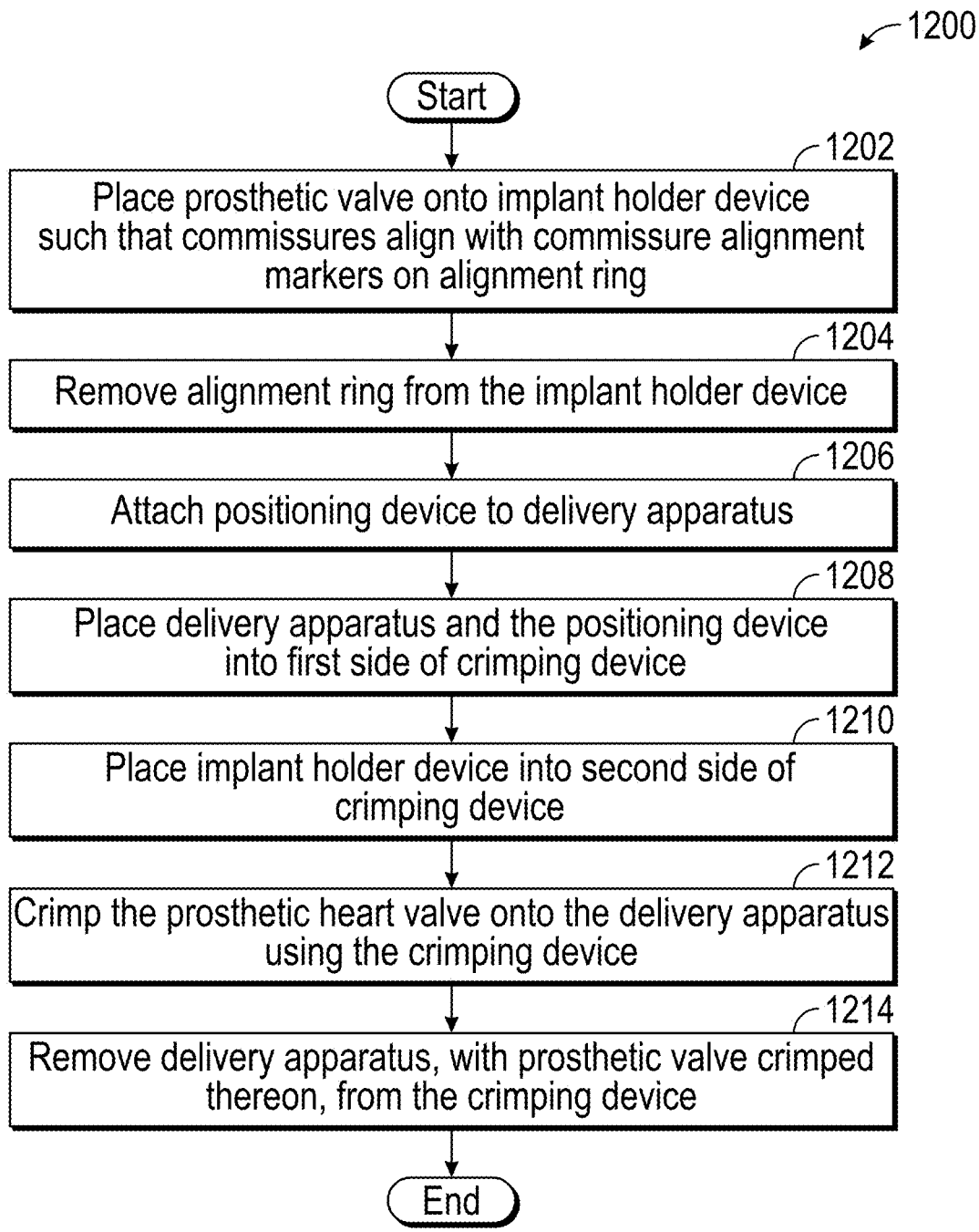
FIG. 56 is a flow chart of an exemplary method for crimping a prosthetic valve into a radially compressed state onto a distal end portion of a delivery apparatus, in a predetermined position and in a predetermined orientation relative to the delivery apparatus.

FIG. 56 is a flow chart of an exemplary method 1200 for crimping a prosthetic valve into a radially compressed state to a distal end portion of a delivery apparatus, in a predetermined position and in a predetermined orientation relative to the delivery apparatus. In some embodiments, method 1200 may utilize one or more components of the mounting assemblies described herein with reference to FIGS. 43-55.

Method 1200 begins at 1202 by placing (e.g., positioning) a prosthetic valve (e.g., prosthetic valve 10 of FIG. 1, prosthetic valve 50 of FIGS. 2A-2B, or prosthetic valve 922 of FIG. 41) onto an implant holder device such that one or more commissures of the prosthetic valve align with one or more corresponding indicators or alignment markers on an alignment ring (or ring body) coupled to the implant holder device. The implant holder device can be configured to receive an at least partially radially expanded prosthetic valve and hold the prosthetic valve in a desired circumferential orientation. In some embodiments, the implant holder device can be the support body 1010 of FIGS. 45 and 48 and the alignment ring can be the ring body 1038 of FIGS. 46-48 and 50. For example, in some embodiments, the method at 1200 can include rotationally aligning the prosthetic valve on a support portion of the support body such that one or more commissures of the prosthetic valve match up and align with corresponding indicators on the ring body (e.g., as shown in FIG. 50). In alternate embodiments, the alignment ring can be one of the alignment rings shown in FIGS. 65-68.

After aligning the commissures of the prosthetic valve on the implant holder device, method 1200 proceeds to 1204, which includes removing the alignment ring from the implant holder device, while the circumferentially aligned prosthetic valve remains attached to the implant holder device.

At 1206, the method includes attaching a positioning device to the delivery apparatus. In some embodiments, attaching the positioning device can include coupling a portion of the positioning device around a shaft of the delivery apparatus, proximal to a valve mounting portion of the delivery apparatus and a proximal portion of an inflatable balloon of the delivery apparatus. In some embodiments, the positioning device can be coupled to and around the intermediate (e.g., balloon shaft) of the delivery apparatus (e.g., intermediate shaft 306, as shown in FIG. 54). The positioning device can be one of the positioning devices described herein (e.g., positioning device 1072 of FIG. 49 or positioning device 1100 of FIGS. 53-55) or another positioning device configured to couple to the delivery apparatus and a crimping device and hold the delivery apparatus in a desired circumferential orientation relative to the crimping device. For example, the method at 1206 can include coupling the positioning device to the delivery apparatus such that a radiopaque marker on the delivery apparatus is held in a desired circumferential orientation within the crimping device, upon coupling the positioning device with the crimping device.

Method 1200 proceeds to 1208 and includes placing (e.g., arranging or coupling) the distal end portion of the delivery apparatus and the positioning device into a first (e.g., proximal) side of a crimping device (e.g., crimping device 1084 of FIGS. 43 and 44 or another crimping device). For example, a flange portion of the positioning device including one or more mating elements can be coupled to the first side of the crimping device such that the one or more mating elements mate with one or more corresponding mating elements in the first side of the crimping device. As a result, the distal end portion of the delivery apparatus, coupled with the positioning device, can be arranged within the crimping device, with the valve mounting portion arranged within a portion of the crimping device configured to press against and crimp the prosthetic valve. In this way, the positioning device and the valve mounting portion of the delivery apparatus can be received within the crimping device in a predetermined circumferential orientation and position.

At 1210, the method includes placing the implant holder device into a second (e.g., distal) side of the crimping device. For example, the method at 1210 can include inserting the implant holder device into the second side of the crimping device such that an alignment member of the implant holder device inserts into and/or mates with a corresponding mating structure or element of the crimping device. In this way, the implant holder device and the prosthetic valve arranged on the implant holder device can be received within the crimping device in a predetermined orientation. For example, when both the implant holder device coupled to the prosthetic valve and the positioning device coupled to the delivery apparatus are coupled with the crimping device, a selected commissure of the prosthetic valve can be offset, in a circumferential direction relative to a central longitudinal axis of the delivery apparatus, from a radiopaque marker (e.g., such as one of the markers shown in FIG. 28, 18A-18B, or 42) on the distal end portion of the delivery apparatus by a predetermined amount.

At 1212, the method includes crimping the prosthetic valve into a radially compressed state onto the valve mounting portion of the delivery apparatus using the crimping device. In some embodiments, crimping the prosthetic valve at 1212 can include crimping the prosthetic valve into its radially compressed state around an inflatable balloon, at the valve mounting portion. Additionally, in some embodiments, crimping the prosthetic valve at 1212 can include crimping the prosthetic valve into the radially compressed state on the valve mounting portion of the delivery apparatus while maintaining the predetermined amount of offset between the radiopaque marker and the selected commissure of the prosthetic valve (e.g., as shown in FIG. 42, as described above). As described further below, the predetermined amount of offset can be determined (e.g., preselected) based on a desired or selected imaging view used to image the distal end portion of the delivery apparatus during an implantation procedure and rotationally align the prosthetic valve with the native anatomy (e.g., to achieve commissure alignment). During crimping at 1212, in some embodiments, the implant holder device can automatically uncouple from the prosthetic valve and/or the crimping device (e.g., as described above with reference to FIGS. 51 and 52).

At 1214, the method includes removing the distal end portion of the delivery apparatus, with the prosthetic valve crimped thereon, from the crimping device. The method at 1214 can further include removing (e.g., uncoupling) the positioning device from the delivery apparatus. In this way, the positioning device can be removably coupled to the delivery apparatus and the implant holder device can be removably coupled to the prosthetic valve, as described above. After removal from the crimping device, the delivery apparatus may then be prepared for insertion into a vessel of a patient and for navigation to the patient's heart.

Figure 57:
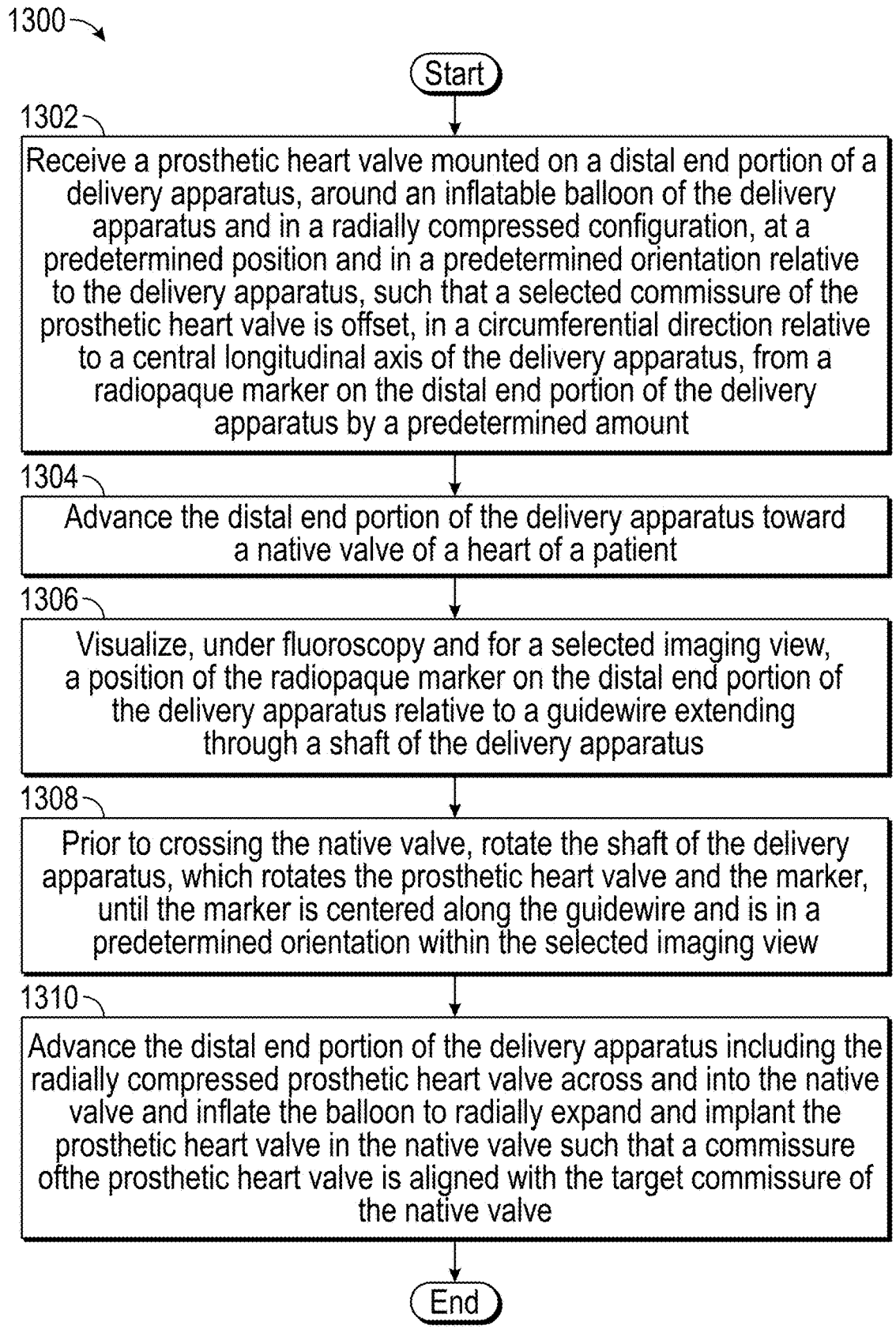
FIG. 57 is a flow chart of an exemplary method for implanting a prosthetic valve at a native valve of a patient with one or more selected commissures of the prosthetic valve in alignment with one or more corresponding commissures of the native valve.

FIG. 57 is a flow chart of an exemplary method 1300 for implanting a prosthetic valve at a native valve of a heart of a patient with one or more selected commissures of the prosthetic valve in alignment (e.g., in a circumferential direction) with one or more corresponding commissures of the native valve. In some embodiments, method 1300 can be carried out with a delivery apparatus that is configured to deploy a radially compressed prosthetic valve mounted on a distal end portion of the delivery apparatus via inflating a balloon of the delivery apparatus. An exemplary delivery apparatus 300 is shown in FIGS. 9-11. The delivery apparatus can include one or more of the components described herein to aid in rotationally aligning the delivery apparatus at the implantation site (e.g., native valve) to achieve the above-described commissure alignment. In alternate embodiments, method 1300 can be carried out with a delivery apparatus that is configured to deploy a radially compressed valve by axially moving a sheath or capsule covering a radially compressed prosthetic valve relative to a shaft of the delivery apparatus (and thus moving the capsule instead of inflating the balloon to deploy the prosthetic valve).

Method 1300 begins at 1302 and includes receiving a prosthetic heart valve mounted on a distal end portion of a delivery apparatus, around an inflatable balloon of the delivery apparatus and in a radially compressed configuration, at a predetermined position and in a predetermined orientation relative to the delivery apparatus, such that a selected commissure of the prosthetic heart valve is offset, in a circumferential direction relative to a central longitudinal axis of the delivery apparatus, from a radiopaque marker on the distal end portion of the delivery apparatus by a predetermined amount. In some embodiments, the predetermined amount is determined based on a selected imaging view, as described further below, with reference to FIGS. 58-68.

In some embodiments, as described above with reference to FIGS. 30-34B, the marker can be reflection asymmetric along an axis that is parallel to the central longitudinal axis. In some embodiments, the marker can be positioned on a polymeric body of the delivery apparatus, such as a proximal shoulder, distal shoulder, or nose cone. In some embodiments, the marker is arranged on and/or embedded in a flared portion of a distal shoulder of the delivery apparatus, the distal shoulder arranged distal to the valve mounting portion of the delivery apparatus (e.g., as shown in FIGS. 32A-32B and 42).

In some embodiments, the method at 1302 can include crimping the prosthetic heart valve onto the distal end portion of the delivery apparatus using a mounting assembly, as described above with reference to the method of FIG. 56.

At 1304, the method includes advancing the distal end portion of the delivery apparatus toward a native valve of a heart of a patient. In some embodiments, the method at 1304 can additionally include, first inserting the distal end portion of the delivery apparatus into vasculature of the patient with an inflation port of an adaptor of the delivery apparatus facing toward a user (e.g., the user performing the implantation procedure) in order to orient the radiopaque marker entering the patient such that it faces a table on which the patient is positioned (e.g., due to the arrangement of the adaptor 312 and rotatable knob 314 relative to the marker, as described above with reference to FIGS. 15-22).

After advancing the distal end portion of the delivery apparatus to a location proximate to the native valve (e.g., within the patient's heart), the method continues to 1306 and includes visualizing, under fluoroscopy and for a selected imaging view, a position of the radiopaque marker on the distal end portion of the delivery apparatus relative to a guidewire extending through a shaft of the delivery apparatus. For example, as described above with reference to FIGS. 29, 31A-31B, and 34A-34B, using medical imaging, such as fluoroscopy, the radiopaque marker can be visualized, along with the guidewire and additional components (e.g., the valve frame of the prosthetic valve mounted on the delivery apparatus). A position of the radiopaque marker relative to the guidewire can be seen in the selected imaging view (e.g., the marker can appear radially offset from the guidewire when not directly in front of or behind the guidewire in the imaging view, as shown in the example of FIG. 29). Thus, since fluoroscopy does not provide perspective to naturally differentiate what is in the front vs. the back of the selected imaging view, this perspective can be provided by visualizing a position of the asymmetric marker relative to the guidewire, as described further below.

As described further below with reference to FIGS. 61-64, a user can select from a plurality of possible imaging views for imaging the heart and the position of the distal end portion of the delivery apparatus relative to the native valve. For each imaging view, a location of a target commissure of the native valve that is to be aligned with a selected commissure of the prosthetic heart valve (after implantation), within the selected imaging view, may be known. An exemplary fluoroscopic image 1400 of a native (e.g., aortic) valve 1402 viewed with a more standard, three-cusp imaging view is shown in FIG. 58. As shown in FIG. 58, the native aortic valve 1402 includes three leaflets: the non-coronary cusp 1404, the right coronary cusp 1406, and the left coronary cusp 1408. In the three-cusp view, the non-coronary cusp 1404 and the left coronary cusp 1408 are arranged opposite one another in the view and are each overlapped by a portion of the right coronary cusp 1406. As such, a commissure between the non-coronary cusp 1404 and the left coronary cusp 1408 is in known to be located in the back of the image 1400.

At 1308, the method includes, prior to crossing the native valve, rotating the shaft of the delivery apparatus, which rotates the prosthetic heart valve and the marker, until the marker is centered along the guidewire and is in a predetermined orientation in the selected imaging view. The method at 1308 can be performed while imaging the heart and viewing the selected imaging view.

In some embodiments, the predetermined orientation in the selected imaging view is a direct back of the imaging view (e.g., away from the viewer). In alternate embodiments, the predetermined orientation in the selected imaging view can be a direct front of the imaging view (e.g., toward the viewer). Thus, in some embodiments, the radiopaque marker can be configured as an asymmetric marker that has a first orientation when it is in front of the guidewire (e.g., in the direct front of the imaging view) and a different, second orientation when it is behind the guidewire (e.g., in the direct back of the imaging view). In this way, the asymmetric marker can help a user differentiate between the marker being positioned in the front and the back of the selected imaging view (as compared to a symmetric marker which would appear the same to a viewer in an imaging view, whether the marker is behind or in front of the guidewire).

For example, in some embodiments, as shown in FIG. 59, the asymmetric marker 600 can be configured as a letter of the alphabet that appears forward (e.g., forward-readable "C", as shown in FIG. 31A) when the marker is centered along the guidewire 606 and is arranged in the direct back of the imaging view (e.g., behind the guidewire, as shown in FIG. 59) and appears backward (e.g., backwards "C", as shown in FIG. 31B) when the marker is centered along the guidewire and is arranged in the direct front of the imaging view. Thus, the method at 1308 can include rotating the shaft of the delivery apparatus, which rotates the prosthetic heart valve and the marker, until the marker appears centered along the guidewire and in its forward orientation, within the selected imaging view, thereby positioning the marker in the direct back of the imaging view.

In alternate embodiments, the asymmetric marker can appear forward when the marker is centered along the guidewire and is arranged in the direct front of the imaging view (e.g., in front of the guidewire) and appears backward when the marker is centered along the guidewire and is arranged in the direct back of the imaging view. Thus, in these embodiments, the method at 1308 can include rotating the shaft of the delivery apparatus, which rotates the prosthetic heart valve and the marker, until the marker appears centered along the guidewire and in its backward orientation, within the selected imaging view, thereby positioning the marker in the direct back of the imaging view.

In still other embodiments, the method at 1308 can include rotating the shaft of the delivery apparatus, which rotates the prosthetic heart valve and the marker, until the marker appears centered along the guidewire and is in a predetermined orientation (backward or forward) within the selected imaging view, thereby positioning the marker in the direct front of the imaging view. In this way, the predetermined offset between the selected commissure of the prosthetic heart valve and the marker on the delivery apparatus can be determined based on both the selected imaging view and the target orientation of the marker in the selected imaging view (direct front or direct back).

By rotating the distal end portion of the delivery apparatus prior to crossing the native valve, blood flow through the native valve (which may be stenosed) may not be occluded by the delivery apparatus. Additionally, in some embodiments, if the crimped prosthetic valve were to be rotated within (e.g., across) the native valve (which may have calcified leaflets), emboli could be generated by knocking off pieces of calcium from the leaflets, which could lead to stroke or other medical complications. Thus, by rotating the distal end portion of the delivery apparatus and the radially compressed prosthetic valve outside of the native valve (e.g., in the ascending aorta), emboli and other complications can be reduced or avoided. Further, a user can take more time for the rotating since the delivery apparatus is not in a position that can occlude blood flow through the native valve.

After achieving the desired rotational positioning of the radiopaque marker relative to the guidewire at 1308, the method continues to 1310, which includes advancing the distal end portion of the delivery apparatus including the radially compressed prosthetic heart valve across and into the native valve and inflating the balloon to radially expand and implant the prosthetic heart valve in the native valve such that the selected commissure of the prosthetic heart valve is aligned with the target commissure of the native valve.

In some embodiments, during the inflating, as the prosthetic heart valve radially expands, the prosthetic heart valve rotates by an amount equal to the predetermined amount of offset between the marker and the selected commissure when the prosthetic heart valve is radially compressed around the balloon. For example, as shown in the exemplary schematic of FIG. 60, when the target commissure 1450 of the native valve 1452 is known to be in the direct back of the selected imaging view used for rotational positioning at the implantation site, and the marker 600 is aligned at the direct back of the selected imaging view, the prosthetic valve 922 can rotate by an amount (as shown by arrow 1454 in FIG. 60) that is equal to the predetermined amount of offset between the marker and the selected commissure 930 of the prosthetic valve 922 when the prosthetic heart valve is radially compressed around the balloon, thereby implanting the prosthetic valve 922 with the selected commissure 930 circumferentially aligned with the target commissure 1450 of the native valve 1452.

In alternate embodiments, during the inflating, as the prosthetic heart valve radially expands, the prosthetic heart valve rotates by an amount that is more or less than the amount of offset between the marker and the selected commissure when the prosthetic heart valve is radially compressed around the balloon. However, this amount of offset can be predetermined based on the selected imaging view and a preexisting knowledge of a location of the target commissure of the native valve within the selected imaging view. In this way, during method 1300, the marker on the delivery apparatus can still be aligned with the guidewire (e.g., in the direct back of the selected imaging view), but the predetermined amount of offset between the marker and the selected commissure of the radially compressed prosthetic valve can be adjusted for different imaging view such that, upon inflation of the balloon, the prosthetic valve rotates and is implanted with commissures in alignment with commissure of the native valve.

Examples of this rotational alignment and adjustment of the circumferential offset between the marker on the delivery apparatus and the selected commissure of the radially compressed prosthetic heart valve, for different imaging views, are described below with reference to FIGS. 61-68.

Figure 62:
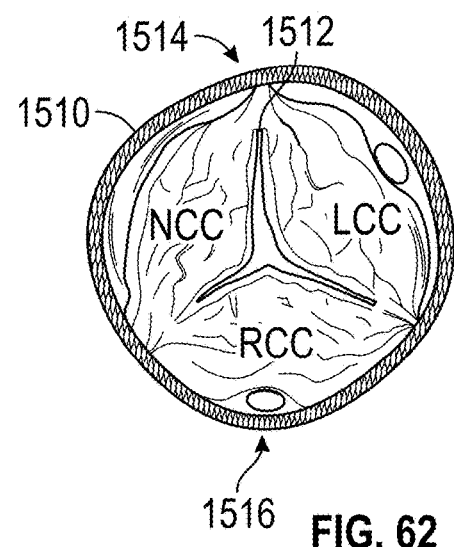
FIG. 62 is a cross-sectional view of a native valve, illustrating a location of commissures of the native valve within the imaging view of FIG. 61.

A schematic of a first embodiment of a more standard, three-cusp imaging view 1500 of a native valve 1510 that can be used for visualizing the delivery apparatus in a patient's heart during an implantation procedure and rotationally aligning the prosthetic valve, as described above, is shown in FIG. 61. In the three-cusp imaging view 1500, the non-coronary cusp 1502 of the native valve (e.g., aortic valve) 1510 and the left coronary cusp 1504 are arranged opposite one another in the view and each are overlapped by a different portion of the right coronary cusp 1506, with all three cusps aligned along a transverse axis 1508. Thus, as shown in the cross-sectional view of the native valve 1510 in FIG. 62, for the three-cusp imaging view 1500, a selected commissure 1512 of the native valve 1510, which is arranged between the non-coronary cusp 1502 and the left coronary cusp 1504 is arranged in the direct back 1514 of the three-cusp imaging view 1500. FIG. 62 also shows the direct front 1516 of the imaging view, in which the right coronary cusp 1506 is located.

In contrast, FIG. 63 shows a schematic of a second embodiment of a different, right/left cusp overlap view 1550 of the native valve 1510 that can be used for visualizing the delivery apparatus in the patient's heart during an implantation procedure and rotationally aligning the prosthetic valve, as described above. In the right/left cusp overlap view 1550, the left coronary cusp 1504 and the right coronary cusp 1506 overlap one another and the non-coronary cusp 1502 is offset from the left coronary cusp 1504 and the right coronary cusp 1506. As shown in the cross-sectional view of the native valve 1510 in FIG. 64, for the right/left cusp overlap view 1550, the selected commissure 1512 is circumferentially offset from the direct back 1514 of the imaging view.

It should be noted that, in alternate embodiments, a different commissure of the native valve (other than the commissure arranged between the arranged between the non-coronary cusp and the left coronary cusp) can be the selected commissure on which the predetermined offset between the marker and the selected commissure of the prosthetic valve is at least partially based.

Thus, for the two different imaging views shown in FIGS. 61 and 63, the circumferential offset between the radiopaque marker on the delivery apparatus and the selected commissure of the radially compressed prosthetic valve can be different predetermined offset values. In some embodiments, the implantation procedure can proceed in a same way for the different imaging views (e.g., the method at 1304, 1306, 1308, and 1310 can proceed as described above, using the different, selected imaging views), including rotationally aligning the radiopaque marker on the delivery apparatus with the guidewire such that the marker is positioned in the direct back of the imaging view (e.g., as shown in FIGS. 59 and 60). However, the mounting of the prosthetic valve to the delivery apparatus can be adjusted such that a different amount of circumferential offset between the marker and the selected commissure of the prosthetic valve is used for the different procedures using the different imaging views, where the determined amount of circumferential offset for the selected imaging view results in the prosthetic valve being implanted in the native valve with commissures in alignment with commissures of the native valve.

It should be noted that the two imaging views shown in FIGS. 61 and 63 are examples of two different imaging views that could be used during a valve implantation procedure for rotationally aligning the prosthetic valve at the native valve. However, additional, different imaging views that position a target commissure of the native valve in a different location relative to the direct back (or front) of the selected imaging view are possible and can also be used with the systems and methods described herein. In this way, a user can select from a plurality of possible imaging views and the circumferential location of the selected (or target) commissure (e.g. commissure 1512 shown in FIGS. 62 and 64) relative to the back (or front) of the selected imaging view can be known (e.g., predetermined).

In some embodiments, different alignment rings (e.g., ring bodies, similar to ring body 1038 shown in FIGS. 46-48) for a mounting assembly or different indicators on an alignment ring denoting an alignment location for one or more commissures of the prosthetic valve arranged on an implant holder device (e.g., such as support body 1010 of FIGS. 45 and 48) can be used for different selected imaging views for the valve implantation procedure.

Figure 65:
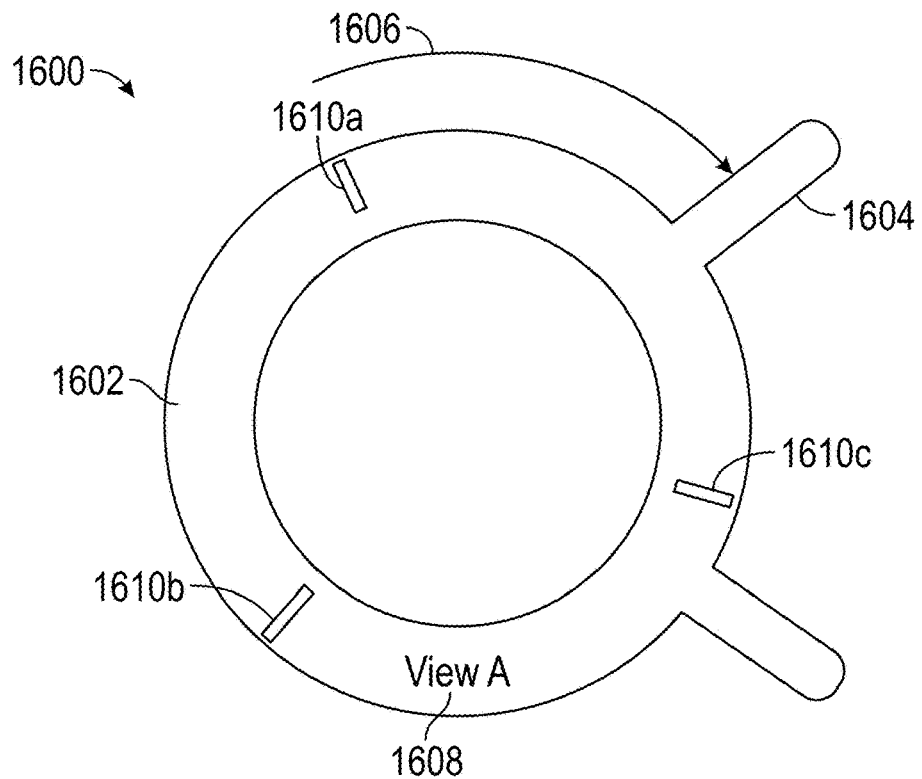
FIG. 65 illustrates an embodiment of an alignment ring configured to rotationally align a prosthetic valve relative to a delivery apparatus for an implantation procedure using a first imaging view.
Figure 66:
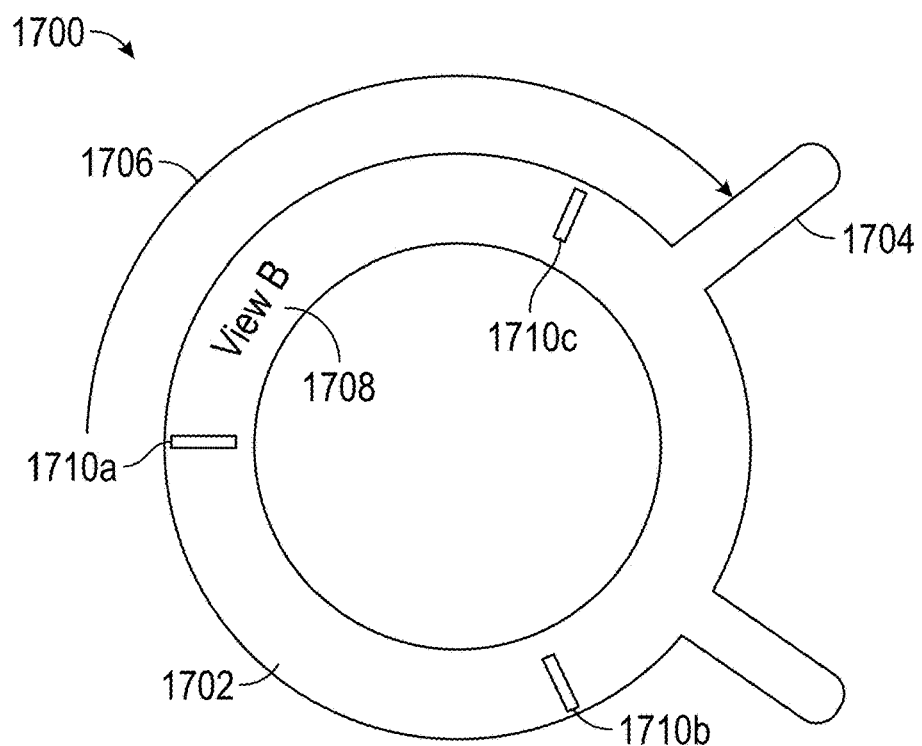
FIG. 66 illustrates another embodiment of an alignment ring configured to rotationally align a prosthetic valve relative to a delivery apparatus for an implantation procedure using a second imaging view.

FIGS. 65-68 show exemplary embodiments of different alignment rings that can be used in a mounting assembly and are configured to rotationally align the prosthetic valve on an implant holder device, thereby resulting in the prosthetic valve being crimped onto a valve mounting portion of a delivery apparatus in a predetermined circumferential orientation relative to a radiopaque marker on the distal end portion of the delivery apparatus. For example, the alignment rings can be configured such that the prosthetic valve is radially compressed onto the delivery apparatus with a selected commissure circumferentially offset from the radiopaque marker on the distal end portion of the delivery apparatus by a predetermined amount that is determined (e.g., selected) based on the selected imaging view for use during an implantation procedure. In some embodiments, as shown in FIGS. 65 and 66, different alignment rings can be similar in overall shape and function but have a different arrangement of indicators or markers that are unique for a selected imaging view intended to be used. For example, the different alignment rings having a unique arrangement of indicators or markers can be configured to align the prosthetic valve on an implant holder device in such a way as to offset a selected commissure of the prosthetic valve relative to the radiopaque marker on the delivery apparatus by the appropriate amount that aligns the commissures of the prosthetic valve with the native valve when the prosthetic valve is deployed from the delivery apparatus with the radiopaque marker aligned with the guidewire, as described above.

FIG. 65 shows one embodiment of an alignment ring 1600 which can be configured to rotationally align a prosthetic valve relative to a delivery apparatus for an implantation procedure using a first imaging view, such as the three-cusp imaging view (e.g., the three-cusp imaging view 1500 of FIG. 61), to rotationally align and implant the prosthetic valve with the delivery apparatus at the native valve. The alignment ring 1600 can be configured to enable mounting of the prosthetic valve onto a delivery apparatus with a selected commissure of the prosthetic valve circumferentially offset from a radiopaque marker on the delivery apparatus by a first predetermined amount, the first predetermined amount resulting in the prosthetic valve being implanted with commissures in alignment with commissures of the native valve following deployment of the prosthetic valve with the delivery apparatus having the radiopaque marker aligned with the guidewire in its predetermined orientation (e.g., which indicates the marker is arranged in the direct back of the imaging view).

The alignment ring 1600 can be configured (e.g., structured) similarly to or the same as the ring body 1038 of FIGS. 46 and 47. For example, the alignment ring 1600 can include one or more indicators (e.g., alignment indicators or markers) 1610a-c arranged on one or more surfaces of a body 1602 of the alignment ring 1600. As described above with reference to FIGS. 46 and 47, the indicators 1610a-c can be depressions (e.g., grooves) or etchings into the one or more surfaces, raised features extending radially outward from the one or more surfaces, and/or markings (e.g., lines printed, painted, or stamped onto) on the one or more surfaces.

As shown in FIG. 65, the alignment ring 1600 includes three indicators 1610a-c spaced apart from one another around a circumference of the alignment ring 1600. However, in alternate embodiments, the alignment ring 1600 can include less than three indicators 1610a-c, such as one or two. The indicators 1610a-c can be configured to indicate a desired orientation for the commissures of the prosthetic valve when mounting the prosthetic valve around an implant holder device (e.g., such as support body 1010 shown in FIGS. 45 and 48) when the alignment ring is coupled to the implant holder device (e.g., as shown in FIG. 48). As shown in FIG. 65, a first indicator 1610a can be spaced apart from a first lever (e.g., radial extension) 1604 by a first arc length 1606.

In some embodiments, the alignment ring 1600 can include an additional marking or indicator that indicates its intended use for alignment of a prosthetic valve to be implanted in an implantation procedure using the three-cusp imaging view. For example, as shown in FIG. 65, the alignment ring includes a first label 1608 ("View A") that indicates the selected imaging view for the implantation procedure. In some embodiments, the selected imaging view (View A) can be the three-cusp imaging view described above. In alternate embodiments, the first label 1608 can be a color coding, a symbol, a numeric code, or the like.

FIG. 66 shows another embodiment of an alignment ring 1700 which can be configured to rotationally align a prosthetic valve relative to a delivery apparatus for an implantation procedure using a second imaging view, such as the right/left cusp overlap imaging view (e.g., right/left cusp overlap view 1550 of FIG. 63), to rotationally align and implant the prosthetic valve with the delivery apparatus at the native valve. The alignment ring 1700 can be configured to enable mounting of the prosthetic valve onto a delivery apparatus with a selected commissure of the prosthetic valve circumferentially offset from a radiopaque marker on the delivery apparatus by a second predetermined amount, the second predetermined amount resulting in the prosthetic valve being implanted with commissures in alignment with commissures of the native valve following deployment of the prosthetic valve with the delivery apparatus having the radiopaque marker aligned with the guidewire in its predetermined orientation (e.g., which indicates the marker is arranged in the direct back of the imaging view). The second predetermined amount can be different than the first predetermined amount described above with reference to the alignment ring 1600.

The alignment ring 1700 can be configured (e.g., structured) similarly to or the same as the ring body 1038 of FIGS. 46 and 47. For example, similarly to the alignment ring 1600, the alignment ring 1700 can include one or more indicators 1710a-c arranged on one or more surfaces of a body 1702 of the alignment ring 1700.

As shown in FIG. 66, the alignment ring 1700 includes three indicators 1710a-c spaced apart from one another around a circumference of the alignment ring 1700. However, in alternate embodiments, the alignment ring 1700 can include less than three indicators 1710a-c, such as one or two. The indicators 1710a-c can be configured to indicate a desired orientation for the commissures of the prosthetic valve when mounting the prosthetic valve around an implant holder device (e.g., such as support body 1010 shown in FIGS. 45 and 48) when the alignment ring is coupled to the implant holder device (e.g., as shown in FIG. 48). As shown in FIG. 66, a first indicator 1710a can be spaced apart from a first lever (e.g., radial extension) 1704 by a second arc length 1706.

In some embodiments, the alignment ring 1700 can include an additional marking or indicator that indicates its intended use for alignment of a prosthetic valve to be implanted in an implantation procedure using the three-cusp imaging view. For example, as shown in FIG. 66, the alignment ring includes a first label 1708 ("View B") that indicates the selected imaging view for the implantation procedure. In some embodiments, the selected imaging view (View B) can be the right/left cusp overlap view, as described above. In alternate embodiments, the first label 1708 can be a color coding, a symbol, a numeric code, or the like.

FIGS. 65 and 66 show two possible embodiments of individual alignment rings that are configured for use with differently selected imaging views for a valve implantation procedure, as described herein. However, additional alignment rings configured similarly to those shown in FIGS. 65 and 66 but with a different orientation of indicators (commissure markers) for differently selected imaging views are also possible. In this way, in some embodiments, a user can select from a plurality of different alignment rings that are unique to a selected imaging view, for an implantation procedure.

Figure 67:
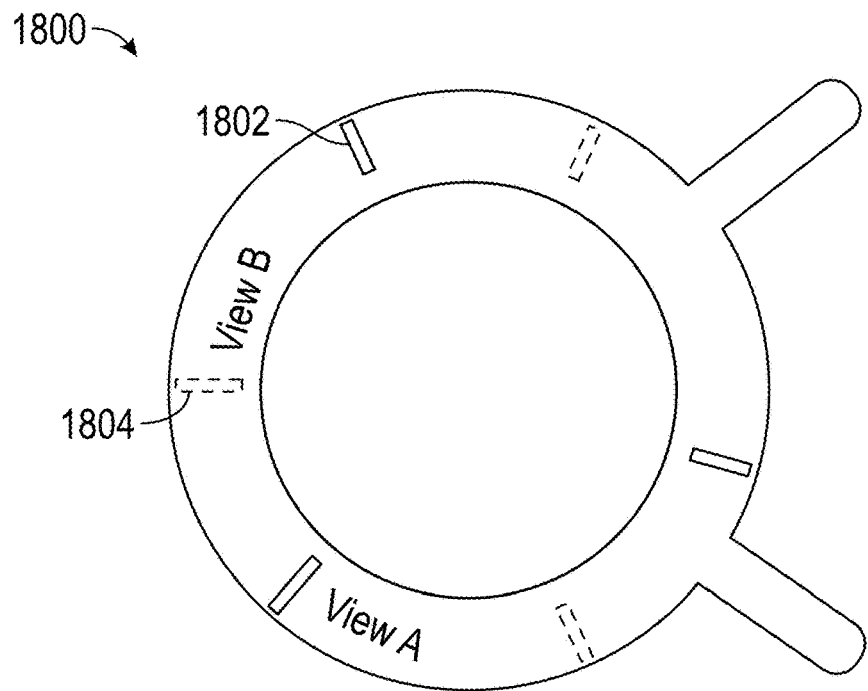
FIG. 67 illustrates another embodiment of an alignment ring including multiple sets of alignment markers for use in two or more implantation procedures utilizing differently selected imaging views.

FIG. 67 shows another embodiment of an alignment ring 1800. The alignment ring 1800 can be similar to the other alignment rings (or ring bodies) described herein but includes multiple sets of indicators (e.g., alignment markers) for use in two or more implantation procedures utilizing differently selected imaging views. For example, the alignment ring 1800 can be configured for intended use with two different fluoroscopic imaging views. In the example of FIG. 67, the alignment ring 1800 includes a first set of indicators 1802 and a second set of indicators 1804 which are circumferentially offset from one another. In one embodiment, the first set of indicators 1802 can be used for an implantation procedure utilizing the three-cusp imaging view and the second set of indicators 1804 can be used for a different implantation procedure utilizing the right/left cusp overlap view.

In some embodiments, the first set of indicators 1802 can have a different color than the second set of indicators 1804. In this way, the different colored indicators can correspond to the different imaging views.

In other embodiments, the first set of indicators 1802 can have a different marking (e.g., lines vs. dots) than the second set of indicators 1804. In still other embodiments, the first set of indicators 1802 can be arranged on a first side (or surface) of the alignment ring 1800 while the second set of indicators 1804 can be arranged on an opposite, second side (or surface) of the alignment ring 1800.

FIG. 68 shows another embodiment of an alignment ring 1900. The alignment ring 1900 can be similar to the other alignment rings (or ring bodies) described herein but includes one or more sets of indicators 1902, each set of indicators including a plurality of graduated indicators (or markings). For example, each set of indicators 1902 can include a first (e.g., standard or base) indicator 1904, a second indicator 1906 that is circumferentially offset from the first indicator 1904 by a first amount (e.g., 10°), a third indicator 1908 that is circumferentially offset from the first indicator 1904 by a second amount (e.g., 20°), and a fourth indicator 1910 that is circumferentially offset from the first indicator 1904 by a third amount (e.g., 30°). In alternate embodiments, the sets of indicators 1902 can include more or less graduated markings than those shown in FIG. 68.

A graduated alignment ring having a plurality of graduated markings for one or more commissure locations, such as alignment ring 1900, can be useful for patients with atypical anatomy or for user-customized imaging views. For example, a user (e.g., physician) can identify from a pre-procedure CT (or other imaging modality) that the patient has a native valve with commissures and/or coronary arteries in unusual (e.g., non-standard) locations. Thus, a more customizable alignment ring, such as the graduated alignment ring 1900, can allow the physician to offset the prosthetic valve commissures from the more standard location. For example, the offset of a native valve commissure from the expected location could be measured in the pre-procedure CT and then physician could then ask a user to offset the prosthetic valve commissures by 20° from standard on the alignment ring and implant holder device (e.g., using the third indicators 1908 shown in FIG. 68).

In this way, methods, assemblies, and/or apparatuses are provided for implanting a prosthetic heart valve at a native valve with commissures of the prosthetic heart valve being circumferentially aligned with commissures of the native valve. As a result, access to the coronary arteries can be increased.

In some embodiments of the delivery apparatuses and/or methods described herein, a distal end portion of the delivery apparatus can include a valve mounting portion that is configured to receive a radially compressed prosthetic valve thereon and a polymeric body arranged proximate to the valve mounting portion. In some embodiments, the polymeric body can include a radiopaque marker that is configured to indicate a location of a commissure of the prosthetic valve after radially expanding the prosthetic valve via inflating a balloon of the delivery apparatus. In some embodiments, the polymeric body can include a radiopaque marker that is configured to be aligned with a guidewire extending through a center of the delivery apparatus in a predetermined orientation such that the prosthetic valve is implanted with commissures in alignment with commissures of a native valve.

In some embodiments, the methods, assemblies, and/or apparatuses can additionally or alternatively include a method of arranging and radially compressing a prosthetic valve onto a valve mounting portion of a delivery apparatus such that a selected commissure of the prosthetic valve is in a predetermined position and orientation relative to the radiopaque marker of the delivery apparatus.

In some embodiments, the methods, assemblies, and/or apparatuses can additionally or alternatively include a method of forming and/or folding the balloon of the delivery apparatus that results in a consistent amount of rotation of the prosthetic valve during deployment of the prosthetic valve into is radially expanded state. As a result, after inflation of the balloon and radially expanding the prosthetic valve, the selected commissure of the prosthetic valve may be aligned, in a circumferential direction, with the radiopaque marker of the delivery apparatus and/or a target commissure of the native valve.

In some embodiments, the methods, assemblies, and/or apparatuses can additionally or alternatively include a delivery apparatus that is configured to rotate the balloon of the delivery apparatus with the crimped (e.g., radially compressed) prosthetic valve without adversely affecting a flexing capability of the distal end portion of the delivery apparatus and/or inflation of the balloon.

In some embodiments, the methods, assemblies, and/or apparatuses can additionally or alternatively include the delivery apparatus with the radiopaque marker, where the radiopaque marker is visible under fluoroscopy and has an asymmetric shape that allows a user to determine whether the maker is positioned in a front or a back of the fluoroscopic view (e.g., as viewed by the user).

In some embodiments, the methods, assemblies, and/or apparatuses can additionally or alternatively include a method for rotating the distal end portion of the delivery apparatus, including the radiopaque marker and the radially compressed prosthetic valve, during an implantation procedure, to rotationally align the marker with a target commissure of the native valve where the prosthetic valve is intended to be implanted, a guidewire extending through the delivery apparatus, and/or predetermined location within a selected imaging view. In some embodiments, the method for rotating can occur during a selected portion of the implantation procedure that reduces a likelihood of clinical complications occurring.

In some embodiments, the methods, assemblies, and/or apparatuses can additionally or alternatively include a method for rotationally aligning the radiopaque marker of the delivery apparatus with a selected commissure of the native valve, using a selected fluoroscopic view obtained during the implantation procedure, and deploying the prosthetic valve within the native valve, with the delivery apparatus, such that the selected commissure of the prosthetic valve is circumferentially aligned with the selected commissure of the native valve.

Each of the above-described features of the methods, assemblies, and/or apparatuses can be combined with any one or more of the other above-described features of the methods, assemblies, and/or apparatuses.

In this way, a prosthetic valve can be more easily deployed at an implantation site such that commissures of the radially expanded prosthetic valve are aligned with commissures of the native valve, thereby avoiding placement of the commissures of the prosthetic valve from blocking and/or being positioned in front of the coronary arteries. As a result, blood flow into and access to the coronary arteries may be increased.

In some embodiments, a balloon cover can be configured to enclose (e.g., encase) a distal end portion of a delivery apparatus (e.g., a portion of the distal end portion 309 of the delivery apparatus 300 shown in FIGS. 10 and 40-42) which includes an inflatable balloon mounted (and folded) thereon during shipping and/or storage prior to use and/or during a de-airing process.

For example, prior to crimping a prosthetic valve on the balloon of a delivery apparatus, the user typically performs a cyclic "de-airing" process that involves pushing inflation fluid into the balloon and then withdrawing the fluid out of the balloon, such as with a syringe fluidly connected to the handle of the delivery apparatus. The de-airing process can be more effective when the balloon is allowed to at least partially inflate. However, inflation of the balloon outside of a balloon cover can result in un-folding of the balloon, which can inhibit or prevent the balloon from returning to its folded state (e.g., as shown in FIG. 37) when the inflation fluid is removed from the balloon. A balloon cover can be configured to prevent complete unfolding of the balloon and/or assist the balloon in returning to its fully folded state after the inflation fluid is removed from the balloon.

Traditional balloon covers can comprise two shell portions or halves that are configured to be arranged and mated together around the distal end portion of the delivery apparatus, including the balloon (e.g., the distal end portion 309 of delivery apparatus 300, with balloon 318 mounted thereon, as shown in FIGS. 9-11 and 40). In some embodiments, a removable sleeve can be slid over and around the assembled balloon cover in order to hold (and couple) the two shell portions of the balloon cover together. When a user is ready to mount or crimp a prosthetic valve onto the delivery apparatus, around the balloon (e.g., as shown in FIG. 41), a user can grab the delivery apparatus and pull to remove the sleeve from the delivery apparatus.

However, when the delivery apparatus includes a positioning device coupled to the distal end portion of the delivery apparatus (e.g., positioning device 1100 coupled to the distal end portion 309 of the delivery apparatus 300, as shown in FIGS. 54 and 55 or positioning device 1072 coupled to a distal end portion of a delivery apparatus, as shown in FIG. 49), a user may grab the positioning device during removal of the sleeve from the balloon cover. For example, a user may grab the positioning device with one hand and then slide the sleeve off the balloon cover and off a distal end of the delivery apparatus with the other hand. This can result in movement of the positioning device relative to the delivery apparatus (and the radiopaque marker on the distal end portion of the delivery apparatus, as described herein). As a result, the prosthetic valve can be subsequently mounted onto the balloon in an improper circumferential orientation relative to the marker, which can result in misalignment of the commissures of the prosthetic valve with the commissures or the native valve, at the implantation site (e.g., during an implantation procedure, as explained above with reference to FIG. 57).

To address such issues, a balloon cover for a balloon mounted on and around a distal end portion of a delivery apparatus can comprise first and second shell members, each having a narrower, first portion configured to receive (and enclose therein) the distal end portion of the delivery apparatus including the balloon and a wider, second portion configured to receive (and at least partially enclose therein) the positioning device. In this way, the second portion can surround the positioning device and prevent a user from directly contacting or grabbing the positioning device, thereby avoiding any unwanted movement (e.g., rotation) of the positioning device relative to the delivery apparatus during removal of the balloon cover from the delivery apparatus.

FIGS. 69-76B and FIGS. 108-114 show embodiments of a balloon cover that is configured to cover a portion of a distal end portion of a delivery apparatus (e.g., distal end portion 309 of delivery apparatus 300, as shown in FIGS. 69, 72-76B, and 108-114) that includes an inflatable balloon (e.g., balloon 318) mounted thereon and a positioning device coupled to the distal end portion of the delivery apparatus, proximal to a valve mounting portion of the delivery apparatus (e.g., positioning device 1100, as shown in FIGS. 69, 72-76B, and 108-114).

Figure 69:
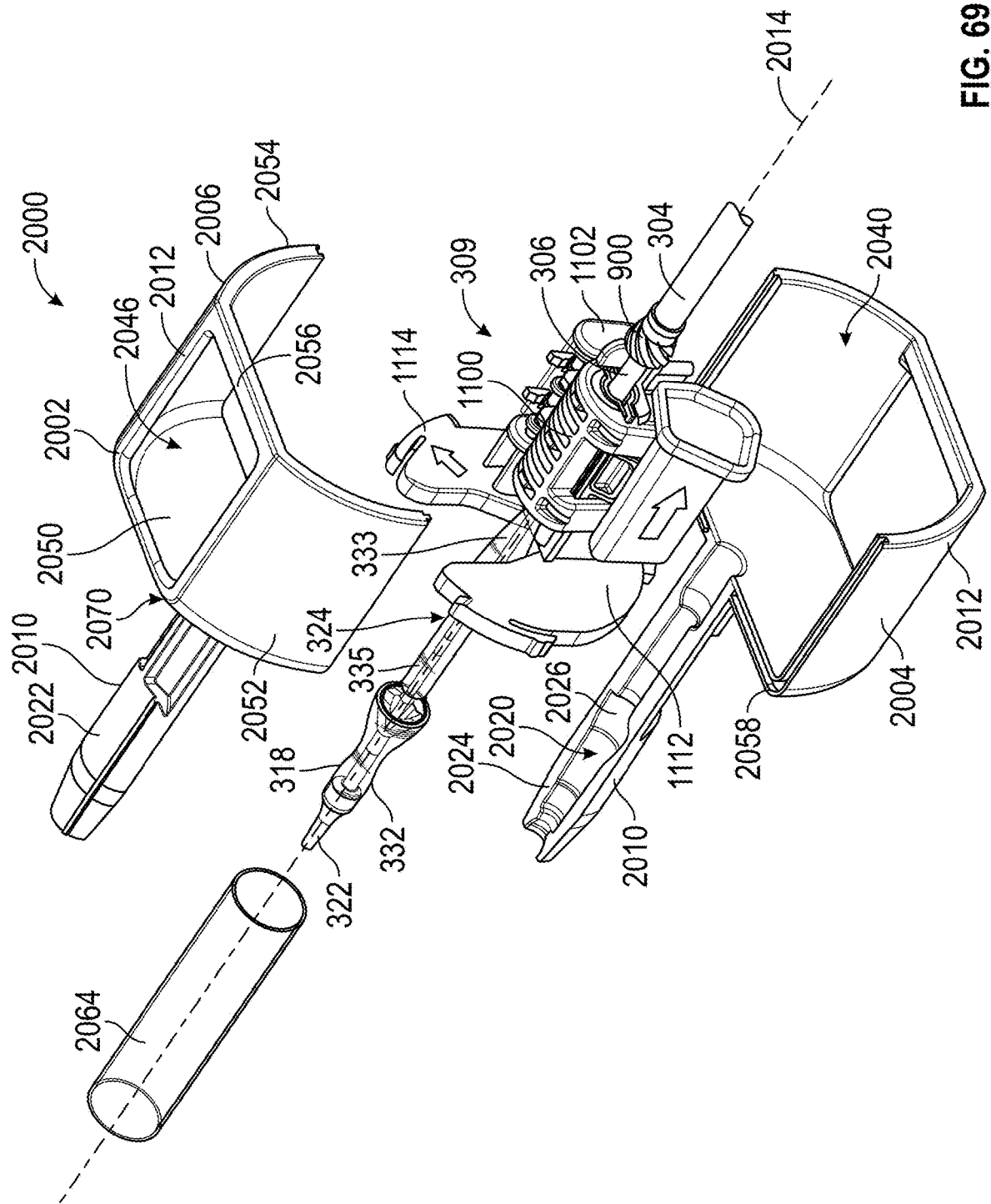
FIG. 69 is an exploded view of an embodiment of a balloon cover for a distal end portion of delivery apparatus which is configured to cover an inflatable balloon and a positioning device mounted on the distal end portion.
Figure 71C:
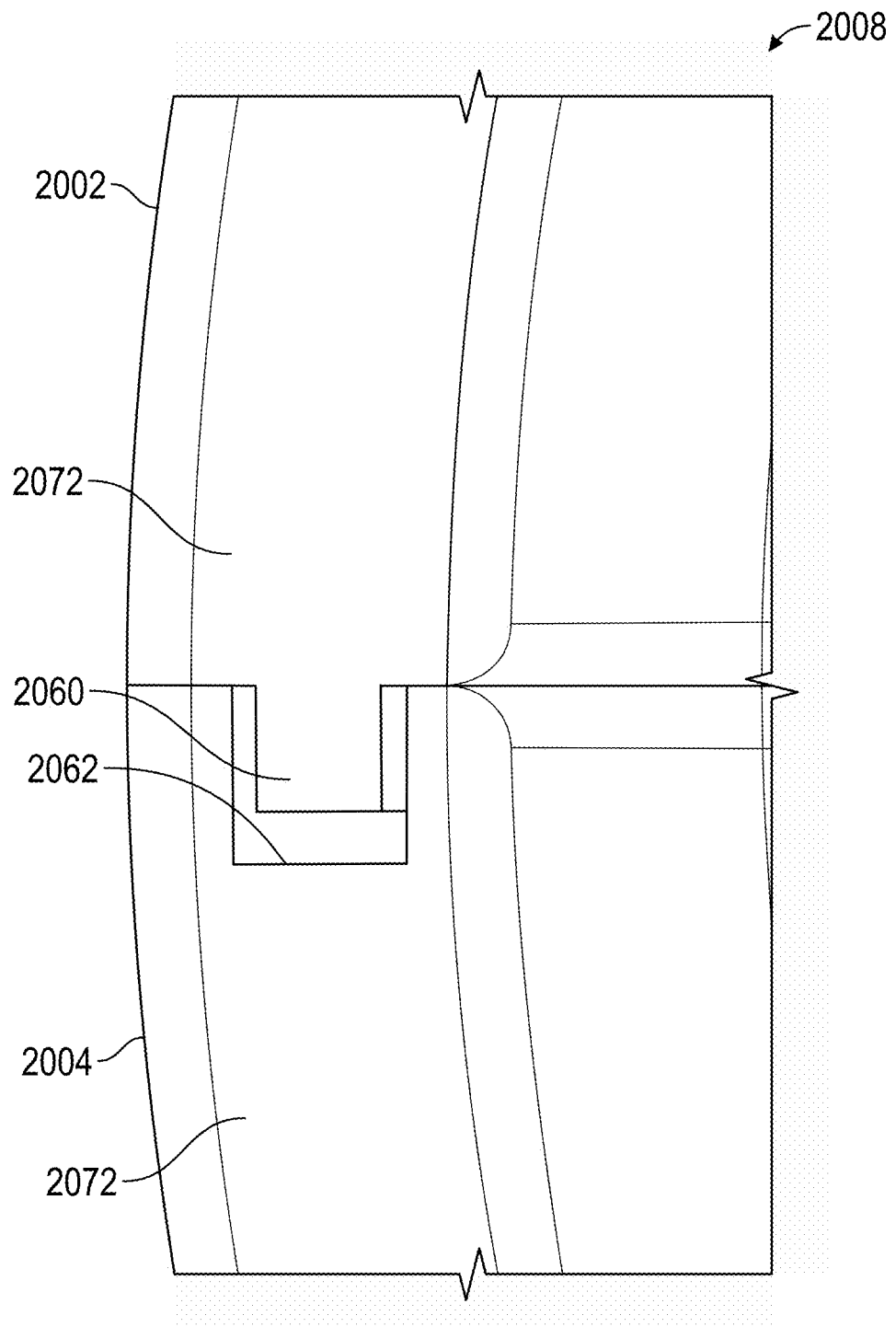
FIG. 71C is a detail view of a portion of a mating interface between two shell members of the balloon cover of FIG. 60, when in an assembled configuration where the mating edges of the two shell members are engaged with one another.
Figure 72:
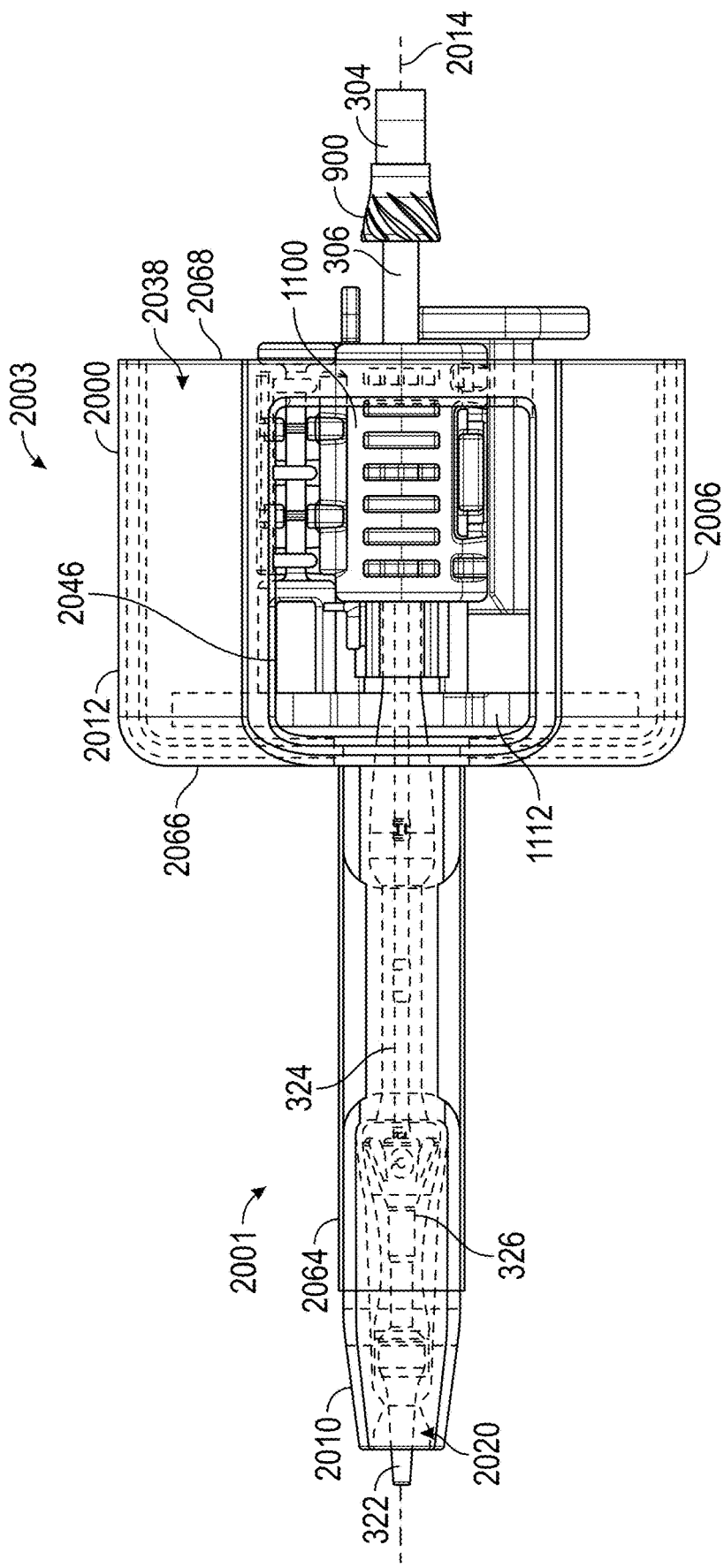
FIG. 72 is a first side view of the balloon cover of FIG. 69 in an assembled configuration and with components arranged inside and covered by the balloon cover being shown with dashed lines.
Figure 73:
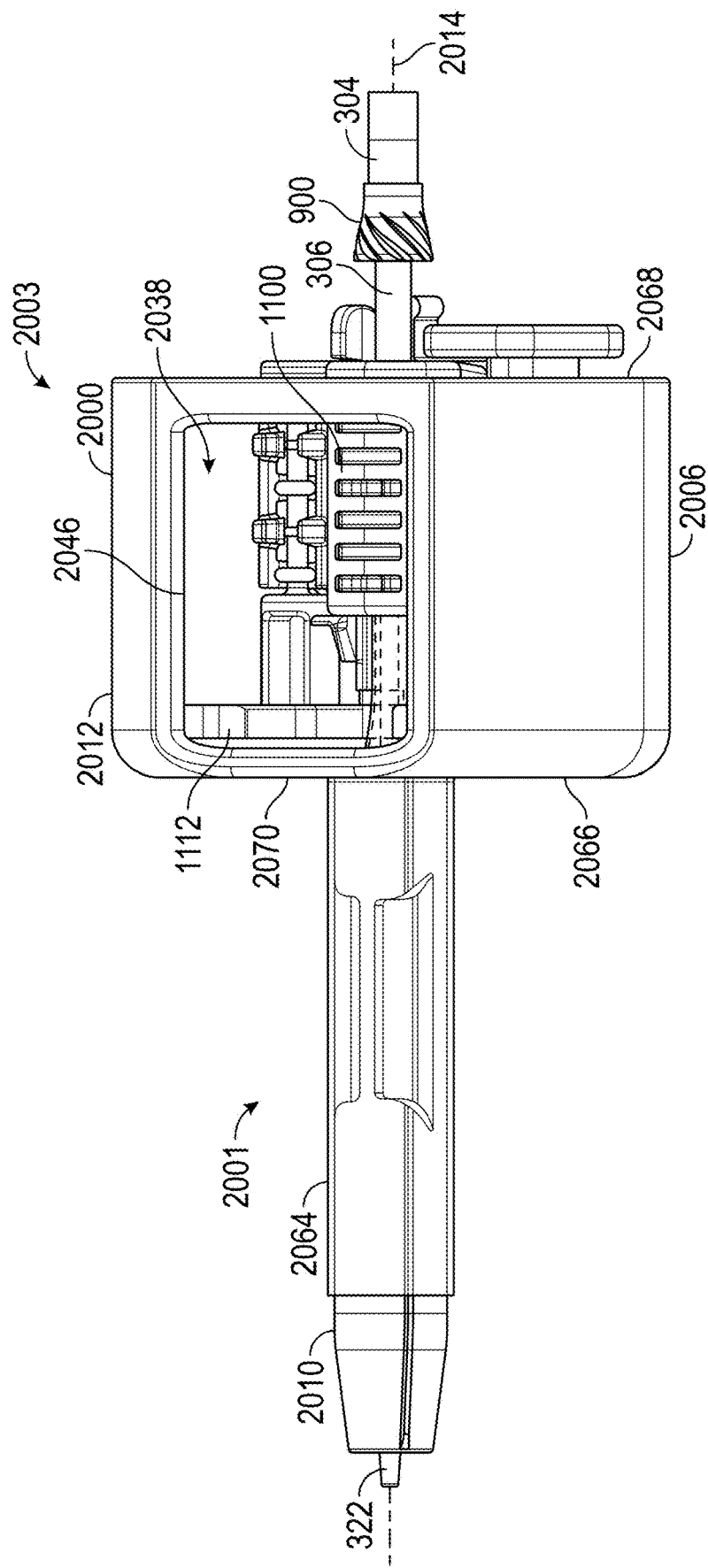
FIG. 73 is a second side view of the balloon cover of FIG. 69 in an assembled configuration, wherein the second side view is rotated from the first side view of FIG. 72.

FIGS. 69-75C show an exemplary embodiment of such a balloon cover (or balloon cover assembly) 2000 comprising a first cover portion 2001 that is configured to cover at least a portion of the distal end portion of the delivery apparatus that includes the balloon and a second cover portion 2003 that is configured to cover the positioning device (cover portions 2001 and 2003 shown in FIGS. 72 and 73). The balloon cover 2000 can comprise a first shell member 2002 and a second shell member 2004 that are configured to matingly engage with each other and be removably coupled to each other. For example, the first shell member 2002 and the second shell member 2004 can comprise two halves of an outer shell 2006 of and/or forming the balloon cover 2000 (FIG. 69).

The outer shell 2006 and balloon cover 2000 are shown in a disassembled configuration in the exploded view of FIG. 69 and in an assembled configuration in the various views of FIGS. 72-75C. FIG. 70 shows the first shell member 2002, disassembled from a remainder of the balloon cover 2000. However, since in some embodiments the first shell member 2002 and the second shell member 2004 can be configured the same (e.g., identically formed), the first shell member 2002 shown in FIG. 70 may alternatively be the second shell member 2004. Additionally, FIGS. 71A-71C show details views of a mating interface 2008 (FIG. 71C) between and related mating interface features or members (FIGS. 71A-71C) of the first shell member 2002 and the second shell member 2004.

Each of the first shell member 2002 and the second shell member 2004 includes a first portion (e.g., first shell portion) 2010 and a second portion (e.g., second shell portion) 2012. In some embodiments, the first portion 2010 and the second portion 2012 of one of the first shell member 2002 and the second shell member 2004 can be continuous with one another (e.g., formed as one piece). In some embodiments, the second portion 2012 can have a second width 2018 that is larger than a first width 2016 of the first portion 2010 (FIG. 70), the widths defined in a radial direction relative to a central longitudinal axis 2014 of the balloon cover 2000 (which can be coaxial with a central longitudinal axis of the delivery apparatus when assembled and coupled around the delivery apparatus). In some embodiments, the first width 2016 and the second width 2018 can be diameters.

When the first shell member 2002 and the second shell member 2004 are assembled together (e.g., in mating engagement), the first portions 2010 of the first shell member 2002 and the second shell member 2004 can form the first cover portion 2001 and define an elongate cavity 2020 (which, in some embodiments can be referred to as a lumen). The cavity 2020 can be configured to receive a distal end portion of a delivery apparatus and at least a portion of a balloon (e.g., a majority portion in some embodiments) mounted on the distal end portion of the delivery apparatus (e.g., balloon 318 of the distal end portion 309, as shown in FIGS. 69 and 72-75C).

For example, the first portion 2010 of the first shell member 2002 (and similarly, the second shell member 2004) comprises an outer surface 2022 (FIGS. 69 and 70) and an inner surface 2024 (FIG. 70). The inner surface 2024 can be a mating surface that is configured to mate with or matingly engage with (e.g., have face-to-face contact with) a respective inner surface of the first portion 2010 of the other (e.g., second) shell member forming the balloon cover 2000. In some embodiments, the inner surface 2024 can be a planar surface.

The first portion 2010 can further include a depression 2026 which is depressed into the inner surface 2024 (toward the outer surface 2022). Together, the depressions 2026 of the first shell member 2002 and the second shell member 2004 can form the cavity 2020. Thus, each depression 2026 of each of the first shell member 2002 and the second shell member 2004 can define a half cavity portion 2021 of the cavity 2020 (FIG. 70).

Each depression 2026 can be shaped to receive a portion of the distal end portion 309 of the delivery apparatus. For example, each depression 2026 can include a distal section 2028, a proximal section 2030, and an intermediate section 2032, the intermediate section 2032 disposed between the distal section 2028 and the proximal section 2030 (FIG. 70).

In some embodiments, the distal section 2028 can be shaped (e.g., configured) to receive the balloon (e.g., balloon 318) and the portion of the delivery apparatus which the balloon overlays. For example, in the embodiment shown in FIGS. 69-75C, the distal section 2028 can be shaped to receive a portion of the nose cone 322 and the distal end portion 332 of the balloon 318 which overlays the distal shoulder 326 of the delivery apparatus 300.

In some embodiments, the intermediate section 2032 can be shaped (e.g., configured) to receive the intermediate portion 335 of the balloon and the portion of the delivery apparatus 300 which the intermediate portion 335 overlays (e.g., the valve mounting portion 324).

In some embodiments, the proximal section 2030 can be shaped (e.g., configured) to receive at least a distal portion of the proximal end portion 333 of the balloon 318. In some embodiments, a more proximal portion of the proximal end portion 333 of the balloon 318 can extend into the second portion 2012 of the first shell member 2002 or the second shell member 2004 (FIGS. 70 and 72). In other embodiments, the proximal section 2030 can be shaped to receive an entirety of the proximal end portion 333 of the balloon 318.

In this way, a shape or contour of the depression 2026 can vary along a first length 2034 of the first portion 2010, the first length 2034 extending in an axial direction relative to the central longitudinal axis 2014 (FIG. 70). For example, as shown in FIG. 70, the intermediate section 2032 is narrower than each of the distal section 2028 and the proximal section 2030. In some embodiments, a width of the intermediate section 2032 is constant along a majority of a length of the intermediate section 2032.

In other embodiments, each depression 2026 can include the distal section 2028 and a proximal section which may resemble the intermediate section 2032 and extend from the distal section 2028 to the second portion 2012. In such embodiments, the proximal section can be configured to receive the intermediate portion 335 of the balloon and the portion of the delivery apparatus 300 which the intermediate portion 335 overlays (e.g., the valve mounting portion 324). In some embodiments, the proximal section can be further configured to receive the proximal end portion 333 of the balloon 318 which may not have a wider diameter portion than the intermediate portion 335 when disposed within the balloon cover 2000. Such an exemplary embodiment is shown in FIGS. 108-114, as described further below.

In some embodiments, the first length 2034 of the first portion 2010 can be longer than a second length 2036 of the second portion 2012.

In other embodiments, the second length 2036 of the second portion 2012 can be the same or longer than the first length 2034 of the first portion 2010.

In some embodiments, the second length 2036 of the second portion 2012 can be selected based on a length and/or size of the positioning device (e.g., positioning device 1100) to be contained within the second portions 2012 of the first shell member 2002 and the second shell member 2004 when they are coupled together in mating engagement. For example, in some embodiments, the second length 2036 can be the same or longer than a length of the positioning device 1100. In some embodiments, the second length 2036 can be shorter than a length of the positioning device 1100, but long enough to cover enough of the positioning device (e.g., a majority portion or wider or larger diameter portions of the positioning device) such that a user is blocked or deterred from grabbing onto the positioning device 1100.

When the first shell member 2002 and the second shell member 2004 are assembled to one another (e.g., coupled together in mating engagement), the second portions 2012 of the first shell member 2002 and the second shell member 2004 can form the second cover portion 2003 and define a cavity 2038 (FIGS. 69 and 72-75A). The cavity 2038 can be configured to receive a positioning device (e.g., positioning device 1100, as shown in FIGS. 69 and 72-75C) mounted on the distal end portion 309 of the delivery apparatus 300, proximal to a valve mounting portion 324 of the distal end portion 309.

Inner surfaces of walls of the second portion 2012 can define one half cavity portion 2040 of the cavity 2038 (FIG. 70). For example, as shown in FIG. 70, the second portion 2012 of the first shell member 2002 (and the second shell member 2004) can be defined by a first wall 2050, a second wall 2052, a third wall 2054, and a fourth wall 2056. The first wall 2050 can be relatively planar and the central longitudinal axis 2014 can be normal to the first wall 2050. The second wall 2052 and the third wall 2054 can be curved (as shown in FIGS. 69-75C). The fourth wall 2056 can be relatively planar and arranged perpendicular to the first wall 2050. In some embodiments, the fourth wall 2056 can define an opening (which can also be referred to herein as a window) 2046 and extend between the second wall 2052 and the third wall 2054 (e.g., in a circumferential direction or in a direction that is perpendicular to the central longitudinal axis 2014).

Figure 76A:
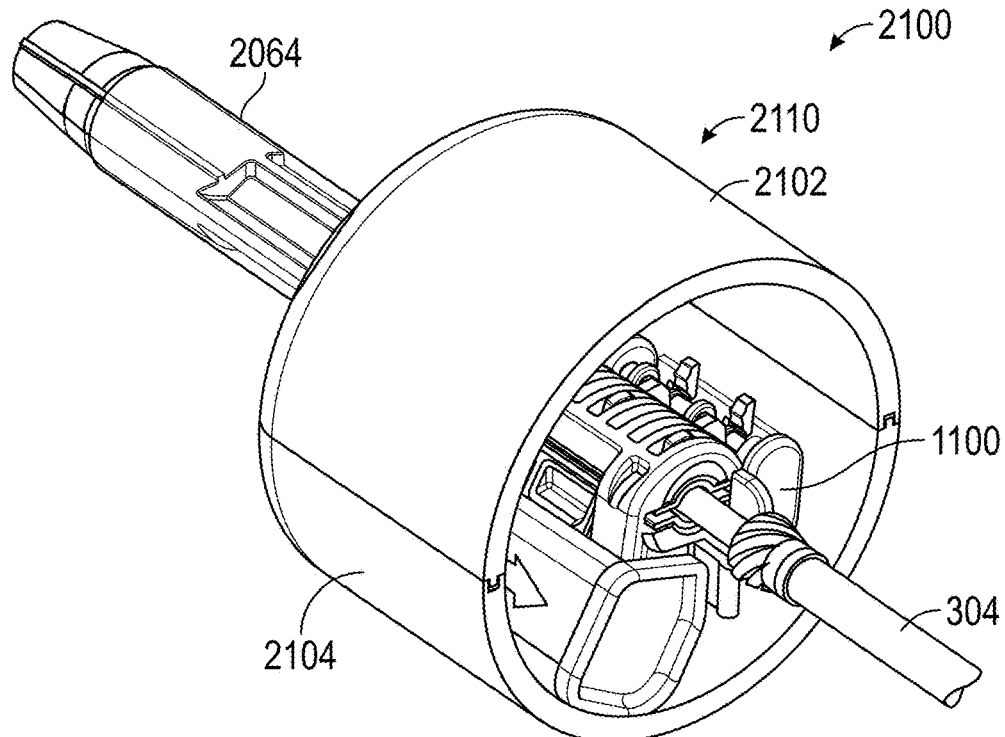
FIG. 76A is a perspective view of another embodiment of a balloon cover for a distal end portion of delivery apparatus which is configured to cover an inflatable balloon and a positioning device mounted on the distal end portion, where a portion of the balloon cover covering the positioning device has walls that fully enclose the positioning device therein.

In other embodiments, as explained further below with reference to FIGS. 76A and 76B, the second portion 2012 may not include the fourth wall 2056 (and the opening 2046) and instead the second wall 2052 and the third wall 2054 can be continuous with one another (e.g., forming one continuously curved wall, forming a complete half cylinder).

Each of the walls of the second portion 2012 can include an inner surface and an outer surface. For example, the first wall 2050 can have a first inner surface 2042, the second wall 2052 can have a second inner surface 2044, the third wall 2054 can have a third inner surface 2043, and the fourth wall 2056 can have a fourth inner surface 2048 (FIG. 70). The first inner surface 2042, the second inner surface 2044, the third inner surface 2043, and the fourth inner surface 2048 can define the half cavity portion 2040.

As shown in FIGS. 69 and 70, in some embodiments, the depression 2026 can extend to the first inner surface 2042. In this way, the depression 2026 can be continuous from the first inner surface 2042 to a distal end of the first portion 2010.

In some embodiments, the second inner surface 2044 and the third inner surface 2043 are each curved and, together, form a half cylinder shape of the second portion 2012. In some embodiments, the second inner surface 2044 and the first inner surface 2042 are separated from one another by the opening 2046 and connected together by the fourth inner surface 2048, at a proximal end of the second portion 2012.

The second portion 2012 of the first shell member 2002 (and similarly, the second shell member 2004) can further included a mating surface 2058 which is configured to mate with a corresponding mating surface of the second shell member 2004 (as shown in FIG. 71C). The mating surface 2058 can be formed along edges of the first wall 2050, the second wall 2052, and the third wall 2054.

In some embodiments, the mating surface 2058 of the second portion 2012 can be continuous with (and/or in a same plane) as the inner surface 2024 of the first portion 2010. In this way, the inner surface 2024 and the mating surface 2058 can form an entire mating surface of the first shell member 2002 or the second shell member 2004.

In some embodiments, the mating surface 2058 can be planar or relatively planar and include a first mating element, which in some embodiments can be configured as a protrusion (or tongue) 2060 extending along a first portion of the mating surface 2058 (e.g., on a first side of the mating surface 2058, relative to the central longitudinal axis 2014) and a second mating element, which in some embodiments can be configured as a groove (or depression) 2062 extending along a second portion of the mating surface 2058 (e.g., on a second side of the mating surface 2058 which is opposite the first side, relative to the central longitudinal axis 2014). A detail view of the first portion of the mating surface 2058 including the protrusion 2060 is shown in FIG. 71A and a detail view of the second portion of the mating surface 2058 including the groove 2062 is shown in FIG. 71B. The protrusion extends outward from the mating surface 2058 and the groove 2062 is depressed into the mating surface 2058.

FIG. 71C is a detail view of the mating interface 2008 between the protrusion 2060 of the first shell member 2002 (e.g., on the first portion of the mating surface 2058 of the first shell member 2002) and the groove 2062 of the second shell member 2004 (e.g., on the second portion of the mating surface 2058 of the second shell member 2004). As shown in FIG. 71C, in some embodiments, the respective mating surfaces 2058 of the respective second portions 2012 of the first shell member 2002 and the second shell member 2004 can be positioned against one another (e.g., in face-to-face contact) and the protrusion 2060 of the first shell member 2002 can extend into (and interface or mate with) the groove 2062 of the second shell member 2004. The reverse of this mating engagement can occur at the second portions of the mating surfaces 2058 of the first shell member 2002 and the second shell member 2004 (e.g., on an opposite side of the balloon cover 2000, the protrusion 2060 of the second shell member 2004 can extend into and interface or mate with the groove 2062 of the first shell member 2002.

In other embodiments, the mating interface 2008 between the first shell member 2002 and the second shell member 2004 can be configured differently with different interlocking or interfacing mating features (e.g., such as other lock-and-key or complementary features). In some embodiments, the mating interface 2008 between the first shell member 2002 and the second shell member 2004 can have different protruding and depressed interlocking features, such as a differently shaped protrusion (e.g., triangular in cross-section or a series of spaced apart protrusions) and a correspondingly shaped groove(s) or depression(s).

The configuration of the mating interface 2008, as described above, can prevent the first shell member 2002 and the second shell member 2004 from sliding past one another when the assembled balloon cover 2000 is grabbed or handled by a user.

Once assembled in mating engagement (as shown in FIGS. 72-75C), the first shell member 2002 and the second shell member 2004 can be held or coupled together (e.g., such that they cannot be pulled apart from one another) via a coupling element. In some embodiments, as shown in FIGS. 69, 72, 73, and 75A, the coupling element can be configured as a sleeve 2064. In some embodiments, the sleeve 2064 can be tubular and configured to slide over and around the mated together first portions 2010 of the first shell member 2002 and the second shell member 2004. For example, the sleeve 2064 can be configured to hold the first shell member 2002 and the second shell member 2004 in mating engagement with one another. As a result, the balloon cover 2000 can be held together (and mounted) on and around the distal end portion 309 of the delivery apparatus.

As introduced above and shown in FIGS. 72 and 73, when assembled together, the first portions 2010 of the first shell member 2002 and the second shell member 2004 can cover and enclose therein a portion of the distal end portion 309 of the delivery apparatus and the balloon 318. In some embodiments, the portion of the delivery apparatus covered by the first portions 2010 of the balloon cover 2000 can include a portion of the nose cone 322, the distal shoulder 326, the valve mounting portion 324, and a portion of the inner shaft 308 which the proximal end portion 333 of the balloon 318 is arranged around, and the portions of the balloon 318 covering these portions of the delivery apparatus (FIG. 72).

Additionally, as shown in FIGS. 72 and 73, when assembled together, the second portions 2012 of the first shell member 2002 and the second shell member 2004 can cover and enclose therein a positioning device (e.g., positioning device 1100) mounted on the distal end portion 309 of the delivery apparatus, proximal to the valve mounting portion 324 of the distal end portion 309 of the delivery apparatus.

In some embodiments, the second portions 2012 of the first shell member 2002 and the second shell member 2004 can cover and enclose an entirety of the positioning device 1100. In other embodiments, the second portions 2012 of the first shell member 2002 and the second shell member 2004 can cover and enclose a majority of the positioning device 1100 (e.g., all but a proximal most portion, as shown in FIGS. 72 and 72).

When assembled together, the second portions 2012 of the first shell member 2002 and the second shell member 2004 can form a closed distal end 2066 (FIGS. 72, 73, and 75A) and an open proximal end 2068 (FIGS. 72-75C). For example, the closed distal end 2066 can be formed by outer surfaces 2070 of the first walls 2050 of the first shell member 2002 and the second shell member 2004.

In other embodiments, the distal end 2066 can be at least partially open with one or more openings or windows in the first walls 2050 of the first shell member 2002 and/or the second shell member 2004.

Figure 74:
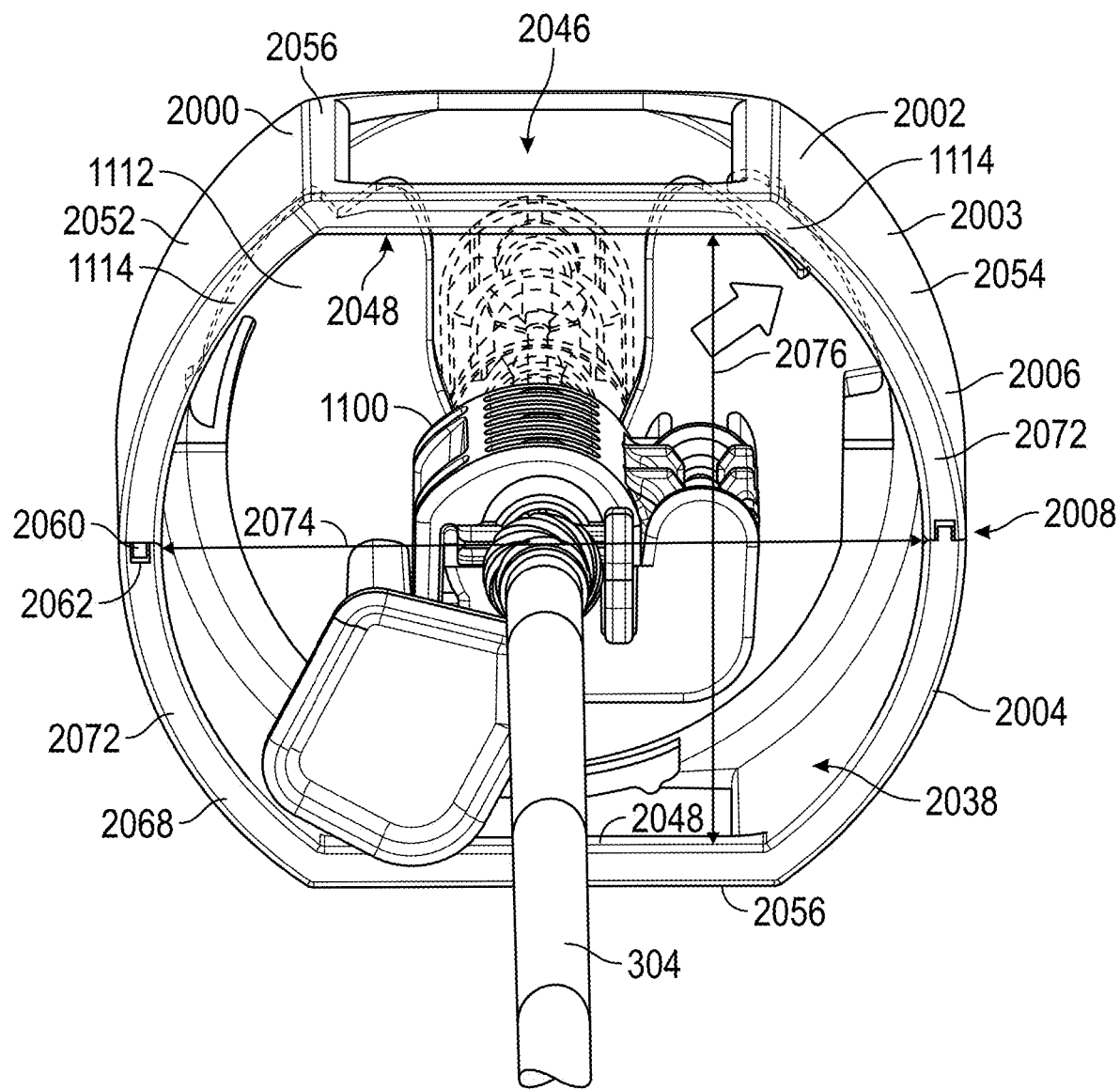
FIG. 74 is a perspective end view of the balloon cover of FIG. 69, from a proximal end of the balloon cover, in an assembled configuration.
Figure 75A:
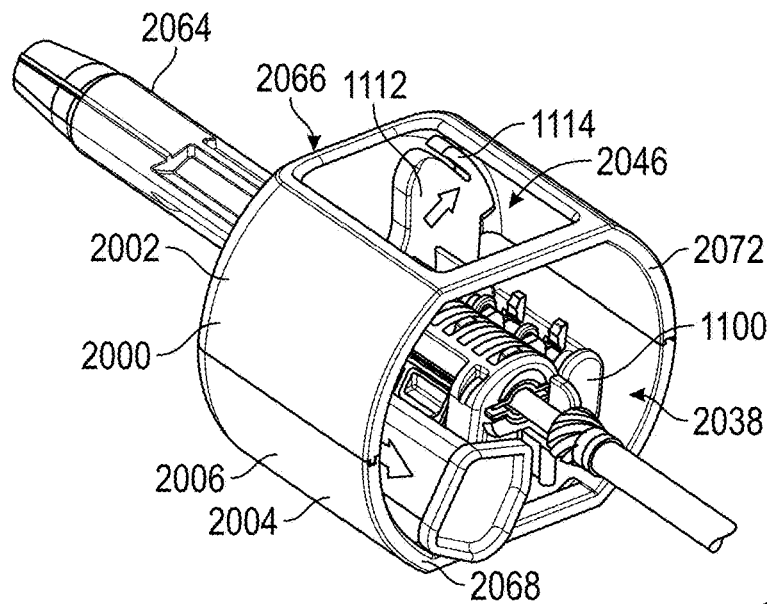
FIG. 75A is a perspective view of the balloon cover of FIG. 69 in an assembled configuration, where the portion of the balloon cover covering the positioning device has walls including one or more windows that are configured to reduce a height of the balloon cover.
Figure 75B:
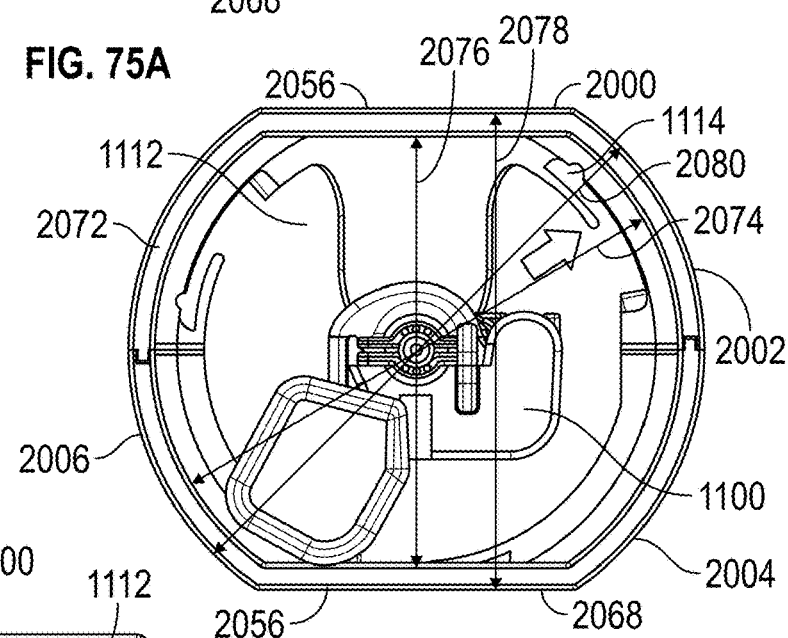
FIG. 75B is an end view of the balloon cover of FIG. 75A.
Figure 75C:
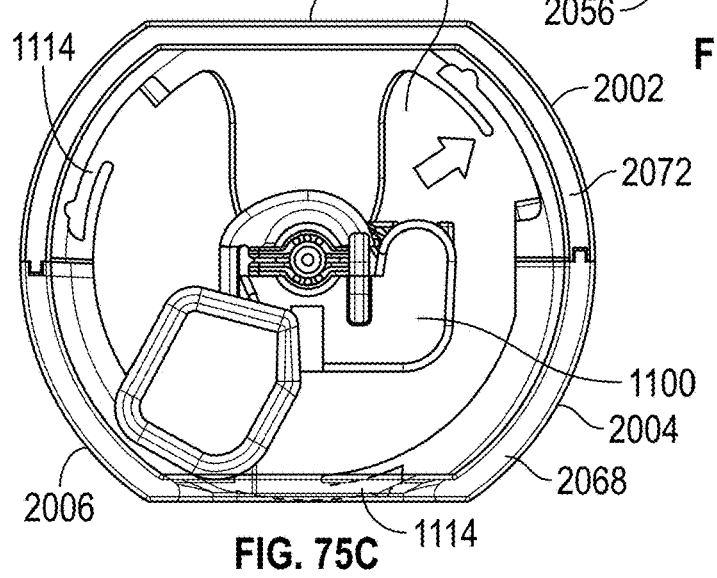
FIG. 75C is a cross-sectional end view of the balloon cover of FIG. 75A.

Additionally, in some embodiments (as shown in FIGS. 74-75C), the open proximal end 2068 can be formed by edge portions 2072 of the second wall 2052 and the third wall 2054 of each of the first shell member 2002 and the second shell member 2004.

In other embodiments, the proximal end 2068 can be at least partially closed. For example, in such embodiments, the edge portions 2072 can extend radially inward to form partial (e.g., not fully enclosed) walls.

The first portions 2010 of the first shell member 2002 and the second shell member 2004 extend distally, in the axial direction, from the closed distal end 2066.

Outer surfaces of the walls of the second portions 2012 of the first shell member 2002 and the second shell member 2004 can form the second cover portion 2003 of the balloon cover 2000 and can provide a surface for a user to grab and/or hold onto when sliding the sleeve 2064 off the first portions 2010 (so that the balloon cover 2000 can be removed from the delivery apparatus).

When the second portions 2012 of the first shell member 2002 and the second shell member 2004 are assembled to form the second cover portion 2003, a cylinder-shaped enclosure (e.g., cylinder) can be formed. Inner dimensions of the cylinder-shaped enclosure can define the cavity 2038. For example, the second cover portion 2003 can have an inner diameter 2074 and an inner height 2076 (FIGS. 74 and 75B). The inner height 2076 can be defined between the fourth inner surface 2048 of the fourth wall 2056 of the first shell member 2002 and the fourth inner surface 2048 of the fourth wall 2056 of the second shell member 2004 (FIG. 74). The inner diameter 2074 can be defined between oppositely arranged curved walls (e.g., second walls 2052, as shown in FIG. 74) of the first shell member 2002 and the second shell member 2004.

As shown in FIGS. 75B and 75C, the inner diameter 2074 and the inner height 2076 can be selected based on a largest dimension of the positioning device to be contained within the cavity 2038. For example, the inner diameter 2074 and the inner height 2076 can be selected such that the flange portion 1112 of the positioning device 1100 fits within the cavity 2038, without touching (e.g., being spaced away from) the second inner surfaces 2044 and the third inner surfaces 2043 of the first shell member 2002 and the second shell member 2004. For example, the inner diameter 2074 can be larger than an outer diameter of the flange portion 1112.

In some embodiments, the inner height 2076 can be the same or slightly smaller than the outer diameter of the flange portion 1112. For example, in some embodiments, as shown in FIG. 75C, one or more portions of the flange portion 1112 of the positioning device 1100 (e.g., an extension portion 1114) can extend into one of the openings 2046 (e.g., between the fourth inner surface 2048 and an outer surface of the fourth wall 2056).

As such, when a user grabs onto the exterior of the second cover portion 2003 (e.g., to remove the sleeve 2064), any movement of the balloon cover 2000 will not result in movement of the positioning device 1100 relative to the delivery apparatus, since the balloon cover 2000 does not directly contact the positioning device 1100. For example, if the balloon cover 2000 is rotated, this rotation will not result in rotation of the positioning device 1100, thereby maintaining the positioning device in a specified and intended circumferential position relative to the delivery apparatus. This can enable a prosthetic valve to be mounted on the valve mounting portion of the delivery apparatus in a predetermined circumferential orientation relative to a radiopaque marker on the delivery apparatus, as discussed herein (e.g., as discussed above with reference to FIG. 57).

In some embodiments, as shown in FIGS. 74-75C, the inner height 2076 can be smaller than the inner diameter 2074. Correspondingly, the second cover portion 2003 can have an outer height 2078 that is smaller than an outer diameter 2080 (FIG. 75B). The reduced inner height 2076 and outer height 2078, as compared to the corresponding diameters, of the second cover portion 2003 can reduce an overall packaging space of the balloon cover 2000. This can reduce material costs of the balloon cover itself and packaging materials used to contain the balloon cover. Thus, the inner diameter 2074 and the inner height 2076 can be selected to be as small as possible to reduce packaging space, while still being large enough to prevent engagement with the positioning device (FIG. 76C).

In some embodiments, the configuration of the openings 2046 in the fourth walls 2056 of the first shell member 2002 and the second shell member 2004 can result in the reduced inner height 2076 and outer height 2078.

In some embodiments, the openings 2046 can also allow a user to visualize the positioning device 1100 and the distal end portion 309 of the delivery apparatus 300, which may allow for easier assembly of the balloon cover 2000 around the delivery apparatus.

In other embodiments, the second cover portion 2003 can be cylindrical and the first shell member 2002 and the second shell member 2004 can have walls that fully enclose the positioning device therein, without any openings. For example, FIGS. 76A and 76B show another exemplary embodiment of a balloon cover 2100 comprising a first shell member 2102 and a second shell member 2104 that are configured to matingly engage with each other and be removably coupled to each other.

Figure 76B:
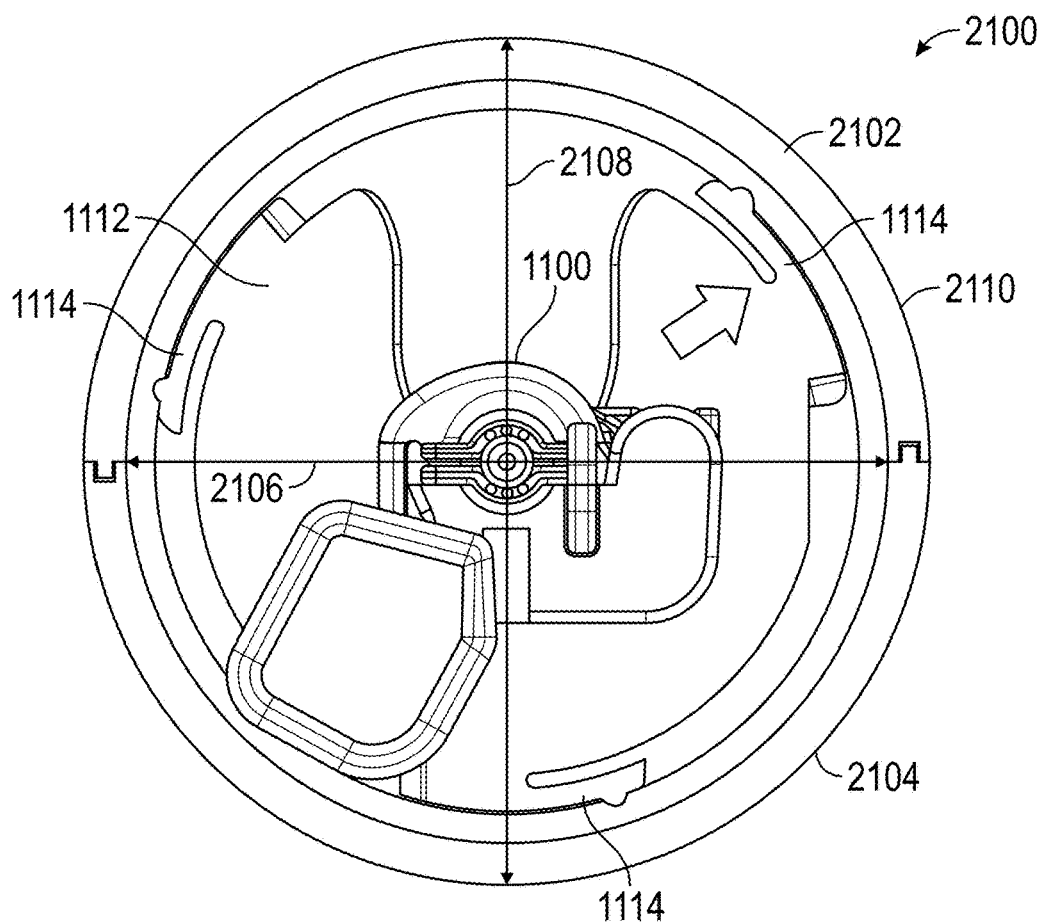
FIG. 76B is an end view of the balloon cover of FIG. 76A.

The first shell member 2102 and the second shell member 2104 can be configured similarly to the first shell member 2002 and the second shell member 2004 of the balloon cover 2000 (FIGS. 69-75C), except the first shell member 2102 and the second shell member 2104 do not include an opening 2046 and an inner diameter 2106 and outer diameter 2108 of a second cover portion 2110 (similar to second cover portion 2003) are constant around a circumference of the second cover portion 2110 (FIG. 76B). As such, the second cover portion 2110 does not have a reduced height (as compared to the balloon cover 2000). Thus, the balloon cover 2100 (FIGS. 76A and 76B) can increase packaging space as compared to the balloon cover 2000 (FIGS. 69-75C).

FIGS. 108-114 show another embodiment of a balloon cover 2600 that is configured to cover a portion of a distal end portion of a delivery apparatus (e.g., distal end portion 309 of delivery apparatus 300) that includes an inflatable balloon (e.g., balloon 318) mounted thereon and a positioning device coupled to the distal end portion of the delivery apparatus, proximal to a valve mounting portion of the delivery apparatus (e.g., positioning device 1100). The balloon cover 2600 can be similar to the balloon cover 2000 of FIGS. 69-75C, except it is configured to receive a portion of the positioning device and prevent rotation of the positioning device and balloon cover 2600 relative to one another. For example, independent rotation between the positioning device and balloon cover 2600 can result in twisting of the balloon, thereby causing unpredictable rotation of the prosthetic heart valve during valve deployment at the implantation site (and thus uncertainty to the positioning of the prosthetic valve commissures relative to the native valve commissures).

The balloon cover 2600 comprises a first cover portion 2601 that is configured to cover at least a portion of the distal end portion of the delivery apparatus that includes the balloon and a second cover portion 2603 that is configured to cover the positioning device. The balloon cover 2600 can comprise a first shell member 2602 and a second shell member 2604 that are configured to matingly engage with each other and be removably coupled to each other (FIGS. 110 and 113). For example, the first shell member 2602 and the second shell member 2604 can comprise two halves of an outer shell 2606 of and/or forming the balloon cover 2600 (FIG. 110).

The outer shell 2606 and balloon cover 2600 are shown in a disassembled configuration in the exploded view of FIG. 110 and in an assembled configuration in the various views of FIGS. 108, 109, 111, and 113. Further, FIG. 113 shows a cross-sectional view of the balloon cover 2600 while FIG. 114 shows one of the shell members (e.g. first shell member 2602) arranged around the delivery apparatus.

In some embodiments, the first shell member 2602 and the second shell member 2604 can have a similar or same mating interface 2008 as that described above with reference to FIGS. 71A-71C.

Each of the first shell member 2602 and the second shell member 2604 includes a first portion (e.g., first shell portion) 2610 and a second portion (e.g., second shell portion) 2612. In some embodiments, the first portion 2610 and the second portion 2612 of one of the first shell member 2602 and the second shell member 2604 can be continuous with one another (e.g., formed as one piece). Similar to the balloon cover 2000, the second portion 2612 of the balloon cover 2600 can have a larger width than the first portion 2610.

When the first shell member 2602 and the second shell member 2604 are assembled together (e.g., in mating engagement), the first portions 2610 of the first shell member 2602 and the second shell member 2604 can form the first cover portion 2601 and define an elongate cavity 2620 (FIGS. 110 and 113). The cavity 2620 can be configured to receive a distal end portion of a delivery apparatus and at least a portion of a balloon (e.g., a majority portion in some embodiments) mounted on the distal end portion of the delivery apparatus (e.g., balloon 318 of the distal end portion 309, as shown in FIGS. 110, 113, and 114).

For example, the first portion 2610 of the first shell member 2602 (and similarly, the second shell member 2604) comprises an outer (radially outward facing) surface 2622 (FIGS. 110, 112, and 113) and an inner (radially inward facing) surface 2624 (FIGS. 110 and 114). The inner surface 2624 can be a mating surface that is configured to mate with or matingly engage with (e.g., have face-to-face contact with) a respective inner surface of the first portion 2610 of the other (e.g., second) shell member forming the balloon cover 2600. In some embodiments, the inner surface 2624 can be a planar surface.

In some embodiments, the first portion 2610 of one of the shell members (the second shell member 2604, as shown in FIGS. 110 and 112) can include an aperture or window 2660 disposed through the outer surface 2622 and the inner surface 2624 and positioned such that the marker 600 on the distal shoulder (or other marker on the distal end portion of the delivery apparatus) can be visualized by a user when the balloon cover is coupled to the delivery apparatus, as described herein.

The first portion 2610 can further include a depression 2626 which is depressed into the inner surface 2624 (toward the outer surface 2622, FIGS. 110 and 114). Together, the depressions 2626 of the first shell member 2602 and the second shell member 2604 can form the cavity 2620.

Each depression 2626 can be shaped to receive a portion of the distal end portion 309 of the delivery apparatus. For example, each depression 2626 can include a distal section 2628 and a proximal section 2630 (FIG. 110). In some embodiments, the distal section 2628 can be shaped (e.g., configured) to receive the balloon (e.g., balloon 318) and the portion of the delivery apparatus which the balloon overlays. For example, in the embodiment shown in FIGS. 108-114, the distal section 2628 can be shaped to receive a portion of the nose cone 322 and the distal end portion 332 of the balloon 318 which overlays the distal shoulder 326 of the delivery apparatus 300 (FIGS. 110, 113, and 114).

In some embodiments, the proximal section 2630 can be shaped (e.g., configured) to receive the intermediate portion 335 of the balloon and the portion of the delivery apparatus 300 which the intermediate portion 335 overlays (e.g., the valve mounting portion 324). In some embodiments, the proximal section 2630 can also be shaped to receive at least a distal portion of the proximal end portion 333 of the balloon 318, but in the embodiment shown in FIGS. 108-114, the proximal end portion 333 of the balloon 318 can have a same profile or diameter as the intermediate portion 335. Thus, the proximal section 2630 can have a constant or relatively constant width along its length (or a majority of its length), from the distal section 2628 to the second portion 2612 of the shell member. In other embodiments, each depression 2626 can be shaped similar to the depression 2026 of the balloon cover 2000 shown in FIGS. 69-75C.

In this way, a shape or contour of the depression 2626 can vary along a length of the first portion 2610. For example, as shown in FIGS. 110, 113, and 114, the proximal section 2630 is narrower than the distal section 2628.

In some embodiments, the length of the first portion 2610 can be longer than a length of the second portion 2612, as described above with reference to FIGS. 69-75C.

The second portion 2012 of each of the first shell member 2602 and the second shell member 2604 can be configured (sized and shaped) based on a length and/or size of the positioning device (e.g., positioning device 1100) to be contained within the second portions 2612 of the first shell member 2602 and the second shell member 2604 when they are coupled together in mating engagement.

When the first shell member 2602 and the second shell member 2604 are assembled to one another (e.g., coupled together in mating engagement), the second portions 2612 of the first shell member 2602 and the second shell member 2604 can form the second cover portion 2603 and define a cavity 2638 (FIGS. 108 and 111-114). The cavity 2638 can be configured to receive a positioning device (e.g., positioning device 1100, as shown in FIGS. 108-114) mounted on the distal end portion 309 of the delivery apparatus 300, proximal to a valve mounting portion 324 of the distal end portion 309. In some embodiments, the overall dimensions of the cavity 2638, apart from the one or more cavities 2652 described further below, can be similar to the cavity 2038 of the balloon cover 2000, as described above.

Similar to the balloon cover 2000 (FIGS. 69-75C), inner surfaces of walls of the second portion 2612 can define one half cavity portion of the cavity 2638. In some embodiments, the second portion 2612 of the second shell member 2604 can be configured the same or similar to the second portion 2012 of the first and second shell members 2002 and 2004 of the balloon cover 2000 (see description of FIGS. 69-75C above). However, the second portion 2612 of the first shell member 2602 can have a first wall 2650 (the wall connecting to the first portion 2610) that is shaped (e.g., keyed) to receive a portion of the positioning device 1100. For example, the first wall 2650 of the second portion 2612 of the first shell member 2602 can be shaped to form one or more cavities 2652 that are shaped to receive and hold therein a portion of the flange portion 1112 of the positioning device 1100 (FIGS. 110, 113, and 114). In some embodiments, the second portion 2612 of the first shell member 2602 can comprise one or more protruding wall portions 2654 that are part of or extend from the first wall 2650 to protrude into the cavity 2638 and form the one or more cavities 2652 (FIGS. 108, 110, 113, and 114).

By configuring the first wall 2650 of the second portion 2612 of the first shell member 2602 to have the one or more cavities 2652, when the balloon cover 2600 is coupled to the delivery apparatus and around the positioning device 1100, the positioning device 1100 and balloon cover 2600 are prevented from rotating relative to one another. As a result, twisting of the balloon 318 can be avoided.

In some embodiments, one of the shell portions of any of the other balloon covers described herein (e.g., with reference to FIGS. 69-86) can have a second portion comprising one or more cavities 2652 that are shaped to receive and hold therein a portion of the flange portion 1112 of the positioning device 1100, as described above with reference to FIGS. 108-114.

Returning to FIGS. 108-114, remaining walls of the second portion 2612 of the first shell member 2602 can be similar to the walls of the second shell member 2604. As described above with reference to the balloon cover 2000, the second portions 2612 of the balloon cover 2600 can define openings 2646.

Once assembled in mating engagement (as shown in FIGS. 108, 109, and 111-113), the first shell member 2602 and the second shell member 2604 can be held or coupled together (e.g., such that they cannot be pulled apart from one another) via a coupling element. In some embodiments, the coupling element can be configured as a sleeve 2664. The sleeve 2664 can be configured the same or similar to the sleeve 2064 of the balloon cover 2000.

As introduced above, when assembled together, the first portions 2610 of the first shell member 2602 and the second shell member 2604 can cover and enclose therein a portion of the distal end portion 309 of the delivery apparatus and the balloon 318 (FIGS. 108, 109, and 111-114). In some embodiments, the portion of the delivery apparatus covered by the first portions 2610 of the balloon cover 2600 can include a portion of the nose cone 322, the distal shoulder 326, the valve mounting portion 324, and a portion of the inner shaft 308, and the portions of the balloon 318 covering these portions of the delivery apparatus (FIGS. 113 and 114).

Similar to as described above with reference to FIGS. 69-75C, outer surfaces of the walls of the second portions 2612 of the first shell member 2602 and the second shell member 2604 can form the second cover portion 2603 of the balloon cover 2600 and can provide a surface for a user to grab and/or hold onto when sliding the sleeve 2664 off the first portions 2610 (so that the balloon cover 2600 can be removed from the delivery apparatus), without grabbing onto the positioning device 1100.

As introduced above with reference to FIGS. 38-41, the distal end portion 309 of the delivery apparatus 300 can include a distal tip portion 900 mounted on or disposed at the distal end of the outer shaft 304. In some embodiments, after mounting the prosthetic valve in a radially compressed state around the valve mounting potion 324 of the delivery apparatus 300, the outer shaft 304 and the intermediate shaft (e.g., balloon shaft) 306 can be moved axially relative to one another such that the distal tip portion 900 is arranged over the proximal end portion 333 of the balloon 318. As a result, the distal tip portion 900 can act as a proximal shoulder on a proximal side of the valve mounting portion 324 and resist movement of the radially compressed prosthetic valve, proximally in the axial direction, during advancing the distal end portion of the delivery apparatus to the target implantation site.

As previously described, prior to crimping the prosthetic valve around the valve mounting portion 324, the balloon 318 can undergo a cyclic de-airing process whereby the inflation fluid is introduced into the balloon and then withdrawn from the balloon. The process of introducing inflation fluid into the balloon 318 and then withdrawing the inflation fluid can be repeated one or more times as needed. During the de-airing process, the distal tip portion 900 is typically positioned proximal to the balloon 318 (e.g., off and away from the proximal end portion 333 of the balloon 318) to facilitate the flow of inflation fluid into the proximal end portion 333 of the balloon 318. In some embodiments, the de-airing process can be carried out while the balloon 318 is contained within a balloon cover. Following the de-airing process, the balloon cover can be removed from the balloon and the outer shaft 304 can be moved axially relative to the intermediate shaft 306 (and the inner shaft 308) to a more distal position extending over the proximal end portion 333 of the balloon 318 (as shown in FIG. 41). When the distal tip portion 900 is moved distally over the proximal end portion 333, residual fluid in the proximal end portion 333 of the balloon from the de-airing process can be pushed distally into the intermediate portion 335 and the distal end portion 332 of the balloon 318.

As introduced above, in order to accommodate this residual fluid without increasing a crimping profile of the prosthetic valve on the delivery apparatus, a radial depression 334 can be initially formed in the distal end portion 332 of the balloon 318 (e.g., prior to moving the distal tip portion 900 over the proximal end portion 333 of the balloon 328, FIG. 40). When the residual inflation fluid in the proximal end portion 333 of the balloon 318 is "squeezed" or pushed into the distal end portion 332 of the balloon 318 by advancing the distal tip portion 900, the displaced residual fluid can dilate the distal end portion 332 of the balloon 318 from the radially depressed state shown in FIG. 40 to the expanded state 924 shown in FIG. 41 (and shown with dashed lines in FIG. 40). As a result, undesirable inflation of the intermediate portion 324, which can thereby expand a crimping profile of the prosthetic valve, can be avoided.

Various techniques and mechanisms can be used to achieve the balloon shape shown in FIG. 40, including a balloon cover having an internal cavity that is shaped to produce the desired shape of the balloon (e.g., the radial depression 334).

Figure 77:
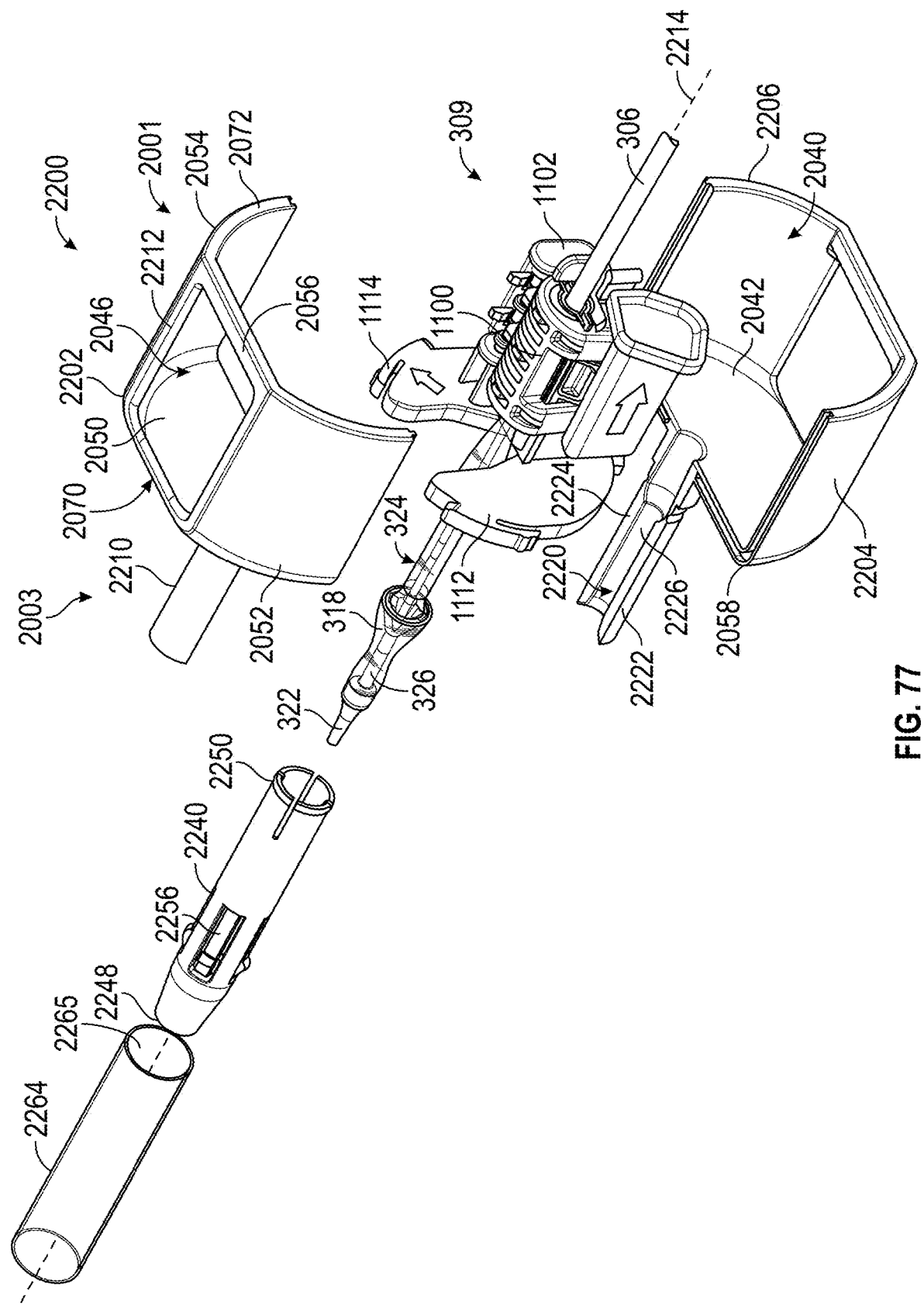
FIG. 77 is an exploded view of another embodiment of a balloon cover for a distal end portion of delivery apparatus which is configured to cover an inflatable balloon and a positioning device mounted on the distal end portion and create a specified, final shape of the inflatable balloon.

FIGS. 77-83B show an exemplary embodiment of a balloon cover 2200 that is configured to receive (and cover) a portion of a distal end portion of a delivery apparatus (e.g., distal end portion 309 of delivery apparatus 300, as shown in FIG. 77) that includes an inflatable balloon (e.g., balloon 318) mounted thereon. In some embodiments, the balloon cover 2200 is configured to additionally receive a positioning device coupled to the distal end portion of the delivery apparatus, proximal to a valve mounting portion of the delivery apparatus (e.g., positioning device 1100, as shown in FIGS. 53-55 and 77).

Figure 83A:
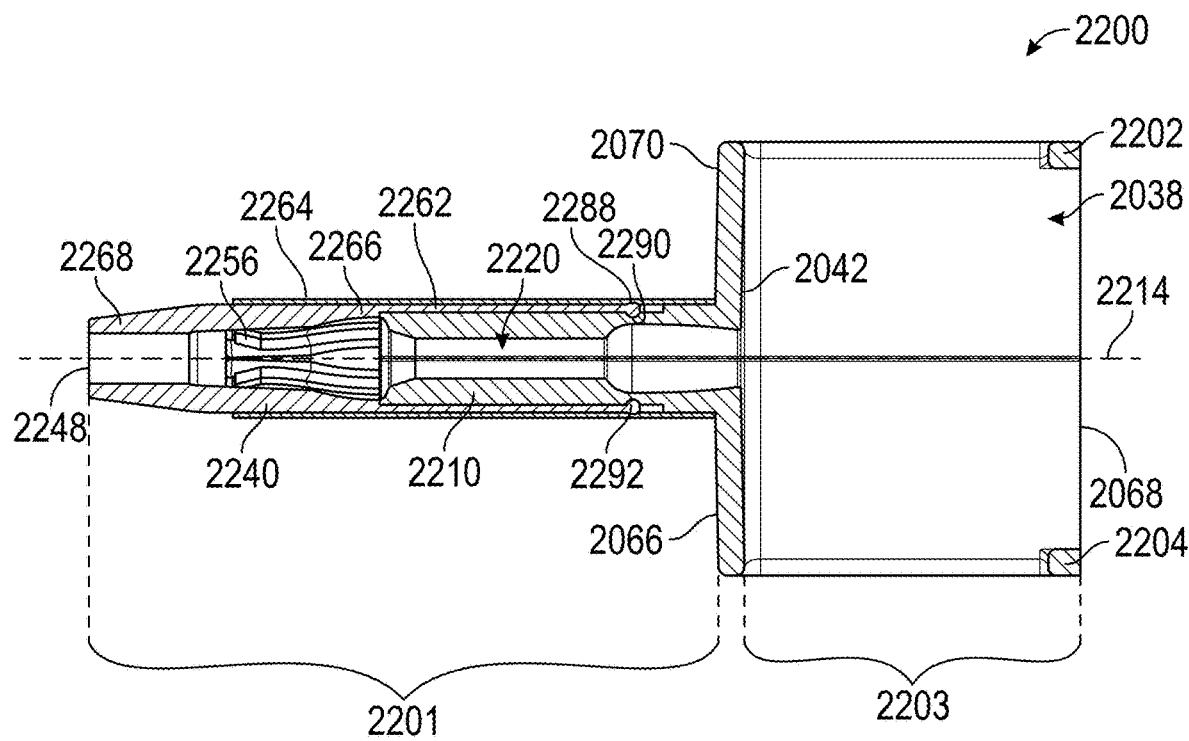
FIG. 83A is a first cross-sectional side view of the assembled balloon cover of FIG. 77.
Figure 83B:
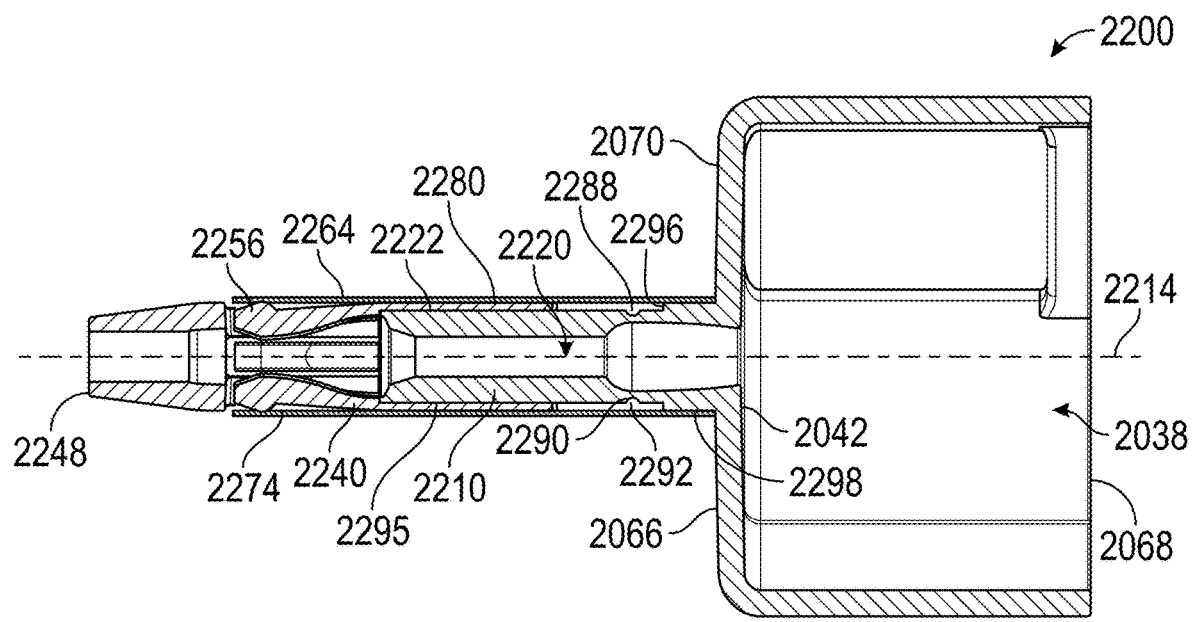
FIG. 83B is a second cross-sectional side view of the assembled balloon cover of FIG. 77.

More specifically, the balloon cover 2200 is configured to receive and create a specified, final shape of the balloon 318 (e.g., such as the shape shown in FIG. 40, which includes the radial depression 334). For example, FIG. 77 is an exploded view of the balloon cover 2200 configured to be assembled around the distal end portion 309 of the delivery apparatus 300. Cross-sectional views of the assembled balloon cover 2200 are shown in FIGS. 83A and 83B. As described more fully below, the balloon cover 2200 can be similar to the balloon cover 2100 described above with reference to FIGS. 69-75C, except for the addition of a depression sleeve that is configured to receive the distal end portion 332 of the balloon 318 and a first cavity (formed by depressions of the shell members) that is configured to receive the intermediate portion 335 and the proximal end portion 333 of the balloon 318.

As shown in FIGS. 77 and 83A, the balloon cover (or balloon cover assembly) 2200 comprises a first cover portion 2201 that is configured to cover at least a portion of the distal end portion of the delivery apparatus that includes the balloon. The balloon cover 2200 can further comprise a second cover portion 2203 that is configured to cover the positioning device (FIGS. 77 and 83A).

The balloon cover 2200 can comprise a first shell member 2202 and a second shell member 2204 that are configured to matingly engage with each other and be removably coupled to each other (similar to the first shell member 2002 and the second shell member 2004 of the balloon cover 2000). For example, the first shell member 2202 and the second shell member 2204 can comprise two halves of a shell 2206 of the balloon cover 2200 (FIGS. 77, 83A, and 83B).

The balloon cover 2200 can further comprise a depression sleeve 2240 (which can also be referred to as a depression cap, member, or tube). The depression sleeve 2240 can be configured to form a shape (e.g., an indented or depressed shape) of a portion of a balloon of the delivery apparatus (e.g., the radial depression 334 in the distal end portion 332 of the balloon 318). The depression sleeve 2240 is described in further detail below with reference to the various views of FIGS. 78-81B.

In some embodiments, the balloon cover 2200 can further comprise a coupling element, which in some embodiments can be a tubular sleeve (e.g., outer sleeve) 2264, which is configured to cover at least a portion of the depress sleeve 2240 and depress one or more depression members 2256 of the depression sleeve 2240 in a radially inward direction, toward the central longitudinal axis 2214, in order to form a negative depression in one or more portions of the balloon.

In some embodiments, the sleeve 2264 can be additionally configured to hold the first shell member 2202 and the second shell member 2204 in mating engagement with one another (e.g., as shown in FIGS. 83A and 83B). The sleeve 2264 can be the same or similar to the sleeve 2064, as described above.

Figure 82:
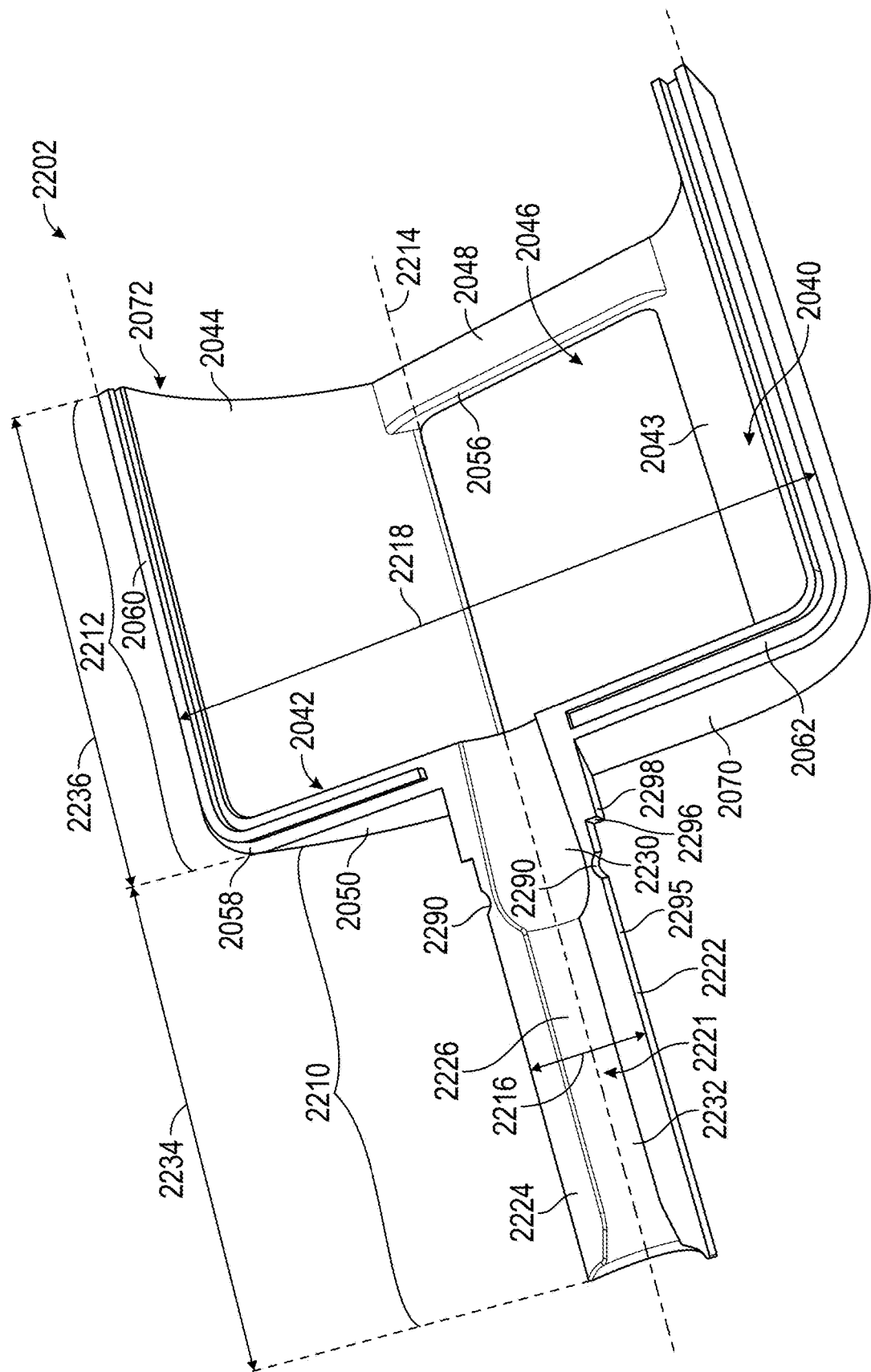
FIG. 82 is a perspective view of a shell member of the balloon cover of FIG. 77 disassembled from a remainder of the balloon cover.

The balloon cover 2200 is shown in a disassembled configuration in the exploded view of FIG. 77 and in an assembled configuration in the various views of FIGS. 83A and 83B. FIG. 82 shows the first shell member 2202 disassembled from a remainder of the balloon cover 2200. However, since in some embodiments the first shell member 2202 and the second shell member 2204 can be configured the same (e.g., identically formed), the first shell member shown in FIG. 82 may alternatively be the second shell member 2204. Additionally, FIGS. 78-81B show different views of the depression sleeve 2240 alone.

As shown in FIGS. 77 and 82, in some embodiments, each of the first shell member 2202 and the second shell member 2204 includes a first portion (e.g., first shell portion) 2210 and a second portion (e.g., second shell portion) 2212. In some embodiments, for each of the first shell member 2202 and the second shell member 2204, the first portion 2210 and the second portion 2212 can be continuous with one another.

In some embodiments, the second portion 2212 can have a second width 2218 that is larger than a first width 2216 of the first portion 2210, the widths defined in a radial direction relative to a central longitudinal axis 2214 of the balloon cover 2200 (which can be coaxial with a central longitudinal axis of the delivery apparatus when assembled and coupled around the delivery apparatus). In some embodiments, the first width 2216 and the second width 2218 can be diameters.

When the first shell member 2202 and the second shell member 2204 are assembled together (e.g., in mating engagement), the first portions 2210 of the first shell member 2202 and the second shell member 2204 can form a portion of the first cover portion 2201 (e.g., which also includes the depression sleeve 2240, as described further below) and define an elongate cavity 2220 (which, in some embodiments can be referred to as a lumen). The cavity 2220 (FIGS. 77, 83A, and 83B) can be configured to receive a distal end portion of a delivery apparatus and at least a portion of a balloon (e.g., an intermediate portion and proximal end portion in some embodiments) mounted on the distal end portion of the delivery apparatus (e.g., balloon 318 of the distal end portion 309, as shown in FIG. 77).

For example, the first portion 2210 of the first shell member 2202 (and similarly, the second shell member 2204) comprises an outer surface 2222 and an inner surface 2224 (FIGS. 77 and 82). The inner surface 2224 can be a mating surface that is configured to mate with or matingly engage with (e.g., have face-to-face contact with) a respective inner surface of the first portion 2210 of the other (e.g., second) shell member forming the balloon cover 2200. In some embodiments, the inner surface 2224 can be a planar surface.

The first portion 2210 can further include a depression 2226 which is depressed into the inner surface 2224, toward the outer surface 2222 (FIG. 82). Together, the depressions 2226 of the first shell member 2202 and the second shell member 2204 can form the cavity 2220 (FIGS. 77, 83A, and 83B). Thus, each depression 2226 of each of the first shell member 2202 and the second shell member 2204 can define a half cavity portion 2221 of the cavity 2220 (FIG. 82).

Each depression 2226 can be shaped to receive a portion of the distal end portion 309 of the delivery apparatus (e.g., a portion of the delivery apparatus which the intermediate and proximal end portions of the balloon 318 overlay). For example, each depression 2226 can include a proximal section 2230 and an intermediate section 2232 (FIG. 82). In some embodiments, the depressions 2226 of the balloon cover 2200 can be similar to the depressions 2026 of the balloon cover 2000 (FIG. 70), except the depressions 2226 do not include a distal section configured to receive the distal end portion 332 of the balloon 318.

For example, in some embodiments, the intermediate section 2232 can be shaped (e.g., configured) to receive the intermediate portion 335 of the balloon and the portion of the delivery apparatus 300 which the intermediate portion 335 overlays (e.g., the valve mounting portion 324).

In some embodiments, the proximal section 2230 can be shaped (e.g., configured) to receive at least a distal portion of the proximal end portion 333 of the balloon 318. In some embodiments, a more proximal portion of the proximal end portion 333 of the balloon 318 can extend into the second portion 2212 of the first shell member 2202 or the second shell member 2204. In other embodiments, the proximal section 2230 can be shaped to receive an entirety of the proximal end portion 333 of the balloon 318.

In this way, a shape or contour of the depression 2226 can vary along a first length 2234 of the first portion 2210, the first length 2234 extending in an axial direction relative to the central longitudinal axis 2214 (FIG. 82). For example, as shown in FIG. 82, the intermediate section 2232 can be narrower than the proximal section 2030. In some embodiments, a width of the intermediate section 2232 is constant along a majority of a length of the intermediate section 2232.

In some embodiments, the first length 2234 of the first portion 2210 can be longer than a second length 2236 of the second portion 2212 (FIG. 82).

In other embodiments, the second length 2236 of the second portion 2212 can be the same or longer than the first length 2234 of the first portion 2210.

In some embodiments, the second length 2236 of the second portion 2212 can be selected based on a length and/or size of the positioning device (e.g., positioning device 1100) to be contained within the second portions 2212 of the first shell member 2202 and the second shell member 2204 when they are coupled together in mating engagement. For example, in some embodiments, the second length 2236 can be the same or longer than a length of the positioning device 1100. In some embodiments, the second length 2236 can be shorter than a length of the positioning device 1100, but long enough to cover enough of the positioning device (e.g., a majority portion or wider or larger diameter portions of the positioning device) such that a user is blocked or deterred from grabbing onto the positioning device 1100.

When the first shell member 2202 and the second shell member 2204 are assembled to one another (e.g., coupled together in mating engagement), the second portions 2212 of the first shell member 2202 and the second shell member 2204 can form the second cover portion 2203 and define the cavity 2038 (FIGS. 83A and 83B). As described above with reference to FIGS. 69-75C, the cavity 2038 can be configured to receive a positioning device (e.g., positioning device 1100 shown in FIG. 77) mounted on the distal end portion 309 of the delivery apparatus 300, proximal to a valve mounting portion 324 of the distal end portion 309.

The second portion 2212 of each of the first shell member 2202 and the second shell member 2204 can be configured similarly to (or the same as) the second portion 2012 of each of the first shell member 2002 and the second shell member 2004 of the balloon cover 2000, as described above with reference to FIGS. 69-75C. Thus, similar components have been labeled similarly in FIGS. 77-83B.

For example, in some embodiments, the walls and inner and outer surfaces of the second portion 2212 can be configured the same is in the second portion 2012 (and thus, are labeled accordingly in FIGS. 77-83B). Further, the second portion 2212 can include the mating surface 2058 with the first mating element (e.g., protrusion 2060) and the second mating element (e.g., groove 2062). In this way, the second portions 2212 of the first shell member 2202 and the second shell member 2204 can be configured to matingly engage with each other in the same way as described above for balloon cover 2000 (e.g., as described above with reference to FIG. 71C).

As shown in FIGS. 77 and 82-83B, in some embodiments, the depression 2226 can extend to the first inner surface 2042. In this way, the depression 2226 can be continuous from the first inner surface 2042 to a distal end of the first portion 2210.

When assembled together, the first portions 2210 of the first shell member 2202 and the second shell member 2204 can cover and enclose therein a portion of the distal end portion 309 of the delivery apparatus and the balloon 318. In some embodiments, the portion of the delivery apparatus covered by the first portions 2210 of the balloon cover 2200 can include the valve mounting portion 324 and a portion of the inner shaft 308 which the proximal end portion 333 of the balloon 318 is arranged around, and the portions of the balloon 318 covering these portions of the delivery apparatus (FIGS. 77, 83A, and 83B).

Additionally, similar to as described above for the balloon cover 2000 (FIGS. 69 and 72-75C), when assembled together, the second portions 2212 of the first shell member 2202 and the second shell member 2204 can cover and enclose therein a positioning device (e.g., positioning device 1100) mounted on the distal end portion 309 of the delivery apparatus, proximal to the valve mounting portion 324 of the distal end portion 309 of the delivery apparatus.

In some embodiments, the second cover portion 2203 and the cavity 2038 can have the same or similar dimensions (e.g., inner and outer diameters and heights) to those described above with reference to the balloon cover 2000.

As introduced above, the balloon cover 2200 can further comprise the depression sleeve 2240 which is configured to form a negative depression in one or more portions of the balloon 318. For example, in some embodiments (as shown in FIGS. 77-83B), the depression sleeve 2240 can be configured to form a negative radial depression in the distal end portion 332 of the balloon 318 (e.g., the radial depression 334).

In other embodiments, the depression sleeve 2240 can be configured to form a depression in an alternate portion of the balloon (e.g., the intermediate portion of the proximal end portion). In these embodiments, the depression sleeve 2240 and the first portions 2210 of the first shell member 2202 and the second shell member 2204 can be modified such that the depression sleeve 2240 covers the alternate portion(s) of the balloon when the balloon cover is assembled around the delivery apparatus. In some embodiments, the depression sleeve 2240 can be configured to form one or more depressions in one or more locations along a length of the balloon (e.g., in the distal end portion 332 and the proximal end portion 333). In this way, a geometry of the depression sleeve 2240 and the first portions 2210 can be selected based on a specified geometry of the balloon which the balloon cover 2200 is configured to cover and at least partially shape.

As shown in FIGS. 77-81B, the depression sleeve 2240 can comprise a first portion 2242, a second portion 2244, and a third portion 2246, the second portion 2244 disposed between the first portion 2242 and the third portion 2246. In some embodiments, the first portion 2242 can be a distal end portion of the depression sleeve 2240 and can extend from a distal end (or first end) 2248 of the depression sleeve 2240 to the second portion 2244. In some embodiments, the third portion 2246 can be a proximal end portion of the depression sleeve 2240 and can extend from a proximal end (or second end) 2250 of the depression sleeve 2240 to the second portion 2244.

In some embodiments, the first portion 2242 can be configured to receive a distal portion of the delivery apparatus, such as a distal end portion of a distal shoulder (e.g., distal shoulder 226) and/or a portion of a nose cone (e.g., nose cone 322). An inner diameter and/or length (in the axial direction) of the first portion 2242 can be configured (e.g., sized) to receive the distal end portion of the delivery apparatus which is distal to the depressed portion of the balloon (e.g., distal to the radial depression 334).

In some embodiments, an inner lumen 2254 of the first portion 2242, defined by an inner surface of the first portion 2242), can have a first lumen portion with a relative constant inner diameter 2251 and a second lumen portion with an inner diameter 2253 that can increase from the first lumen portion to the second portion 2244 of the depression sleeve 2240 (FIG. 81A).

In some embodiments, the first portion 2242 is tapered and can have an outer diameter 2252 (FIG. 81A) that tapers (e.g., decreases) from its proximal end (at or which connects to the second portion 2244) to the distal end 2248.

The second portion 2244 can also be referred to herein as a depression portion of the depression sleeve 2240. The second portion 2244 can comprise one or more depression members 2256 (FIGS. 78-81B). In some embodiments, the second portion 2244 can include multiple (e.g., two or more) depression members 2256 spaced apart from one another around a circumference of the second portion 2244. In some embodiments, as shown in FIGS. 78-83B, the second portion 2244 includes four depression members 2256. However, in alternate embodiments, the second portion 2244 can includer more or fewer than four depression members 2256 (e.g., such as two, three, five, six, or the like).

Figure 78:
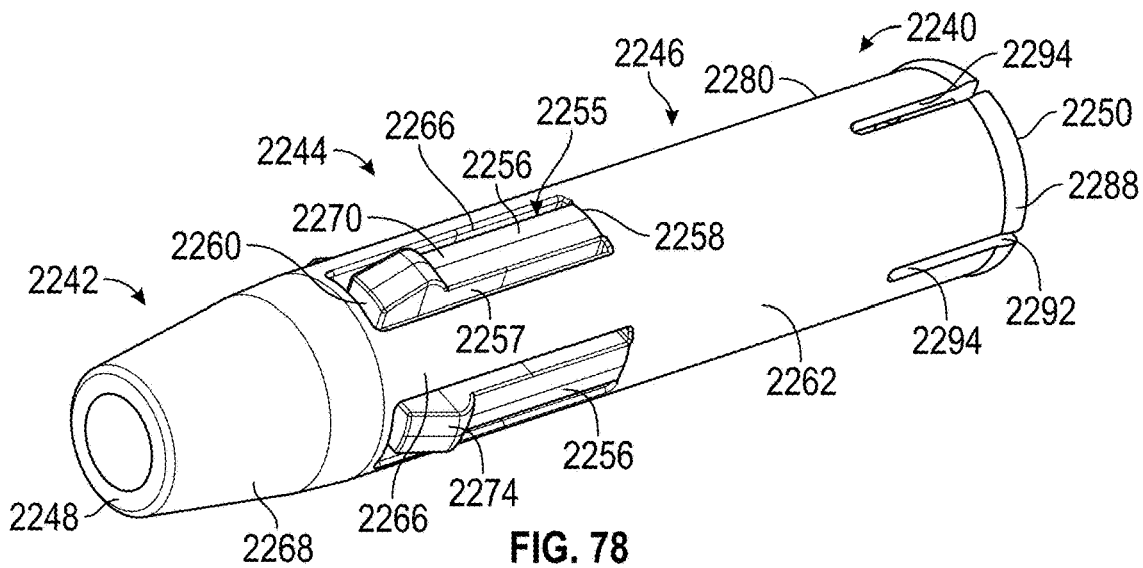
FIG. 78 is a perspective view of a depression sleeve of the balloon cover of FIG. 77, the depression sleeve including one or more depression members.
Figure 79:
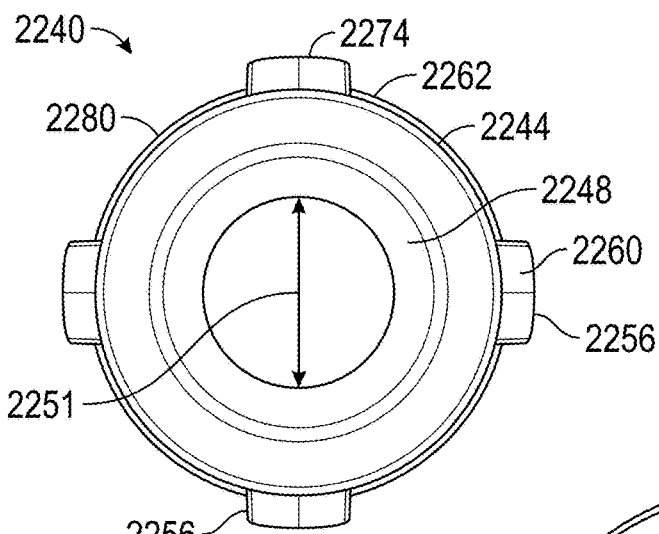
FIG. 79 is an end view of the depression sleeve of FIG. 78.
Figure 80:
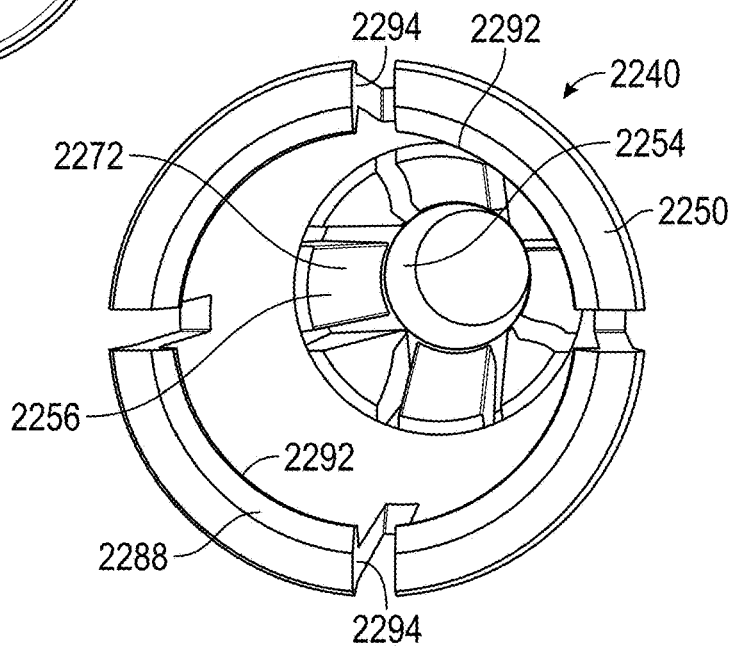
FIG. 80 is another perspective view of the depression sleeve of FIG. 78.

Each depression member 2256 can have an attached end 2258 that is attached to and/or integral with a remainder of the second portion 2244 and/or the third portion 2246 (FIGS. 78, 81A, and 81B). Each depression member 2256 can also have a free end 2260 that is unattached to the remainder of the second portion 2244 and any other portion of the depression sleeve 2240 (e.g., such as the first portion 2242). In this way, the free end 2260 of the depression member 2256 can freely move and can be configured to bend, flex, or deflect radially inward toward the central longitudinal axis 2214 (e.g., in response to inward pressure applied to the free end 2260, as described further below with reference to FIGS. 81B, 83A, and 83B).

In some embodiments, each depression member 2256 can be an elongate member extending in the axial direction from the attached end 2258 to the free end 2260. In some embodiments, the attached end 2258 can be coupled to and/or continuous with a wall 2262 of the third portion 2246 (FIGS. 78, 81A, and 81B). Additionally, in some embodiments, the wall 2262 of the third portion 2246 can be continuous with a wall 2266 of the second portion 2244 (FIGS. 78 and 81A). Further, in some embodiments, the wall 2266 of the second portion 2244 can be continuous with a wall 2268 of the first portion 2242 (FIGS. 78 and 81A). In this way, the first portion 2242, second portion 2244, and third portion 2246 of the depression sleeve 2240 can all be continuously formed with each other (e.g., formed or molded together as one piece).

In other embodiments, one or more of the first portion 2242, second portion 2244, and third portion 2246 of the depression sleeve 2240 can be formed separately and attached (e.g., via mechanical or chemical bonding) to a remainder of the portions of the depression sleeve 2240.

Each depression member 2256 can be disposed within an opening 2255 formed in the wall 2266 of the second portion 2244 (FIGS. 78, 81A, and 81B). For example, side edges 2257 and the free end 2260 of each depression member 2256 can be spaced away from (e.g., and non-contacting with) surfaces of the wall 2266 that define the corresponding opening 2255. In this way, in some embodiments, each depression member 2256 can be configured as a cantilever.

Each depression member 2256 can include an outer surface 2270 and an inner surface 2272 (where the outer surface 2270 and the inner surface 2272 are relative to an interior of the depression sleeve 2240). In some embodiments, the outer surface 2270 can be a relatively planar outer surface, except for a protrusion (e.g., bump or outer protrusion) 2274 disposed at, adjacent to, or proximate to its free end 2260 (FIGS. 78, 79, 81A, and 81B). For example, as shown in FIG. 81A, the protrusion 2274 can extend radially outward (away from the central longitudinal axis 2214) relative to a remainder of (e.g., the planar portion) of the outer surface 2270. Further, when the depression members 2256 are in the state or configuration shown in FIG. 81A (e.g., an unbiased, unflexed, undeflected, or relaxed state, as described further below), the protrusion 2274 can extend radially outward relative to an outer surface of the wall 2262 and an outer surface of the wall 2268.

In some embodiments, the inner surface 2272 can be contoured along its axial length (e.g., between the attached end 2258 and the free end 2260). For example, the inner surface 2272 can extend further radially inward (toward the central longitudinal axis 2214) along its axial length, from the attached end 2258 to a location proximate to (e.g., adjacent to) the free end 2260. For example, the inner surface 2272 can include a protrusion (e.g., inner protrusion) 2276 disposed proximate to and/or adjacent to the free end 2260. In some embodiments, the protrusion 2276 can be additionally disposed at a same or similar axial position as the protrusion 2274 in the outer surface 2270 (FIGS. 81A and 81B).

The protrusion 2276 can be configured as a bump, extension member, rib, or the like. For example, the protrusion 2276 can extend radially inward, toward the central longitudinal axis 2214, relative to a remainder of the inner surface 2272. The inner surface 2272 can slope radially inward from the attached end 2258, to the protrusion 2276. In this way, a thickness or width of the depression member 2256 (e.g., in the radial direction) can be largest at the axial location of the protrusion 2276 (and protrusion 2274).

In some embodiments, a shape and/or contour of the inner surface 2272, including the protrusion 2276, can be configured based on a specified, final shape of a portion of the balloon (e.g., balloon 318) which it is configured to cover and surround. For example, in some embodiments (as shown in FIGS. 77-83B), the inner surface 2272 can be shaped according to a specified final shape or contour of the distal end portion 332 of the balloon 318 (e.g., as shown in FIG. 40). For example, in some embodiments, the shape and/or contour of the inner surface 2272, including dimensions of the protrusion 2276, can be selected to form the negative radial depression 334 in the distal end portion 332 of the balloon 318 (or, in other embodiment, a negative radial depression in another or additional portion of the balloon).

In some embodiments, an inner lumen 2278, configured to receive the distal end portion 332 of the balloon therein, can be formed by the inner surface 2272 of the depression members 2256 and a remaining inner surface of the second portion 2244 (e.g., the inner surface between the depression members 2256).

The third portion 2246 can configured to receive at least a portion of the first portions 2210 of the first shell member 2202 and the second shell member 2204 (e.g., when the first shell member 2002 and the second shell member 2204 are assembled together in mating engagement with each other). For example, in some embodiments, the third portion 2246 can be configured as a sleeve or shell member that is configured to fit around and couple to the first portions 2210 of the first shell member 2202 and the second shell member 2204.

In some embodiments, the wall 2262 of the third portion 2246 can have an outer surface 2280 and an inner surface 2282 (FIGS. 81A and 81B). The outer surface 2280 can be relatively planar and configured to receive the sleeve 2264 thereon. The inner surface 2282 can be relatively planar and define a lumen 2284 with an inner diameter 2286. In some embodiments, the inner diameter 2286 can be slightly larger than and/or similar to the first width 2216 of the first portions 2210.

In some embodiments, the third portion 2246 can include a flanged portion 2288 at the proximal end 2250 (FIGS. 78, 80, 81A, and 81B) that is configured to interface (e.g., mate or couple) with corresponding retaining elements 2290 in the first portions 2210 of the first shell member 2202 and the second shell member 2204 (FIGS. 82, 83A, and 83B). For example, in some embodiments, the flanged portion 2288 can include one or more protrusions 2292 that extend radially inward (toward the central longitudinal axis 2214) and are configured to mate with the corresponding retaining elements 2290 (FIGS. 78 and 80-81B).

In some embodiments, the retaining elements 2290 can be configured as notches or depressions in the outer surface 2222 (e.g., which depress inward toward the central longitudinal axis). The retaining elements 2290 can be shaped to receive a corresponding protrusion 2292.

In some embodiments, the proximal end of the third portion 2246 can include one or more axially extending slots 2294 spaced apart around a circumference of the third portion 2246 (FIGS. 78 and 80-81B). Each slot 2294 can extend from the proximal end 2250 and the flanged portion 2288, toward the second portion 2244. In some embodiments, the slots 2294 can increase a flexibility of the flanged portion 2288 such that the protrusions 2292 of the flanged portion 2288 can slide axially over the outer surface 2222 and extend (e.g., snap or couple) into the corresponding retaining elements 2290 in the first portions 2210 of the first shell member 2202 and the second shell member 2204.

Additionally, in some embodiments, the first portions 2210 of the first shell member 2202 and the second shell member 2204 can include a step 2296 between a smaller width portion 2295 and a larger width (e.g., stepped) portion 2298 of the respective first portion 2210 (FIG. 82). The step 2296 can be configured to receive the proximal end 2250 of the depression sleeve 2240.

Once the first shell member 2202 and the second shell member 2204 are assembled in mating engagement with each other (as shown in FIGS. 83A and 83B), the depression sleeve 2240 can be slid over the outer surfaces 2222 of the smaller width portions 2295 of the first portions 2210 of the first shell member 2202 and the second shell member 2204, until the proximal end 2250 hits the steps 2296. In this configuration, the outer surface 2280 of the third portion 2246 can be relatively planar and flush with an outer surface of the larger width portion 2298 of the first portions 2210 (FIG. 83B).

In some embodiments, the first shell member 2202 and the second shell member 2204 can be held or coupled together (e.g., such that they cannot be pulled apart from one another) via the depression sleeve 2240.

When the depression sleeve 2240 is coupled to the first shell member 2202 and the second shell member 2204, as described above, the depression members 2256 can be in the relaxed or undeflected state shown in FIG. 81A (e.g., not depressed radially inward toward the central longitudinal axis 2214).

In some embodiments, an additional coupling element, such as the sleeve 2264 (FIGS. 77, 83A, and 83B) can be slid over and around the depression sleeve 2240. In some embodiments, the sleeve 2264 can also be arranged around the larger width portion 2298 of the first portions 2210 of the first shell member 2202 and the second shell member 2204.

When the sleeve 2264 is slid over and around the depression sleeve 2240, to the position shown in FIGS. 83A and 83B, for example, the free end 2260 of each depression member 2256 is pressed radially inward, toward the central longitudinal axis 2214, as shown in FIG. 81B. More specifically, as the sleeve 2264 slides over and past the first portion 2242 of the depression sleeve 2240, the sleeve 2264 can come into contact with the free end 2260 of each depression member 2256 of the second portion 2244. As the sleeve 2264 continues to slide along each depression member 2256, an inner surface of the sleeve can contact and exert a radially inward pressure on the protrusions 2274, thereby causing the free ends 2260 to bend radially inward and the protrusions 2276 to extend radially inward. Once the sleeve 2264 is in place over and around the depression sleeve 2240 (FIGS. 83A and 83B), the depression members 2256 are held in the flexed (e.g., bent or deflected) and radially inward configuration shown in FIG. 81B.

In other embodiments, an alternate coupling element (instead of the sleeve 2264) can be slid, coupled, or clamped around the depression members 2256 of the depression sleeve 2240 and configured to depress or deflect the free ends 2260 of the depression members 2256 radially inward, as explained above. Such a coupling element may comprise a ring, c-clamp, or the like.

In some embodiments, the outer surface 2270 of each depression member 2256 can be sloped from the free end 2260 to a peak of the protrusion 2274. As a result, the sleeve 2264 can be more smoothly advanced over the protrusions 2274, toward the proximal end 2250 of the depression sleeve 2240. When the sleeve 2264 is arranged over the second portion 2244 (and the entire depression sleeve 2240), as shown in FIGS. 83A and 83B, an inner surface 2265 of the sleeve 2264 contacts the protrusions 2274.

In this way, the depression members 2256 of the depression sleeve 2240 are configured to move from an unflexed or resting configuration or state (FIG. 81A) to the flexed or radially inward configuration or state (FIG. 81B). In the resting configuration (FIG. 81A), the protrusions 2274 of the depression members 2256 are disposed radially outward relative to a remainder of the outer surfaces 2270 of the depression members 2256 and the outer surface 2280 of the third portion 2246. In this configuration, the inner protrusions 2276 of the depression members 2256 are positioned further away from the central longitudinal axis 2214.

In the flexed configuration (FIG. 81B), the protrusions 2274 of the depression members 2256 and pressed radially inward by the sleeve 2264 and the protrusions 2274 are disposed approximately at a same radial position (e.g., flush with) the outer surface 2280 of the third portion 2246 (e.g., due to the sleeve extend across the entire outer surface of the depression sleeve 2240). Further, in this configuration, since the free ends 2260 of the depression members 2256 are deflected radially inward, the inner protrusions 2276 of the depression members 2256 are positioned closer to the central longitudinal axis (as compared to their position in FIG. 81A). As such, when a portion of a folded balloon (e.g., the distal end portion 332 of the balloon 318) is covered by and disposed within the inner lumen 2278 of the second portion 2244 of the depression sleeve 2240, the protrusions 2276 can press radially inward against the balloon and form a negative radial depression in the portion of the balloon (e.g., the radial depression 334 shown in FIG. 40).

In this way, the balloon cover 2200 including the depression sleeve 2240 illustrated in FIGS. 77-83B can be configured to cover a distal end portion of a delivery apparatus including an inflatable balloon and form a negative radial depression in a portion of the balloon. In some embodiments, as shown in FIGS. 77-83B, the balloon cover 2200 and depression sleeve 2240 can be configured to form the radial depression 334 in the distal end portion 332 of the balloon 318 (FIGS. 10 and 40).

However, in other embodiments, the balloon cover 2200 and depression sleeve 2240 can be configured to form a negative radial depression in an alternate or additional portion of the balloon (e.g., balloon 318). For example, the depression members 2256 can be included in an alternate portion of the depression sleeve 2240 and/or the first shell member 2202 and the second shell member 2204 can be modified such that the depression members 2256 of the depression sleeve 2240 surround an alternate or additional portion of the balloon.

Figure 84:
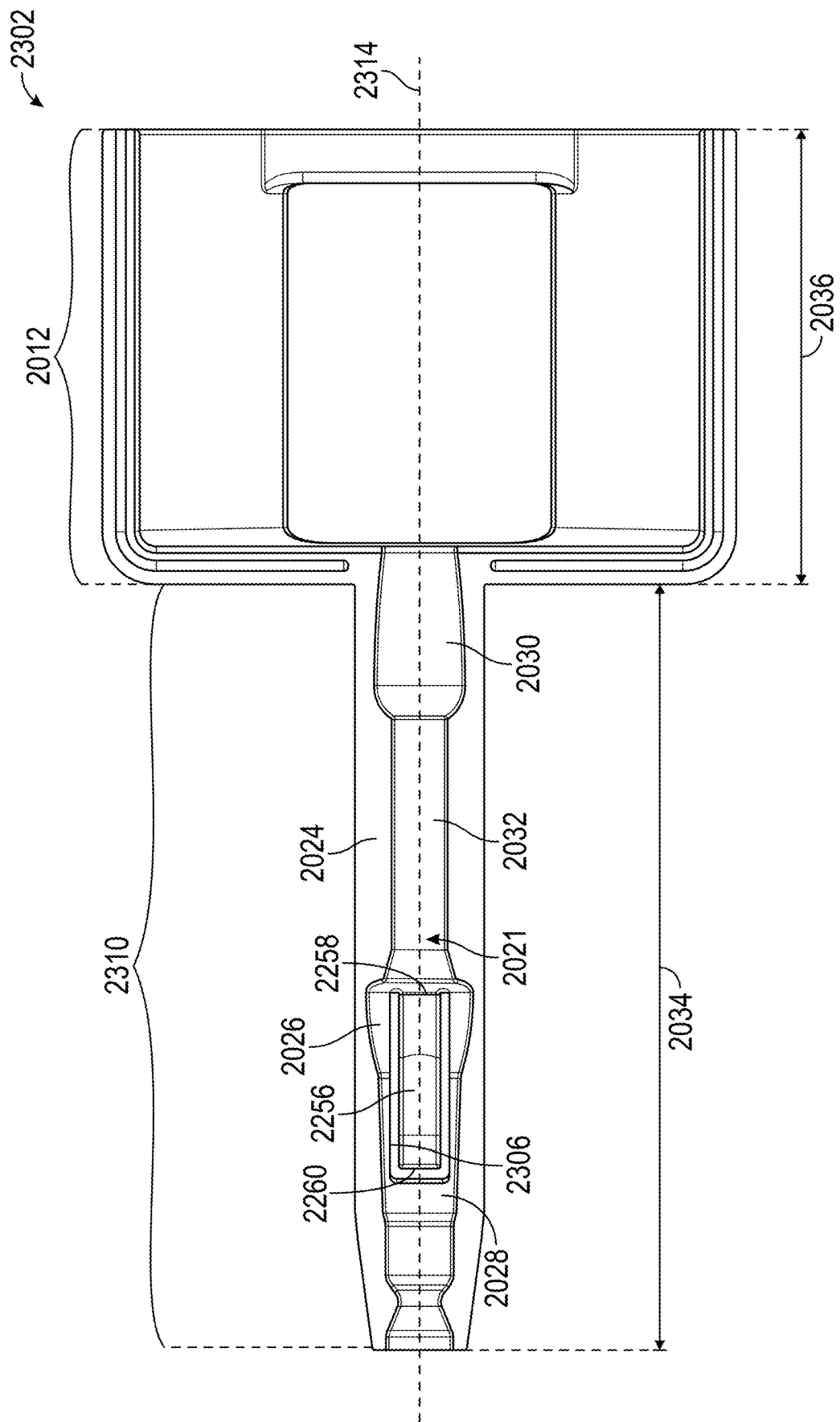
FIG. 84 is a plan view of another exemplary embodiment of a shell member for a balloon cover that is configured to receive a portion of a distal end portion of a delivery apparatus that includes an inflatable balloon and a positioning device mounted thereon and form a specified, final shape of the balloon around the delivery apparatus.
Figure 85:
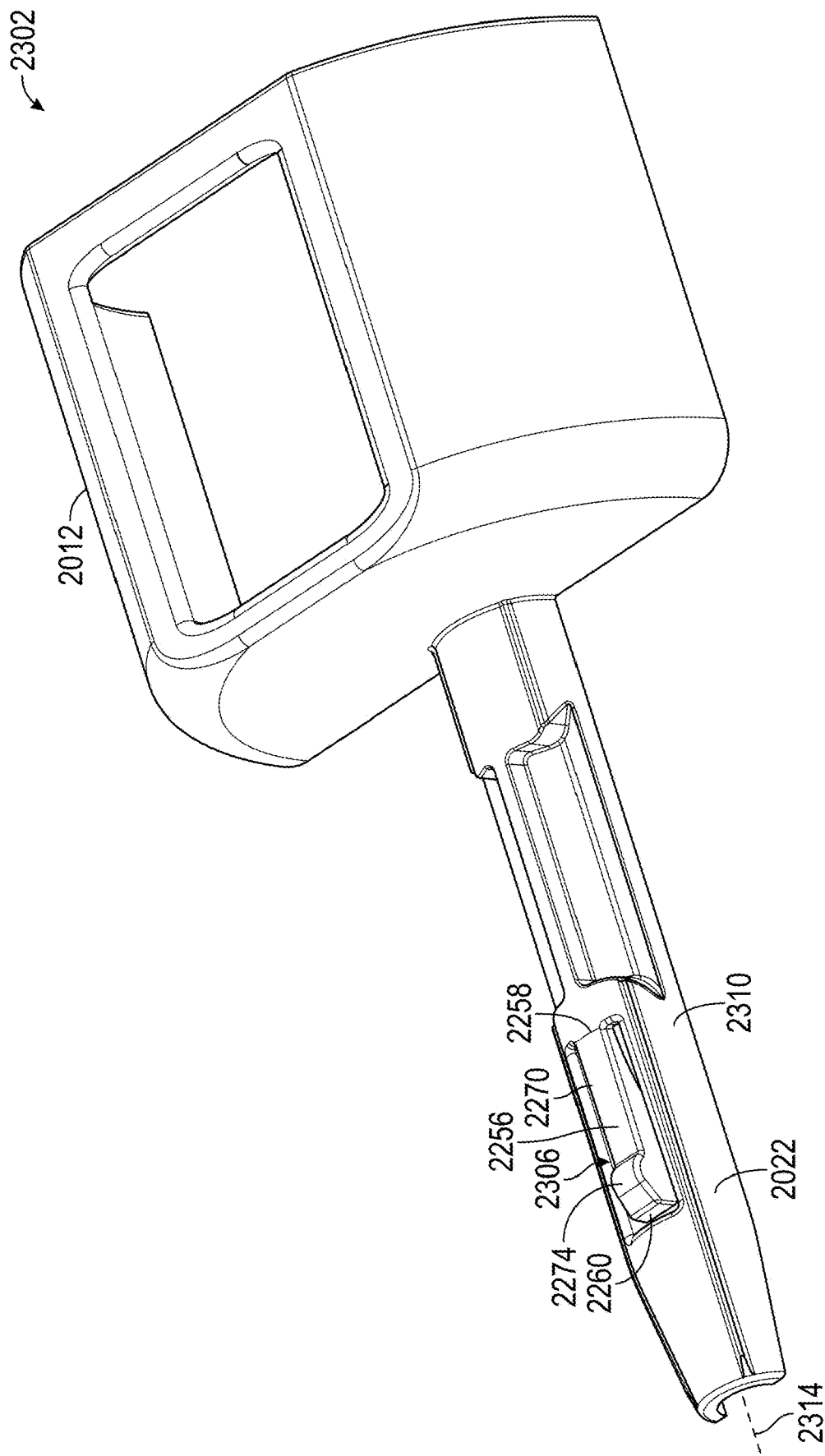
FIG. 85 is a perspective view of the shell member of FIG. 84.
Figure 86:
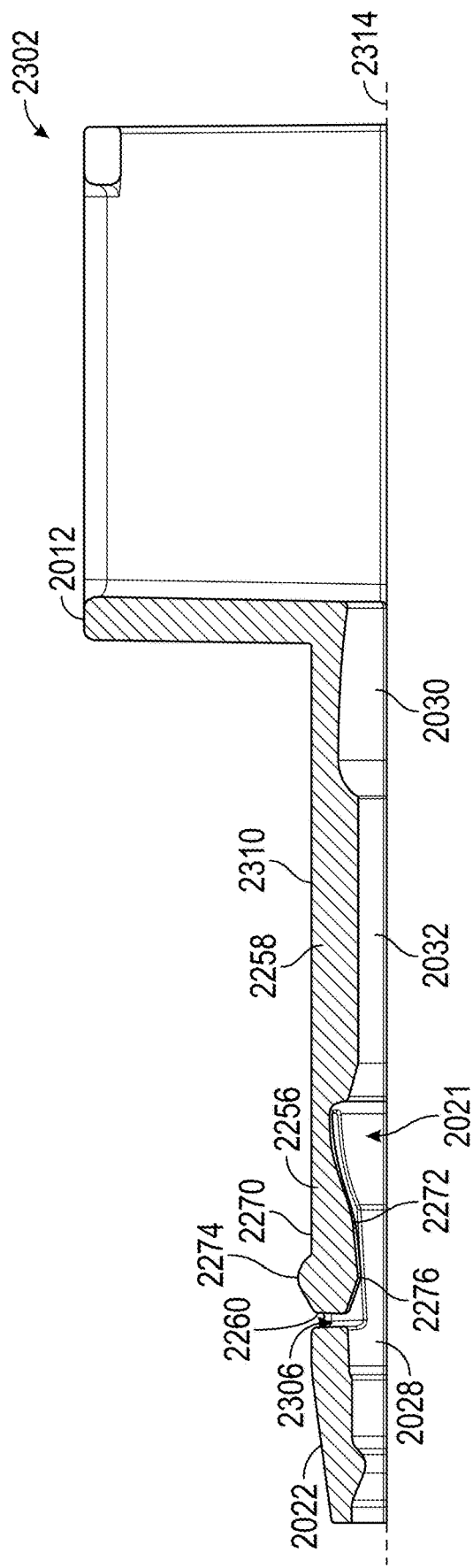
FIG. 86 is a cross-sectional side view of the shell member of FIG. 84.

FIGS. 84-86 show another exemplary embodiment of a shell member 2302 for a balloon cover that is configured to receive a portion of a distal end portion of a delivery apparatus that includes an inflatable balloon and a positioning device mounted thereon and form a specified, final shape of the balloon around the delivery apparatus. For example, in some embodiments, the balloon cover formed from two shell members 2302 and can be configured to receive the distal end portion 309 of the delivery apparatus 300, the balloon 318 mounted thereon, and the positioning device 1100 that is coupled to the distal end portion of the delivery apparatus, proximal to the valve mounting portion 324. Further, in some embodiments, the balloon cover formed from the shell members 2302 can be configured to form the specified, final shape of the balloon mounted on the distal end portion of the delivery apparatus (e.g., the radial depression 334 of the distal end portion 332 of the balloon 318).

For example, a balloon cover that is similar to the balloon cover 2000 (FIGS. 69-75C) can be formed by coupling (e.g., in mating engagement) two of the shell members 2302 with each other and holding the shell members 2302 together with the sleeve 2064 (e.g., as described above with reference to FIGS. 69-75C). For example, the shell member 2302 shown in FIGS. 84-86 can be configured the same or similar to the first shell member 2002 and/or the second shell member 2004 of the balloon cover 2000 (FIGS. 69-75C), except the shell member 2302 can include one or more depression members 2256 formed in the first portion 2010 of the shell member 2302, as described further below.

As shown in the embodiment of FIGS. 84-86, the shell member 2302 includes one depression member 2256. Thus, a balloon cover formed by mating and coupling together two shell members 2302 would include two depressions members 2256 (e.g., one in each shell member).

In other embodiments, the shell member 2302 can include more than one depression member 2256 (e.g., two, three, or the like) and/or only one of the two shell members 2302 forming the balloon cover can include one or more depression members 2256 (and the other shell member may not include any depression members 2256).

The one or more depression members 2256 of the shell member 2302 can be configured to be moved into a radially inward configuration, in response to an applied radially inward force, and as a result, form a negative radial depression in one or more portions of the balloon received within the shell member 2302. The depression member(s) 2256 can function and be configured the same or similar to the depression members 2256 of the balloon cover 2200 (FIGS. 77-83B). However, instead of being disposed in a depression sleeve (e.g., depression sleeve 2240 of balloon cover 2200), the one or more depression members 2256 can be disposed or formed within the shell member 2302.

As shown in FIGS. 84-86, the shell member 2302 comprises a first portion 2310 and a second portion 2012. In some embodiments, the first portion 2310 and the second portion 2012 can be continuous with one another. The second portion 2012 can be configured to receive a positioning device therein. Additionally, the second portion 2012 can be configured the same or similar to the second portion 2012 of the first shell member 2002 and the second shell member 2004 of the balloon cover 2000 (e.g., as shown in FIGS. 69-71B), and thus, is labeled similarly in FIGS. 84-86.

The first portion 2310 can be configured similar to the first portion 2010 of the first shell member 2002 and the second shell member 2004 of the balloon cover 2000 (e.g., as shown in FIGS. 69-71B), except for the addition of the depression member 2256.

Similar to the depression members described above with reference to FIGS. 78-81B, the depression member 2256 of the shell member 2302 can have an attached end 2258 that is attached to and/or integral with (e.g., integrally formed with or molded as one part with) a remainder of the first portion 2010 (FIGS. 84-86). The depression member 2256 of the shell member 2302 can also have a free end 2260 that is unattached to the remainder of the first portion 2010. In this way, the free end 2260 of the depression member 2256 can freely move and can be configured to bend, flex, or deflect radially inward toward a central longitudinal axis 2314 of the shell member 2302 (e.g., in response to inward pressure applied to the free end 2260, as described herein).

The depression member 2256 can be an elongate member extending in the axial direction from the attached end 2258 to the free end 2260, along a portion of the first length 2034 of the first portion 2310. In the embodiment of FIGS. 84-86, the depression member 2256 is disposed in the distal section 2028 of the depression 2026 (as described above with reference to FIG. 70, the depression 2026 formed in the first portion 2010 can include the distal section 2028, the proximal section 2030, and the intermediate section 2032).

Though only a single depression member 2256 is shown in FIGS. 84-86, in other embodiments, the shell member 2302 can include additional depression members 2256 disposed in a different portion of the first portion 2310 (e.g., axially spaced away from the depression member 2256 shown in FIGS. 84-86). In other embodiments, the single depression member 2256 of the shell member 2302 can be disposed at a different axial location along the depression (e.g., in the proximal section 2030 or intermediate section 2032).

The depression member 2256 can be disposed within an opening 2306 defined in the first portion 2310 of the shell member 2302 (FIGS. 84-86). For example, as shown in FIG. 86, the opening 2306 can extend from the outer surface 2022 to and through the depression 2026. For example, side edges 2257 and the free end 2260 of the depression member 2256 can be spaced away from (e.g., and non-contacting with) surfaces of the first portion 2310 that define the opening 2306 (FIGS. 84 and 85).

The outer surface 2270 of the depression member 2256 can be a relatively planar outer surface, except for the protrusion (e.g., bump) 2274 disposed at or proximate to its free end 2260 (FIGS. 85 and 86). For example, as shown in FIG. 86, the protrusion 2274 can extend radially outward (away from the central longitudinal axis 2314) relative to a remainder of (e.g., the planar portion) of the outer surface 2270. Further, when the depression member 2256 is in the state or configuration shown in FIG. 86 (e.g., an unbiased, unflexed, undeflected, or relaxed state, as described above with reference to FIG. 81A), the protrusion 2274 can extend radially outward relative to the outer surface 2022.

In some embodiments, the inner surface 2272 of the depression member 2256 can be contoured along its axial length (FIG. 86). The inner surface 2272 can extend further radially inward (toward the central longitudinal axis 2314) along its axial length, from the attached end 2258 to a location proximate to the free end 2260. For example, the inner surface 2272 can include the protrusion 2276 which extends radially inward, toward the central longitudinal axis 2314, relative to a remainder of the inner surface 2272 (FIG. 86). The inner surface 2272 can slope radially inward from the attached end 2258, to the protrusion 2276. In this way, a thickness or width of the depression member 2256 can be largest at the axial location of the protrusion 2276 (and protrusion 2274, as shown in FIG. 86).

In some embodiments, the shape and/or contour of the inner surface 2272 (and the protrusion 2276) can be configured based on a specified, final shape of a portion of the balloon (e.g., balloon 318) which it is configured to cover and surround. For example, in some embodiments (as described above), the inner surface 2272 can be shaped according to a specified final shape or contour of the distal end portion 332 of the balloon 318 (e.g., which, as shown in FIG. 40, includes the radial depression 334 in the distal end portion 332 of the balloon 318).

Thus, the free end 2260 of the depression member 2256 can be configured to move radially inward in response to an applied force (e.g., applied by sleeve 2064 when covering the first portion 2010 of the shell member 2302). As such, when two of the shell members 2302 are coupled together around the distal end portion of the delivery apparatus (as described above), and the sleeve or another coupling element is arranged over and against the outer surfaces 2022 of the first portions 2310 of the shell members 2302, the depression members 2256 of each shell member 2302 can be depressed radially inward, thereby pressing against the balloon (e.g., balloon 318) and forming a negative radial depression (e.g., shaped according to the shape and contour of the protrusion 2276 and inner surface 2272) in the balloon.

Returning to the discussion of the delivery apparatus, as introduced above with reference to FIGS. 9 and 14, the intermediate shaft 306 of the delivery apparatus 300 can include the proximal end portion 310 that extends proximally from a proximal end of the handle 302, to an adaptor (e.g., adaptor 312 of FIGS. 9, 14, and 15 or adaptor 402 of FIG. 23). In some embodiments, the adaptor can be bonded to the proximal end portion 310 of the intermediate shaft 306 (e.g., via applying an adhesive material to the adaptor and/or the proximal end of the intermediate shaft 306 and curing the adhesive material via UV light). After bonding the adaptor to the intermediate shaft 306, the two parts can be permanently fixed to one another (e.g., not reversibly or removably coupled to each other). However, in some instances, this type of connection or bonding between the adaptor and the intermediate shaft 306 can result in leaks between the two parts and/or a weak connection that can degrade over time and/or during use.

Thus, in some embodiments, instead of bonding the intermediate shaft 306 and the adaptor to each other, these components can be coupled to each other via a shaft connector release assembly. The shaft connector release assembly can be configured to provide a tight and leak-proof connection between the intermediate shaft 306 and the adaptor. Further, the shaft connector release assembly can be configured to more quickly and easily couple the intermediate shaft 306 and the adaptor to one another.

FIGS. 87A-96 show an exemplary embodiment of such a shaft connector release assembly 2400 for the intermediate shaft 306 and an adaptor 2410 (e.g., an adaptor similar to and/or that would take the place of the adaptor 312 in the delivery apparatus 300). The shaft connector release assembly 2400 can comprise a release sleeve 2402 and an adaptor insert 2404.

Figure 87A:
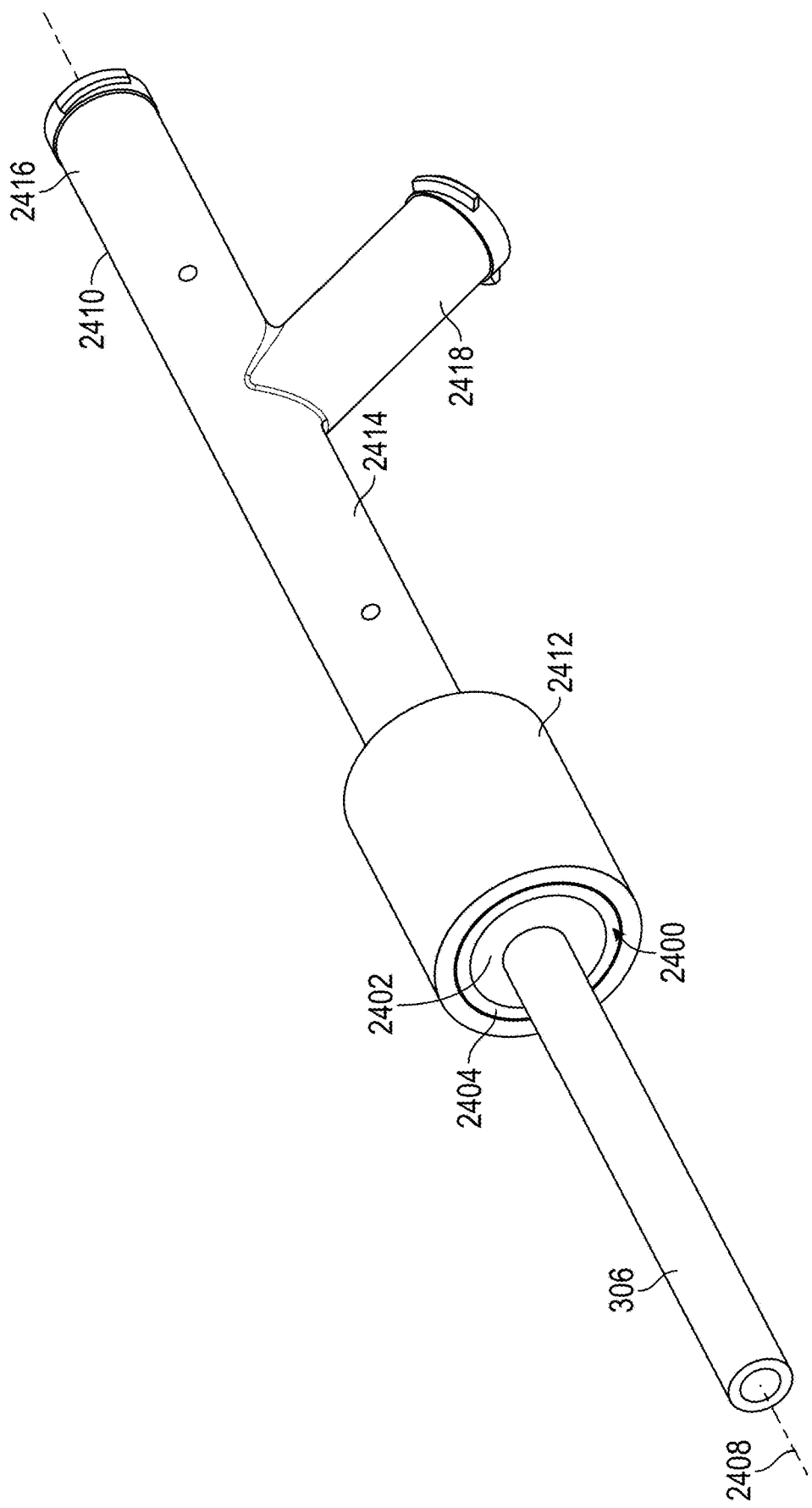
FIG. 87A is a perspective view of a shaft connector release assembly coupling a proximal end portion of a rotatable shaft of a delivery apparatus to an adaptor.
Figure 87B:
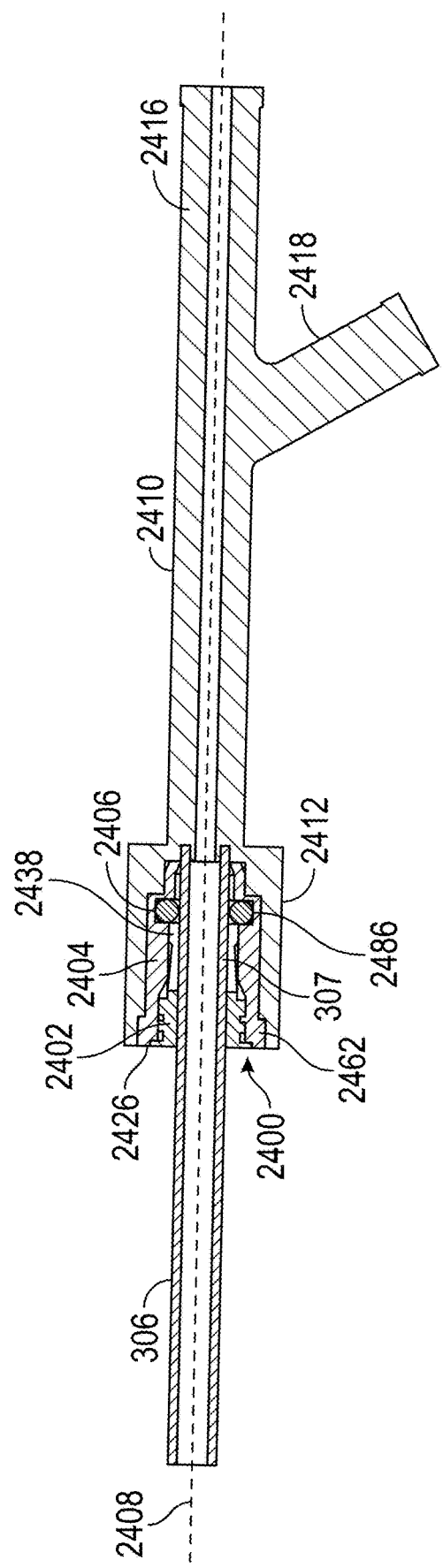
FIG. 87B is a cross-sectional view of the shaft connector release assembly of FIG. 87A coupling the proximal end portion of the rotatable shaft to the adaptor.
Figure 88:
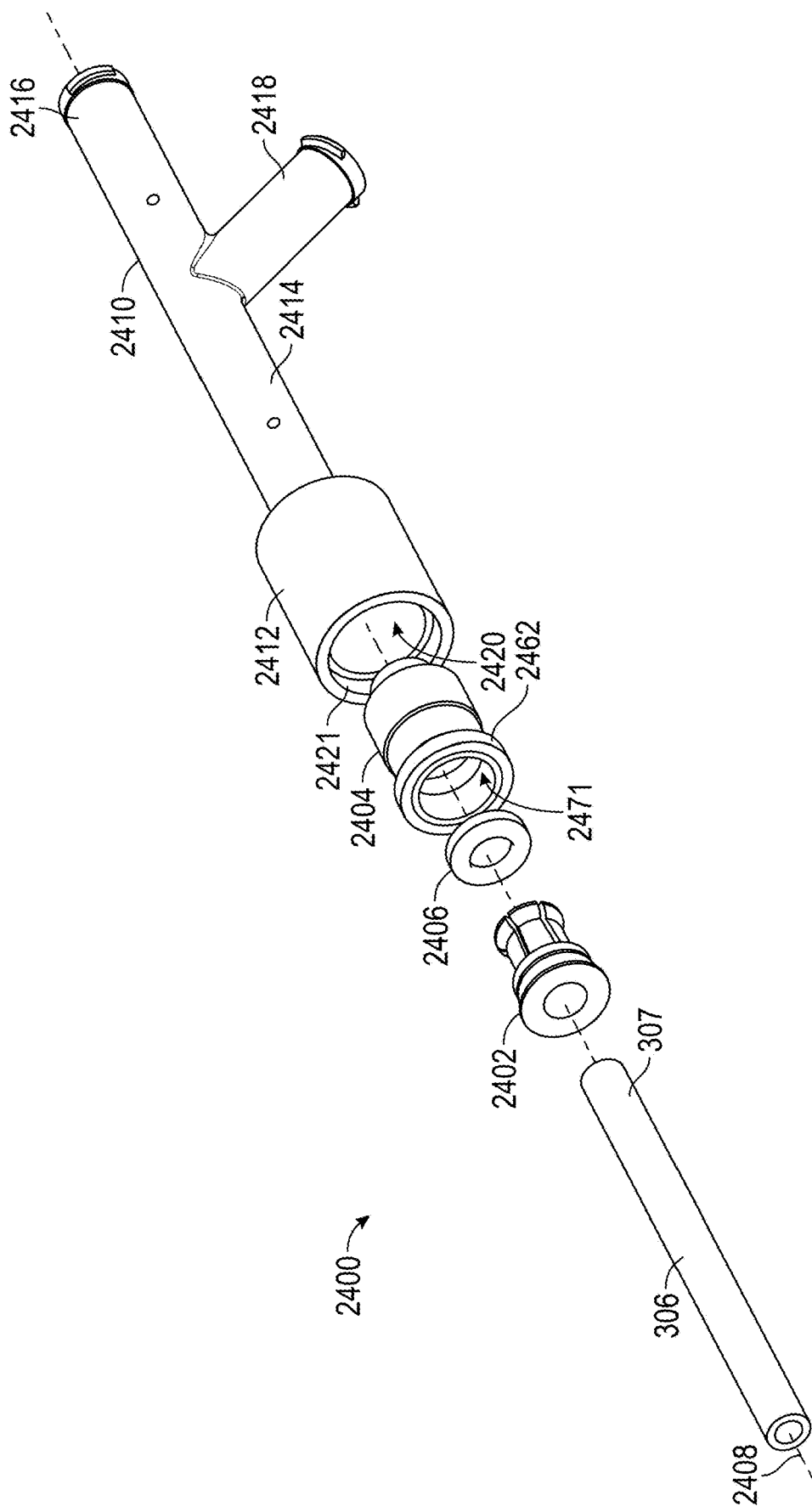
FIG. 88 is an exploded view of the shaft connector release assembly, proximal end portion of the rotatable shaft, and the adaptor of FIG. 87A.
Figure 89:
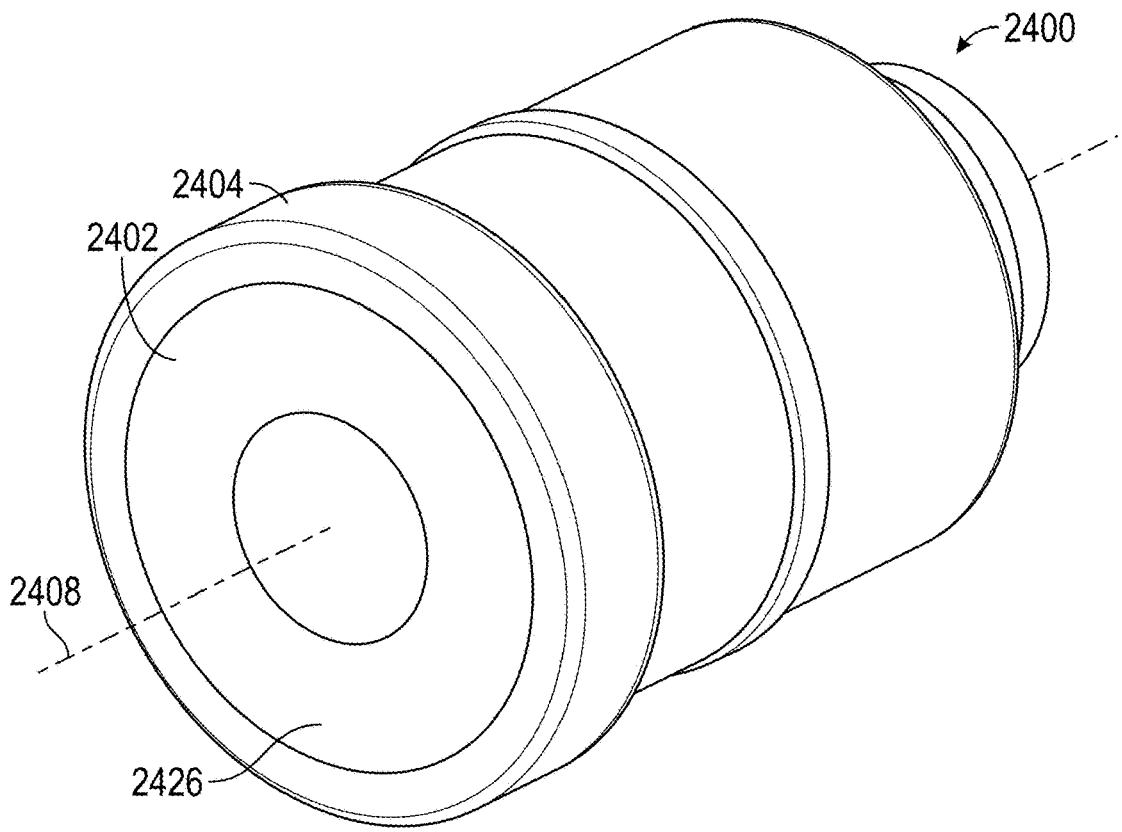
FIG. 89 is a perspective view of the shaft connector release assembly of FIG. 87A, alone, in an assembled configuration.
Figure 90:
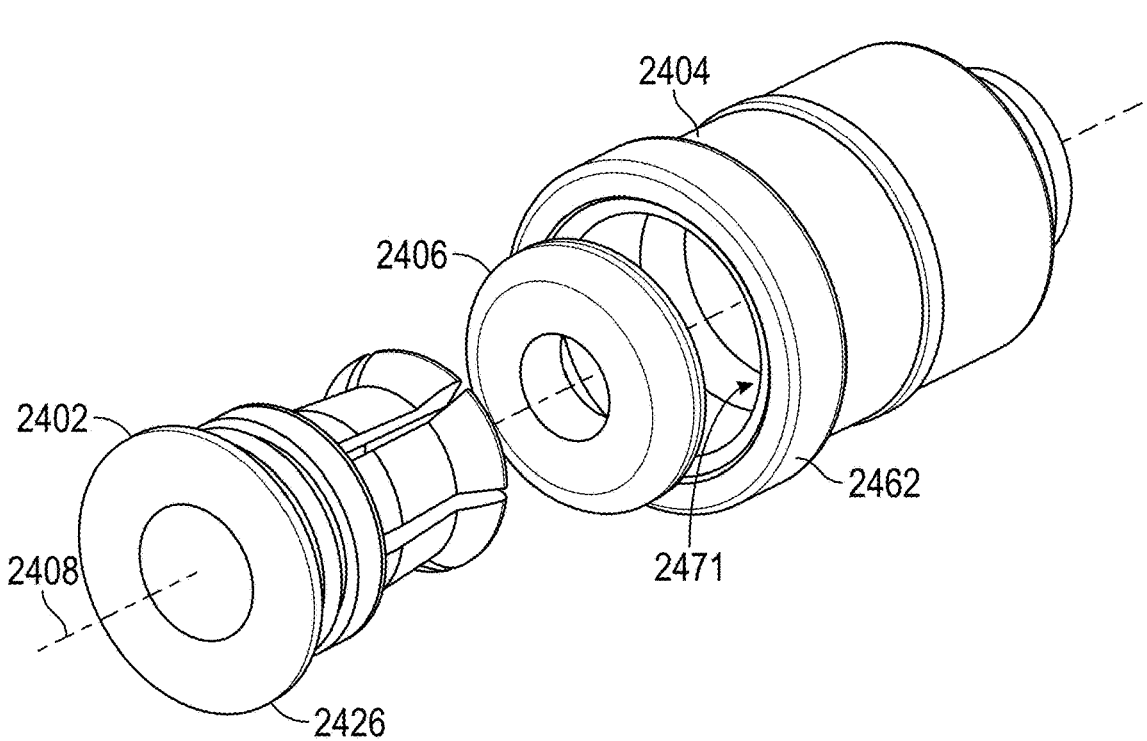
FIG. 90 is an exploded view of the shaft connector release assembly of FIG. 89.
Figure 91:
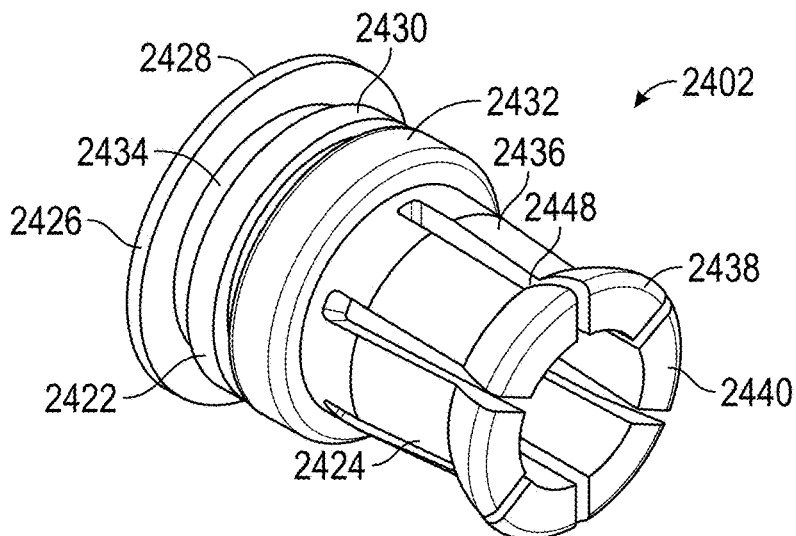
FIG. 91 is a perspective view of an embodiment of a release sleeve of the shaft connector release sleeve of FIG. 89.
Figure 92:
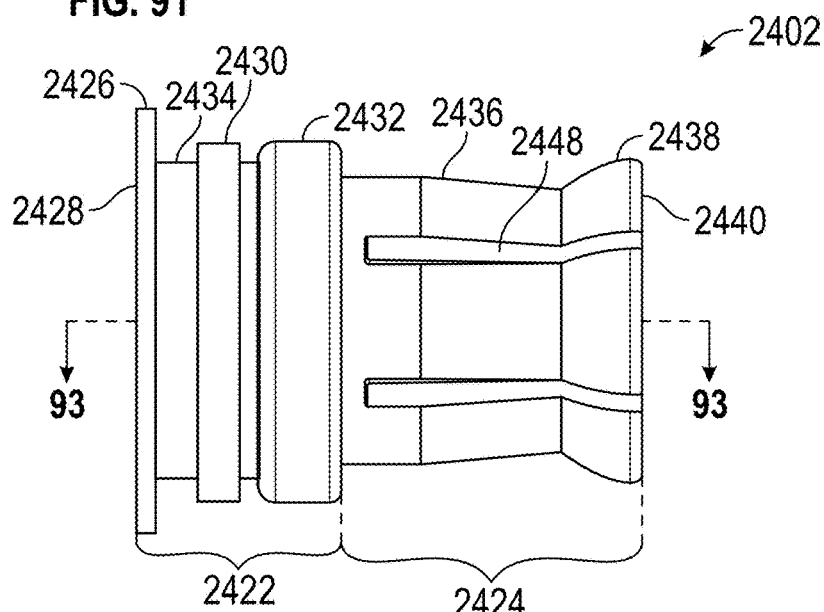
FIG. 92 is a side view of the release sleeve of FIG. 91.
Figure 93:
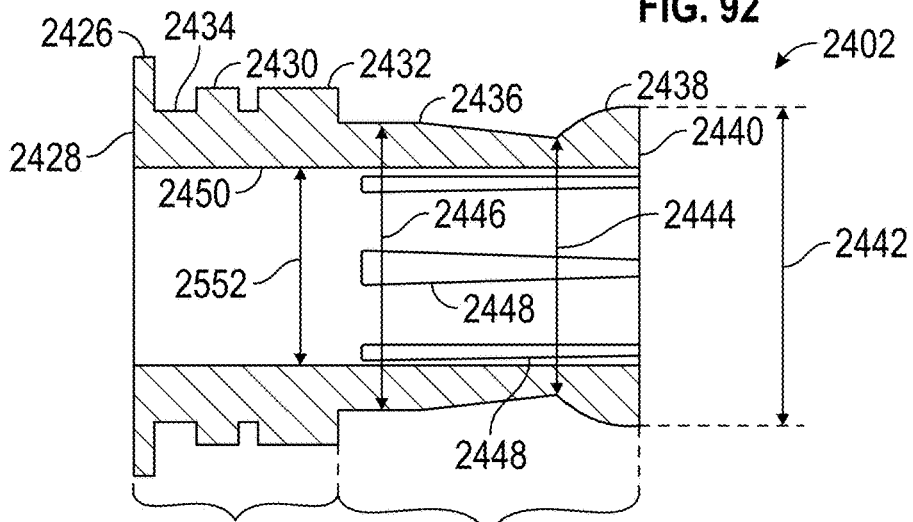
Figure 94:
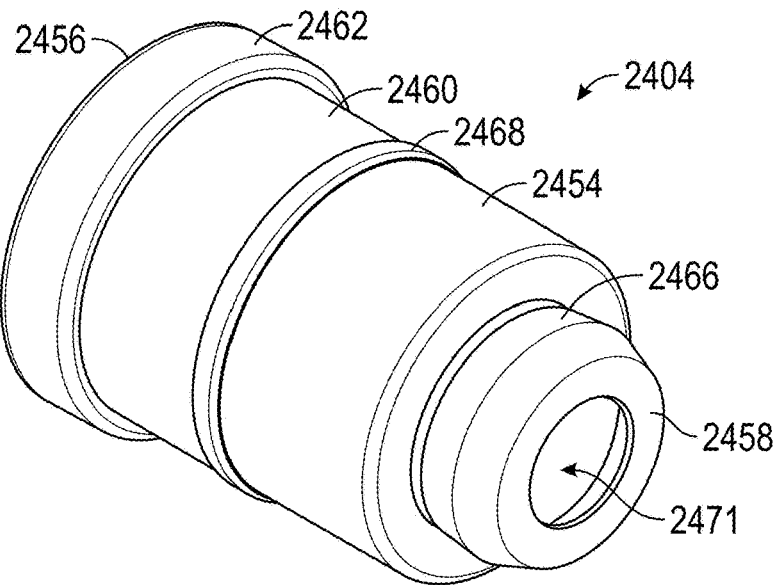
Figure 95:
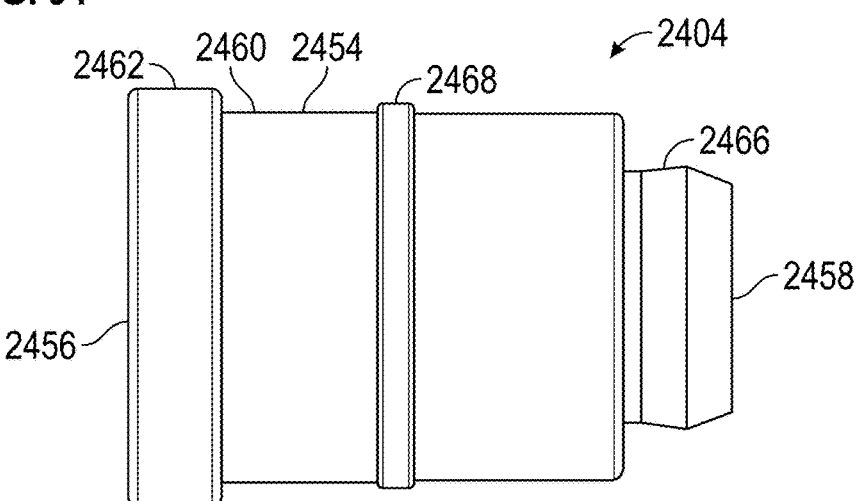
Figure 96:
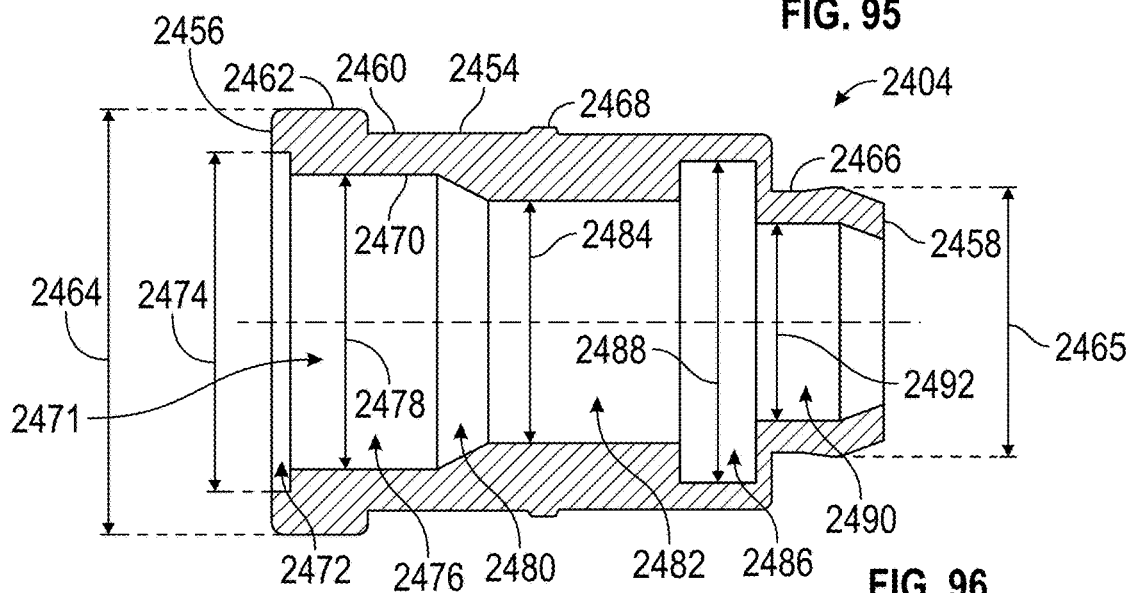

FIGS. 87A and 87B show different views of the shaft connector release assembly 2400 in an assembled configuration and coupled to each of the intermediate shaft 306 and the adaptor 2410 (which, in some embodiments, can be the same as or similar to the adaptor 312). FIG. 88 is an exploded view that shows the shaft connector release assembly 2400 in a disassembled configuration and disassembled from the intermediate shaft 306 and the adaptor 2410. FIGS. 89 and 90 show the shaft connector release assembly 2400, alone, in an assembled configuration (FIG. 89) and a disassembled configuration (FIG. 90). FIGS. 91-93 show different views of the release sleeve 2402 alone and FIGS. 94-96 show different views of the adaptor insert 2404 alone.

The shaft connector release assembly 2400 can have a central longitudinal axis 2408 (FIGS. 87-90). In some embodiments, when the shaft connector release assembly 2400 is coupled to the intermediate shaft 306 and the adaptor 2410, as shown in FIGS. 87A and 87B, the central longitudinal axis 2408 can be coaxial with the central longitudinal axis 320 of the delivery apparatus.

As shown in FIGS. 87A-88, the release sleeve 2402 is configured to receive and couple to and/or around a proximal end 307 (e.g., of the proximal end portion 310) of the intermediate shaft 306. For example, the release sleeve 2402 can be directly coupled to the proximal end 307 of the intermediate shaft 306. As used herein, directly coupled can refer to the coupling between two components without any intervening components arranged therebetween.

The release sleeve 2402 is further configured to fit within and be removably coupled to the adaptor insert 2404. In some embodiments, the release sleeve 2402 and the adaptor insert 2404 can be directly coupled to one another.

Additionally, the adaptor insert 2404 can be configured to fit within and coupled to a connecting portion 2412 of the adaptor 2410. In some embodiments, the adaptor insert can be directly coupled to/within the connecting portion 2412.

In some embodiments, the connecting portion 2412 can also be referred to herein as an adaptor connecting portion 2412 and can either be integrally formed with a remainder of the adaptor 2410 or configured to be coupled to an adaptor, such as the adaptor 2410.

As shown in the perspective view of FIG. 87A and the cross-sectional side view of FIG. 87B, when the shaft connector release assembly 2400 is assembled and connects the intermediate shaft 306 to the adaptor 2410, the connecting portion 2412 of the adaptor 2410 surrounds (e.g., is disposed around) the adaptor insert 2404, the adaptor insert 2404 surrounds the release sleeve 2402, and the release sleeve 2402 surrounds the proximal end 307 of the intermediate shaft 306.

In some embodiments, the adaptor 2410 can comprise the connecting portion 2412 and a branch portion 2414. In other embodiments, the connecting portion 2412 and the branch portion 2414 can be initially separate from one another and then connected together (e.g., via welding or other mechanical or chemical fixation means, as described further below).

In some embodiments, the branch portion 2414 can be similar to the adaptor 312 (FIGS. 9 and 14-16). For example, the branch portion 2414 can include a first port 2416 configured to receive a guidewire therethrough (e.g., similar to the first port 338 of adaptor 312) and a second port 2418 configured to receive fluid (e.g., inflation fluid) from a fluid source (e.g., similar to the second port 340 of adaptor 312). The second port 2418 can be fluidly coupled to an inner lumen of the intermediate shaft 306, as described above.

In some embodiments, the branch portion 2414 can be configured similarly to the adaptor 402 of FIGS. 23-27 with the second port 2418 being rotatable relative to a body of the branch portion 2414.

As shown in FIGS. 87A-88, in some embodiments, the connecting portion 2412 of the adaptor 2410 can have a larger outer diameter than the branch portion 2414 and the intermediate shaft 306.

As shown in FIG. 88, the connecting portion 2412 can include a cavity 2420 that is configured (e.g., shaped) to receive the adaptor insert 2404 therein. For example, as described in further detail below, in some embodiments, the cavity 2420 and an outer surface of the adaptor insert 2404 can be correspondingly shaped such that the adaptor insert 2404 and the connecting portion 2412 can be press fit together (e.g., in mating engagement).

Turning to FIGS. 91-93, a perspective, side, and cross-sectional view, respectively, of the release sleeve 2402 is shown. The release sleeve 2402 can comprise a first (e.g., distal) portion 2422 and a second (e.g., proximal) portion 2424.

The first portion 2422 can comprise a first flange 2426 disposed at a first (e.g., distal) end 2428 of the release sleeve 2402. In some embodiments, the first portion 2422 can comprise one or more additional flanges, extension portions, or ring portions that extend radially outward from a body 2434 of the first portion 2422, around a circumference of the release sleeve 2402 (as such, they can also be referred to as outwardly extending ring portions).

In some embodiments, as shown in FIGS. 91-93, the release sleeve 2402 can include two additional flanges, including a second flange 2430 and a third flange 2432 which are spaced apart from one another in the axial direction (and are also spaced apart from the first flange 2426). In other embodiments, the release sleeve 2402 can include more or less than two additional flanges (e.g., zero, one, three, four, or the like).

The second portion 2424 can be configured to flex or bend radially inward, relative to the central longitudinal axis 2408 (which can also be a central longitudinal axis of the release sleeve 2402 when included in the shaft connector release assembly 2400, as shown in FIGS. 89 and 90).

As shown in FIGS. 91-93, the second portion 2424 can comprise a body 2436 that narrows from the first portion 2422 to a wider, collar portion 2438 disposed at a second (e.g., proximal) end 2440 of the release sleeve 2402. The second portion 2424 can also be referred to as a flexible portion of the release sleeve 2402.

The collar portion 2438 can extend radially outward from a narrower portion of the body 2436. For example, as shown in FIG. 93, at the second end 2440, the collar portion 2438 can have a first diameter 2442 which is larger than a second diameter 2444 of the narrow portion of the body 2436. The first diameter 2442 can also be larger than a third diameter 2446 of a wider portion of the body 2436 which is disposed adjacent to the first portion 2422 (e.g., when the release sleeve 2402 is disassembled from the adaptor insert 2404, as shown in FIGS. 90-93).

The second portion 2424 can also include one or more slots 2448 that extend axially through the body 2436 and the collar portion 2438, to the second end 2440. The one or more slots 2448 can be configured to provide flexibility to the second portion 2424 such that the collar portion 2438 can flex radially inward, toward the central longitudinal axis 2408 in response to a radially inward pressure from the adaptor insert 2404 (e.g., when arranged within the adaptor insert 2404 in the shaft connector release assembly 2400, as described further below). In some embodiments, the second portion 2424 can include a plurality of slots 2448 that are spaced apart from one another around a circumference of the body 2436.

In some embodiments, the release sleeve 2402 can include an inner lumen 2450 with an inner diameter 2552 that is relatively constant along its length, from the first end 2428 to the second end 2440 when disassembled, as shown in FIG. 93. However, as described above and further below, the collar portion 2438 can be pushed or depressed radially inward, thereby narrowing the inner lumen 2450 at the second end 2440 of the release sleeve 2402.

Turning to FIGS. 94-96, a perspective, side, and cross-sectional view, respectively, of the adaptor insert 2404 is shown. The adaptor insert 2404 can comprise a body 2454 which extends from a first (e.g., distal) end 2456 to a second (e.g., proximal) end 2458 of the adaptor insert 2404.

In some embodiments, at the first end 2456, an outer surface 2460 of the body 2454 can have a wider, flanged portion 2462 with a first outer diameter 2464. The flanged portion 2462 can be configured (e.g., sized) to fit within a wider cavity portion 2421 of the cavity 2420 of the connecting portion 2412 of the adaptor 2410 (FIGS. 87A-88)

In some embodiments, at the second end 2458, the body 2454 can have a narrower portion 2466 and the outer surface 2460 at the narrower portion 2466 can have a second outer diameter 2465. In some embodiments, the second outer diameter 2465 can vary along the axial length of the narrower portion 2466 (as shown in FIG. 96). However, in other embodiments, the second outer diameter 2465 can be constant along the axial length of the narrower portion 2466.

In some embodiments, the outer surface 2460 of the body 2454 can have one or more additional geometric features, such as a ring portion 2468. In other embodiments, the body 2454 may not include the ring portion 2468.

The body 2454 of the adaptor insert 2404 can include an inner surface (or lumen) 2470 with a diameter that varies along the axial length of the adaptor insert 2404 and defines an interior cavity 2471 that can comprise a plurality of cavity portions with varying diameters (FIG. 96).

In some embodiments, the cavity portions defined by the inner surface 2470 include a first cavity portion 2472 with a first inner diameter 2474. The first cavity portion 2472 can be configured to receive the first flange 2426 therein (FIGS. 87B and 89).

In some embodiments, the cavity portions defined by the inner surface 2470 include a second cavity portion 2476 with a second inner diameter 2478 (FIG. 96). In some embodiments, the second cavity portion 2476 can include a tapered portion 2480 that narrows (in diameter) to a third cavity portion 2482 having a third inner diameter 2484. Thus, the third inner diameter 2484 can be smaller than the second inner diameter 2478 (FIG. 96).

In some embodiments, the cavity portions defined by the inner surface 2470 can include a fourth cavity portion 2486 that is configured to receive the sealing member 2406 therein (FIGS. 96 and 87B). The fourth cavity portion 2486 can have a fourth inner diameter 2488 that is larger than the third inner diameter 2484.

In some embodiments, the cavity portions defined by the inner surface 2470 can include a fifth cavity portion 2490 which is part of the narrower portion 2466 and has a fifth inner diameter 2492. In some embodiments, as shown in FIG. 96, the fifth inner diameter 2492 is smaller than the third inner diameter 2484.

As shown in FIG. 87B, a majority of the second portion 2424 of the release sleeve 2402 can be configured to fit and be received within the third cavity portion 2482 of the adaptor insert 2404. Further, a majority of the first portion 2422 of the release sleeve 2402 can be configured to fit and be received within the second cavity portion 2476 of the adaptor insert 2404. In some embodiments, as shown in FIG. 87B and introduced above, the first flange 2426 of the release sleeve 2402 can be configured to fit and be received within the first cavity portion 2472 of the adaptor insert 2404.

For example, during insertion of the release sleeve 2402 into the adaptor insert 2404, the collar portion 2438 of the second portion 2424 of the release sleeve 2402 can begin to depress radially inward is it comes into contact with (and slides against) the inner surface 2470 in the tapered portion 2480 of the second cavity portion 2476. For example, the first diameter 2442 of the collar portion 2438 (when disassembled from the adaptor insert, as shown in FIG. 93) can be larger than the third inner diameter 2484 of the third cavity portion 2482. Thus, when the collar portion 2438 is arranged within the third cavity portion 2482 of the adaptor insert 2404, as shown in FIG. 87B, the collar portion 2438 of the release sleeve 2402 is depressed radially inward and, when disposed around the intermediate shaft 306 (as shown in FIG. 87B), can press against the intermediate shaft 306. As a result, the release sleeve 2402 can couple tightly to and around the intermediate shaft 306. For example, the release sleeve 2402 can be held in coupling contact with the proximal end 307 of the intermediate shaft 306 via radially inward pressure from the adaptor insert 2404.

For example, in some embodiments, when the release sleeve 2402 is received within the interior cavity 2471 of the adaptor insert 2404 and the collar portion 2438 is arranged within the third cavity portion 2482, the first diameter 2442 of the collar portion 2438 can be smaller or equal to the third inner dimeter 2484 of the third cavity portion 2482.

Further, in some embodiments, as shown in FIG. 87B, the sealing member 2406 can be positioned within the fourth cavity 2486 of the adaptor insert and adjacent to the collar portion 2438. As a result, the sealing member 2406 can encircle and seal around the intermediate shaft 306 and reduce a likelihood of fluid passing through the adaptor 2410 and to the inner lumen of the intermediate shaft 306 from escaping via the adaptor 2410. As such, the shaft connector release assembly 2400 is configured to provide a secure and fluid-tight connection between the intermediate shaft 306 and the adaptor 2410 (or a similar adaptor, such as one of the other adaptors described herein)

The components of the shaft connector release assembly 2400 (e.g., as shown in the exploded view of FIG. 90) can be assembled together and to the adaptor 2410 (or a similar adaptor) and/or the intermediate shaft 306 in various manners to form the final, assembled shaft connector release assembly 2400 which connects the intermediate shaft 306 and the adaptor 2410 to one another (as shown in FIGS. 87A, 87B, and 89).

In some embodiments, to assemble the shaft connector release assembly 2400 to the intermediate shaft 306 and the adaptor 2410, the release sleeve 2402 can be positioned around the proximal end 307 of the intermediate shaft 306 (or another shaft to be coupled to a connector). In some embodiments, the sealing member 2406 can be arranged within the adaptor insert (e.g., in the fourth cavity 2486). Together, the release sleeve 2402 and the intermediate shaft 306 can be slid into the adaptor insert (as described above). In some embodiments, the release sleeve 2402 and the adaptor insert 2404 can be sized such that they can be securely press fit together in coupling engagement with one another and to the intermediate shaft.

In some embodiments, the assembled shaft connector release assembly 2400 can be configured to be press fit into the connecting portion 2412 of the adaptor 2410. For example, as described above, the adaptor insert 2404 can be shaped to fit tightly within and couple securely to the connecting portion 2412 (as shown in FIG. 87B). As a result, the shaft connector release assembly 2400 can be securely coupled to the adaptor 2410, thereby coupling the intermediate shaft 306 to the adaptor 2410.

In other embodiments, the adaptor 2410 (or other adaptor) can be manufactured as two parts. For example, the connecting portion 2412 can be separate from a remainder of the adaptor 2410 (e.g., the branch portion 2414). In such embodiments, the assembled shaft connector release assembly 2400 (assembled around the intermediate shaft 306) can be press fit into the connecting portion 2412 or the assembled shaft connector release assembly 2400 can be welded (e.g., via sonic welding) to and within the connecting portion 2412. In either case, the connecting portion 2412, coupled to the assembled shaft connector release assembly 2400, can then be permanently fixed or welded (e.g., via sonic welding) to the branch portion 2414 of the adaptor 2410.

In some embodiments, when the connecting portion 2412 is manufactured as a separate piece from the adaptor, the adaptor could be one of the other adaptors described herein (e.g., adaptor 312 shown in FIGS. 14 and 15 or adaptor 402 shown in FIGS. 23-27) and then the connecting portion 2412 can be welded to the adaptor, as described above.

In still other embodiments, the adaptor insert 2404 and the adaptor 2410 can be formed as one piece. For example, the adaptor insert 2404 and the adaptor 2410 can be molded together (e.g., via overmolding). In such embodiments, the release sleeve 2402, coupled around the intermediate shaft 306, can then be insert into the adaptor insert 2404 (as described above). As a result, the intermediate shaft 306 and the adaptor 2410 would be coupled securely together.

In some embodiments, the rotatable knob 314 shown in FIGS. 15-22 can be attached the intermediate shaft 306 (as described above), distal to the connecting portion 2412 of the adaptor (e.g., the adaptor 2410 and the shaft connector release assembly 2400 can replace the adaptor 312 shown in FIGS. 15-17).

Additional Examples of the Disclosed Technology

In view of the above described implementations of the disclosed subject matter, this application discloses the additional examples enumerated below. It should be noted that one feature of an example in isolation or more than one feature of the example taken in combination and, optionally, in combination with one or more features of one or more further examples are further examples also falling within the disclosure of this application.

Example 1. A delivery apparatus comprising a first shaft that is configured to rotate around a central longitudinal axis of the delivery apparatus to rotationally align a prosthetic valve mounted on the delivery apparatus with native anatomy at a target implantation site; a second shaft extending through the first shaft and having a distal end portion extending distally beyond a distal end portion of the first shaft; an inflatable balloon coupled to the distal end portion of the first shaft; and a shoulder arranged within the balloon and a radiopaque marker mounted on or embedded within the shoulder at a location spaced radially outward from an outer surface of the distal end portion of the second shaft, wherein the marker is reflection asymmetric along an axis that is parallel to the central longitudinal axis, and wherein the shoulder is configured such that when the prosthetic valve is mounted on the balloon in a radially compressed state, the shoulder resists movement of the prosthetic valve relative to the balloon in an axial direction.

Example 2. The delivery apparatus of any example herein, particularly example 1, wherein the shoulder comprises a polymeric body and the marker is mounted on or embedded within the polymeric body.

Example 3. The delivery apparatus of any example herein, particularly either example 1 or 2, wherein the shoulder is a distal shoulder arranged within a distal end portion of the balloon and mounted on the distal end portion of the second shaft.

Example 4. The delivery apparatus of any example herein, particularly example 3, wherein the distal shoulder is arranged proximal and adjacent to a nose cone of the delivery apparatus, the nose cone mounted to the distal end portion of the second shaft.

Example 5. The delivery apparatus of any example herein, particularly example 3 or example 4, wherein the distal shoulder comprises a base portion and a flared portion, the flared portion extending radially outward from the base portion, toward a valve mounting portion of the delivery apparatus, the valve mounting portion configured to receive the prosthetic valve in a radially compressed state, and wherein the marker is arranged on or embedded within the flared portion.

Example 6. The delivery apparatus of any example herein, particularly example 5, wherein the flared portion includes a plurality of wings flaring radially outward from the base portion, in a proximal direction and at an angle relative to the central longitudinal axis, and wherein the marker is arranged on or embedded within one of the plurality of wings.

Example 7. The delivery apparatus of any example herein, particularly any one of examples 3-6, wherein the marker is positioned at a proximal end of the distal shoulder, the proximal end arranged adjacent to a valve mounting portion of the delivery apparatus, the valve mounting portion configured to receive the prosthetic valve in the radially compressed state, and wherein the balloon overlays the valve mounting portion.

Example 8. The delivery apparatus of any example herein, particularly any one of examples 1-7, wherein a proximal end portion of the balloon is coupled to the distal end portion of the first shaft and a distal end portion of the balloon is coupled to a nose cone coupled to the distal end portion of the second shaft.

Example 9. The delivery apparatus of any example herein, particularly example 1 or example 2, wherein the shoulder is a proximal shoulder arranged within a proximal end portion of the balloon, the proximal shoulder arranged proximal to a valve mounting portion of the delivery apparatus.

Example 10. The delivery apparatus of any example herein, particularly any one of examples 1-9, wherein the marker is shaped as a letter of an alphabet.

Example 11. The delivery apparatus of any example herein, particularly any one of examples 1-10, wherein the marker comprises tantalum.

Example 12. The delivery apparatus of any example herein, particularly any one of examples 1-11, wherein the marker comprises a platinum-iridium alloy.

Example 13. The delivery apparatus of any example herein, particularly example 12, wherein an alloy proportion of the platinum-iridium alloy is 90:10.

Example 14. The delivery apparatus of any example herein, particularly any one of examples 1-13, wherein the delivery apparatus further includes a nose cone coupled to the distal end portion of the second shaft and wherein the nose cone is arranged distal to the shoulder.

Example 15. The delivery apparatus of any example herein, particularly any one of examples 1-14, wherein the first shaft is arranged within and configured to rotate relative to a third shaft of the delivery apparatus, wherein the distal end portion of the first shaft extends distally beyond a distal end of the third shaft, and further comprising a handle portion including a steering mechanism configured to selectively adjust a curvature of the third shaft.

Example 16. The delivery apparatus of any example herein, particularly any one of examples 1-15, wherein the first shaft comprises a first layer of braided material and a second layer of braided material embedded therein, wherein the first layer of braided material extends along an entire length of the first shaft, from a proximal end to a distal end of the first shaft, and the second layer of braided material extends a majority of the entire length of the first shaft, from the proximal end to a distance spaced away from the distal end.

Example 17. The delivery apparatus of any example herein, particularly any one of examples 1-16, further comprising a handle portion and wherein the first shaft extends distally from the handle portion and has a proximal end portion that extends proximally from the handle portion to an adaptor, the adaptor including a body coupled to the proximal end portion, a first port extending axially from the body, relative to the central longitudinal axis, and a second port extending at an angle from the body, relative to the central longitudinal axis.

Example 18. The delivery apparatus of any example herein, particularly example 17, wherein an inner lumen of the second port is fluidly coupled to an annular space defined between an inner surface of the first shaft and an outer surface of the second shaft and a fluid passageway formed between the outer surface of the distal end portion of the second shaft and an inner surface of the balloon.

Example 19. The delivery apparatus of any example herein, particularly example 17 or example 18, wherein the second port is configured to rotate around the central longitudinal axis and relative to the body and the first port of the adaptor.

Example 20. The delivery apparatus of any example herein, particularly any one of examples 17-19, further comprising a knob mounted on the proximal end portion of the first shaft, the knob configured to rotate the first shaft.

Example 21. The delivery apparatus of any example herein, particularly example 20, wherein the knob comprises an outer housing and an anchor arranged within the outer housing, wherein the anchor is configured to couple the knob to the proximal end portion of the first shaft.

Example 22. The delivery apparatus of any example herein, particularly example 21, wherein the outer housing includes two or more housing portions that are configured to be removably coupled to one another and couple together around the anchor.

Example 23. The delivery apparatus of any example herein, particularly example 21 or example 22, wherein the anchor includes an aligning tab configured to align the adaptor relative to the marker of the shoulder.

Example 24. The delivery apparatus of any example herein, particularly example 23, wherein the anchor includes a shaft portion defining an inner lumen configured to receive and couple around the proximal end portion of the first shaft and wherein the aligning tab extends radially outward from the shaft portion.

Example 25. The delivery apparatus of any example herein, particularly example 24, wherein the shaft portion of the anchor includes one or more centering ribs spaced apart around a circumference of the inner lumen and extending along the inner lumen.

Example 26. The delivery apparatus of any example herein, particularly any one of examples 22-25, wherein the outer housing comprises an internal cavity configured to receive the adaptor and wherein the two or more housing portions are configured to be removably coupled to one another and couple together around the adaptor.

Example 27. The delivery apparatus of any example herein, particularly example 26, wherein the knob further comprises a cap configured to be coupled to a proximal end of the outer housing such that the two or more housing portions are held together.

Example 28. The delivery apparatus of any example herein, particularly example 27, wherein a proximal end of the first port of the adaptor extends outward in a proximal direction from the cap.

Example 29. The delivery apparatus of any example herein, particularly any one of examples 22-28, wherein the outer housing comprises one or more indicators that indicate to a user which way the knob should be rotated in order to align the radiopaque marker with a guidewire running through a center of the delivery apparatus.

Example 30. The delivery apparatus of any example herein, particularly example 29, where each indicator comprises a printed marking including a line representing the guidewire, a visual of the radiopaque marker on either side of the line, and an arrow on either side of the line indicating to the user which way to rotate the knob if the radiopaque marker does not appear aligned with the guidewire under fluoroscopy during an implantation procedure with the delivery apparatus.

Example 31. The delivery apparatus of any example herein, particularly any one of examples 1-30, wherein the balloon includes a plurality of overlapping pleats wrapped around the second shaft.

Example 32. The delivery apparatus of any example herein, particularly any one of examples 1-31, further comprising a third shaft surrounding the first shaft, wherein the first shaft is configured to rotate within the third shaft and the first shaft and third shaft are configured to translate axially relative to one another, and wherein the third shaft includes a distal tip portion including a plurality of internal helical expansion grooves and a plurality of external helical expansion grooves that are configured to allow the distal tip portion to flex radially outward.

Example 33. The delivery apparatus of any example herein, particularly example 32, wherein the distal tip portion comprises a coupling portion mounted around a distal end of the first shaft and a flex portion extending distally outward from the coupling portion and wherein the plurality of internal helical expansion grooves are arranged in an inner surface of the flex portion and curve around the central longitudinal axis, from a proximal end of the flex portion to a distal end of the distal tip portion.

Example 34. The delivery apparatus of any example herein, particularly example 33, wherein the distal tip portion is axially movable from a first position where the distal tip portion is arranged away from and off the balloon and the distal end portion of the first shaft extends distally past the distal end of the distal tip portion to a second position wherein the distal tip portion is arranged over a proximal end portion of the balloon and a distal end portion of the third shaft surrounds the distal end portion of the first shaft, and wherein the plurality of internal helical expansion grooves are configured to reduce engagement between pleats of the balloon and the plurality of internal helical expansion grooves when the balloon is rotated with rotation of the first shaft when the distal tip portion is in the second position.

Example 35. The delivery apparatus of any example herein, particularly example 34, wherein the shoulder is a distal shoulder arranged within a distal end portion of the balloon and mounted on the distal end portion of the second shaft and wherein, when the distal tip portion is in the first position, a distal end portion of the balloon includes a radial depression that is depressed inward, toward the central longitudinal axis, relative to an outermost radial surface of the distal shoulder.

Example 36. The delivery apparatus of any example herein, particularly example 35, wherein the radial depression of the distal end portion of the balloon is configured to radially expand when the distal tip portion is moved from the first position to the second position.

Example 37. A delivery apparatus, comprising: a first shaft configured to rotate around a central longitudinal axis of the delivery apparatus to rotationally align a prosthetic valve mounted on the delivery apparatus with native anatomy at a target implantation site; a second shaft extending through the first shaft and having a distal end portion extending distally beyond a distal end portion of the first shaft; an inflatable balloon coupled to the distal end portion of the first shaft; and a polymeric body mounted on the distal end portion of the second shaft and a radiopaque marker mounted on or embedded within the polymeric body.

Example 38. The delivery apparatus of any example herein, particularly example 37, wherein the polymeric body is a distal shoulder arranged within a distal end portion of the balloon and mounted on the distal end portion of the second shaft.

Example 39. The delivery apparatus of any example herein, particularly example 37 or example 33, wherein the distal shoulder is arranged proximal and adjacent to a nose cone of the delivery apparatus, the nose cone mounted to the distal end portion of the second shaft and wherein the distal shoulder is configured such that when the prosthetic valve is mounted on the balloon in a radially compressed state, the distal shoulder resists movement of the prosthetic valve relative to the balloon in an axial direction.

Example 40. The delivery apparatus of any example herein, particularly any one of examples 37-39, wherein the distal shoulder comprises a base portion and a flared portion, the flared portion extending radially outward from the base portion, toward a valve mounting portion of the delivery apparatus, the valve mounting portion configured to receive the prosthetic valve in a radially compressed state, and wherein the marker is arranged on or embedded within the flared portion.

Example 41. The delivery apparatus of any example herein, particularly example 40, wherein the flared portion includes a plurality of wings flaring radially outward from the base portion, in a proximal direction and at an angle relative to the central longitudinal axis, and spaced apart from one another around a circumference of the flared portion, and wherein the marker is centered on one of the plurality of wings such that the marker is centered along the central longitudinal axis.

Example 42. The delivery apparatus of any example herein, particularly example 37, wherein the polymeric body is a nose cone mounted on the distal end portion of the delivery apparatus and wherein the nose cone is arranged distal to a valve mounting portion of the delivery apparatus, the valve mounting portion configured to receive the prosthetic valve in a radially compressed state and wherein the balloon overlays the valve mounting portion.

Example 43. The delivery apparatus of any example herein, particularly example 37, wherein the polymeric body is a proximal shoulder arranged within a proximal end portion of the balloon, the proximal shoulder arranged proximal to a valve mounting portion of the delivery apparatus, the valve mounting portion configured to receive the prosthetic valve in a radially compressed state.

Example 44. The delivery apparatus of any example herein, particularly any one of examples 37-43, wherein the polymeric body is not radiopaque.

Example 45. The delivery apparatus of any example herein, particularly any one of examples 37-44, wherein the marker is reflection asymmetric along an axis that is parallel to the central longitudinal axis.

Example 46. The delivery apparatus of any example herein, particularly example 45, wherein the marker is shaped as a letter of an alphabet.

Example 47. The delivery apparatus of any example herein, particularly any one of examples 37-46, wherein the marker comprises tantalum.

Example 48. The delivery apparatus of any example herein, particularly any one of examples 37-47, wherein the marker comprises a platinum-iridium alloy.

Example 49. The delivery apparatus of any example herein, particularly any one of examples 37-48, wherein the second shaft includes an inner lumen configured to receive a guidewire and wherein an annular space is defined between an outer surface of the second shaft and an inner surface of the first shaft, the annular spaced configured to receive an inflation fluid and fluidly coupled to a fluid passageway formed between the outer surface of the distal end portion of the second shaft and an inner surface of the balloon.

Example 50. The delivery apparatus of any example herein, particularly any one of examples 37-49, wherein the first shaft comprises a first layer of braided material and a second layer of braided material embedded therein, wherein the first layer of braided material extends along an entire length of the first shaft, from a proximal end to a distal end of the first shaft, and the second layer of braided material extends a majority of the entire length of the first shaft, from the proximal end to a distance spaced away from the distal end.

Example 51. The delivery apparatus of any example herein, particularly any one of examples 37-50, wherein the first shaft is arranged within and configured to rotate relative to a third shaft of the delivery apparatus and further comprising a handle portion including a steering mechanism configured to selectively adjust a curvature of the third shaft.

Example 52. The delivery apparatus of any example herein, particularly any one of examples 37-51, further comprising a handle including one or more adjustment mechanisms configured to adjust operation of the delivery apparatus, wherein the first shaft extends distally from the handle to the distal end portion of the first shaft, wherein the first shaft has a proximal end portion that extends proximally from the handle to an adaptor, and further comprising a rotatable knob mounted on the proximal end portion of the first shaft, the knob configured to rotate the first shaft.

Example 53. The delivery apparatus of any example herein, particularly example 52, wherein the adaptor comprises a body coupled to the proximal end portion, a first port extending axially from the body, relative to the central longitudinal axis, and a second port extending at an angle from the body, relative to the central longitudinal axis, wherein the first port is coupled to an inner lumen of the second shaft and configured to receive a guidewire, and wherein the second port is fluidly coupled to an annular space defined between an outer surface of the second shaft and an inner surface of the first shaft, the annular spaced fluidly coupled to a fluid passageway formed between the outer surface of the distal end portion of the second shaft and an inner surface of the balloon.

Example 54. The delivery apparatus of any example herein, particularly example 53, wherein the second port is configured to rotate around the central longitudinal axis and relative to the body and the first port of the adaptor.

Example 55. The delivery apparatus of any example herein, particularly any one of examples 52-54, wherein the knob comprises an outer housing and an anchor arranged within the outer housing, wherein the anchor is configured to couple the knob to the proximal end portion of the first shaft.

Example 56. The delivery apparatus of any example herein, particularly example 55, wherein the outer housing includes two or more housing portions that are configured to be removably coupled to one another and couple together around the anchor and around the adaptor such that the anchor and the adaptor are enclosed within the outer housing.

Example 57. The delivery apparatus of any example herein, particularly example 56, wherein the knob further comprises a cap configured to be coupled to a proximal end of the outer housing such that the two or more housing portions are held together.

Example 58. The delivery apparatus of any example herein, particularly any one of examples 55-57, wherein the outer housing comprises one or more indicators that indicate to a user which way the knob should be rotated in order to align the radiopaque marker with a guidewire running through a center of the delivery apparatus.

Example 59. The delivery apparatus of any example herein, particularly example 58, where each indicator comprises a printed marking including a line representing the guidewire, a visual of the radiopaque marker on either side of the line, and an arrow on either side of the line indicating to the user which way to rotate the knob if the radiopaque marker does not appear aligned with the guidewire under fluoroscopy during an implantation procedure with the delivery apparatus.

Example 60. The delivery apparatus of any example herein, particularly example 55 or example 56, wherein the anchor includes an aligning tab configured to circumferentially align the adaptor relative to the marker of the polymeric body.

Example 61. The delivery apparatus of any example herein, particularly example 60, wherein the anchor includes a shaft portion defining an inner lumen configured to receive and couple around the proximal end portion of the first shaft and wherein the aligning tab extends radially outward from the shaft portion.

Example 62. The delivery apparatus of any example herein, particularly example 61, wherein the shaft portion of the anchor includes one or more centering ribs spaced apart around a circumference of the inner lumen and extending along the inner lumen and an aperture extending between an outer surface and an inner surface of the shaft portion and arranged in a central portion of the shaft portion.

Example 63. The delivery apparatus of any example herein, particularly any one of examples 37-62, wherein the balloon includes a plurality of overlapping pleats wrapped around the second shaft and overlaying a valve mounting portion of the delivery apparatus, the valve mounting portion configured to receive the prosthetic valve in a radially compressed state.

Example 64. The delivery apparatus of any example herein, particularly any one of examples 37-63, further comprising a third shaft surrounding the first shaft, wherein the first shaft is configured to rotate within the third shaft and the first shaft and third shaft are configured to translate axially relative to one another, and wherein the third shaft includes a distal tip portion including a plurality of helical expansion grooves arranged in an inner surface of the distal tip portion and configured to allow the distal tip portion to flex radially outward.

Example 65. The delivery apparatus of any example herein, particularly example 64, wherein the distal tip portion is axially movable from a first position where the distal tip portion is arranged away from and off the balloon and the distal end portion of the first shaft extends distally past a distal end of the distal tip portion to a second position where the distal tip portion is arranged over a proximal end portion of the balloon and a distal end portion of the third shaft surrounds the distal end portion of the first shaft, and wherein the plurality of helical expansion grooves are configured to reduce engagement between pleats of the balloon and the plurality of helical expansion grooves when the balloon is rotated with rotation of the first shaft when the distal tip portion is in the second position.

Example 66. The delivery apparatus of any example herein, particularly example 65, further comprising a distal shoulder arranged within a distal end portion of the balloon and mounted on the distal end portion of the second shaft and wherein, when the distal tip portion is in the first position, the distal end portion of the balloon includes a radial depression that is depressed inward, toward the central longitudinal axis, relative to an outermost radial surface of the distal shoulder.

Example 67. The delivery apparatus of any example herein, particularly example 66, wherein the radial depression of the distal end portion of the balloon is configured to radially expand when the distal tip portion is moved from the first position to the second position.

Example 68. A medical assembly for replacing a native valve of a heart, comprising: a delivery apparatus, the delivery apparatus comprising: a first shaft configured to rotate around a central longitudinal axis of the delivery apparatus; a second shaft extending through the first shaft and having a distal end portion extending distally beyond a distal end portion of the first shaft; an inflatable balloon coupled to the distal end portion of the first shaft; and a radiopaque marker arranged on a distal end portion of the delivery apparatus. The medical assembly further comprising a prosthetic heart valve mounted in a radially compressed configuration onto and around the balloon, wherein the marker is offset, in a circumferential direction relative to the central longitudinal axis, from a location of a selected commissure of the prosthetic heart valve, wherein the first shaft is configured to rotate to rotationally align the marker at the native valve such that, after inflating the balloon to radially expand the prosthetic heart valve, the prosthetic heart valve is implanted with the selected commissure of the prosthetic heart valve circumferentially aligned with a target commissure of the native valve.

Example 69. The medical assembly of any example herein, particularly example 68, wherein the radiopaque marker is reflection asymmetric along an axis that is parallel to a central longitudinal axis of the delivery apparatus.

Example 70. The medical assembly of any example herein, particularly example 68 or example 69, wherein the marker is mounted on or embedded within a polymeric body mounted on the distal end portion of the second shaft.

Example 71. The medical assembly of any example herein, particularly example 70, wherein the marker is mounted on or embedded within the polymeric body at a location spaced radially outward from an outer surface of the distal end portion of the second shaft.

Example 72. The medical assembly of any example herein, particularly example 70 or example 71, wherein the polymeric body is a distal shoulder arranged inside the balloon, distal to the prosthetic heart valve.

Example 73. The medical assembly of any example herein, particularly example 70 or example 71, wherein the polymeric body is a proximal shoulder arranged inside balloon, proximal to the prosthetic heart valve.

Example 74. The medical assembly of any example herein, particularly example 70 or example 71, wherein the polymeric body is a nose cone, the nose cone coupled to the distal end portion of the second shaft, distal to the prosthetic heart valve.

Example 75. The medical assembly of any example herein, particularly any one of examples 68-74, wherein the balloon is pleated and radially wrapped around the second shaft, underneath the radially compressed prosthetic heart valve.

Example 76. The medical assembly of any example herein, particularly any one of examples 68-75, further comprising a guidewire extending though the second shaft and through a center of the distal end portion of the delivery apparatus.

Example 77. The medical assembly of any example herein, particularly any one of examples 68-76, wherein the marker is configured to indicate a location of the selected commissure of the prosthetic heart valve after radially expanding the prosthetic heart valve via inflating the balloon.

Example 78. The medical assembly of any example herein, particularly any one of examples 68-77, wherein the first shaft comprises two layers of a braided material embedded therein, wherein a first layer of the two layers of the braided material extends along an entire length of the first shaft and a second layer of the two layers of the braided material is shorter than the first layer.

Example 79. The medical assembly of any example herein, particularly any one of examples 68-78, wherein the delivery apparatus further comprises a third shaft and a steering mechanism configured to selectively adjust a curvature of the third shaft and wherein the first shaft is configured to rotate within the third shaft.

Example 80. The medical assembly of any example herein, particularly any one of examples 68-79, further comprising a handle including one or more adjustment mechanisms configured to adjust operation of the delivery apparatus, wherein the first shaft extends distally from the handle to the distal end portion of the first shaft, wherein the first shaft has a proximal end portion that extends proximally from the handle, and further comprising a rotatable knob mounted on the proximal end portion of the first shaft, the knob configured to rotate the first shaft.

Example 81. The medical assembly of any example herein, particularly example 80, further comprising an adaptor mounted to the proximal end portion of the first shaft, wherein the adaptor comprises a body coupled to the proximal end portion, a first port extending axially from the body, relative to the central longitudinal axis, and a second port extending at an angle from the body, relative to the central longitudinal axis, wherein the first port is coupled to an inner lumen of the second shaft and configured to receive a guidewire, and wherein the second port is fluidly coupled to an annular space defined between an outer surface of the second shaft and an inner surface of the first shaft, the annular spaced fluidly coupled to a fluid passageway formed between the outer surface of the distal end portion of the second shaft and an inner surface of the balloon.

Example 82. The medical assembly of any example herein, particularly example 81, wherein the second port is configured to rotate around the central longitudinal axis and relative to the body and the first port of the adaptor.

Example 83. The medical assembly of any example herein, particularly any one of examples 81-82, wherein the knob comprises an outer housing and an anchor arranged within the outer housing, wherein the anchor is configured to couple the knob to the proximal end portion of the first shaft.

Example 84. The medical assembly of any example herein, particularly example 83, wherein the outer housing includes two or more housing portions that are configured to be removably coupled to one another and couple together around the anchor and the adaptor.

Example 85. The medical assembly of any example herein, particularly example 83 or example 76, wherein the anchor includes an aligning tab configured to circumferentially align the adaptor relative to the marker of the distal end portion of the delivery apparatus.

Example 86. The medical assembly of any example herein, particularly example 85, wherein the anchor includes a shaft portion defining an inner lumen configured to receive and couple around the proximal end portion of the first shaft and wherein the aligning tab extends radially outward from the shaft portion.

Example 87. The medical assembly of any example herein, particularly example 86, wherein anchor includes one or more extension portions extending radially outward from the shaft portion and configured to mate with corresponding apertures arranged in the outer housing.

Example 88. The medical assembly of any example herein, particularly any one of examples 68-87, further comprising a third shaft surrounding the first shaft, wherein the first shaft is configured to rotate within the third shaft and the first shaft and third shaft are configured to translate axially relative to one another, and wherein the third shaft includes a distal tip portion including a plurality of helical expansion grooves arranged in an inner surface of the distal tip portion.

Example 89. The medical assembly of any example herein, particularly example 88, wherein the distal tip portion is axially movable from a first position where the distal tip portion is arranged away from and off the balloon and the distal end portion of the first shaft extends distally past a distal end of the distal tip portion to a second position where the distal tip portion is arranged over a proximal end portion of the balloon and a distal end portion of the third shaft surrounds the distal end portion of the first shaft, and wherein the plurality of helical expansion grooves are configured to reduce engagement between pleats of the balloon and the plurality of helical expansion grooves when the balloon is rotated with rotation of the first shaft when the distal tip portion is in the second position.

Example 90. The medical assembly of any example herein, particularly example 89, further comprising a distal shoulder arranged within a distal end portion of the balloon and mounted on the distal end portion of the second shaft and wherein, when the distal tip portion is in the first position, the distal end portion of the balloon includes a radial depression that is depressed inward, toward the central longitudinal axis, relative to an outermost radial surface of the distal shoulder.

Example 91. The medical assembly of any example herein, particularly example 82, wherein the radial depression of the distal end portion of the balloon is configured to radially expand when the distal tip portion is moved from the first position to the second position.

Example 92. The medical assembly of any of any example herein, particularly example 82 or example 83, wherein the marker is arranged on or embedded within the distal shoulder.

Example 93. The medical assembly of any example herein, particularly any one of examples 68-92, wherein the prosthetic heart valve includes three commissures and is configured to be deployed in a native aortic valve.

Example 94. A method, comprising: advancing a distal end portion of a delivery apparatus toward a native valve of a heart, wherein a prosthetic heart valve is radially compressed around an inflatable balloon of the delivery apparatus, at a valve mounting portion of the delivery apparatus; visualizing, under fluoroscopy and for a selected imaging view, a position of a radiopaque marker on the distal end portion of the delivery apparatus relative to a guidewire extending through a shaft of the delivery apparatus, wherein the marker is circumferentially offset from a selected commissure of the radially compressed prosthetic heart valve by a predetermined amount that is determined based on the selected imaging view, and wherein the marker is reflection asymmetric along an axis that is parallel to a central longitudinal axis of the delivery apparatus; prior to crossing the native valve, rotating the shaft of the delivery apparatus, which rotates the prosthetic heart valve and the marker, until the marker is centered along the guidewire and is in a predetermined orientation in the selected imaging view; and advancing the distal end portion of the delivery apparatus including the radially compressed prosthetic heart valve across and into the native valve and inflating the balloon to radially expand and implant the prosthetic heart valve in the native valve such that the selected commissure of the prosthetic heart valve is aligned with a target commissure of the native valve, wherein during the inflating, as the prosthetic heart valve radially expands, the prosthetic heart valve rotates.

Example 95. The method of any example herein, particularly example 94, wherein for a first selected imaging view the predetermined amount of offset is a first amount and wherein for a second selected imaging view the predetermined amount of offset is a second amount.

Example 96. The method of any example herein, particularly example 95, wherein the first selected imaging view is a three-cusp imaging view and the second selected imaging view is a right/left cusp overlap imaging view and wherein the native valve is a native aortic valve.

Example 97. The method of any example herein, particularly any one of examples 94-96, wherein the rotating the shaft of the delivery apparatus includes rotating a knob disposed on a proximal end portion of the shaft that extends proximally from a handle of the delivery apparatus and wherein the shaft of the delivery apparatus extends through the handle and distally to the distal end portion of the delivery apparatus.

Example 98. The method of any example herein, particularly example 97, wherein the balloon is coupled to a distal end of the shaft.

Example 99. The method of any example herein, particularly any one of examples 94-98, wherein the predetermined orientation in the selected imaging view is a direct back of the selected imaging view.

Example 100. The method of any example herein, particularly example 99, wherein the marker has a first orientation when it is arranged in front of the guidewire within the selected imaging view and a different, second orientation when it is arranged behind the guidewire within the selected imaging view and wherein rotating the shaft of the delivery apparatus, which rotates the prosthetic heart valve and the marker, includes rotating the shaft until the marker is centered along the guidewire and in its second orientation within the selected imaging view, thereby positioning the marker in the direct back of the selected imaging view.

Example 101. The method of any example herein, particularly any one of examples 94-98, wherein the predetermined orientation in the selected imaging view is a direct front of the selected imaging view.

Example 102. The method of any example herein, particularly example 101, wherein the marker has a first orientation when it is arranged in front of the guidewire within the selected imaging view and a different, second orientation when it is arranged behind the guidewire within the selected imaging view and wherein rotating the shaft of the delivery apparatus, which rotates the prosthetic heart valve and the marker, includes rotating the shaft until the marker is centered along the guidewire and in its first orientation within the selected imaging view, thereby positioning the marker in the direct front of the selected imaging view.

Example 103. The method of any example herein, particularly any one of examples 94-102, wherein during the inflating, as the prosthetic heart valve radially expands, the prosthetic heart valve rotates by an amount equal to the predetermined amount of offset between the marker and the selected commissure of the prosthetic heart valve when the prosthetic heart valve is radially compressed around the balloon.

Example 104. The method of any example herein, particularly any one of examples 94-103, wherein the shaft is a first shaft, wherein a second shaft extends through the first shaft and has a distal end portion extending distally beyond a distal end portion of the first shaft, and wherein the marker is arranged on or embedded within a polymeric body mounted on the distal end portion of the second shaft.

Example 105. The method of any example herein, particularly example 104, wherein the polymeric body is a distal shoulder mounted on the distal end portion of the second shaft, distal to the prosthetic heart valve when the prosthetic heart valve is radially compressed around the balloon, and wherein the distal shoulder is configured to resist movement of the prosthetic heart valve relative to the balloon when the prosthetic heart valve is radially compressed around the balloon.

Example 106. A method, comprising: receiving a prosthetic heart valve mounted on a distal end portion of a delivery apparatus, around an inflatable balloon of the delivery apparatus and in a radially compressed configuration, at a predetermined position and in a predetermined orientation relative to the delivery apparatus, such that a selected commissure of the prosthetic heart valve is offset, in a circumferential direction relative to a central longitudinal axis of the delivery apparatus, from a radiopaque marker on the distal end portion of the delivery apparatus by a predetermined amount, wherein the marker is reflection asymmetric across a longitudinal axis of the marker that is parallel to the central longitudinal axis; advancing the distal end portion toward a native valve of a heart; prior to crossing the native valve with the distal end portion of the delivery apparatus and while imaging the heart, rotating together, the balloon and the radially compressed prosthetic heart valve, until the marker is in a selected orientation relative to a guidewire extending through a shaft of the delivery apparatus, within an imaging view; and advancing the radially compressed prosthetic heart valve with the delivery apparatus into the native valve and inflating the balloon to radially expand and implant the prosthetic heart valve in the native valve such that the selected commissure of the prosthetic heart valve is aligned with a target commissure of the native valve.

Example 107. The method of any example herein, particularly example 106, wherein the selected orientation includes the longitudinal axis of the marker being axially aligned with the guidewire and the marker being in a first orientation of two orientations that are mirror images of one another.

Example 108. The method of any example herein, particularly example 107, wherein the marker is a letter of an alphabet and wherein the first orientation of the marker is a forward-readable orientation of the letter of the alphabet.

Example 109. The method of any example herein, particularly example 107, wherein the marker is a letter of an alphabet and wherein the first orientation of the marker is a backward-readable orientation of the letter of the alphabet.

Example 110. The method of any example herein, particularly any one of examples 107-109, wherein the selected orientation of the marker indicates the marker is behind the guidewire in the imaging view and the marker is in a back of the imaging view.

Example 111. The method of any example herein, particularly any one of examples 107-109, wherein the selected orientation of the marker indicates the marker is in front of the guidewire in the imaging view and the marker is in a front of the imaging view.

Example 112. The method of any example herein, particularly any one of examples 106-111, wherein the rotating includes rotating the shaft within and relative to an outer shaft of the delivery apparatus, wherein the outer shaft is configured to flex.

Example 113. The method of any example herein, particularly any one of examples 106-112, wherein the predetermined amount of offset is determined based on a radial wrapping of the balloon around the shaft of the delivery apparatus and a resulting amount of rotation that occurs during inflating balloon to radially expand the valve.

Example 114. The method of any example herein, particularly example 113, wherein the predetermined amount of offset is further based on the imaging view used during the imaging the heart, the imaging view selected from a plurality of possible imaging views.

Example 115. The method of any example herein, particularly any one of examples 106-114, wherein the marker is arranged on or embedded within a polymeric body mounted on a distal end portion of the shaft of the delivery apparatus.

Example 116. The method of any example herein, particularly example 115, wherein the polymeric body is a distal shoulder mounted on the distal end portion of the shaft, distal to the prosthetic heart valve, and configured to resist movement of the prosthetic heart valve relative to the balloon.

Example 117. The method of any example herein, particularly any one of examples 106-116, wherein the target commissure of the native valve is a commissure between a non-coronary cusp and a left coronary cusp of the native valve.

Example 118. The method of any example herein, particularly any one of examples 106-117, wherein the shaft of the delivery apparatus is a first shaft that is arranged within and includes a distal end portion extending beyond a distal end portion of a second shaft of the delivery apparatus and wherein the rotating together, the balloon and the radially compressed prosthetic heart valve includes actuating a rotatable knob to rotate the second shaft, the balloon coupled to the distal end portion of the second shaft.

Example 119. A method, comprising: positioning a prosthetic valve, in a radially expanded state, around a distal end portion of a delivery apparatus, around an inflatable balloon of the delivery apparatus, at a predetermined position and in a predetermined orientation relative to the delivery apparatus, such that a selected commissure of the prosthetic valve is offset, in a circumferential direction relative to a central longitudinal axis of the delivery apparatus, from a radiopaque marker on the distal end portion of the delivery apparatus by a predetermined amount, wherein the marker is reflection asymmetric along an axis that is parallel to the central longitudinal axis; and crimping the prosthetic valve into a radially compressed state to and around the balloon and the delivery apparatus and maintaining the offset between the selected commissure of the prosthetic valve and the marker.

Example 120. The method of any example herein, particularly example 119, wherein the positioning comprises: positioning the prosthetic valve onto an implant holder device such that one or more commissures of the prosthetic valve align with one or more corresponding alignment markers on an alignment ring coupled to the implant holder device and coupling the implant holder device to a first side of a crimping device; and attaching a positioning device to the delivery apparatus and coupling the positioning device to a second side of the crimping device such that prosthetic heart valve is positioned around the distal end portion of the delivery apparatus, around the balloon, within the crimping device.

Example 121. The method of any example herein, particularly example 120, wherein the prosthetic heart valve, in the radially expanded state, is received on a conical support portion of the implant holder device, the conical support portion extending outward from a coupling portion of the implant holder device, the coupling portion including an alignment element configured to mate with a corresponding mating interface in the first side of the crimping device.

Example 122. The method of any example herein, particularly example 121, wherein the crimping includes automatically sliding the implant holder device away from the prosthetic valve and out of the crimping device during the crimping.

Example 123. The method of any example herein, particularly any one of examples 120-122, further comprising selecting the alignment ring from one or more alignment rings based on a desired imaging view for visualizing the prosthetic valve on the distal end portion of the delivery apparatus during an implantation procedure, wherein each alignment ring of the one or more alignment rings has a different predetermined arrangement of the one or more alignment markers on the alignment ring.

Example 124. The method of any example herein, particularly any one of examples 120-122, further comprising selecting a set of alignment markers on the alignment ring from multiple sets of alignment markers that are circumferentially offset from one another, based on a desired imaging view for visualizing the prosthetic valve on the distal end portion of the delivery apparatus during an implantation procedure and positioning the prosthetic valve onto the implant holder device such that one or more commissures of the prosthetic valve align with one or more corresponding alignment markers of the selected set of alignment markers on the alignment ring coupled to the implant holder device.

Example 125. The method of any example herein, particularly any one of examples 120-122, further comprising selecting a set of alignment markers on the alignment ring from multiple sets of alignment markers that are circumferentially offset from one another, based on a determined native anatomy of a heart of a patient in which the prosthetic valve is to be implanted, and positioning the prosthetic valve onto the implant holder device such that one or more commissures of the prosthetic valve align with one or more corresponding alignment markers of the selected set of alignment markers on the alignment ring coupled to the implant holder device.

Example 126. The method of any example herein, particularly any one of examples 120-125, wherein attaching the positioning device to the delivery apparatus includes coupling a portion of the positioning device around a shaft of the delivery apparatus, proximal to a valve mounting portion of the delivery apparatus and a proximal portion of the balloon of the delivery apparatus.

Example 127. A delivery apparatus, comprising: a first shaft including a tapered distal tip portion; a second shaft extending through the first shaft and configured to rotate within the first shaft, around a central longitudinal axis of the delivery apparatus, wherein the first shaft and the second shaft are configured to translate axially relative to one another; a third shaft extending through the second shaft and having a distal end portion extending distally beyond a distal end portion of the second shaft; an inflatable balloon coupled to the distal end portion of the second shaft, the balloon arranged around the distal end portion of the third shaft and overlaying a valve mounting portion of the delivery apparatus that is configured to receive a prosthetic valve in a radially compressed state; and wherein the distal tip portion of the first shaft includes a proximal end portion and a distal end portion that has an outer diameter than increases in a distal direction, the distal end portion including a plurality of helical internal grooves arranged on an inner surface of the distal end portion, the plurality of helical internal grooves configured to reduce engagement between pleats of the balloon and the plurality of helical internal grooves when the balloon is rotated with rotation of the second shaft.

Example 128. The delivery apparatus of any example herein, particularly example 127, wherein the helical internal grooves of the plurality of helical internal grooves are spaced apart from one another around a circumference of the distal tip portion and wherein each helical internal groove of the plurality of helical internal grooves curves around the central longitudinal axis.

Example 129. The delivery apparatus of any of any example herein, particularly example 128, wherein the distal end portion of the distal tip portion includes a plurality of helical external grooves arranged on an outer surface of the distal end portion and spaced apart from one another around a circumference of the distal tip portion.

Example 130. The delivery apparatus of any example herein, particularly example 129, wherein the plurality of helical internal grooves are circumferentially offset from the plurality of helical external grooves such that a location where one helical external groove depresses into the outer surface of the distal tip portion is arranged between where two adjacent helical internal grooves of the plurality of helical internal grooves depress into the inner surface of the distal tip portion.

Example 131. The delivery apparatus of any example herein, particularly any one of examples 127-130, wherein the distal tip portion is axially movable from a first position where the distal tip portion is arranged away from and off the balloon and the distal end portion of the second shaft extends distally past a distal end of the distal tip portion to a second position wherein the distal tip portion is arranged over a proximal end portion of the balloon and adjacent to a proximal side of the valve mounting portion.

Example 132. The delivery apparatus of any example herein, particularly example 131, wherein the distal tip portion is configured to resist movement of the prosthetic valve relative to the balloon in an axial direction when the distal tip portion is in the second position.

Example 133. The delivery apparatus of any of any example herein, particularly example 132, further comprising a distal shoulder arranged within a distal end portion of the balloon and mounted on the distal end portion of the third shaft, wherein the distal shoulder includes a flared portion arranged adjacent to the valve mounting portion configured such that when the prosthetic valve is mounted on the balloon in the radially compressed state, the distal shoulder resists movement of the prosthetic valve relative to the balloon in an axial direction.

Example 134. The delivery apparatus of any example herein, particularly example 133, wherein, when the distal tip portion is in the first position, the distal end portion of the balloon includes a radial depression that is depressed radially inward, toward the central longitudinal axis, relative to an outermost radial surface of the flared portion of the distal shoulder.

Example 135. The delivery apparatus of any example herein, particularly example 134, further comprising a nose cone mounted on the distal end portion of the third shaft, distal to the distal shoulder, and wherein the distal end portion of the balloon extends over the flared portion of the distal shoulder, then depress radially inward, toward a base portion of the distal shoulder, and then extends back radially outward to a proximal end of the nose cone to form the radial depression.

Example 136. The delivery apparatus of any example herein, particularly example 134 or example 135, wherein the radial depression of the distal end portion of the balloon is configured to radially expand when the distal tip portion is moved from the first position to the second position.

Example 137. The delivery apparatus of any example herein, particularly any one of examples 133-136, wherein a radiopaque marker is arranged on or embedded within the distal shoulder.

Example 138. The delivery apparatus of any example herein, particularly any one of examples 133-137, wherein a radiopaque marker is arranged on or embedded within the flared portion of the distal shoulder.

Example 139. The delivery apparatus of any example herein, particularly example 137 or example 138, wherein the radiopaque marker is asymmetric across an axis that is parallel to the central longitudinal axis.

Example 140. The delivery apparatus of any example herein, particularly any one of examples 127-139, wherein the second shaft comprises a first layer of braided material and a second layer of braided material embedded therein, wherein the first layer of braided material extends along an entire length of the second shaft, from a proximal end to a distal end of the second shaft, and the second layer of braided material extends a majority of the entire length of the second shaft, from the proximal end to a distance spaced away from the distal end.

Example 141. The delivery apparatus of any example herein, particularly any one of examples 127-140, further comprising: a handle portion, wherein the second shaft extends distally from the handle portion and has a proximal end portion that extends proximally from the handle portion; and a knob mounted on the proximal end portion of the second shaft and configured to rotate the second shaft relative to the first shaft.

Example 142. The delivery apparatus of any example herein, particularly example 141, further comprising an adaptor coupled to the proximal end portion of the second shaft, the adaptor including a body coupled to the proximal end portion of the second shaft, a first port extending axially from the body, relative to the central longitudinal axis, and a second port extending at an angle from the body, relative to the central longitudinal axis.

Example 143. The delivery apparatus of any example herein, particularly example 142, wherein an inner lumen of the second port is fluidly coupled to an annular space defined between an inner surface of the second shaft and an outer surface of the third shaft and a fluid passageway formed between the outer surface of the distal end portion of the third shaft and an inner surface of the balloon.

Example 144. The delivery apparatus of any example herein, particularly example 142 or example 143, wherein the second port is configured to rotate around the central longitudinal axis and relative to the body and the first port of the adaptor.

Example 145. The delivery apparatus of any example herein, particularly any one of examples 142-144, wherein the knob comprises an outer housing and an anchor arranged within the outer housing, wherein the anchor is configured to couple the knob to the proximal end portion of the second shaft.

Example 146. The delivery apparatus of any example herein, particularly example 145, wherein the outer housing includes two or more housing portions that are configured to be removably coupled to one another and couple together around the anchor.

Example 147. The delivery apparatus of any example herein, particularly example 145 or example 146, wherein the anchor includes an aligning tab configured to align the adaptor relative to a radiopaque marker arranged on or embedded within a polymeric body mounted to the distal end portion of the third shaft.

Example 148. The delivery apparatus of any example herein, particularly example 147, wherein the anchor includes a shaft portion defining an inner lumen configured to receive and couple around the proximal end portion of the second shaft and wherein the aligning tab extends radially outward from the shaft portion.

Example 149. The delivery apparatus of any example herein, particularly example 148, wherein the shaft portion of the anchor includes one or more centering ribs spaced apart around a circumference of the inner lumen and extending along the inner lumen.

Example 150. The delivery apparatus of any example herein, particularly example 147 or example 148, wherein a distal end of the shaft portion of the anchor includes one or more radial extensions extending around a circumference of the shaft portion and spaced apart from one another, in an axial direction, and wherein the one or more radial extensions are configured to mate with an interior of a sleeve element arranged around the proximal end portion of the second shaft and the distal end of the shaft portion of the anchor, the sleeve element configured to relieve strain between the knob and the proximal end portion of the second shaft.

Example 151. The delivery apparatus of any example herein, particularly any one of examples 127-150, wherein the balloon includes a plurality of overlapping pleats wrapped around the second shaft.

Example 152. A delivery apparatus, comprising: a handle portion; a rotatable shaft extending distally from the handle portion and having a proximal end portion that extends proximally from the handle portion to an adaptor, the adaptor including a body connected to the proximal end portion, a first port extending axially from the body, and a second port extending at an angle from the body, in a direction intersecting a central longitudinal axis of the delivery apparatus; a knob mounted on the proximal end portion of the rotatable shaft, the knob configured to rotate the rotatable shaft; and an inflatable balloon coupled to a distal end portion of the rotatable shaft and configured to inflate upon receiving inflation fluid from the second port.

Example 153. The delivery apparatus of any example herein, particularly example 152, wherein the handle portion includes one or more adjustment members configured to control operation of the delivery apparatus.

Example 154. The delivery apparatus of any example herein, particularly example 152, wherein a first adjustment member of the one or more adjustment members is configured as a rotatable knob that is configured to adjust a curvature of a distal end portion of the delivery apparatus.

Example 155. The delivery apparatus of any example herein, particularly example 153 or example 154, wherein a second adjustment member of the one or more adjustment members is configured as a rotatable knob configured to adjust an axial position of the rotatable shaft relative to an outer shaft of the delivery apparatus that surrounds the rotatable shaft.

Example 156. The delivery apparatus of any example herein, particularly any one of examples 152-155, wherein the second port is rotatable around and relative to the body of the adaptor.

Example 157. The delivery apparatus of any example herein, particularly example 156, wherein the second port includes a base portion arranged around a circumference of a proximal portion of the body of the adaptor and wherein the second port includes an inner channel extending from an opening in the second port, through a shaft portion of the second port, and through a portion of the base portion connected with the shaft portion.

Example 158. The delivery apparatus of any example herein, particularly example 157, wherein a seal is arranged between the base portion and the proximal portion of the body of the adaptor.

Example 159. The delivery apparatus of any example herein, particularly example 157 or example 158, wherein the proximal portion of the body of the adaptor includes an annular groove defining an annular channel extending around at least a portion of a circumference of the proximal portion of the body of the adaptor, wherein the annular channel is configured to fluidly couple the inner channel to an interior of the balloon.

Example 160. The delivery apparatus of any example herein, particularly example 159, wherein the annular channel fluidly couples the inner channel to an annular space defined between an outer surface of an inner shaft of the delivery apparatus extending through the rotatable shaft and through the proximal portion of the body of the adaptor and an inner surface of the proximal portion of the body of the adaptor.

Example 161. The delivery apparatus of any example herein, particularly any one of examples 157-160, wherein the proximal portion of the body of the adaptor is bonded to the first port.

Example 162. The delivery apparatus of any example herein, particularly any one of examples 152-161, wherein the adaptor is connected to the proximal end portion of the rotatable shaft by a shaft connector release assembly, the shaft connector release assembly comprising: a release sleeve directly coupled to the proximal end portion of the rotatable shaft; and an adaptor insert directly coupled to the adaptor, wherein the release sleeve is received within an interior cavity of the adaptor insert.

Example 163. An assembly comprising: an adaptor connecting portion configured to be coupled to or integrally formed with an adaptor; an adaptor insert configured to be received within an interior cavity of the adaptor connecting portion and comprising an interior cavity including a plurality of cavity portions, the plurality of cavity portions including a first cavity portion with a first diameter and a second cavity portion with a second diameter, the second diameter smaller than the first diameter; and a release sleeve comprising a wider, first portion configured to be received within the first cavity portion and a narrower, second portion configured to be received within the second cavity portion, wherein the second portion of the release sleeve is configured to bend radially inward relative to a central longitudinal axis of the assembly.

Example 164. The assembly of any example herein, particularly example 163, wherein the second portion of the release sleeve comprises a body that narrows from the first portion of the release sleeve to a wider, collar portion of the second portion of the release sleeve.

Example 165. The assembly of any example herein, particularly example 164, wherein the collar portion extends radially outward from a narrower portion of the body of the second portion of the release sleeve to an end of the release sleeve and wherein the collar portion has a third diameter at the end of the release sleeve which is larger than a fourth diameter of a wider portion of the body that is disposed adjacent to the first portion of the release sleeve.

Example 166. The assembly of any example herein, particularly example 165, wherein, when the release sleeve is arranged outside of the adaptor insert, the third diameter of the collar portion is greater than the second diameter of the second cavity portion of the adaptor insert and wherein, when the release sleeve is received within the interior cavity of the adaptor insert and the collar portion is arranged within the second cavity portion, the third diameter of the collar portion is smaller or equal to the second diameter of the second cavity portion.

Example 167. The assembly of any example herein, particularly example 164 or example 236, wherein the second portion of the release sleeve comprises one or more slots that extend axially through the body and the collar portion of the second portion of the release sleeve and wherein the one or more slots are configured to enable the second portion of the release sleeve to bend radially inward.

Example 168. The assembly of any example herein, particularly example 167, wherein the one or more slots include a plurality of slots that are spaced apart from one another around a circumference of the second portion of the release sleeve.

Example 169. The assembly of any example herein, particularly any one of examples 163-168, wherein the interior cavity of the adaptor insert further includes a third cavity portion with a fifth diameter that is larger than the first diameter and wherein the first portion of the release sleeve comprises a flange that is configured to be received within the third cavity portion.

Example 170. The assembly of any example herein, particularly any one of examples 163-169, further comprising a sealing member disposed within a fourth cavity portion of the interior cavity of the adaptor insert, the fourth cavity portion disposed adjacent to the second cavity portion and having a sixth diameter that is larger than the second diameter of the second cavity portion.

Example 171. The assembly of any example herein, particularly any one of examples 163-169, further comprising a shaft received within the release sleeve and coupled to the release sleeve at the second portion of the release sleeve and wherein the shaft is coupled to the adaptor connecting portion by the release sleeve and the adaptor insert.

Example 172. A delivery apparatus comprising: a handle portion; a rotatable shaft extending distally from the handle portion and having a proximal end portion that extends proximally from the handle portion; an adaptor in fluid communication with an inner lumen of the rotatable shaft; a shaft connector release assembly coupling the proximal end portion of the rotatable shaft to the adaptor, the shaft connector release assembly comprising: an adaptor insert coupled to the adaptor and comprising an interior cavity; and a release sleeve disposed around the proximal end portion of the rotatable shaft and positioned within the interior cavity of the adaptor insert, the release sleeve coupled to the adaptor insert, wherein a flexible, first portion of the release sleeve is depressed radially inward and held in coupling contact with the proximal end portion of the rotatable shaft via radially inward pressure from the adaptor insert; and an inflatable balloon coupled to a distal end portion of the rotatable shaft and configured to inflate upon receiving inflation fluid from the adaptor.

Example 173. The delivery apparatus of any example herein, particularly example 172, wherein the release sleeve comprises the first portion and a second portion and wherein the second portion is larger in diameter than the first portion.

Example 174. The delivery apparatus of any example herein, particularly example 173, wherein the first portion of the release sleeve comprises a body that narrows from the second portion of the release sleeve to a wider, collar portion of the first portion of the release sleeve.

Example 175. The delivery apparatus of any example herein, particularly example 174, wherein the collar portion extends radially outward from a narrower portion of the body of the first portion of the release sleeve to an end of the release sleeve and wherein, when the release sleeve is arranged outside of the adaptor insert, a diameter of the collar portion, at the end of the release sleeve, is larger than a diameter of a wider portion of the body that is disposed adjacent to the second portion of the release sleeve.

Example 176. The delivery apparatus of any example herein, particularly example 174 or example 175, wherein the first portion of the release sleeve comprises one or more slots that extend axially through the body and the collar portion of the first portion of the release sleeve and wherein the one or more slots are configured to enable the first portion of the release sleeve to bend radially inward.

Example 177. The delivery apparatus of any example herein, particularly example 176, wherein the one or more slots include a plurality of slots that are spaced apart from one another around a circumference of the second portion of the release sleeve.

Example 178. The delivery apparatus of any example herein, particularly any one of examples 173-177, wherein the interior cavity of the adaptor insert includes a plurality of cavity portions, the plurality of cavity portions including a first cavity portion with a first diameter and a second cavity portion with a second diameter, the second diameter smaller than the first diameter and wherein the second portion of the release sleeve is disposed within the first cavity portion and the first portion of the release sleeve is disposed within the second cavity portion.

Example 179. The delivery apparatus of any example herein, particularly example 178, wherein the shaft connector release assembly further comprises a sealing member disposed within a third cavity portion of the interior cavity of the adaptor insert and disposed around an outer surface of the proximal end portion of the rotatable shaft, the third cavity portion disposed adjacent to the second cavity portion and having a third diameter that is larger than the second diameter of the second cavity portion.

Example 180. The delivery apparatus of any example herein, particularly any one of examples 172-179, wherein the shaft connector release assembly further comprises a sealing member disposed around the proximal end portion of the rotatable shaft and within the interior cavity of the adaptor insert, adjacent to an end of the first portion of the release sleeve.

Example 181. The delivery apparatus of any example herein, particularly any one of examples 172-180, wherein the adaptor insert is configured to be received within an interior cavity of a connecting portion of the adaptor.

Example 182. The delivery apparatus of any example herein, particularly any one of examples 172-181, further comprising a knob mounted on the proximal end portion of the rotatable shaft, distal to the adaptor, the knob configured to rotate the rotatable shaft.

In view of the many possible embodiments to which the principles of the disclosed technology may be applied, it should be recognized that the illustrated embodiments are only preferred examples of the disclosed technology and should not be taken as limiting the scope of the claimed subject matter. Rather, the scope of the claimed subject matter is defined by the following claims and their equivalents.

I claim:

1. A method comprising:
advancing a distal end portion of a delivery apparatus toward a native valve of a heart, wherein a prosthetic heart valve is radially compressed around an inflatable balloon of the delivery apparatus, at a valve mounting portion of the delivery apparatus;
visualizing, under fluoroscopy and for a selected imaging view, a position of a radiopaque marker on the distal end portion of the delivery apparatus relative to a guidewire extending through a shaft of the delivery apparatus, wherein the marker is circumferentially offset from a selected commissure of the radially compressed prosthetic heart valve by a predetermined amount that is determined based on the selected imaging view, and wherein the marker is reflection asymmetric along an axis that is parallel to a central longitudinal axis of the delivery apparatus;
prior to crossing the native valve, rotating the shaft of the delivery apparatus, which rotates the prosthetic heart valve and the marker, until the marker is centered along the guidewire and is in a predetermined orientation in the selected imaging view; and
advancing the distal end portion of the delivery apparatus including the radially compressed prosthetic heart valve across and into the native valve and inflating the balloon to radially expand and implant the prosthetic heart valve in the native valve such that the selected commissure of the prosthetic heart valve is aligned with a target commissure of the native valve, wherein during the inflating, as the prosthetic heart valve radially expands, the prosthetic heart valve rotates.

2. The method of claim 1, wherein for a first selected imaging view the predetermined amount of offset is a first amount, and wherein for a second selected imaging view the predetermined amount of offset is a second amount.

3. The method of claim 2, wherein the first selected imaging view is a three-cusp imaging view, and the second selected imaging view is a right/left cusp overlap imaging view, and wherein the native valve is a native aortic valve.

4. The method of claim 1, wherein the rotating the shaft of the delivery apparatus includes rotating a knob disposed on a proximal end portion of the shaft that extends proximally from a handle of the delivery apparatus, and wherein the shaft of the delivery apparatus extends through the handle and distally to the distal end portion of the delivery apparatus.

5. The method of claim 4, wherein the balloon is coupled to a distal end of the shaft.

6. The method of claim 1, wherein the predetermined orientation in the selected imaging view is a direct back of the selected imaging view.

7. The method of claim 6, wherein the marker has a first orientation when it is arranged in front of the guidewire within the selected imaging view and a different, second orientation when it is arranged behind the guidewire within the selected imaging view, and wherein rotating the shaft of the delivery apparatus, which rotates the prosthetic heart valve and the marker, includes rotating the shaft until the marker is centered along the guidewire and in its second orientation within the selected imaging view, thereby positioning the marker in the direct back of the selected imaging view.

8. The method of claim 1, wherein the predetermined orientation in the selected imaging view is a direct front of the selected imaging view.

9. The method of claim 8, wherein the marker has a first orientation when it is arranged in front of the guidewire within the selected imaging view and a different, second orientation when it is arranged behind the guidewire within the selected imaging view, and wherein rotating the shaft of the delivery apparatus, which rotates the prosthetic heart valve and the marker, includes rotating the shaft until the marker is centered along the guidewire and in its first orientation within the selected imaging view, thereby positioning the marker in the direct front of the selected imaging view.

10. The method of claim 1, wherein during the inflating, as the prosthetic heart valve radially expands, the prosthetic heart valve rotates by an amount equal to the predetermined amount of offset between the marker and the selected commissure of the prosthetic heart valve when the prosthetic heart valve is radially compressed around the balloon.

11. The method of claim 1, wherein the shaft is a first shaft, wherein a second shaft extends through the first shaft and has a distal end portion extending distally beyond a distal end portion of the first shaft, and wherein the marker is arranged on or embedded within a polymeric body mounted on the distal end portion of the second shaft.

12. The method of claim 11, wherein the polymeric body is a distal shoulder mounted on the distal end portion of the second shaft, distal to the prosthetic heart valve when the prosthetic heart valve is radially compressed around the balloon, and wherein the distal shoulder is configured to resist movement of the prosthetic heart valve relative to the balloon when the prosthetic heart valve is radially compressed around the balloon.

* * * * *